US006303295B1

(12) United States Patent
Taylor et al.

(10) Patent No.: US 6,303,295 B1
(45) Date of Patent: Oct. 16, 2001

(54) SELENOPROTEINS, CODING SEQUENCES AND METHODS

(75) Inventors: Ethan Will Taylor; Ram Gopal Nadimpalli; Chandra Sekar Ramanathan, all of Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 08/679,493

(22) Filed: Jul. 12, 1996

Related U.S. Application Data

(60) Provisional application No. 60/001,203, filed on Jul. 14, 1995, now abandoned, and provisional application No. 60/003,112, filed on Sep. 1, 1995, now abandoned.

(51) Int. Cl.[7] ................................................ C12Q 1/68
(52) U.S. Cl. ........................ 435/6; 530/400; 530/350; 536/23.1; 536/23.74
(58) Field of Search .................................. 530/400, 350; 435/6; 536/23.1, 23.5, 23.72, 23.74

(56) References Cited

U.S. PATENT DOCUMENTS

| | | | |
|---|---|---|---|
| 4,341,757 | * 7/1982 | Spallholz | 424/8 |
| 4,599,234 | * 7/1986 | Amer | 424/164 |
| 4,744,984 | * 5/1988 | Ragland | 424/92 |
| 5,019,561 | * 5/1991 | Birkmayer | 514/52 |

FOREIGN PATENT DOCUMENTS

| | | | |
|---|---|---|---|
| 0 345 247 A2 | * 12/1989 | (EP) | A61K/31/095 |
| 0 465 081 A1 | * 1/1992 | (EP) | A61K/9/16 |
| WO 95/06719 | * 3/1995 | (WO) | C12N/9/08 |

OTHER PUBLICATIONS

Low et al., J. Biological Chem. 270:(37):21659–21664, Sep. 1995.*
Berry et al., EMBO J., 12:3315–3322, 1993.*
Le, S–Y. et al. (1989) J. theor. Biol. 138:495–510.*
Behne, D. et al. (1995) Analyst 120:823–825.*
Gomez, B. et al. (1989) Biochimica et Biophysica Acta. 979:20–26.*
Sanchez, A. et al. (1996) Proc. Natl. Acad. Sci. USA 93:3602–3607.*
Lanfear, J. et al. (1994) Carcinogenesis 15:1387–1392.*
Buttke, T. M. et al. (1995) Free Rad. Res. 22:389–397.*
Michael, N.L. et al. (1994) Journal of Virology 68:979–987.*
Rima, B.K. Biochemical Society Transactions vol. 24, Royal Irish Academy Lecture, U. College Dublin, Sep. 14, 1995.*
Wyatt, J.R. et al. (1993) The RNA World Cold Spring Harbor Laboratory Press pp. 465–496.*
Chen, X. et al. (1995) The EMBO Journal 14; 842–852.*
Kozak, Marilyn (1989) The Journal of Cell Biology 108:229–241.*
Kollmus, H. et al. (1996) Nucleic Acids Research 24:1195–1201.*
Battigello, J–M. A. et al. (1995) Bioorganic & Medicinal Chemistry 3:839–849.*
Jacks, T. et al. (1988) Nature 331:280–283.*
Puglisi, J.D. et al. (1988) Nature 331:283–286.*
Dworkin, Brad M. (1994) Chemico–Biological Interactions 91:181–186.*
Taylor, E. W. et al. (1995) Journal of Orthomolecular Medicine 10:131–138.*
Martin, G.W. et al. (1996) RNA 2:171–182.*
Low, S. C. et al. (1996) TIBS 21:203–208.*
Sappey, C. et al. (1994) AIDS Research and Human Retroviruses 10:1451–1461.*
Bologna, R. et al. (1994) Journal of Nutritional Immunology 3:41–49.*
Schuhmacher, M. et al. (1994) Trace Elements and Electrolytes 11:130–134.*
Sergeant, C. et al. (1994) Oxidative Stress, Cell Activation and Viral Infection pp. 341–351.*
Mantero–Atienza, E. et al. and Oliviero, R. et al. (1991) Journal of Parenteral and Enteral Nutrition, Letters to the Editor 15:693–694.*
Allavena, C. et al. (1995) Biological Trace Elements Research 47:133–138.*
Cubitt, B. et al. (1994) Virus Research 34:69–79.*
Schrauzer, G. N. et al. (1989) Biological Trace Element Research 20:169–178.*
Olmsted, L. et al. (1989) Biological Trace Element Research 20:59–65.*
Kennedy, J. R. (1992) Medical Hypotheses 37:16–19.*
Beck, K. W. et al. (1990) Biological Trace Element Research 25:89–96.*
Dworkin, B. M. et al. (1988) Biological Trace Element Research 15:167–177.*
Schinazi, R. F. et al. (1994) Antimocrobial Agents and Chemotherapy 38:268–274.*
Schrauzer, Gerhard N. (1992) Biological Trace Element Research 33:51–62.*
Schrauzer, G. N. et al. (1989) Biological Trace Element Research 20:169–178.*
Cohen, E. A. et al. (1990) Journal of Acquired Immune Deficiency Syndromes 3:601–608.*

(List continued on next page.)

Primary Examiner—Scott W. Houtteman
(74) Attorney, Agent, or Firm—Greenlee Winner and Sullivan, P.C.

(57) ABSTRACT

The present disclosure provides a method for the identification of nucleotide sequences which encode selenoproteins. Nucleotide sequences are translated in all potential reading frames, those with a relatively large number of UGA or TGA codons are noted, and frameshift-dependent open reading frames and SECIS elements are identified as associated with selenoprotein coding sequences, especially those within or overlapping known open reading frames. Further provided are selenoprotein coding sequences which are associated with certain viruses (e.g., HIV and Ebola), cancer-related genes and coding sequences related to normal functioning of the immune system.

16 Claims, 28 Drawing Sheets

OTHER PUBLICATIONS

Katz, David H. (1993) *Aids Research and Human Retroviruses* 9:489–493.*

Cirelli, A. et al. (1991) *Clinical Biochemistry* 24:211–214.*

Hedge, R. S. et al. (1992) *Nature* 359:505–512.*

Kato, H. et al. (1991) *Science* 251:1476–1479.*

Meeting Reports (1996) *International Antiviral News* 4:84–86.*

Ramanathan, C. S. et al. (1995) *Antiviral Research* 26:A271 #85.*

Taylor, E. W. et al. (1995) *Antiviral Research* 26:A271 #86.*

Hou, J.C. et al. (1993) *Chung–Hua–I–Hsueh–Tsa–Chih* 73:645–6, 699 English Abstract only.*

Adler, T. "Diet Causes Viral Mutation in Mice" *Science News* 147:276.*

Beck et al. (1995) "Rapid genomic evolution of a non–virulent Coxsackievirus B3 in selenium–deficient mice results in selection of identical virulent isolates" *Nature Medicine* 1(5):433–436.*

Borman, S. (1994) "AIDS Virus Predicted To Have Up To Four Unexpected New Genes" *Chemical & Engineering News, ACS* 23–25.*

Facchiano, A. (1995) Investigating Hypothetical Products from Noncoding Frames (HyPNoFs) *J. Mol. Evol.* 40:570–577.*

Gauntt, C. and Tracy, S. (1995) "Deficient diet evokes nasty heart virus" *Nature Medicine* 1(5):405–406.*

Levander, O. (1994) "Nutrient Deficiency Unleases Jeckyll–Hyde Virus" *Agricultural Research* 14–15.*

Taylor et al. (1994) "A Basis for New Approaches to the chemotherapy of AIDS: Novel Genes in HIV–1 Potentially Encode Selenoproteins Expressed by Ribosomal Frameshifting and Termination Suppression" *J. Med. Chem.* 37:2637–2654.*

Taylor, E. (1995) "From Pseudoknots to Selenium: A New Theory of HIV Pathogenesis" *International Antiviral News* 3(2):18–20.*

Williams, P. (1995) "Can selenium help slow down AIDS?" *Record* 20–23.*

* cited by examiner

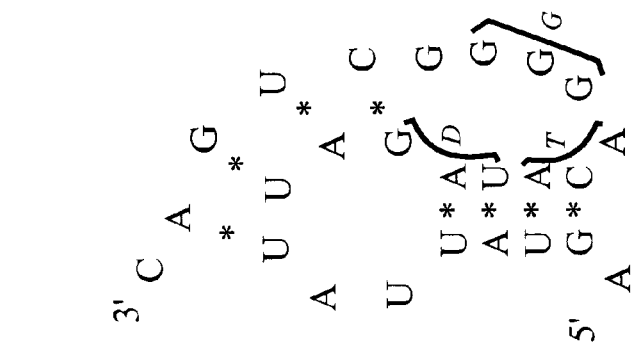
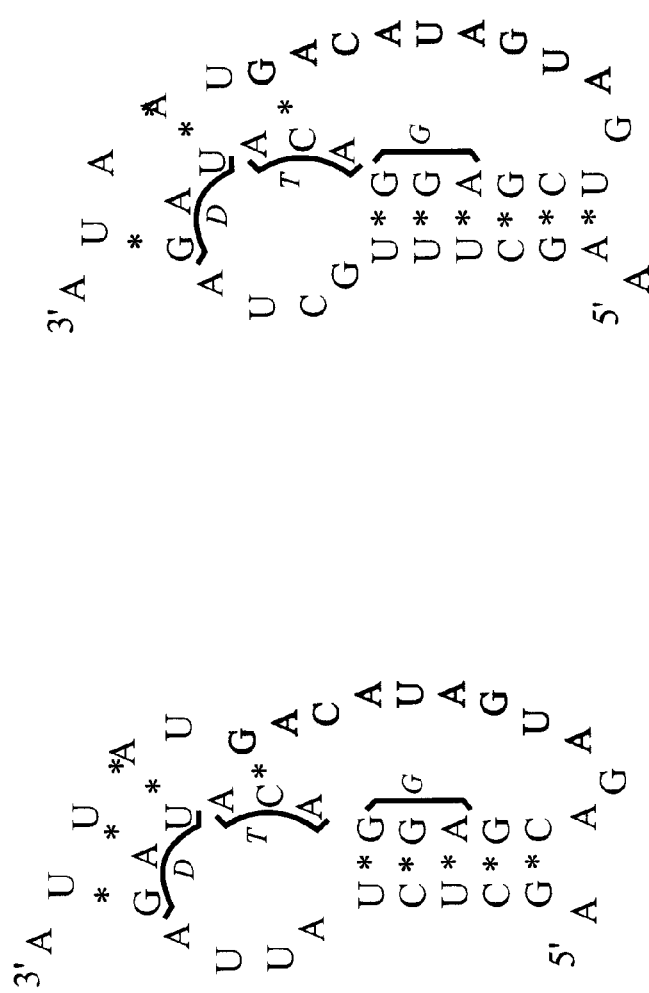
FIG. 3A  FIG. 3B  FIG. 3C

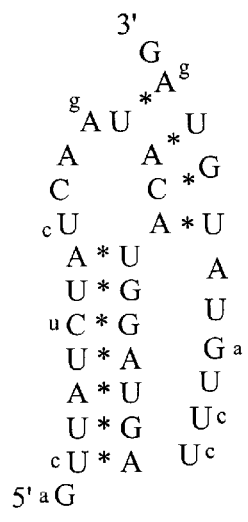 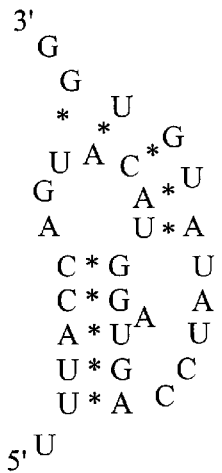 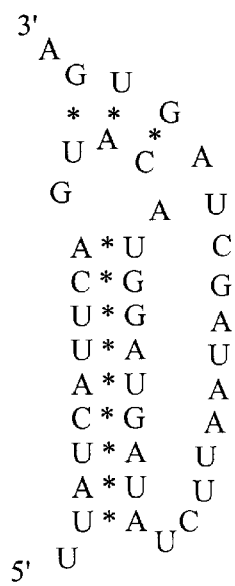
FIG. 5A  FIG. 5B  FIG. 5C

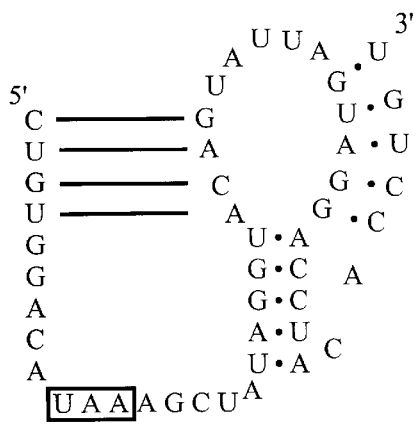 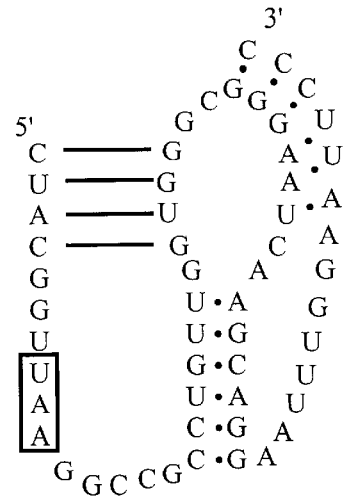 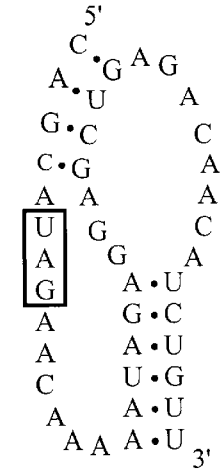
FIG. 11A  FIG. 11B  FIG. 11C
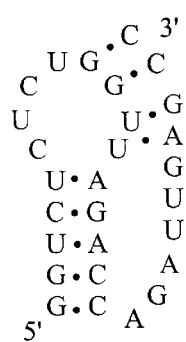 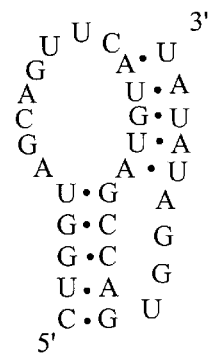 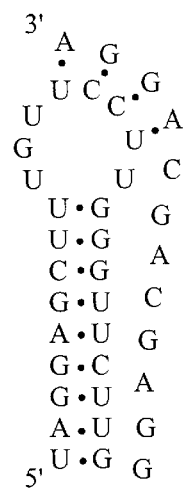
FIG. 12A  FIG. 12B  FIG. 12C

```
                            20         30         40         50
CD4-SP      RKQESCIRKCTWWCCEPLSSRKICPVRCGDPPPLSCCAC

:|   :|  :|::  || |  :::   || :|  | |  :|  |:

MCSP        PKSPCCPPKSP--CCPPKPCP--CPPPCPCPATCPCPL
                  40         50         60         70

60         70         80         90
CD4-SP      NWRTRRQRSRSGRRRCGCCTLRRGC--GSVCCVTRDRSCW

: :   :|:::: :::|:||: :: |    ::|| : :::

MCSP        KPPCCPQKCSCCPKKCTCCPQPPPCCAQPTCCSSENKTES
                 80         90        100        110
```

FIG. 13

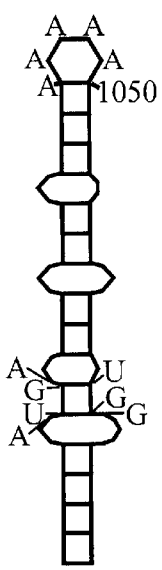 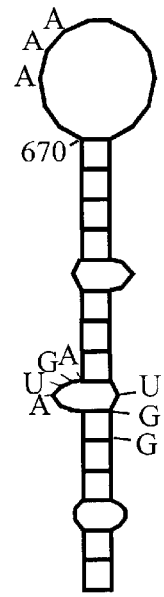 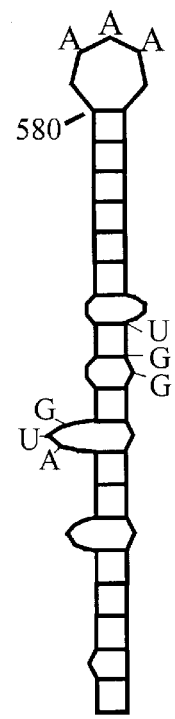
FIG. 14A  FIG. 14B  FIG. 14C
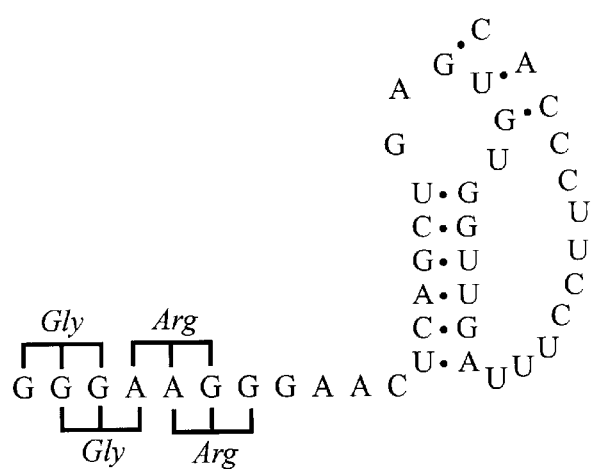
FIG. 15

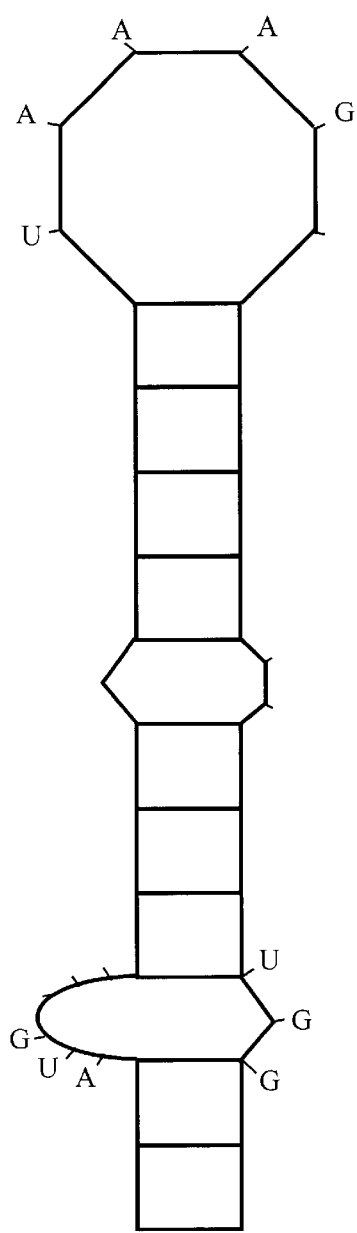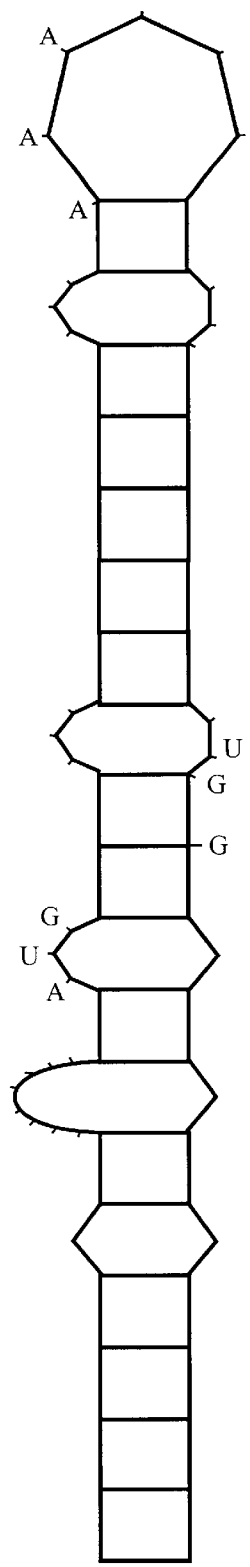
FIG. 16A
FIG. 16B

|  |  |  |  | Met |  |  |
|---|---|---|---|---|---|---|
| IDEAL | gcc | gcc | a<br>gcc | <u>atg</u> | g |  |
| IL2α<br>selenoprotein | +<br>acc | x<br>tcc | acc | <u>atg</u> | g | p<3x10⁻⁵ →<u>Better</u> |
| IL2α main gene | +<br>gtc | +xx<br>agg | xx<br>aag | <u>atg</u> | g | p<3x10⁻³ | x = mismatch, purine to pyrimidine

+ = mismatch, Y:Y or R:R

FIG. 17

UGA-rich PPCR

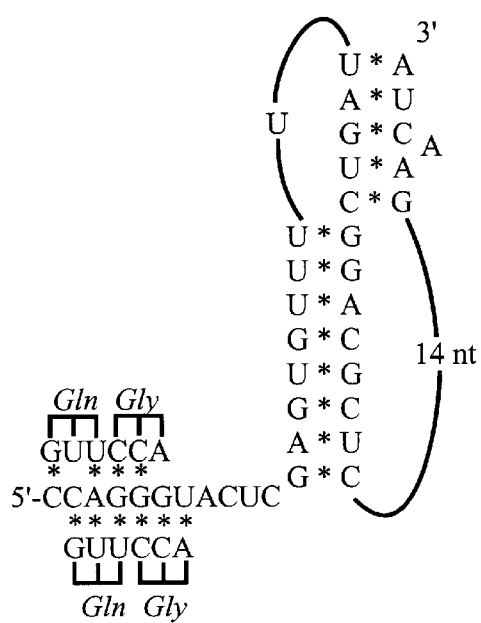
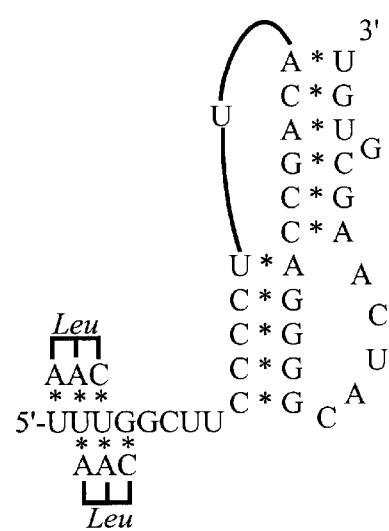
FIG. 25A
FIG. 25B

```
                                            +1 FS signal?
                                              CCCUGA
    -1:         Sec                          Pro (Sec)
             CUUGAU... 27 nt ...UUCCCUGAU
    nef:     Leu  Asp              Phe  Pro  Asp
              i                     ii   iii
```

*nef* codons in known HIV-1 sequence isolates:

i.  Leu, CUU (73/76): could be CUU,CUC,YUA,YUG
ii. Phe, UUC (75/76): could be UUC or UUU
iii. Pro, CCU (74/76): could be CCU,CCC,CCA,CCG

FIG. 28

SEQUENCE LISTING

<160> NUMBER OF SEQ ID NOS: 216

<210> SEQ ID NO 1
<211> LENGTH: 51
<212> TYPE: RNA
<213> ORGANISM: Human immunodeficiency virus type 1

<400> SEQUENCE: 1
uaaaggaagc ucuauuagau acaggagcag augauacagu auuagaagaa a       51

<210> SEQ ID NO 2
<211> LENGTH: 11
<212> TYPE: RNA
<213> ORGANISM: Human immunodeficiency virus type 1

<400> SEQUENCE: 2
ugguuagacc a       11

<210> SEQ ID NO 3
<211> LENGTH: 29
<212> TYPE: RNA
<213> ORGANISM: Human immunodeficiency virus type 1

<400> SEQUENCE: 3
ggucucucug guuagaccag auuugagcc       29

<210> SEQ ID NO 4
<211> LENGTH: 35
<212> TYPE: RNA
<213> ORGANISM: Human immunodeficiency virus type 1

<400> SEQUENCE: 4
aguuaucuau caauacaaug gaugauuuau augua       35

<210> SEQ ID NO 5
<211> LENGTH: 4
<212> TYPE: PRT
<213> ORGANISM: Human immunodeficiency virus type 1

<400> SEQUENCE: 5

Tyr Met Asp Asp
 1

<210> SEQ ID NO 6
<211> LENGTH: 38
<212> TYPE: RNA
<213> ORGANISM: chimpanzee immunodeficiency virus

<400> SEQUENCE: 6
aagcuuugcu agauacagga gcugaugaua caguaaua       38

<210> SEQ ID NO 7
<211> LENGTH: 25
<212> TYPE: RNA
<213> ORGANISM: Simian immunodeficiency virus

<400> SEQUENCE: 7
aguauuauua gauacagggg cugac       25

<210> SEQ ID NO 8
<211> LENGTH: 39
<212> TYPE: RNA

```
<213> ORGANISM: Human immunodeficiency virus type 1

<400> SEQUENCE: 8
ucuggccuuc cuacaaggga aggccaggga auuuucuuc                               39

<210> SEQ ID NO 9
<211> LENGTH: 34
<212> TYPE: RNA
<213> ORGANISM: chimpanzee immunodeficiency virus

<400> SEQUENCE: 9
acuauuuacc aguacaugga ugaccuauau gugg                                   34

<210> SEQ ID NO 10
<211> LENGTH: 40
<212> TYPE: RNA
<213> ORGANISM: Human immunodeficiency virus type 2

<400> SEQUENCE: 10
uuaucauuca guacauggau gauaucuuaa uagcuaguga                             40

<210> SEQ ID NO 11
<211> LENGTH: 62
<212> TYPE: RNA
<213> ORGANISM: Coxsackievirus B
<220> FEATURE:
<221> NAME/KEY: misc_feature
<222> LOCATION: (1)..(62)
<223> OTHER INFORMATION: N is A, U, G or C.

<400> SEQUENCE: 11
nnnnnnnnnn nnaugnnnnn nnnnnnnnnn aaaannnnnn nnnnnnnuga nnnnnnnnnn       60 nn                                                                      62

<210> SEQ ID NO 12
<211> LENGTH: 68
<212> TYPE: RNA
<213> ORGANISM: Human immunodeficiency virus type 1
<220> FEATURE:
<221> NAME/KEY: misc_feature
<222> LOCATION: (1)..(68)
<223> OTHER INFORMATION: N is A, U, G or C.

<400> SEQUENCE: 12
nnnnnnnaug nnnnnnnnnn nnnnnnnnnn nnnnnnaaaa annnnnnnnn nnnnnnnnug       60 annnnnnn                                                                68

<210> SEQ ID NO 13
<211> LENGTH: 231
<212> TYPE: RNA
<213> ORGANISM: Human immunodeficiency virus type 1
<220> FEATURE:
<221> NAME/KEY: misc_feature
<222> LOCATION: (1)..(231)
<223> OTHER INFORMATION: N is A, U, G or C.

<400> SEQUENCE: 13
nnnnnnnnnu ggunnnacca nnugannnnn nnnnnnnnnn nnnnnnnnnn nnnnnnnnnn       60
nnnnnnnnnn nnnuaaagnn nnnnnnnnnn nnnnnnnnnn nnnnnnnnnn nnnnnnnnnn      120
nnnnnnnnnn nnnnnnnnnn nnnnnnnnnn nnnnnnnaaa annnnnnnnn nnnnnnnnnn      180
nnnnnnnuga nnnnnnnnnn nnnnnnnnnn nnnnnnnnnn nnnnnnnnnn n               231
```

<210> SEQ ID NO 14
<211> LENGTH: 82
<212> TYPE: RNA
<213> ORGANISM: Human immunodeficiency virus type 1
<220> FEATURE:
<221> NAME/KEY: misc_feature
<222> LOCATION: (1)..(82)
<223> OTHER INFORMATION: N is A, U, G or C.

<400> SEQUENCE: 14
nnnnnnnnnn nnnnnnnnnn nnnnuaaag nnnnnnnnnn nnnnnnnnnn nnnnnnnnnn      60
nnnnnnnuga nnnnnnnnnn nn                                              82

<210> SEQ ID NO 15
<211> LENGTH: 119
<212> TYPE: RNA
<213> ORGANISM: Human immunodeficiency virus type 1
<220> FEATURE:
<221> NAME/KEY: misc_feature
<222> LOCATION: (1)..(119)
<223> OTHER INFORMATION: N is A, U, G or C.

<400> SEQUENCE: 15
nnnnnnnnnn nnnnnnnnnn nnnnnnnnnn nnnnnnnnnn nnnaguannn nnnnnnnnnn      60
nnnnnaunnn nnnnnnnnnn naaaagannn nnnnnnnnnn nnnnnnnnnn nnnnnnnn       119

<210> SEQ ID NO 16
<211> LENGTH: 37
<212> TYPE: RNA
<213> ORGANISM: Human immunodeficiency virus type 1
<220> FEATURE:
<221> NAME/KEY: misc_feature
<222> LOCATION: (1)..(37)
<223> OTHER INFORMATION: N is A, U, G or C.

<400> SEQUENCE: 16
nnnnnaugnn nnnacaagnn nnnnnnnnug annnnnn                               37

<210> SEQ ID NO 17
<211> LENGTH: 90
<212> TYPE: RNA
<213> ORGANISM: Coxsackievirus B
<220> FEATURE:
<221> NAME/KEY: misc_feature
<222> LOCATION: (1)..(90)
<223> OTHER INFORMATION: N is A, U, G or C.

<400> SEQUENCE: 17
nnnnnnnnnn nnnnnnnnnn nnnagaaaac nnnnnnnnnn ugannnnnnn nnnnnnnnnn      60
nnnnnnnnnn nnnnnnnnnn nnnnnnnnnn                                       90

<210> SEQ ID NO 18
<211> LENGTH: 99
<212> TYPE: RNA
<213> ORGANISM: Visna virus
<220> FEATURE:
<221> NAME/KEY: misc_feature
<222> LOCATION: (1)..(99)
<223> OTHER INFORMATION: N is A, U, G or C.

<400> SEQUENCE: 18
nnnnnnnnnn nnnnnnnnnn nnnnnngaaa nnnnnnnnnn nnnnnnnnnn nnnnnnnnnn      60
nnnnnnnnnn nnnnnnnnnn nnnugannnn nnnnnnnn                              99

<210> SEQ ID NO 19

-continued

<211> LENGTH: 61
<212> TYPE: RNA
<213> ORGANISM: polio type 1 Mahoney
<220> FEATURE:
<221> NAME/KEY: misc_feature
<222> LOCATION: (1)..(61)
<223> OTHER INFORMATION: N is A, U, G or C.

<400> SEQUENCE: 19
nnnnnnnnnn nnnnnnnnnn nnnnnnnuaa agnnnnnnnn ugannnnnnn nnnnnnnnnn 60 n 61

<210> SEQ ID NO 20
<211> LENGTH: 60
<212> TYPE: RNA
<213> ORGANISM: Equine infectious anemia virus
<220> FEATURE:
<221> NAME/KEY: misc_feature
<222> LOCATION: (1)..(60)
<223> OTHER INFORMATION: N is A, U, G or C.

<400> SEQUENCE: 20
nnnnnnnnnn nnnnnnnnnu gannnnnnnn nnnnaaagnn nnnnnnnnnn nnnnnnnnnn 60

<210> SEQ ID NO 21
<211> LENGTH: 49
<212> TYPE: RNA
<213> ORGANISM: Coxsackievirus B
<220> FEATURE:
<221> NAME/KEY: misc_feature
<222> LOCATION: (1)..(49)
<223> OTHER INFORMATION: N is A, U, G or C.

<400> SEQUENCE: 21
nnnnnnnnnn nnugannnnn nuaaaagnnn nnnnnnnnnn nnnnnnnnn 49

<210> SEQ ID NO 22
<211> LENGTH: 123
<212> TYPE: PRT
<213> ORGANISM: Homo sapiens
<220> FEATURE:
<221> NAME/KEY: VARIANT
<222> LOCATION: (1)..(123)
<223> OTHER INFORMATION: X is selenocysteine.

<400> SEQUENCE: 22

```
Met Leu Ala Leu Glu Thr Ser Pro Trp Pro Leu Lys Arg Lys Gln Glu
  1               5                  10                  15

Ser Cys Ile Arg Lys Cys Thr Trp Trp Cys Cys Glu Pro Leu Ser Ser
             20                  25                  30

Arg Lys Ile Cys Pro Val Arg Cys Gly Asp Pro Pro Pro Leu Ser Cys
         35                  40                  45

Cys Cys Ala Cys Asn Trp Arg Thr Arg Arg Gln Arg Ser Arg Ser Gly
     50                  55                  60

Arg Arg Arg Cys Gly Cys Cys Thr Leu Arg Arg Gly Cys Gly Ser Val
 65                  70                  75                  80

Cys Cys Val Thr Arg Asp Arg Ser Cys Trp Asn Pro Thr Ser Arg Phe
                 85                  90                  95

Cys Pro His Gly Pro Pro Arg Cys Ser Gln Trp Pro Cys Leu Cys Trp
            100                 105                 110

Gly Ala Ser Pro Ala Ser Cys Phe Ser Leu Gly
        115                 120
```

-continued

```
<210> SEQ ID NO 23
<211> LENGTH: 226
<212> TYPE: PRT
<213> ORGANISM: Homo sapiens
<220> FEATURE:
<221> NAME/KEY: VARIANT
<222> LOCATION: (1)..(226)
<223> OTHER INFORMATION: X is selenocysteine.

<400> SEQUENCE: 23

Met Gln Ala Gly Ser Phe Ser Ile Ser Gln Ala Cys Ser Arg Lys Thr
 1               5                  10                  15

Val Ala Ser Thr Ser Ala Cys Ser Ser Gly Ala Pro Ser Cys Pro Ser
                20                  25                  30

Gly Arg Glu Leu Ser Cys Val Trp Leu Ile Ser Phe Pro Pro Leu Pro
            35                  40                  45

Ser Pro Pro Arg Ser Pro Pro Ser Arg Arg Glu Cys Ala Gly Tyr Pro
        50                  55                  60

Gly Gln Arg Pro Arg Arg Ala His Phe Val Ala Pro Ser Pro Leu Ala
 65                  70                  75                  80

Cys Trp Trp Leu Ala Ser Trp Phe Cys Trp Pro Trp Glu Trp Pro
                85                  90                  95

Ser Thr Cys Ala Ala Gly Gly Gly Glu Pro Gly Phe Val Ser Cys Asn
                100                 105                 110

Asn Phe Thr Asn Lys Gln Arg Ile Arg Phe Trp Cys Pro Ala Thr Lys
            115                 120                 125

Arg His Arg Ser Val Met Ser Thr Met Trp Lys Asn Glu Arg Arg Asp
        130                 135                 140

Thr Phe Asn Pro Gly Glu Phe Asn Gly Cys Cys Ser Cys Leu Leu Phe
145                 150                 155                 160

Thr Ala Ala Arg Pro Phe Cys Val Cys Cys Ala Trp Glu Gln Leu Val
                165                 170                 175

Arg Gly Ser Ser Gly Ile Leu Gly Arg Arg Phe His Cys Pro Gln Gly
                180                 185                 190

Thr Ser Gln Ser Val Leu Glu Asp Cys Val Arg Asn Ala Ala His Ala
            195                 200                 205

Thr Ala Ser Gly Ser Cys Ala Phe Pro Glu Leu Gly Pro Leu Val Val
        210                 215                 220

Ala Ile
225

<210> SEQ ID NO 24
<211> LENGTH: 158
<212> TYPE: PRT
<213> ORGANISM: Homo sapiens
<220> FEATURE:
<221> NAME/KEY: VARIANT
<222> LOCATION: (1)..(158)
<223> OTHER INFORMATION: X is selenocysteine.

<400> SEQUENCE: 24

Met Thr Ser Ala Thr Leu Ser Pro Thr Met Ser Asn Cys Pro Cys Trp
 1               5                  10                  15

Ala Gly Ala Leu Gly Pro Arg Arg Ala Ser Ala Ala Glu Pro Cys
                20                  25                  30

Thr Gln Ala Phe Pro Ser Trp Cys Leu Cys Ser Ser Leu Ala Arg Pro
            35                  40                  45

Pro Pro Pro Thr Ser Cys Thr Ser Ser Arg Ala Gly Trp Thr Asn Cys
        50                  55                  60
```

```
Gln Ser Pro Pro Arg Thr Cys Ser Trp Arg Thr Cys Ala Cys Ser Phe
 65                  70                  75                  80

Pro Ser Leu Pro Ser Leu Cys Ala Arg Cys Ala Trp Pro Pro Arg Cys
             85                  90                  95

Cys Cys Arg Arg Cys Pro Trp Glu Pro Cys Pro Arg Gly Pro Cys Arg
            100                 105                 110

Met Pro Pro Ser Met Ala Thr Cys Gln Arg Thr Met Cys Cys Thr Cys
            115                 120                 125

Ser Arg Met Leu Thr Pro Cys Arg Cys Thr Arg His Cys Arg Gly Ala
        130                 135                 140

Ser Arg Arg Thr Cys Asp Thr Leu Arg Thr Pro Trp Arg Pro
145                 150                 155

<210> SEQ ID NO 25
<211> LENGTH: 213
<212> TYPE: PRT
<213> ORGANISM: Human immunodeficiency virus type 1
<220> FEATURE:
<221> NAME/KEY: VARIANT
<222> LOCATION: (1)..(213)
<223> OTHER INFORMATION: X is selenocysteine.

<400> SEQUENCE: 25

Met Gly Ala Arg Ala Ser Val Leu Ser Gly Gly Glu Leu Asp Arg Trp
  1               5                  10                  15

Glu Lys Ile Arg Leu Arg Pro Gly Gly Lys Lys Tyr Lys Leu Lys
             20                  25                  30

His Ile Val Trp Ala Ser Arg Glu Leu Glu Arg Phe Ala Val Asn Pro
             35                  40                  45

Gly Leu Leu Glu Thr Ser Glu Gly Cys Arg Gln Ile Leu Gly Gln Leu
         50                  55                  60

Gln Pro Ser Leu Gln Thr Gly Ser Glu Glu Leu Arg Ser Leu Tyr Asn
 65                  70                  75                  80

Thr Val Ala Thr Leu Tyr Cys Val His Gln Arg Ile Glu Ile Lys Asp
             85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly His Ser Ser Gln Val
            115                 120                 125

Ser Gln Asn Tyr Pro Ile Val Gln Asn Ile Gln Gly Gln Met Val His
        130                 135                 140

Gln Ala Ile Ser Pro Arg Thr Leu Asn Cys Met Gly Lys Ser Ser Arg
145                 150                 155                 160

Arg Glu Gly Phe Gln Pro Arg Ser Asp Thr His Val Phe Ser Ile Ile
                165                 170                 175

Arg Arg Ser His Pro Thr Arg Phe Lys His Ala Lys His Ser Gly
            180                 185                 190

Gly Thr Ser Ser Ser His Ala Asn Val Lys Arg Asp His Gln Xaa Gly
        195                 200                 205

Ser Cys Arg Met Gly
    210

<210> SEQ ID NO 26
<211> LENGTH: 101
<212> TYPE: PRT
<213> ORGANISM: Human immunodeficiency virus type 1
<220> FEATURE:
```

```
<221> NAME/KEY: VARIANT
<222> LOCATION: (1)..(101)
<223> OTHER INFORMATION: X is selenocysteine.

<400> SEQUENCE: 26

Pro Gln Ile Thr Leu Trp Gln Arg Pro Leu Val Thr Ile Lys Ile Gly
 1               5                  10                  15

Gly Gln Leu Lys Glu Ser Ser Ile Arg Tyr Arg Ser Arg Xaa Tyr Ser
             20                  25                  30

Ile Arg Arg Asn Glu Phe Ala Arg Lys Met Glu Thr Lys Asn Asp Arg
         35                  40                  45

Gly Asn Trp Arg Phe Tyr Gln Ser Lys Thr Val Xaa Ser Asp Thr His
     50                  55                  60

Arg Asn Leu Trp Thr Xaa Ser Tyr Arg Tyr Ser Ile Ser Arg Thr Tyr
 65                  70                  75                  80

Thr Cys Gln His Asn Trp Lys Lys Ser Val Asp Ser Asp Trp Leu His
             85                  90                  95

Phe Lys Phe Ser His
            100

<210> SEQ ID NO 27
<211> LENGTH: 48
<212> TYPE: RNA
<213> ORGANISM: Human immunodeficiency virus type 1

<400> SEQUENCE: 27
cuguggacau aaagcuauag guacaguauu aguaggaccu acaccugu                48

<210> SEQ ID NO 28
<211> LENGTH: 56
<212> TYPE: RNA
<213> ORGANISM: Human immunodeficiency virus type 1

<400> SEQUENCE: 28
cuacgguuaa ggccggcugu ugguggggcgg gaaucaagca ggaauuugga auuccc     56

<210> SEQ ID NO 29
<211> LENGTH: 41
<212> TYPE: RNA
<213> ORGANISM: Human immunodeficiency virus type 1

<400> SEQUENCE: 29
cagcauagaa caaaaauaga ggagcugaga caacaucugu u                      41

<210> SEQ ID NO 30
<211> LENGTH: 28
<212> TYPE: RNA
<213> ORGANISM: Human immunodeficiency virus type 1

<400> SEQUENCE: 30
ggucucucug guuagaccag auugagcc                                     28

<210> SEQ ID NO 31
<211> LENGTH: 32
<212> TYPE: RNA
<213> ORGANISM: Human immunodeficiency virus type 1

<400> SEQUENCE: 31
cugguagcag uucauguagc caguggauau au                                32

<210> SEQ ID NO 32
```

```
<211> LENGTH: 38
<212> TYPE: RNA
<213> ORGANISM: Human immunodeficiency virus type 1

<400> SEQUENCE: 32
uaggagcuuu guuccuuggg uucuugggag cagcagga                           38

<210> SEQ ID NO 33
<211> LENGTH: 74
<212> TYPE: PRT
<213> ORGANISM: Mus sp.

<400> SEQUENCE: 33
```

Pro Lys Ser Pro Cys Cys Pro Lys Ser Pro Cys Cys Pro Lys
 1               5                  10                  15

Pro Cys Pro Cys Pro Pro Pro Cys Pro Cys Pro Ala Thr Cys Pro Cys
            20                  25                  30

Pro Leu Lys Pro Pro Cys Cys Pro Gln Lys Cys Ser Cys Pro Lys
         35                  40                  45

Lys Cys Thr Cys Cys Pro Gln Pro Pro Pro Cys Cys Ala Gln Pro Thr
     50                  55                  60

Cys Cys Ser Ser Glu Asn Lys Thr Glu Ser
 65                  70

```
<210> SEQ ID NO 34
<211> LENGTH: 62
<212> TYPE: RNA
<213> ORGANISM: Homo sapiens
<220> FEATURE:
<221> NAME/KEY: misc_feature
<222> LOCATION: (1)..(62)
<223> OTHER INFORMATION: N is A, U, G or C.

<400> SEQUENCE: 34
nnnnnnnaug annnnnnnnn nnnnnnnnaa aaannnnnnn nnnnnnnnnn uggnnnnnnn    60 nn                                                                  62

<210> SEQ ID NO 35
<211> LENGTH: 60
<212> TYPE: RNA
<213> ORGANISM: Homo sapiens
<220> FEATURE:
<221> NAME/KEY: misc_feature
<222> LOCATION: (1)..(60)
<223> OTHER INFORMATION: N is A, U, G or C.

<400> SEQUENCE: 35
nnnnnnnnnn naugannnnn nnnnnaaan nnnnnnnnnn nnnnnnnnug gnnnnnnnnn     60

<210> SEQ ID NO 36
<211> LENGTH: 69
<212> TYPE: RNA
<213> ORGANISM: Homo sapiens
<220> FEATURE:
<221> NAME/KEY: misc_feature
<222> LOCATION: (1)..(69)
<223> OTHER INFORMATION: N is A, U, G or C.

<400> SEQUENCE: 36
nnnnnnnnnn nnnnnaugn nnnnnnnnnn nnnnnnnaa annnnnnnnn nnnnnuggn      60 nnnnnnnnn                                                           69

<210> SEQ ID NO 37
```

```
<211> LENGTH: 41
<212> TYPE: RNA
<213> ORGANISM: Homo sapiens

<400> SEQUENCE: 37
gggaagggaa cucagcugag ugugguugau uuccuuccca c                    41

<210> SEQ ID NO 38
<211> LENGTH: 11
<212> TYPE: RNA
<213> ORGANISM: Homo sapiens
<220> FEATURE:
<221> NAME/KEY: misc_feature
<222> LOCATION: (1)..(11)
<223> OTHER INFORMATION: N is A, U, G or C.

<400> SEQUENCE: 38
augnaaanug r                                                     11

<210> SEQ ID NO 39
<211> LENGTH: 40
<212> TYPE: RNA
<213> ORGANISM: Homo sapiens
<220> FEATURE:
<221> NAME/KEY: misc_feature
<222> LOCATION: (1)..(40)
<223> OTHER INFORMATION: N is A, U, G or C.

<400> SEQUENCE: 39
nnnaugnnnn nnnnnnnnnu aaagnnnnnn nnnnnuggnn                      40

<210> SEQ ID NO 40
<211> LENGTH: 70
<212> TYPE: RNA
<213> ORGANISM: Homo sapiens
<220> FEATURE:
<221> NAME/KEY: misc_feature
<222> LOCATION: (1)..(70)
<223> OTHER INFORMATION: N is A, U, G or C.

<400> SEQUENCE: 40
nnnnnnnnnn nnnnnnnnau gnnnnnnnnn nnnnnnnaaa nnnnnnnnnn nnnuggnnn  60 nnnnnnnnnn                                                       70

<210> SEQ ID NO 41
<211> LENGTH: 80
<212> TYPE: RNA
<213> ORGANISM: Homo sapiens
<220> FEATURE:
<221> NAME/KEY: misc_feature
<222> LOCATION: (1)..(80)
<223> OTHER INFORMATION: N is A, U, G or C.

<400> SEQUENCE: 41
nnnnnnnnnn nnaugnnnnn nnnnnnnnnn nnnnnnnnaa annnnnnnnn nnnnnnnnnn  60
nuggnnnnnn nnnnnnnnnn                                            80

<210> SEQ ID NO 42
<211> LENGTH: 57
<212> TYPE: RNA
<213> ORGANISM: Homo sapiens
<220> FEATURE:
<221> NAME/KEY: misc_feature
<222> LOCATION: (1)..(57)
<223> OTHER INFORMATION: N is A, U, G or C.

<400> SEQUENCE: 42
```

```
nnnnnnnnau gnnnnnnnn nnnnnnaaan nnnnnnnnnn nnnngggnnn nnnnnnn      57
```

<210> SEQ ID NO 43
<211> LENGTH: 53
<212> TYPE: RNA
<213> ORGANISM: Homo sapiens

<400> SEQUENCE: 43

```
ggaaauuugc guguggagua uuuggaugac agaaacacuu uucgacauag ugu          53
```

<210> SEQ ID NO 44
<211> LENGTH: 79
<212> TYPE: RNA
<213> ORGANISM: Ebola virus
<220> FEATURE:
<221> NAME/KEY: misc_feature
<222> LOCATION: (1)..(79)
<223> OTHER INFORMATION: N is A, U, G or C.

<400> SEQUENCE: 44

```
nnnnnnnnnn nnnnaugnnn nnnnnnnnnn nnnnnnnnnn nnnaaannnn nnnnnnnnnn   60
nugannnnnn nnnnnnnnn                                                79
```

<210> SEQ ID NO 45
<211> LENGTH: 67
<212> TYPE: RNA
<213> ORGANISM: Ebola virus
<220> FEATURE:
<221> NAME/KEY: misc_feature
<222> LOCATION: (1)..(67)
<223> OTHER INFORMATION: N is A, U, G or C.

<400> SEQUENCE: 45

```
nnnnnnnnna ugnnnnnnnn nnnnnnnnnn nnnnaaaann nnnnnnnnnn nnnnnugann   60 nnnnnnn                                                             67
```

<210> SEQ ID NO 46
<211> LENGTH: 59
<212> TYPE: RNA
<213> ORGANISM: Ebola virus
<220> FEATURE:
<221> NAME/KEY: misc_feature
<222> LOCATION: (1)..(59)
<223> OTHER INFORMATION: N is A, U, G or C.

<400> SEQUENCE: 46

```
nnnnnnnnna ugnnnnnnnn nnnnnnnaaa nnnnnnnnnn nnnnnnnnnn ugannnnnn    59
```

<210> SEQ ID NO 47
<211> LENGTH: 49
<212> TYPE: RNA
<213> ORGANISM: Ebola virus

<400> SEQUENCE: 47

```
uuucccucaa cuaucggcaa uugcacucgg agucgccaca gcacacggg              49
```

<210> SEQ ID NO 48
<211> LENGTH: 43
<212> TYPE: RNA
<213> ORGANISM: Ebola virus

<400> SEQUENCE: 48

```
ggaaaagaaa auucuuauga acuuccauca gaaaagaac gaa                     43
```

<210> SEQ ID NO 49
<211> LENGTH: 53
<212> TYPE: RNA
<213> ORGANISM: Coxsackievirus B
<220> FEATURE:
<221> NAME/KEY: misc_feature
<222> LOCATION: (1)..(53)
<223> OTHER INFORMATION: N is A, U, G or C.

<400> SEQUENCE: 49
ccaggguacu cgaguguuuu uagucggacg cucnnnnnnn nnnnnnngaa cua 53

<210> SEQ ID NO 50
<211> LENGTH: 37
<212> TYPE: RNA
<213> ORGANISM: Coxsackievirus B

<400> SEQUENCE: 50
uuuggcuucc ccuuacagcc aggggcauca agcgugu 37

<210> SEQ ID NO 51
<211> LENGTH: 43
<212> TYPE: RNA
<213> ORGANISM: Human immunodeficiency virus type 1

<400> SEQUENCE: 51
uuuuuuaggg aagaucuggc cuuccuacaa gggaaggcca ggg 43

<210> SEQ ID NO 52
<211> LENGTH: 45
<212> TYPE: RNA
<213> ORGANISM: Human immunodeficiency virus type 1

<400> SEQUENCE: 52
aaaggaagcu cuauuagaua caggagcaga ugauacagua uuaga 45

<210> SEQ ID NO 53
<211> LENGTH: 58
<212> TYPE: RNA
<213> ORGANISM: Feline leukemia virus
<220> FEATURE:
<221> NAME/KEY: misc_feature
<222> LOCATION: (1)..(58)
<223> OTHER INFORMATION: N is A, U, G or C.

<400> SEQUENCE: 53
uaggagagug ggccaggacc cccccccuga gcccnnnnnn nnnnnnnnnn nngggggg 58

<210> SEQ ID NO 54
<211> LENGTH: 72
<212> TYPE: RNA
<213> ORGANISM: Human immunodeficiency virus type 1
<220> FEATURE:
<221> NAME/KEY: misc_feature
<222> LOCATION: (1)..(72)
<223> OTHER INFORMATION: N is A, U, G or C.

<400> SEQUENCE: 54
uuuaaaagaa aaggggggac uggaagggcu aauucacucc cnnnnnnnnn nnnnnnnnnn 60
nnnnnnuggu cu 72

<210> SEQ ID NO 55
<211> LENGTH: 42
<212> TYPE: RNA
<213> ORGANISM: Human immunodeficiency virus type 1

```
<220> FEATURE:
<221> NAME/KEY: misc_feature
<222> LOCATION: (1)..(42)
<223> OTHER INFORMATION: N is A, U, G or C.

<400> SEQUENCE: 55
cuugaunnnn nnnnnnnnnn nnnnnnnnnn nnnuucccug au                  42

<210> SEQ ID NO 56
<211> LENGTH: 12
<212> TYPE: RNA
<213> ORGANISM: Human immunodeficiency virus type 1

<400> SEQUENCE: 56
cuucucyuay ug                                                   12

<210> SEQ ID NO 57
<211> LENGTH: 12
<212> TYPE: RNA
<213> ORGANISM: Human immunodeficiency virus type 1

<400> SEQUENCE: 57
ccucccccac cg                                                   12

<210> SEQ ID NO 58
<211> LENGTH: 60
<212> TYPE: RNA
<213> ORGANISM: Mouse mammary tumor virus

<400> SEQUENCE: 58
aaagggagau cugacuuuua cguuccugu aguuuuaug ggagacagug augaugauga   60

<210> SEQ ID NO 59
<211> LENGTH: 87
<212> TYPE: RNA
<213> ORGANISM: Hepatitis B virus
<220> FEATURE:
<221> NAME/KEY: misc_feature
<222> LOCATION: (1)..(87)
<223> OTHER INFORMATION: N is A, U, G or C.

<400> SEQUENCE: 59 uuuccccac uguuggcuu ucagcnnnnn nnnnaugug guauuggggg ccaagunnnn    60
nnnnnnnnnn nnnnnnnnuu auaccgc                                    87

<210> SEQ ID NO 60
<211> LENGTH: 139
<212> TYPE: RNA
<213> ORGANISM: Human immunodeficiency virus type 1
<220> FEATURE:
<221> NAME/KEY: misc_feature
<222> LOCATION: (1)..(139)
<223> OTHER INFORMATION: N is A, U, G or C.

<400> SEQUENCE: 60
nnnnnnnnnn nnnnnnnnng augauacnnn nnnnnaagaa annnnnnnnn nnnnnnnnnn  60
nnnnnnnaaa annnnnnnnn nnnnnnnnnn nnnnnnnnnn nnnnnnnngu augaucnnnn 120
nnnnnnnnnn nnnnnnnnn                                             139

<210> SEQ ID NO 61
<211> LENGTH: 12
<212> TYPE: DNA
<213> ORGANISM: Papillomavirus sylvilagi
<220> FEATURE:
```

```
<221> NAME/KEY: misc_feature
<222> LOCATION: (1)..(12)
<223> OTHER INFORMATION: N is A, T, G or C.

<400> SEQUENCE: 61
accgnnnncg gt                                                              12

<210> SEQ ID NO 62
<211> LENGTH: 11
<212> TYPE: DNA
<213> ORGANISM: Human immunodeficiency virus type 1

<400> SEQUENCE: 62
tggttagacc a                                                               11

<210> SEQ ID NO 63
<211> LENGTH: 9
<212> TYPE: PRT
<213> ORGANISM: Human immunodeficiency virus type 1

<400> SEQUENCE: 63

Pro Phe Arg Lys Gln Asn Pro Arg His
  1               5

<210> SEQ ID NO 64
<211> LENGTH: 12
<212> TYPE: RNA
<213> ORGANISM: Human immunodeficiency virus type 1

<400> SEQUENCE: 64
auccauuuca ga                                                              12

<210> SEQ ID NO 65
<211> LENGTH: 11
<212> TYPE: RNA
<213> ORGANISM: Human immunodeficiency virus type 1

<400> SEQUENCE: 65
aucguuucag a                                                               11

<210> SEQ ID NO 66
<211> LENGTH: 11
<212> TYPE: RNA
<213> ORGANISM: Human immunodeficiency virus type 1

<400> SEQUENCE: 66
acaacaaaag a                                                               11

<210> SEQ ID NO 67
<211> LENGTH: 11
<212> TYPE: RNA
<213> ORGANISM: Human immunodeficiency virus type 1

<400> SEQUENCE: 67
augacaaaag a                                                               11

<210> SEQ ID NO 68
<211> LENGTH: 12
<212> TYPE: RNA
<213> ORGANISM: Human immunodeficiency virus type 1

<400> SEQUENCE: 68
augacccuga ga                                                              12
```

```
<210> SEQ ID NO 69
<211> LENGTH: 12
<212> TYPE: RNA
<213> ORGANISM: Human immunodeficiency virus type 1

<400> SEQUENCE: 69
auaaaggaga ga                                                        12

<210> SEQ ID NO 70
<211> LENGTH: 155
<212> TYPE: PRT
<213> ORGANISM: Human immunodeficiency virus type 1
<220> FEATURE:
<221> NAME/KEY: VARIANT
<222> LOCATION: (1)..(155)
<223> OTHER INFORMATION: X is Q or Y.

<400> SEQUENCE: 70

Phe Leu Asp Gly Ile Asp Lys Ala Gln Asp Glu His Glu Lys Tyr His
 1               5                  10                  15

Ser Asn Trp Arg Ala Met Ala Ser Asp Phe Asn Leu Pro Pro Val Val
                20                  25                  30

Ala Lys Glu Ile Val Ala Ser Cys Asp Lys Cys Gln Leu Lys Gly Glu
            35                  40                  45

Ala Met His Gly Gln Val Asp Cys Ser Pro Gly Ile Trp Gln Leu Asp
        50                  55                  60

Cys Thr His Leu Glu Gly Lys Ser Tyr Pro Gly Ser Ser Ser Cys Ser
 65                  70                  75                  80

Gln Trp Ile Tyr Arg Ser Arg Ser Tyr Ser Arg Asn Arg Ala Gly
                85                  90                  95

Asn Ser Ile Leu Ser Phe Lys Ile Ser Arg Lys Met Ala Ser Lys Asn
            100                 105                 110

Asn Thr Tyr Arg Gln Trp Gln Gln Phe His Gln Tyr Tyr Gln Gln Xaa
        115                 120                 125

Arg Leu Leu Val Gly Gly Asn Gln Ala Gly Ile Trp Asn Ser Leu Gln
    130                 135                 140

Ser Pro Lys Ser Arg Ser Ser Arg Ile Tyr Glu
145                 150                 155

<210> SEQ ID NO 71
<211> LENGTH: 327
<212> TYPE: PRT
<213> ORGANISM: Human immunodeficiency virus type 1
<220> FEATURE:
<221> NAME/KEY: VARIANT
<222> LOCATION: (1)..(327)
<223> OTHER INFORMATION: X is selenocysteine.

<400> SEQUENCE: 71

Pro Ile Ser Pro Ile Glu Thr Val Pro Val Lys Leu Lys Pro Gly Met
 1               5                  10                  15

Asp Gly Pro Lys Val Lys Gln Trp Pro Leu Thr Glu Glu Lys Ile Lys
                20                  25                  30

Ala Leu Val Glu Ile Cys Thr Glu Met Glu Lys Glu Gly Lys Ile Ser
            35                  40                  45

Lys Ile Gly Pro Glu Asn Pro Tyr Asn Thr Pro Val Phe Ala Ile Lys
        50                  55                  60

Lys Lys Asp Ser Thr Lys Trp Arg Lys Leu Val Asp Phe Arg Glu Leu
 65                  70                  75                  80
```

-continued

```
Asn Lys Arg Thr Gln Asp Phe Trp Glu Val Gln Leu Gly Ile Pro His
                85                  90                  95

Pro Ala Gly Leu Lys Lys Glu Lys Ile Ser Asn Ser Thr Gly Cys Gly
            100                 105                 110

Xaa Cys Ile Phe Phe Ser Ser Leu Asp Glu Asp Phe Arg Lys Tyr Thr
        115                 120                 125

Ala Phe Thr Ile Pro Ser Ile Asn Asn Glu Thr Pro Gly Ile Arg Tyr
    130                 135                 140

Gln Tyr Asn Val Leu Pro Gln Gly Trp Lys Gly Ser Pro Ala Ile Phe
145                 150                 155                 160

Gln Ser Ser Met Thr Lys Ile Leu Glu Pro Phe Arg Lys Gln Asn Pro
                165                 170                 175

Asp Ile Val Ile Tyr Gln Tyr Met Asp Asp Leu Tyr Val Gly Ser Asp
            180                 185                 190

Leu Glu Ile Gly Gln His Arg Thr Lys Ile Glu Glu Leu Arg Gln His
        195                 200                 205

Leu Leu Arg Trp Gly Leu Thr Thr Pro Asp Lys Lys His Gln Lys Glu
    210                 215                 220

Pro Pro Phe Leu Trp Met Gly Tyr Glu Leu His Pro Asp Lys Trp Thr
225                 230                 235                 240

Val Gln Pro Ile Val Leu Pro Glu Lys Asp Ser Trp Thr Val Asn Asp
                245                 250                 255

Ile Gln Lys Leu Val Gly Lys Leu Asn Trp Ala Ser Gln Ile Tyr Pro
            260                 265                 270

Gly Ile Lys Val Arg Gln Leu Cys Lys Leu Leu Arg Gly Thr Lys Ala
        275                 280                 285

Leu Thr Glu Val Ile Pro Leu Thr Glu Glu Ala Glu Leu Glu Leu Ala
    290                 295                 300

Glu Asn Arg Glu Ile Leu Lys Glu Pro Val His Gly Val Tyr Tyr Asp
305                 310                 315                 320

Pro Ser Lys Asp Leu Ile Ala
                325

<210> SEQ ID NO 72
<211> LENGTH: 327
<212> TYPE: PRT
<213> ORGANISM: Human immunodeficiency virus type 1
<220> FEATURE:
<221> NAME/KEY: VARIANT
<222> LOCATION: (1)..(327)
<223> OTHER INFORMATION: X is selenocysteine.

<400> SEQUENCE: 72

Pro Ile Ser Pro Ile Glu Thr Val Pro Val Lys Leu Lys Pro Gly Met
1               5                   10                  15

Asp Gly Pro Lys Val Lys Gln Trp Pro Leu Thr Glu Glu Lys Ile Lys
            20                  25                  30

Ala Leu Val Glu Ile Cys Thr Glu Met Glu Lys Glu Gly Lys Ile Ser
        35                  40                  45

Lys Ile Gly Pro Glu Asn Pro Tyr Asn Thr Pro Val Phe Ala Ile Lys
    50                  55                  60

Lys Lys Asp Ser Thr Lys Trp Arg Lys Leu Val Asp Phe Arg Glu Leu
65                  70                  75                  80

Asn Lys Arg Thr Gln Asp Phe Trp Glu Val Gln Leu Gly Ile Pro His
                85                  90                  95

Pro Ala Gly Leu Lys Lys Lys Lys Ser Val Thr Val Leu Asp Val Gly
```

-continued

```
                100                 105                 110
Asp Ala Tyr Phe Ser Val Pro Leu Asp Glu Asp Phe Arg Lys Tyr Thr
            115                 120                 125

Ala Phe Thr Ile Pro Ser Ile Asn Asn Glu Thr Pro Gly Ile Arg Tyr
        130                 135                 140

Gln Tyr Asn Val Leu Pro Gln Gly Trp Lys Gly Ser Pro Ala Ile Phe
145                 150                 155                 160

Gln Ser Ser Met Thr Lys Ile Leu Glu Pro Phe Arg Lys Gln Asn Pro
                165                 170                 175

Arg His Ser Tyr Leu Ser Ile His Gly Xaa Phe Val Cys Arg Ile Xaa
                180                 185                 190

Leu Glu Ile Gly Gln His Arg Thr Lys Ile Glu Glu Leu Arg Gln His
            195                 200                 205

Leu Leu Arg Trp Gly Leu Thr Thr Pro Asp Lys Lys His Gln Lys Glu
        210                 215                 220

Pro Pro Phe Leu Trp Met Gly Tyr Glu Leu His Pro Asp Lys Trp Thr
225                 230                 235                 240

Val Gln Pro Ile Val Leu Pro Glu Lys Asp Ser Trp Thr Val Asn Asp
                245                 250                 255

Ile Gln Lys Leu Val Gly Lys Leu Asn Trp Ala Ser Gln Ile Tyr Pro
            260                 265                 270

Gly Ile Lys Val Arg Gln Leu Cys Lys Leu Leu Arg Gly Thr Lys Ala
        275                 280                 285

Leu Thr Glu Val Ile Pro Leu Thr Glu Glu Ala Glu Leu Glu Leu Ala
290                 295                 300

Glu Asn Arg Glu Ile Leu Lys Glu Pro Val His Gly Val Tyr Tyr Asp
305                 310                 315                 320

Pro Ser Lys Asp Leu Ile Ala
                325
```

<210> SEQ ID NO 73
<211> LENGTH: 237
<212> TYPE: PRT
<213> ORGANISM: Human immunodeficiency virus type 1
<220> FEATURE:
<221> NAME/KEY: VARIANT
<222> LOCATION: (199)
<223> OTHER INFORMATION: X is Q or Y.
<221> NAME/KEY: VARIANT
<222> LOCATION: (1)..(237)
<223> OTHER INFORMATION: X at positions 186, 192, 237 and 233 is
      selenocysteine.

<400> SEQUENCE: 73

```
Pro Ile Ser Pro Ile Glu Thr Val Pro Val Lys Leu Lys Pro Gly Met
  1               5                  10                  15

Asp Gly Pro Lys Val Lys Gln Trp Pro Leu Thr Glu Glu Lys Ile Lys
            20                  25                  30

Ala Leu Val Glu Ile Cys Thr Glu Met Glu Lys Glu Gly Lys Ile Ser
        35                  40                  45

Lys Ile Gly Pro Glu Asn Pro Tyr Asn Thr Pro Val Phe Ala Ile Lys
    50                  55                  60

Lys Lys Asp Ser Thr Lys Trp Arg Lys Leu Val Asp Phe Arg Glu Leu
65                  70                  75                  80

Asn Lys Arg Thr Gln Asp Phe Trp Glu Val Gln Leu Gly Ile Pro His
                85                  90                  95

Pro Ala Gly Leu Lys Lys Lys Lys Ser Val Thr Val Leu Asp Val Gly
```

```
                    100                 105                 110
Asp Ala Tyr Phe Ser Val Pro Leu Asp Glu Asp Phe Arg Lys Tyr Thr
                115                 120                 125

Ala Phe Thr Ile Pro Ser Ile Asn Asn Glu Thr Pro Gly Ile Arg Tyr
    130                 135                 140

Gln Tyr Asn Val Leu Pro Gln Gly Trp Lys Gly Ser Pro Ala Ile Phe
145                 150                 155                 160

Gln Ser Ser Met Thr Lys Ile Leu Glu Pro Phe Arg Lys Thr Lys Ser
                165                 170                 175

Arg His Ser Tyr Leu Ser Ile His Gly Xaa Phe Val Cys Arg Ile Xaa
                180                 185                 190

Leu Arg Asn Arg Ala Ala Xaa Asn Lys Asn Arg Gly Ala Glu Thr Thr
                195                 200                 205

Ser Val Glu Val Gly Thr Tyr His Thr Arg Gly Lys Thr Ser Glu Arg
    210                 215                 220

Thr Ser Ile Pro Leu Asp Gly Leu Xaa Thr Pro Ser Xaa
225                 230                 235
```

<210> SEQ ID NO 74
<211> LENGTH: 151
<212> TYPE: PRT
<213> ORGANISM: Human immunodeficiency virus type 1
<220> FEATURE:
<221> NAME/KEY: VARIANT
<222> LOCATION: (1)..(151)
<223> OTHER INFORMATION: X is selenocysteine.

<400> SEQUENCE: 74

```
Met Gly Gly Lys Trp Ser Lys Ser Ser Val Val Gly Trp Pro Thr Val
 1               5                  10                  15

Arg Glu Arg Met Arg Arg Ala Glu Pro Ala Ala Asp Gly Val Gly Ala
                20                  25                  30

Ala Ser Arg Asp Leu Glu Lys His Gly Ala Ile Thr Ser Ser Asn Thr
            35                  40                  45

Ala Ala Thr Asn Ala Ala Cys Ala Trp Leu Glu Ala Gln Glu Glu Glu
        50                  55                  60

Glu Val Gly Phe Pro Val Thr Pro Gln Val Pro Leu Arg Pro Met Thr
65                  70                  75                  80

Tyr Lys Ala Ala Val Asp Leu Ser His Phe Leu Lys Arg Lys Gly Gly
                85                  90                  95

Thr Gly Arg Ala Asn Ser Leu Pro Thr Lys Thr Arg Tyr Pro Xaa Ser
                100                 105                 110

Val Asp Leu Pro His Thr Arg Leu Leu Pro Xaa Leu Ala Glu Leu His
            115                 120                 125

Thr Arg Ala Arg Gly Gly Ile Ser Thr Asp Leu Trp Met Val Leu Gln
        130                 135                 140

Ala Ser Thr Ser Xaa Ala Arg
145                 150
```

<210> SEQ ID NO 75
<211> LENGTH: 206
<212> TYPE: PRT
<213> ORGANISM: Human immunodeficiency virus type 1
<220> FEATURE:
<221> NAME/KEY: VARIANT
<222> LOCATION: (1)..(206)
<223> OTHER INFORMATION: X is selenocysteine.

<400> SEQUENCE: 75

```
Met Gly Gly Lys Trp Ser Lys Ser Ser Val Val Gly Trp Pro Thr Val
  1               5                   10                  15

Arg Glu Arg Met Arg Arg Ala Glu Pro Ala Ala Asp Gly Val Gly Ala
             20                  25                  30

Ala Ser Arg Asp Leu Glu Lys His Gly Ala Ile Thr Ser Ser Asn Thr
         35                  40                  45

Ala Ala Thr Asn Ala Ala Cys Ala Trp Leu Glu Ala Gln Glu Glu Glu
     50                  55                  60

Glu Val Gly Phe Pro Val Thr Pro Gln Val Pro Leu Arg Pro Met Thr
 65                  70                  75                  80

Tyr Lys Ala Ala Val Asp Leu Ser His Phe Leu Lys Arg Lys Gly Gly
                 85                  90                  95

Thr Gly Arg Ala Asn Ser Leu Pro Thr Lys Thr Arg Tyr Pro Xaa Ser
            100                 105                 110

Val Asp Leu Pro His Thr Arg Leu Leu Pro Asp Trp Gln Asn Tyr Thr
        115                 120                 125

Pro Gly Pro Gly Val Arg Tyr Pro Leu Thr Phe Gly Trp Cys Tyr Lys
    130                 135                 140

Leu Val Pro Val Glu Pro Asp Lys Val Glu Glu Ala Asn Lys Gly Glu
145                 150                 155                 160

Asn Thr Ser Leu Leu His Pro Val Ser Leu His Gly Met Asp Asp Pro
                165                 170                 175

Glu Arg Glu Val Leu Glu Trp Arg Phe Asp Ser Arg Leu Ala Phe His
            180                 185                 190

His Val Ala Arg Glu Leu His Pro Glu Tyr Phe Lys Asn Cys
        195                 200                 205

<210> SEQ ID NO 76
<211> LENGTH: 239
<212> TYPE: PRT
<213> ORGANISM: Human immunodeficiency virus type 1
<220> FEATURE:
<221> NAME/KEY: VARIANT
<222> LOCATION: (1)..(239)
<223> OTHER INFORMATION: X os selenocysteine.

<400> SEQUENCE: 76

Met Gly Gly Lys Trp Ser Lys Ser Ser Val Val Gly Trp Pro Thr Val
  1               5                   10                  15

Arg Glu Arg Met Arg Arg Ala Glu Pro Ala Ala Asp Gly Val Gly Ala
             20                  25                  30

Ala Ser Arg Asp Leu Glu Lys His Gly Ala Ile Thr Ser Ser Asn Thr
         35                  40                  45

Ala Ala Thr Asn Ala Ala Cys Ala Trp Leu Glu Ala Gln Glu Glu Glu
     50                  55                  60

Glu Val Gly Phe Pro Val Thr Pro Gln Val Pro Leu Arg Pro Met Thr
 65                  70                  75                  80

Tyr Lys Ala Ala Val Asp Leu Ser His Phe Leu Lys Glu Lys Gly Gly
                 85                  90                  95

Leu Glu Gly Leu Ile His Ser Gln Arg Arg Gln Asp Ile Leu Asp Leu
            100                 105                 110

Trp Ile Tyr His Thr Gln Gly Tyr Phe Pro Asp Trp Gln Asn Tyr Thr
        115                 120                 125

Pro Gly Pro Gly Val Arg Tyr Pro Leu Thr Phe Gly Trp Cys Tyr Lys
    130                 135                 140
```

-continued

```
Leu Val Pro Val Glu Pro Asp Lys Val Glu Ala Asn Lys Gly Glu
145                 150                 155                 160

Asn Thr Ser Leu Leu His Pro Val Ser Leu His Gly Met Asp Asp Pro
                165                 170                 175

Glu Arg Glu Val Leu Glu Trp Arg Phe Asp Ser Arg Leu Ala Phe His
                180                 185                 190

His Val Ala Arg Glu Leu His Pro Glu Tyr Phe Lys Asn Cys Xaa His
                195                 200                 205

Arg Ala Cys Tyr Lys Gly Leu Ser Ala Gly Asp Phe Pro Gly Arg Arg
                210                 215                 220

Gly Leu Gly Gly Thr Gly Glu Trp Arg Ala Leu Arg Cys Cys Ile
225                 230                 235
```

<210> SEQ ID NO 77
<211> LENGTH: 617
<212> TYPE: PRT
<213> ORGANISM: Human immunodeficiency virus type 1
<220> FEATURE:
<221> NAME/KEY: VARIANT
<222> LOCATION: (1)..(617)
<223> OTHER INFORMATION: X is selenocysteine.

<400> SEQUENCE: 77

```
Met Arg Val Lys Glu Lys Tyr Gln His Leu Trp Arg Trp Gly Trp Lys
1               5                   10                  15

Trp Gly Thr Met Leu Leu Gly Ile Leu Met Ile Cys Ser Ala Thr Glu
                20                  25                  30

Lys Leu Trp Val Thr Val Tyr Tyr Gly Val Pro Val Trp Lys Glu Ala
                35                  40                  45

Thr Thr Thr Leu Phe Cys Ala Ser Asp Ala Lys Ala Tyr Asp Thr Glu
            50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
                100                 105                 110

Asp Gln Ser Leu Lys Pro Cys Val Lys Leu Thr Pro Leu Cys Val Ser
            115                 120                 125

Leu Lys Cys Thr Asp Leu Gly Asn Ala Thr Asn Thr Asn Ser Ser Asn
130                 135                 140

Thr Asn Ser Ser Ser Gly Glu Met Met Met Glu Lys Gly Glu Ile Lys
145                 150                 155                 160

Asn Cys Ser Phe Asn Ile Ser Thr Ser Ile Arg Gly Lys Val Gln Lys
                165                 170                 175

Glu Tyr Ala Phe Phe Tyr Lys Leu Asp Ile Ile Pro Ile Asp Asn Asp
                180                 185                 190

Thr Thr Ser Tyr Thr Leu Thr Ser Cys Asn Thr Ser Val Ile Thr Gln
            195                 200                 205

Ala Cys Pro Lys Val Ser Phe Glu Pro Ile Pro Ile His Tyr Cys Ala
210                 215                 220

Pro Ala Gly Phe Ala Ile Leu Lys Cys Asn Asn Lys Thr Phe Asn Gly
225                 230                 235                 240

Thr Gly Pro Cys Thr Asn Val Ser Thr Val Gln Cys Thr His Gly Ile
                245                 250                 255

Arg Pro Val Val Ser Thr Gln Leu Leu Leu Asn Gly Ser Leu Ala Glu
```

-continued

|   |   |   |   |   | 260 |   |   |   |   | 265 |   |   |   |   | 270 |   |   |
|---|---|---|---|---|---|---|---|---|---|---|---|---|---|---|---|---|---|

Glu Glu Val Val Ile Arg Ser Ala Asn Phe Thr Asp Asn Ala Lys Thr
              275                 280                 285

Ile Ile Val Gln Leu Asn Gln Ser Val Glu Ile Asn Cys Thr Arg Pro
290                 295                 300

Asn Asn Asn Thr Arg Lys Ser Ile Arg Ile Gln Arg Gly Pro Gly Arg
305                 310                 315                 320

Ala Phe Val Thr Ile Gly Lys Ile Gly Asn Met Arg Gln Ala His Cys
                325                 330                 335

Asn Ile Ser Arg Ala Lys Trp Asn Ala Thr Leu Lys Gln Ile Ala Ser
                340                 345                 350

Lys Leu Arg Glu Gln Phe Gly Asn Asn Lys Thr Ile Ile Phe Lys Gln
                355                 360                 365

Ser Ser Gly Gly Asp Pro Glu Ile Val Thr His Ser Phe Asn Cys Gly
370                 375                 380

Gly Glu Phe Phe Tyr Cys Asn Ser Thr Gln Leu Phe Asn Ser Thr Trp
385                 390                 395                 400

Phe Asn Ser Thr Trp Ser Thr Glu Gly Ser Asn Asn Thr Glu Gly Ser
                405                 410                 415

Asp Thr Ile Thr Leu Pro Cys Arg Ile Lys Gln Phe Ile Asn Met Trp
                420                 425                 430

Gln Glu Val Gly Lys Ala Met Tyr Ala Pro Pro Ile Ser Gly Gln Ile
                435                 440                 445

Arg Cys Ser Ser Asn Ile Thr Gly Leu Leu Leu Thr Arg Asp Gly Gly
                450                 455                 460

Asn Asn Asn Asn Gly Ser Glu Ile Phe Arg Pro Gly Gly Gly Asp Met
465                 470                 475                 480

Arg Asp Asn Trp Arg Ser Glu Leu Tyr Lys Tyr Lys Val Val Lys Ile
                485                 490                 495

Glu Pro Leu Gly Val Ala Pro Thr Lys Ala Lys Arg Arg Val Val Gln
                500                 505                 510

Arg Glu Lys Lys Ser Ser Gly Asn Arg Ser Phe Val Pro Trp Val Leu
                515                 520                 525

Gly Ser Ser Arg Lys His Tyr Gly Arg Thr Val Asn Asp Ala Asp Gly
530                 535                 540

Thr Gly Gly Thr Ile Ile Val Trp Tyr Ser Ala Ala Glu Gln Phe
545                 550                 555                 560

Ala Glu Gly Tyr Xaa Gly Ala Thr Ala Ser Val Ala Thr His Ser Leu
                565                 570                 575

Gly His Gln Ala Ala Pro Gly Lys Asn Pro Gly Cys Gly Lys Ile Pro
                580                 585                 590

Lys Gly Ser Thr Ala Pro Gly Asp Leu Gly Leu Leu Trp Lys Thr His
                595                 600                 605

Leu His His Cys Cys Ala Leu Glu Cys
610                 615

<210> SEQ ID NO 78
<211> LENGTH: 119
<212> TYPE: PRT
<213> ORGANISM: Coxsackievirus B
<220> FEATURE:
<221> NAME/KEY: VARIANT
<222> LOCATION: (1)..(119)
<223> OTHER INFORMATION: X is selenocysteine.

<400> SEQUENCE: 78

-continued

```
Met Xaa Tyr Tyr Ser Gln Met Ser Val His Asn Gly Ser Val Leu Leu
  1               5                  10                  15

Cys Val Gln Lys Gln Ala Leu Pro Asn Phe Val Xaa Arg Thr Arg Ser
             20                  25                  30

Ser Arg Gly Pro Arg Glu Xaa Ile Leu Pro Gln Glu Ile Pro Ile Pro
         35                  40                  45

Cys Ala Phe Ser Ser Trp Ile Phe Arg Thr Arg Xaa Leu Trp Arg Tyr
     50                  55                  60

Pro Lys Val Xaa Ala Trp Cys His Trp His Cys Asp His Gly Gly Xaa
 65                  70                  75                  80

Arg Arg Gly Arg Leu Cys Arg His Pro Xaa Ser Pro Val Ala Gly Arg
                 85                  90                  95

Xaa Cys Asn Gly Thr Gly Ser Glu Gly Leu Cys Gly Thr Ala Trp Lys
            100                 105                 110

Cys Thr Arg Leu Arg Leu Tyr
        115

<210> SEQ ID NO 79
<211> LENGTH: 208
<212> TYPE: PRT
<213> ORGANISM: Coxsackievirus B
<220> FEATURE:
<221> NAME/KEY: VARIANT
<222> LOCATION: (1)..(208)
<223> OTHER INFORMATION: X is selenocysteine.

<400> SEQUENCE: 79

Gly Pro Pro Val Tyr Arg Glu Ile Lys Ile Ser Val Ala Pro Glu Thr
  1               5                  10                  15

Pro Pro Pro Pro Ala Ile Ala Asp Leu Leu Lys Ser Val Asp Ser Glu
             20                  25                  30

Ala Val Arg Glu Tyr Cys Lys Glu Lys Gly Trp Leu Val Pro Glu Ile
         35                  40                  45

Asn Ser Thr Leu Gln Ile Glu Lys His Val Ser Arg Ala Phe Ile Cys
     50                  55                  60

Leu Gln Ala Leu Thr Thr Phe Val Ser Val Ala Gly Ile Ile Tyr Ile
 65                  70                  75                  80

Ile Tyr Lys Leu Phe Ala Gly Phe Ser Arg Cys Leu Tyr Arg Ser Ala
                 85                  90                  95

Gln Pro Glu Ala Gln Ser Ala Tyr Pro Glu Ala Ser Lys Ser Ala Arg
            100                 105                 110

Pro Cys Leu Xaa Val Arg Cys Arg Asn Asp Glu Lys Glu Leu Lys Gln
        115                 120                 125

Gly Glu Asn Xaa Ile Trp Arg Val Tyr His Ala Gly His Leu Xaa Gln
    130                 135                 140

Val Gly Arg Phe Ala Thr Pro Arg Gln Thr Trp Ala Asn His Leu Asp
145                 150                 155                 160

Glu Xaa Ser Arg Gly Trp Cys Ala Arg Cys Gly Gly Ala Ser Arg Gln
                165                 170                 175

Gly Arg His Gln Leu Arg Thr Asp Thr Thr Gln Ile Glu Pro Glu Xaa
            180                 185                 190

Glu Val Gln Arg His Gln Arg Leu Leu Ser Gln Gly Gly Ser Gly Gly
        195                 200                 205

<210> SEQ ID NO 80
<211> LENGTH: 43
```

```
<212> TYPE: PRT
<213> ORGANISM: Coxsackievirus B
<220> FEATURE:
<221> NAME/KEY: VARIANT
<222> LOCATION: (1)..(43)
<223> OTHER INFORMATION: X is selenocysteine.

<400> SEQUENCE: 80

Met Leu Glu Arg Arg Ser Thr Leu Trp Lys His Thr Arg Tyr Leu Xaa
 1               5                  10                  15

Asp Pro Met Lys Asp Leu Glu Arg Lys Tyr Ser Ala Phe His Cys Asn
            20                  25                  30

Gln Gly Thr Arg Val Phe Leu Val Gly Arg Ser
        35                  40

<210> SEQ ID NO 81
<211> LENGTH: 182
<212> TYPE: PRT
<213> ORGANISM: Coxsackievirus B
<220> FEATURE:
<221> NAME/KEY: VARIANT
<222> LOCATION: (1)..(182)
<223> OTHER INFORMATION: X is selenocysteine.

<400> SEQUENCE: 81

Met Leu Glu Arg Arg Ser Thr Leu Trp Lys His Thr Arg Tyr Leu Xaa
 1               5                  10                  15

Asp Pro Met Lys Asp Leu Glu Arg Lys Tyr Ser Ala Phe His Cys Asn
            20                  25                  30

Gln Gly Tyr Ser Ser Val Phe Ser Arg Thr Leu Leu Gly Glu Ile Leu
        35                  40                  45

Asn Tyr Tyr Thr His Trp Ser Gly Ser Ile Lys Leu Thr Phe Met Phe
50                  55                  60

Cys Gly Ser Ala Met Ala Thr Gly Lys Phe Leu Leu Ala Tyr Ser Pro
65                  70                  75                  80

Pro Gly Ala Gly Ala Pro Thr Lys Arg Val Asp Ala Met Leu Gly Thr
                85                  90                  95

His Val Val Trp Asp Val Gly Leu Gln Ser Ser Cys Val Leu Cys Ile
            100                 105                 110

Pro Trp Ile Ser Gln Thr His Tyr Arg Phe Val Ala Ser Asp Glu Tyr
        115                 120                 125

Thr Ala Gly Gly Phe Ile Thr Cys Trp Tyr Gln Thr Asn Ile Val Val
    130                 135                 140

Pro Ala Asp Ala Gln Ser Ser Cys Tyr Ile Met Cys Phe Val Ser Ala
145                 150                 155                 160

Cys Asn Asp Phe Ser Val Arg Leu Leu Lys Asp Thr Pro Phe Ile Ser
                165                 170                 175

Gln Gln Asn Phe Phe Gln
            180

<210> SEQ ID NO 82
<211> LENGTH: 6
<212> TYPE: PRT
<213> ORGANISM: Homo sapiens
<220> FEATURE:
<221> NAME/KEY: VARIANT
<222> LOCATION: (1)..(6)
<223> OTHER INFORMATION: X is any amino acid.

<400> SEQUENCE: 82

Ser Cys Cys Cys Xaa Cys
```

-continued

```
<210> SEQ ID NO 83
<211> LENGTH: 12
<212> TYPE: DNA
<213> ORGANISM: Homo sapiens

<400> SEQUENCE: 83
ccctgcccca gg                                                          12

<210> SEQ ID NO 84
<211> LENGTH: 147
<212> TYPE: PRT
<213> ORGANISM: Human immunodeficiency virus type 1

<400> SEQUENCE: 84

Asp Lys Ala Gln Asp Glu His Glu Lys Tyr His Ser Asn Trp Arg Ala
  1               5                  10                  15

Met Ala Ser Asp Phe Asn Leu Pro Pro Val Val Ala Lys Glu Ile Val
                 20                  25                  30

Ala Ser Cys Asp Lys Cys Gln Leu Lys Gly Glu Ala Met His Gly Gln
             35                  40                  45

Val Asp Cys Ser Pro Gly Ile Trp Gln Leu Asp Cys Thr His Leu Glu
         50                  55                  60

Gly Lys Ser Tyr Pro Gly Ser Ser Cys Ser Gln Trp Ile Tyr Arg
 65                  70                  75                  80

Ser Arg Ser Tyr Ser Ser Arg Asn Arg Ala Gly Asn Ser Ile Leu Ser
                 85                  90                  95

Phe Lys Ile Ser Arg Lys Met Ala Ser Lys Asn Asn Thr Tyr Arg Gln
                100                 105                 110

Trp Gln Gln Phe His Gln Tyr Tyr Gly Gln Gly Arg Leu Leu Val Gly
            115                 120                 125

Gly Asn Gln Ala Gly Ile Trp Asn Ser Leu Gln Ser Pro Lys Ser Arg
        130                 135                 140

Ser Ser Arg
145

<210> SEQ ID NO 85
<211> LENGTH: 149
<212> TYPE: PRT
<213> ORGANISM: Escherichia coli

<400> SEQUENCE: 85

Asp Lys Ala Gln Asp Glu Arg Asp Trp Val Leu Asn Glu Phe Arg Thr
  1               5                  10                  15

Gly Lys Ser Pro Ile Met Val Ala Thr Asp Val Ala Ser Arg Gly Ile
                 20                  25                  30

Asp Val Lys Gly Ile Thr His Val Phe Asn Tyr Asp Phe Pro Gly Asn
             35                  40                  45

Thr Glu Asp Tyr Val His Arg Ile Gly Arg Thr Gly Arg Ala Gly Ala
         50                  55                  60

Lys Gly Thr Ala Tyr Thr Tyr Phe Thr Ser Asp Asn Ala Lys Gln Ala
 65                  70                  75                  80

Arg Glu Leu Val Ser Ile Leu Ser Glu Ala Lys Gln Asp Ile Asp Pro
                 85                  90                  95

Lys Leu Glu Glu Met Ala Arg Tyr Ser Ser Gly Gly Arg Gly Gly Asn
                100                 105                 110
```

```
Tyr Arg Arg Gly Gly Tyr Gly Arg Gly Phe Arg Arg Gly Gly Gly
        115                 120                 125
Tyr Gly Asn Arg Asn Arg Gly Phe Thr Gly Ser Asn Ser Ala Pro Leu
130                 135                 140
Ala Arg Ser Arg Trp
145
```

```
<210> SEQ ID NO 86
<211> LENGTH: 50
<212> TYPE: RNA
<213> ORGANISM: Homo sapiens

<400> SEQUENCE: 86
ggaaaaugaa gccacagaga gaauuuauca uuucguggug gggcagaugg          50

<210> SEQ ID NO 87
<211> LENGTH: 66
<212> TYPE: RNA
<213> ORGANISM: Human immunodeficiency virus type 1

<400> SEQUENCE: 87
uuuaaaugca ugdguaaaag uaguagaaga gaaggcuuuc agcccagaag ugauacccau    60
guuuuc                                                              66

<210> SEQ ID NO 88
<211> LENGTH: 64
<212> TYPE: RNA
<213> ORGANISM: Human immunodeficiency virus type 1

<400> SEQUENCE: 88
aaaaaagaaa aaaucaguaa caguacugga uguggugau gcauauuuuu caguucccuu    60
agau                                                                64

<210> SEQ ID NO 89
<211> LENGTH: 45
<212> TYPE: RNA
<213> ORGANISM: Human immunodeficiency virus type 1

<400> SEQUENCE: 89
aggaaaaguu auccugguag caguucaugu agccagugga uauau                   45

<210> SEQ ID NO 90
<211> LENGTH: 56
<212> TYPE: RNA
<213> ORGANISM: Human immunodeficiency virus type 1

<400> SEQUENCE: 90
aaaaagagca guggaauag gagcuuuguu ccuuggguuc uugggagcag caggaa         56

<210> SEQ ID NO 91
<211> LENGTH: 100
<212> TYPE: RNA
<213> ORGANISM: Human immunodeficiency virus type 1
<220> FEATURE:
<221> NAME/KEY: misc_feature
<222> LOCATION: (1)..(100)
<223> OTHER INFORMATION: N is A, U, G or C.

<400> SEQUENCE: 91
uuuaaaagaa aagggggggac uggaagggcu aauucacucc caacgaagac aagauauccu   60
ugaucugugg aunnnnnnnn nnnnnnnnnn nnncccugau                         100
```

<210> SEQ ID NO 92
<211> LENGTH: 11
<212> TYPE: PRT
<213> ORGANISM: Human immunodeficiency virus type 1

<400> SEQUENCE: 92

Pro Gln Ile Thr Leu Trp Gln Arg Pro Leu Val
1               5                   10

<210> SEQ ID NO 93
<211> LENGTH: 90
<212> TYPE: PRT
<213> ORGANISM: Human immunodeficiency virus type 1

<400> SEQUENCE: 93

Thr Ile Lys Ile Gly Gly Gln Leu Lys Gly Ser Ser Ile Arg Tyr Arg
1               5                   10                  15

Ser Arg Cys Tyr Ser Ile Arg Arg Asn Glu Phe Ala Arg Lys Met Glu
            20                  25                  30

Thr Lys Asn Asp Arg Gly Asn Trp Arg Phe Tyr Gln Ser Lys Thr Val
        35                  40                  45

Cys Ser Asp Thr His Arg Asn Leu Trp Thr Gln Ser Tyr Arg Tyr Ser
50                  55                  60

Ile Ser Gly Thr Tyr Thr Cys Asn His Asn Trp Lys Lys Ser Val Asp
65                  70                  75                  80

Ser Asp Trp Leu His Phe Lys Phe Ser His
                85                  90

<210> SEQ ID NO 94
<211> LENGTH: 87
<212> TYPE: PRT
<213> ORGANISM: Pappiloma virus

<400> SEQUENCE: 94

Cys Pro Cys Leu Leu Gly Thr Ile Ser Gly Asn Gly Asn Gln Val Lys
1               5                   10                  15

Cys Tyr Ser Phe Arg Val Lys Arg Trp His Asp Arg Asp Lys Tyr His
            20                  25                  30

His Thr Thr Thr Trp Trp Ala Val Gly Gly Gln Gly Ser Glu Arg Pro
        35                  40                  45

Gly Asp Ala Thr Val Ile Val Thr Phe Lys Asp Gln Ser Gln Arg Ser
50                  55                  60

His Phe Leu Gln Gln Val Pro Leu Pro Pro Gly Met Ser Ala His Gly
65                  70                  75                  80

Val Thr Met Thr Val Asp Phe
                85

<210> SEQ ID NO 95
<211> LENGTH: 85
<212> TYPE: PRT
<213> ORGANISM: Bovine papillomavirus type 1

<400> SEQUENCE: 95

Ser Cys Phe Ala Leu Ile Ser Gly Thr Ala Asn Gln Val Lys Cys Tyr
1               5                   10                  15

Arg Phe Arg Val Lys Lys Asn His Arg His Arg Tyr Glu Asn Cys Thr
            20                  25                  30

Thr Thr Trp Phe Thr Val Ala Asp Asn Gly Ala Glu Arg Gln Gly Gln
        35                  40                  45

```
Ala Gln Ile Leu Ile Thr Phe Gly Ser Pro Ser Gln Arg Gln Asp Phe
         50                  55                  60

Leu Lys His Val Pro Leu Pro Pro Gly Met Asn Ile Ser Gly Phe Thr
 65                  70                  75                  80

Ala Ser Leu Asp Phe
             85

<210> SEQ ID NO 96
<211> LENGTH: 84
<212> TYPE: PRT
<213> ORGANISM: Pappiloma virus

<400> SEQUENCE: 96

Pro Pro Val Ile Cys Leu Lys Gly Gly His Asn Gln Leu Lys Cys Leu
 1               5                  10                  15

Arg Tyr Arg Leu Lys Ser Lys His Ser Ser Leu Phe Asp Cys Ile Ser
             20                  25                  30

Thr Thr Trp Ser Trp Val Asp Thr Thr Ser Thr Cys Arg Leu Gly Ser
         35                  40                  45

Gly Arg Met Leu Ile Lys Phe Ala Asp Ser Glu Gln Arg Asp Lys Phe
         50                  55                  60

Leu Ser Arg Val Pro Leu Pro Ser Thr Thr Gln Val Phe Leu Gly Asn
 65                  70                  75                  80

Phe Tyr Gly Leu

<210> SEQ ID NO 97
<211> LENGTH: 84
<212> TYPE: PRT
<213> ORGANISM: bovine papillomavirus type 8

<400> SEQUENCE: 97

Pro Pro Val Ile Leu Val Arg Gly Gly Ala Asn Thr Leu Lys Cys Phe
 1               5                  10                  15

Arg Asn Arg Ala Arg Val Arg Tyr Arg Gly Leu Phe Lys Tyr Phe Ser
             20                  25                  30

Thr Thr Trp Ser Trp Val Ala Gly Asp Ser Thr Glu Arg Leu Gly Arg
         35                  40                  45

Ser Arg Met Leu Ile Leu Phe Thr Ser Ala Gly Gln Arg Glu Lys Pro
         50                  55                  60

Asp Glu Thr Val Lys Tyr Pro Lys Gly Val Asp Thr Ser Tyr Gly Asn
 65                  70                  75                  80

Leu Asp Ser Leu

<210> SEQ ID NO 98
<211> LENGTH: 84
<212> TYPE: PRT
<213> ORGANISM: Bovine papillomavirus type 1

<400> SEQUENCE: 98

Pro Pro Val Val Cys Val Lys Gly Gly Ala Asn Gln Leu Lys Cys Leu
 1               5                  10                  15

Arg Tyr Arg Leu Lys Ala Ser Thr Gln Val Asp Phe Asp Ser Thr Ser
             20                  25                  30

Thr Thr Trp His Trp Thr Asp Arg Lys Asn Thr Glu Arg Ile Gly Ser
         35                  40                  45

Ala Arg Met Leu Val Lys Phe Ile Asp Glu Ala Gln Arg Glu Lys Phe
         50                  55                  60
```

-continued

Leu Glu Arg Val Ala Leu Pro Arg Ser Val Ser Val Phe Leu Gly Gln
 65                  70                  75                  80

Phe Asn Gly Ser

<210> SEQ ID NO 99
<211> LENGTH: 84
<212> TYPE: PRT
<213> ORGANISM: bovine papillomavirus type 11

<400> SEQUENCE: 99

Thr Pro Ile Val Gln Leu Gln Gly Asp Ser Asn Cys Leu Lys Cys Phe
 1               5                  10                  15

Arg Tyr Arg Leu Asn Asp Lys Tyr Lys His Leu Phe Glu Leu Ala Ser
             20                  25                  30

Ser Thr Trp His Trp Ala Ser Pro Glu Ala Pro His Lys Asn Ala Ile
         35                  40                  45

Val Thr Leu Thr Tyr Ser Ser Glu Glu Gln Arg Gln Gln Phe Leu Asn
     50                  55                  60

Ser Val Lys Ile Pro Pro Thr Ile Arg His Lys Val Gly Phe Met Ser
 65                  70                  75                  80

Leu His Leu Leu

<210> SEQ ID NO 100
<211> LENGTH: 84
<212> TYPE: PRT
<213> ORGANISM: Bovine papillomavirus type 6

<400> SEQUENCE: 100

Thr Pro Ile Val Gln Phe Phe Gly Glu Ser Asn Cys Leu Lys Cys Phe
 1               5                  10                  15

Arg Tyr Arg Leu Asn Arg Asp His Arg His Leu Phe Asp Leu Ile Ser
             20                  25                  30

Ser Thr Trp His Trp Ala Ser Ser Lys Ala Pro His Lys His Ala Ile
         35                  40                  45

Val Thr Val Thr Tyr Asp Ser Glu Glu Gln Arg Arg Arg Phe Leu Asp
     50                  55                  60

Val Val Lys Ile Pro Pro Thr Ile Ser His Lys Leu Gly Phe Met Ser
 65                  70                  75                  80

Leu His Leu Leu

<210> SEQ ID NO 101
<211> LENGTH: 80
<212> TYPE: PRT
<213> ORGANISM: bovine papillomavirus type 18

<400> SEQUENCE: 101

Thr Pro Ile Ile His Leu Lys Gly Asp Arg Asn Ser Leu Lys Cys Leu
 1               5                  10                  15

Arg Tyr Arg Leu Arg Lys His Ser Asp His Tyr Arg Asp Ile Ser Ser
             20                  25                  30

Thr Trp His Trp Thr Gly Ala Gly Asn Glu Lys Thr Gly Ile Leu Thr
         35                  40                  45

Val Thr Tyr His Ser Glu Thr Gln Arg Thr Lys Phe Leu Asn Thr Val
     50                  55                  60

Ala Ile Pro Asp Ser Val Gln Ile Leu Val Gly Tyr Met Thr Met Tyr
 65                  70                  75                  80

<210> SEQ ID NO 102
<211> LENGTH: 80
<212> TYPE: PRT
<213> ORGANISM: bovine papillomavirus type 16

<400> SEQUENCE: 102

Thr Pro Ile Val His Leu Lys Gly Asp Ala Asn Thr Leu Lys Cys Leu
 1               5                  10                  15

Arg Tyr Arg Phe Lys Lys His Cys Thr Leu Tyr Thr Ala Val Ser Ser
            20                  25                  30

Thr Trp His Trp Thr Gly His Asn Tyr Lys His Lys Ser Ala Ile Val
        35                  40                  45

Thr Leu Thr Tyr Asp Ser Glu Trp Gln Arg Asp Gln Phe Leu Ser Gln
    50                  55                  60

Val Lys Ile Pro Lys Thr Ile Thr Val Ser Thr Gly Phe Met Ser Ile
65                  70                  75                  80

<210> SEQ ID NO 103
<211> LENGTH: 81
<212> TYPE: PRT
<213> ORGANISM: bovine papillomavirus type 33

<400> SEQUENCE: 103

Ala Pro Ile Val His Leu Lys Gly Glu Ser Asn Ser Leu Lys Cys Leu
 1               5                  10                  15

Arg Tyr Arg Leu Lys Pro Tyr Asn Glu Leu Tyr Ser Ser Met Ser Ser
            20                  25                  30

Thr Trp His Trp Thr Ser Asp Asn Lys Asn Ser Lys Asn Gly Ile Val
        35                  40                  45

Thr Val Thr Phe Val Thr Gly Gln Gln Gln Gln Met Phe Leu Gly Thr
    50                  55                  60

Val Lys Ile Pro Pro Thr Val Gln Ile Ser Thr Gly Phe Met Thr Leu
65                  70                  75                  80

Val

<210> SEQ ID NO 104
<211> LENGTH: 12
<212> TYPE: PRT
<213> ORGANISM: Simian immunodeficiency virus
<220> FEATURE:
<221> NAME/KEY: VARIANT
<222> LOCATION: (1)..(12)
<223> OTHER INFORMATION: X is selenocysteine.

<400> SEQUENCE: 104

Ser Ser Thr Arg Tyr Arg Ser Xaa Xaa Tyr His Leu
 1               5                  10

<210> SEQ ID NO 105
<211> LENGTH: 12
<212> TYPE: PRT
<213> ORGANISM: Simian immunodeficiency virus
<220> FEATURE:
<221> NAME/KEY: VARIANT
<222> LOCATION: (1)..(12)
<223> OTHER INFORMATION: X is selenocysteine.

<400> SEQUENCE: 105

Ser Ile Ile Arg Tyr Gly Gly Arg Xaa Tyr His Tyr
 1               5                  10

-continued

```
<210> SEQ ID NO 106
<211> LENGTH: 12
<212> TYPE: PRT
<213> ORGANISM: Simian immunodeficiency virus
<220> FEATURE:
<221> NAME/KEY: VARIANT
<222> LOCATION: (1)..(12)
<223> OTHER INFORMATION: X is selenocysteine.

<400> SEQUENCE: 106

Val Leu Leu Gly Tyr Arg Gly Xaa Xaa Phe Tyr Cys
 1               5                  10

<210> SEQ ID NO 107
<211> LENGTH: 12
<212> TYPE: PRT
<213> ORGANISM: Simian immunodeficiency virus
<220> FEATURE:
<221> NAME/KEY: VARIANT
<222> LOCATION: (1)..(12)
<223> OTHER INFORMATION: X is selenocysteine.

<400> SEQUENCE: 107

Ser Ile Ile Arg Tyr Arg Gly Xaa Arg Phe Asn Cys
 1               5                  10

<210> SEQ ID NO 108
<211> LENGTH: 12
<212> TYPE: PRT
<213> ORGANISM: Simian immunodeficiency virus
<220> FEATURE:
<221> NAME/KEY: VARIANT
<222> LOCATION: (1)..(12)
<223> OTHER INFORMATION: X is selenocysteine.

<400> SEQUENCE: 108

Ser Ile Ile Gly Tyr Arg Gly Xaa Xaa Phe Tyr Cys
 1               5                  10

<210> SEQ ID NO 109
<211> LENGTH: 12
<212> TYPE: PRT
<213> ORGANISM: Human immunodeficiency virus type 2
<220> FEATURE:
<221> NAME/KEY: VARIANT
<222> LOCATION: (1)..(12)
<223> OTHER INFORMATION: X is selenocysteine.

<400> SEQUENCE: 109

Ser Leu Val Arg His Arg Gly Xaa Arg Leu Asn Ser
 1               5                  10

<210> SEQ ID NO 110
<211> LENGTH: 12
<212> TYPE: PRT
<213> ORGANISM: Human immunodeficiency virus type 1
<220> FEATURE:
<221> NAME/KEY: VARIANT
<222> LOCATION: (1)..(12)
<223> OTHER INFORMATION: X is selenocysteine.

<400> SEQUENCE: 110

Ser Ser Ile Arg Tyr Arg Ser Arg Xaa Tyr Ser Ile
 1               5                  10

<210> SEQ ID NO 111
<211> LENGTH: 12
<212> TYPE: PRT
<213> ORGANISM: Human immunodeficiency virus
```

```
<220> FEATURE:
<221> NAME/KEY: VARIANT
<222> LOCATION: (1)..(12)
<223> OTHER INFORMATION: X is selenocysteine.

<400> SEQUENCE: 111

Ser Ser Ile Arg Tyr Arg Ser Arg Xaa Tyr Ser Ile
  1               5                  10

<210> SEQ ID NO 112
<211> LENGTH: 12
<212> TYPE: PRT
<213> ORGANISM: Human immunodeficiency virus type 2
<220> FEATURE:
<221> NAME/KEY: VARIANT
<222> LOCATION: (1)..(12)
<223> OTHER INFORMATION: X is selenocysteine.

<400> SEQUENCE: 112

Ser Phe Thr Arg His Arg Gly Xaa Arg Leu Asn Ser
  1               5                  10

<210> SEQ ID NO 113
<211> LENGTH: 12
<212> TYPE: PRT
<213> ORGANISM: respiratory syncytial virus
<220> FEATURE:
<221> NAME/KEY: VARIANT
<222> LOCATION: (1)..(12)
<223> OTHER INFORMATION: X is selenocysteine.

<400> SEQUENCE: 113

Gly Thr Ala Arg His Arg Gly Arg Xaa His His Asn
  1               5                  10

<210> SEQ ID NO 114
<211> LENGTH: 12
<212> TYPE: PRT
<213> ORGANISM: Simian immunodeficiency virus
<220> FEATURE:
<221> NAME/KEY: VARIANT
<222> LOCATION: (1)..(12)
<223> OTHER INFORMATION: x is selenocysteine.

<400> SEQUENCE: 114

Ser Ile Ile Arg Tyr Arg Gly Xaa Xaa Phe Asn Cys
  1               5                  10

<210> SEQ ID NO 115
<211> LENGTH: 12
<212> TYPE: PRT
<213> ORGANISM: Simian immunodeficiency virus
<220> FEATURE:
<221> NAME/KEY: VARIANT
<222> LOCATION: (1)..(12)
<223> OTHER INFORMATION: X is selenocysteine.

<400> SEQUENCE: 115

Ser Leu Val Arg Tyr Arg Ser Arg Xaa His Tyr Asn
  1               5                  10

<210> SEQ ID NO 116
<211> LENGTH: 12
<212> TYPE: PRT
<213> ORGANISM: Simian immunodeficiency virus
<220> FEATURE:
<221> NAME/KEY: VARIANT
<222> LOCATION: (1)..(12)
<223> OTHER INFORMATION: X is selenocysteine.
```

<400> SEQUENCE: 116

Ser Ile Ile Arg Tyr Arg Gly Xaa Xaa Phe Asn Cys
 1               5                   10

<210> SEQ ID NO 117
<211> LENGTH: 12
<212> TYPE: PRT
<213> ORGANISM: Simian immunodeficiency virus
<220> FEATURE:
<221> NAME/KEY: VARIANT
<222> LOCATION: (1)..(12)
<223> OTHER INFORMATION: X is selenocysteine.

<400> SEQUENCE: 117

Asn Val Ser Arg Tyr Arg Gly Arg Xaa Tyr Tyr Asn
 1               5                   10

<210> SEQ ID NO 118
<211> LENGTH: 12
<212> TYPE: PRT
<213> ORGANISM: Human immunodeficiency virus
<220> FEATURE:
<221> NAME/KEY: VARIANT
<222> LOCATION: (1)..(12)
<223> OTHER INFORMATION: X is selenocysteine.

<400> SEQUENCE: 118

Ser Ser Ile Arg His Arg Ser Arg Xaa Tyr Ser Ile
 1               5                   10

<210> SEQ ID NO 119
<211> LENGTH: 12
<212> TYPE: PRT
<213> ORGANISM: chimpanzee immunodeficiency virus
<220> FEATURE:
<221> NAME/KEY: VARIANT
<222> LOCATION: (1)..(12)
<223> OTHER INFORMATION: X is selenocysteine.

<400> SEQUENCE: 119

Ser Phe Ala Arg Tyr Arg Ser Xaa Xaa Tyr Ser Asn
 1               5                   10

<210> SEQ ID NO 120
<211> LENGTH: 21
<212> TYPE: RNA
<213> ORGANISM: Human immunodeficiency virus type 1

<400> SEQUENCE: 120
aucuaucaau acauggauga u                                              21

<210> SEQ ID NO 121
<211> LENGTH: 21
<212> TYPE: RNA
<213> ORGANISM: Human immunodeficiency virus

<400> SEQUENCE: 121
aucuaucagu acauggauga u                                              21

<210> SEQ ID NO 122
<211> LENGTH: 21
<212> TYPE: RNA
<213> ORGANISM: Drosophila melanogaster

<400> SEQUENCE: 122

-continued guauuauuau auguagauga u                                              21

<210> SEQ ID NO 123
<211> LENGTH: 21
<212> TYPE: RNA
<213> ORGANISM: Human immunodeficiency virus

<400> SEQUENCE: 123
auauaccaau acauggauga u                                              21

<210> SEQ ID NO 124
<211> LENGTH: 21
<212> TYPE: RNA
<213> ORGANISM: Human immunodeficiency virus type 2

<400> SEQUENCE: 124
aucguucagu acauggauga u                                              21

<210> SEQ ID NO 125
<211> LENGTH: 21
<212> TYPE: RNA
<213> ORGANISM: Human immunodeficiency virus type 2

<400> SEQUENCE: 125
aucauucagu acauggauga u                                              21

<210> SEQ ID NO 126
<211> LENGTH: 21
<212> TYPE: RNA
<213> ORGANISM: Human immunodeficiency virus type 2

<400> SEQUENCE: 126
cucauccaau acauggauga u                                              21

<210> SEQ ID NO 127
<211> LENGTH: 21
<212> TYPE: RNA
<213> ORGANISM: Human T-cell lymphotropic virus

<400> SEQUENCE: 127
auucuucaau acauggauga c                                              21

<210> SEQ ID NO 128
<211> LENGTH: 21
<212> TYPE: RNA
<213> ORGANISM: chimpanzee immunodeficiency virus

<400> SEQUENCE: 128
auuuaccagu acauggauga c                                              21

<210> SEQ ID NO 129
<211> LENGTH: 21
<212> TYPE: RNA
<213> ORGANISM: Simian immunodeficiency virus

<400> SEQUENCE: 129
uuaguccagu auauggauga c                                              21

<210> SEQ ID NO 130
<211> LENGTH: 21
<212> TYPE: RNA
<213> ORGANISM: Simian immunodeficiency virus

<400> SEQUENCE: 130

```
auuguccaau acauggacga u                                              21

<210> SEQ ID NO 131
<211> LENGTH: 21
<212> TYPE: RNA
<213> ORGANISM: Simian immunodeficiency virus

<400> SEQUENCE: 131
auugugcaau acauggauga c                                              21

<210> SEQ ID NO 132
<211> LENGTH: 21
<212> TYPE: RNA
<213> ORGANISM: Simian immunodeficiency virus

<400> SEQUENCE: 132
auuguacaau acauggauga u                                              21

<210> SEQ ID NO 133
<211> LENGTH: 21
<212> TYPE: RNA
<213> ORGANISM: Simian immunodeficiency virus

<400> SEQUENCE: 133
uuauaucaau acauggauga u                                              21

<210> SEQ ID NO 134
<211> LENGTH: 21
<212> TYPE: RNA
<213> ORGANISM: Simian immunodeficiency virus

<400> SEQUENCE: 134
cugauccaau acauggauga c                                              21

<210> SEQ ID NO 135
<211> LENGTH: 21
<212> TYPE: RNA
<213> ORGANISM: Simian immunodeficiency virus

<400> SEQUENCE: 135
uuaguccagu auauggauga c                                              21

<210> SEQ ID NO 136
<211> LENGTH: 21
<212> TYPE: RNA
<213> ORGANISM: Simian immunodeficiency virus

<400> SEQUENCE: 136
cugauccaau acauggauga c                                              21

<210> SEQ ID NO 137
<211> LENGTH: 21
<212> TYPE: RNA
<213> ORGANISM: Simian immunodeficiency virus

<400> SEQUENCE: 137
cuaauacagu acauggauga c                                              21

<210> SEQ ID NO 138
<211> LENGTH: 21
<212> TYPE: RNA
<213> ORGANISM: Simian immunodeficiency virus
```

```
<400> SEQUENCE: 138
cugauccaau acauggauga c                                              21

<210> SEQ ID NO 139
<211> LENGTH: 21
<212> TYPE: RNA
<213> ORGANISM: Feline immunodeficiency virus

<400> SEQUENCE: 139
auuuaccaau auauggauga c                                              21

<210> SEQ ID NO 140
<211> LENGTH: 21
<212> TYPE: RNA
<213> ORGANISM: panther

<400> SEQUENCE: 140
auauaucaau auauggauga u                                              21

<210> SEQ ID NO 141
<211> LENGTH: 21
<212> TYPE: RNA
<213> ORGANISM: puma

<400> SEQUENCE: 141
guauaucaau auauggauga u                                              21

<210> SEQ ID NO 142
<211> LENGTH: 21
<212> TYPE: RNA
<213> ORGANISM: Bovine immunodeficiency virus

<400> SEQUENCE: 142
uuguaucaau auauggauga u                                              21

<210> SEQ ID NO 143
<211> LENGTH: 21
<212> TYPE: RNA
<213> ORGANISM: Equine infectious anemia virus

<400> SEQUENCE: 143
uuguaucaau auauggauga u                                              21

<210> SEQ ID NO 144
<211> LENGTH: 21
<212> TYPE: RNA
<213> ORGANISM: mouse mammary leukemia virus

<400> SEQUENCE: 144
cugcuacagu acguggauga c                                              21

<210> SEQ ID NO 145
<211> LENGTH: 21
<212> TYPE: RNA
<213> ORGANISM: Visna virus

<400> SEQUENCE: 145
uuuggaauau acauggauga u                                              21

<210> SEQ ID NO 146
<211> LENGTH: 100
<212> TYPE: PRT
<213> ORGANISM: rat
```

```
<400> SEQUENCE: 146

Met Ala Pro Pro Thr Arg Arg Leu Leu Asn Ala Ala Leu Leu Leu Leu
  1               5                  10                  15

Leu Leu Leu Met Ala Thr Ser His Gln Pro Ser Gly Thr Val Val Ala
             20                  25                  30

Arg Glu Leu Arg Cys Gln Cys Leu Lys Thr Leu Pro Arg Val Asp Phe
         35                  40                  45

Glu Asn Ile Gln Ser Leu Thr Val Thr Pro Pro Gly Pro His Cys Thr
     50                  55                  60

Gln Thr Glu Val Ile Ala Thr Leu Lys Asp Gly Gln Glu Val Cys Leu
 65                  70                  75                  80

Asn Pro Gln Ala Pro Arg Leu Gln Lys Ile Ile Gln Lys Leu Leu Lys
             85                  90                  95

Ser Pro Ser Leu
            100

<210> SEQ ID NO 147
<211> LENGTH: 96
<212> TYPE: PRT
<213> ORGANISM: rat

<400> SEQUENCE: 147

Met Val Ser Ala Thr Arg Ser Leu Leu Cys Ala Ala Leu Pro Val Leu
  1               5                  10                  15

Ala Thr Ser Arg Gln Ala Thr Gly Ala Pro Val Ala Asn Glu Leu Arg
             20                  25                  30

Cys Gln Cys Leu Gln Thr Val Ala Gly Ile His Phe Lys Asn Ile Gln
         35                  40                  45

Ser Leu Lys Val Met Pro Pro Gly Pro His Cys Thr Gln Thr Glu Val
     50                  55                  60

Ile Ala Thr Leu Lys Asn Gly Arg Glu Ala Cys Leu Asp Pro Glu Ala
 65                  70                  75                  80

Pro Met Val Gln Lys Ile Val Gln Lys Met Leu Lys Gly Val Pro Lys
             85                  90                  95

<210> SEQ ID NO 148
<211> LENGTH: 106
<212> TYPE: PRT
<213> ORGANISM: Homo sapiens

<400> SEQUENCE: 148

Met Ala Arg Ala Ala Leu Ser Ala Ala Pro Ser Asn Pro Arg Leu Leu
  1               5                  10                  15

Arg Val Ala Leu Leu Leu Leu Leu Val Ala Ala Gly Arg Arg Ala
             20                  25                  30

Ala Gly Ala Ser Val Ala Thr Glu Leu Arg Cys Gln Cys Leu Gln Thr
         35                  40                  45

Leu Gln Gly Ile His Pro Lys Asn Ile Gln Ser Val Asn Val Lys Ser
     50                  55                  60

Pro Gly Pro His Cys Ala Gln Thr Glu Val Ile Ala Thr Leu Lys Asn
 65                  70                  75                  80

Gly Arg Lys Cys Leu Asn Pro Ala Ser Pro Ile Val Lys Lys Ile Ile
             85                  90                  95

Glu Lys Met Leu Asn Ser Asp Lys Ser Asn
            100                 105
```

```
<210> SEQ ID NO 149
<211> LENGTH: 114
<212> TYPE: PRT
<213> ORGANISM: Homo sapiens

<400> SEQUENCE: 149

Met Ser Leu Leu Ser Ser Arg Ala Ala Arg Val Pro Gly Pro Ser Ser
 1               5                  10                  15

Ser Leu Cys Ala Leu Val Leu Leu Leu Thr Gln Pro Gly
            20                  25                  30

Pro Ile Ala Ser Ala Gly Pro Ala Ala Val Leu Arg Glu Leu Arg
            35                  40                  45

Cys Val Cys Leu Gln Thr Thr Gln Gly Val His Pro Lys Met Ile Ser
 50                  55                  60

Asn Leu Gln Val Phe Ala Ile Gly Pro Gln Cys Ser Lys Val Glu Val
 65                  70                  75                  80

Val Ala Ser Leu Lys Asn Gly Lys Glu Ile Cys Leu Asp Pro Glu Ala
                 85                  90                  95

Pro Phe Leu Lys Lys Val Ile Gln Lys Ile Leu Asp Gly Gly Asn Lys
                100                 105                 110

Glu Asn

<210> SEQ ID NO 150
<211> LENGTH: 99
<212> TYPE: PRT
<213> ORGANISM: Homo sapiens

<400> SEQUENCE: 150

Met Thr Ser Lys Leu Ala Val Ala Leu Leu Ala Ala Phe Leu Ile Ser
 1               5                  10                  15

Ala Ala Leu Cys Glu Gly Ala Val Leu Pro Arg Ser Ala Lys Glu Leu
                20                  25                  30

Arg Cys Gln Cys Ile Lys Thr Tyr Ser Lys Pro Phe His Pro Lys Phe
            35                  40                  45

Ile Lys Glu Leu Arg Val Ile Glu Ser Gly Pro His Cys Ala Asn Thr
 50                  55                  60

Glu Ile Ile Val Lys Leu Ser Asp Gly Arg Glu Leu Cys Leu Asp Pro
 65                  70                  75                  80

Lys Glu Asn Trp Val Gln Arg Val Val Glu Lys Phe Leu Lys Arg Ala
                 85                  90                  95

Glu Asn Ser

<210> SEQ ID NO 151
<211> LENGTH: 98
<212> TYPE: PRT
<213> ORGANISM: Homo sapiens

<400> SEQUENCE: 151

Met Asn Gln Thr Ala Ile Leu Ile Cys Cys Leu Ile Phe Leu Thr Leu
 1               5                  10                  15

Ser Gly Ile Gln Gly Val Pro Leu Ser Arg Thr Val Arg Cys Thr Cys
                20                  25                  30

Ile Ser Ile Ser Asn Gln Pro Val Asn Pro Arg Ser Leu Glu Lys Leu
            35                  40                  45

Glu Ile Ile Pro Ala Ser Gln Phe Cys Pro Arg Val Glu Ile Ile Ala
 50                  55                  60
```

```
Thr Met Lys Lys Lys Gly Glu Lys Arg Cys Leu Asn Pro Glu Ser Lys
 65                  70                  75                  80

Ala Ile Lys Asn Leu Leu Lys Ala Val Ser Lys Glu Met Ser Lys Arg
                 85                  90                  95

Ser Pro

<210> SEQ ID NO 152
<211> LENGTH: 99
<212> TYPE: PRT
<213> ORGANISM: Homo sapiens

<400> SEQUENCE: 152

Met Lys Val Ser Ala Ala Leu Leu Cys Leu Leu Leu Ile Ala Ala Thr
 1               5                  10                  15

Phe Ile Pro Gln Gly Leu Ala Gln Pro Asp Ala Ile Asn Ala Pro Val
                 20                  25                  30

Thr Cys Cys Tyr Asn Phe Thr Asn Arg Lys Ile Ser Val Gln Arg Leu
             35                  40                  45

Ala Ser Tyr Arg Arg Ile Thr Ser Ser Lys Cys Pro Lys Glu Ala Val
         50                  55                  60

Ile Phe Lys Thr Ile Val Ala Lys Glu Ile Cys Ala Asp Pro Lys Gln
 65                  70                  75                  80

Lys Trp Val Gln Asp Ser Met Asp His Leu Asp Lys Gln Thr Gln Thr
                 85                  90                  95

Pro Lys Thr

<210> SEQ ID NO 153
<211> LENGTH: 109
<212> TYPE: PRT
<213> ORGANISM: Homo sapiens

<400> SEQUENCE: 153

Met Trp Lys Pro Met Pro Ser Pro Ser Asn Met Lys Ala Ser Ala Ala
 1               5                  10                  15

Leu Leu Cys Leu Leu Leu Thr Ala Ala Ala Phe Ser Pro Gln Gly Leu
                 20                  25                  30

Ala Gln Pro Val Gly Ile Asn Thr Ser Thr Thr Cys Cys Tyr Arg Phe
             35                  40                  45

Ile Asn Lys Lys Ile Pro Lys Gln Arg Leu Glu Ser Tyr Arg Arg Thr
         50                  55                  60

Thr Ser Ser His Cys Pro Arg Glu Ala Val Ile Phe Lys Thr Lys Leu
 65                  70                  75                  80

Asp Lys Glu Ile Cys Ala Asp Pro Thr Gln Lys Trp Val Gln Asp Phe
                 85                  90                  95

Met Lys His Leu Asp Lys Lys Thr Gln Thr Pro Lys Leu
                100                 105

<210> SEQ ID NO 154
<211> LENGTH: 96
<212> TYPE: PRT
<213> ORGANISM: rat

<400> SEQUENCE: 154

Met Lys Val Ser Thr Ala Phe Leu Cys Leu Leu Leu Thr Val Ser Ala
 1               5                  10                  15

Phe Ser Ala Gln Val Leu Ala His Pro Gln Ile Pro Ser Ala Cys Cys
                 20                  25                  30
```

-continued

```
Phe Arg Val Thr Asn Lys Lys Ile Ser Phe Gln Arg Leu Lys Ser Tyr
            35                  40                  45

Lys Ile Ile Thr Ser Ser Lys Cys Pro Gln Thr Ala Ile Val Phe Glu
 50                  55                  60

Ile Lys Pro Asp Lys Met Ile Cys Ala Asp Pro Lys Lys Lys Trp Val
 65                  70                  75                  80

Gln Asp Ala Lys Lys Tyr Leu Gly Gln Ile Ser Gln Thr Thr Lys Pro
                 85                  90                  95
```

<210> SEQ ID NO 155
<211> LENGTH: 91
<212> TYPE: PRT
<213> ORGANISM: Homo sapiens

<400> SEQUENCE: 155

```
Met Lys Val Ser Ala Ala Leu Ala Val Ile Leu Ile Ala Thr Ala
 1               5                  10                  15

Leu Cys Ala Pro Ala Ser Ala Ser Pro Tyr Ser Ser Asp Thr Thr Pro
                 20                  25                  30

Cys Cys Phe Ala Tyr Ile Ala Arg Pro Leu Pro Arg Ala His Ile Lys
             35                  40                  45

Glu Tyr Phe Tyr Thr Ser Gly Lys Cys Ser Asn Pro Ala Val Val Phe
 50                  55                  60

Val Thr Arg Lys Asn Arg Gln Val Cys Ala Asn Pro Glu Lys Lys Trp
 65                  70                  75                  80

Val Arg Glu Tyr Ile Asn Ser Leu Glu Met Ser
                 85                  90
```

<210> SEQ ID NO 156
<211> LENGTH: 91
<212> TYPE: PRT
<213> ORGANISM: Mus sp.

<400> SEQUENCE: 156

```
Met Lys Ile Ser Ala Ala Leu Thr Ile Ile Leu Thr Ala Ala Ala
 1               5                  10                  15

Leu Cys Ala Pro Ala Pro Ala Ser Pro Tyr Gly Ser Asp Thr Thr Pro
                 20                  25                  30

Cys Cys Phe Ala Tyr Leu Ser Leu Ala Leu Pro Arg Ala His Val Lys
             35                  40                  45

Glu Tyr Phe Tyr Thr Ser Ser Lys Cys Ser Asn Leu Ala Val Val Phe
 50                  55                  60

Val Thr Arg Arg Asn Arg Gln Val Cys Ala Asn Pro Glu Lys Lys Trp
 65                  70                  75                  80

Val Gln Glu Tyr Ile Asn Tyr Leu Glu Met Ser
                 85                  90
```

<210> SEQ ID NO 157
<211> LENGTH: 92
<212> TYPE: PRT
<213> ORGANISM: Homo sapiens

<400> SEQUENCE: 157

```
Met Lys Leu Cys Val Thr Val Leu Ser Leu Leu Met Leu Val Ala Ala
 1               5                  10                  15

Phe Cys Ser Pro Ala Leu Ser Ala Pro Met Gly Ser Asp Pro Pro Thr
                 20                  25                  30

Ala Cys Cys Phe Ser Tyr Thr Ala Arg Lys Leu Pro Arg Asn Phe Val
```

-continued

```
                35                  40                  45
Val Asp Tyr Tyr Glu Thr Ser Ser Leu Cys Ser Gln Pro Ala Val Val
     50                  55                  60

Phe Gln Thr Lys Arg Ser Lys Gln Val Cys Ala Asp Pro Ser Glu Ser
 65                  70                  75                  80

Trp Val Gln Glu Tyr Val Tyr Asp Leu Glu Leu Asn
                 85                  90

<210> SEQ ID NO 158
<211> LENGTH: 92
<212> TYPE: PRT
<213> ORGANISM: Homo sapiens

<400> SEQUENCE: 158

Met Lys Leu Cys Val Thr Val Leu Ser Leu Leu Met Leu Val Ala Ala
 1               5                  10                  15

Phe Cys Ser Pro Ala Leu Ser Ala Pro Met Gly Ser Asp Pro Pro Thr
                 20                  25                  30

Ala Cys Cys Phe Ser Tyr Thr Ala Arg Lys Leu Pro Arg Asn Phe Val
             35                  40                  45

Val Asp Tyr Tyr Glu Thr Ser Ser Leu Cys Ser Gln Pro Ala Val Val
     50                  55                  60

Phe Gln Thr Lys Arg Ser Lys Gln Val Cys Ala Asp Pro Ser Glu Ser
 65                  70                  75                  80

Trp Val Gln Glu Tyr Val Tyr Asp Leu Glu Leu Asn
                 85                  90

<210> SEQ ID NO 159
<211> LENGTH: 92
<212> TYPE: PRT
<213> ORGANISM: Homo sapiens

<400> SEQUENCE: 159

Met Lys Leu Cys Val Thr Val Leu Ser Leu Leu Met Leu Val Ala Ala
 1               5                  10                  15

Phe Cys Ser Pro Ala Leu Ser Ala Pro Met Gly Ser Asp Pro Pro Thr
                 20                  25                  30

Ala Cys Cys Phe Ser Tyr Thr Ala Arg Lys Leu Pro Arg Asn Phe Val
             35                  40                  45

Val Asp Tyr Tyr Glu Thr Ser Ser Leu Cys Ser Gln Pro Ala Val Val
     50                  55                  60

Phe Gln Thr Lys Arg Gly Lys Gln Val Cys Ala Asp Pro Ser Glu Ser
 65                  70                  75                  80

Trp Val Gln Glu Tyr Val Tyr Asp Leu Glu Leu Asn
                 85                  90

<210> SEQ ID NO 160
<211> LENGTH: 92
<212> TYPE: PRT
<213> ORGANISM: Homo sapiens

<400> SEQUENCE: 160

Met Lys Leu Cys Val Thr Val Leu Ser Leu Leu Met Leu Val Ala Ala
 1               5                  10                  15

Phe Cys Ser Leu Ala Leu Ser Ala Pro Met Gly Ser Asp Pro Pro Thr
                 20                  25                  30

Ala Cys Cys Phe Ser Tyr Thr Ala Arg Lys Leu Pro Arg Asn Phe Val
             35                  40                  45
```

-continued

```
Val Asp Tyr Tyr Glu Thr Ser Ser Leu Cys Ser Gln Pro Ala Val Val
         50                  55                  60
Phe Gln Thr Lys Arg Ser Lys Gln Val Cys Ala Asp Pro Ser Glu Ser
 65                  70                  75                  80
Trp Val Gln Glu Tyr Val Asp Tyr Leu Glu Leu Asn
                 85                  90

<210> SEQ ID NO 161
<211> LENGTH: 92
<212> TYPE: PRT
<213> ORGANISM: 'Axial Seamount' polynoid polychaete

<400> SEQUENCE: 161

Met Gln Val Ser Thr Ala Ala Leu Ala Val Leu Leu Cys Thr Met Ala
 1               5                  10                  15
Leu Cys Asn Gln Phe Ser Ala Ser Leu Ala Ala Asp Thr Pro Thr Ala
                 20                  25                  30
Cys Cys Phe Ser Tyr Thr Ser Arg Gln Ile Pro Gln Asn Phe Ile Ala
             35                  40                  45
Asp Tyr Phe Glu Thr Ser Ser Gln Cys Ser Lys Pro Gly Val Ile Phe
         50                  55                  60
Leu Thr Lys Arg Ser Arg Gln Val Cys Ala Asp Pro Ser Glu Glu Trp
 65                  70                  75                  80
Val Gln Lys Tyr Val Ser Asp Leu Glu Leu Ser Ala
                 85                  90

<210> SEQ ID NO 162
<211> LENGTH: 96
<212> TYPE: PRT
<213> ORGANISM: Mus sp.

<400> SEQUENCE: 162

Met Gln Ile Ile Thr Thr Ala Leu Val Cys Leu Leu Leu Ala Gly Met
 1               5                  10                  15
Trp Pro Glu Asp Val Asp Ser Lys Ser Met Gln Val Pro Phe Ser Arg
                 20                  25                  30
Cys Cys Phe Ser Phe Ala Glu Gln Glu Ile Pro Leu Arg Ala Ile Leu
             35                  40                  45
Cys Tyr Arg Asn Thr Ser Ser Ile Cys Ser Asn Glu Gly Leu Ile Phe
         50                  55                  60
Lys Leu Lys Arg Gly Lys Glu Ala Cys Ala Leu Asp Thr Val Gly Trp
 65                  70                  75                  80
Val Gln Arg His Arg Lys Met Leu Arg His Cys Pro Ser Lys Arg Lys
                 85                  90                  95

<210> SEQ ID NO 163
<211> LENGTH: 114
<212> TYPE: PRT
<213> ORGANISM: Mus sp.

<400> SEQUENCE: 163

Met Arg Leu Leu Leu Thr Phe Leu Gly Val Cys Cys Leu Thr Pro
 1               5                  10                  15
Trp Val Val Glu Gly Val Gly Thr Glu Val Leu Glu Glu Ser Ser Cys
                 20                  25                  30
Val Asn Leu Gln Thr Gln Arg Leu Pro Val Gln Lys Ile Lys Thr Tyr
             35                  40                  45
```

```
Ile Ile Trp Glu Gly Ala Met Arg Ala Val Ile Phe Val Thr Lys Arg
 50                  55                  60

Gly Leu Lys Ile Cys Ala Asp Pro Glu Ala Lys Trp Val Lys Ala Ala
 65                  70                  75                  80

Ile Lys Thr Val Asp Gly Arg Ala Ser Thr Arg Lys Asn Met Ala Glu
                 85                  90                  95

Thr Val Pro Thr Gly Ala Gln Arg Ser Thr Ser Thr Ala Val Thr Leu
            100                 105                 110

Thr Gly

<210> SEQ ID NO 164
<211> LENGTH: 495
<212> TYPE: PRT
<213> ORGANISM: Ebola virus
<220> FEATURE:
<221> NAME/KEY: VARIANT
<222> LOCATION: (1)..(495)
<223> OTHER INFORMATION: X is selenocysteine.

<400> SEQUENCE: 164

Met Asp Ser Arg Pro Gln Lys Ile Trp Met Ala Pro Ser Leu Thr Glu
  1               5                  10                  15

Ser Asp Met Asp Tyr His Lys Ile Leu Thr Ala Gly Leu Ser Val Gln
             20                  25                  30

Gln Gly Ile Val Arg Gln Arg Val Ile Pro Val Tyr Gln Val Asn Asn
         35                  40                  45

Leu Glu Glu Ile Cys Gln Leu Ile Ile Gln Ala Phe Glu Ala Gly Val
     50                  55                  60

Asp Phe Gln Glu Ser Ala Asp Ser Phe Leu Leu Met Leu Cys Leu His
 65                  70                  75                  80

His Ala Tyr Gln Gly Asp Tyr Lys Leu Phe Leu Glu Ser Gly Ala Val
                 85                  90                  95

Lys Tyr Leu Glu Gly His Gly Phe Arg Phe Glu Val Lys Lys Arg Asp
            100                 105                 110

Gly Val Lys Arg Leu Glu Glu Leu Pro Ala Val Ser Ser Gly Lys
         115                 120                 125

Asn Ile Lys Arg Thr Leu Ala Ala Met Pro Glu Glu Glu Thr Thr Glu
130                 135                 140

Ala Asn Ala Gly Gln Phe Leu Ser Phe Ala Ser Leu Phe Leu Pro Lys
145                 150                 155                 160

Leu Val Val Gly Glu Lys Ala Cys Leu Arg Lys Val Gln Arg Gln Ile
                165                 170                 175

Gln Val His Ala Glu Gln Gly Leu Ile Gln Tyr Pro Thr Ala Trp Gln
            180                 185                 190

Ser Val Gly His Met Met Val Ile Phe Arg Leu Met Arg Thr Asn Phe
        195                 200                 205

Leu Ile Lys Phe Leu Leu Ile His Gln Gly Met His Met Val Ala Gly
    210                 215                 220

His Asp Ala Asn Asp Ala Val Ile Ser Asn Ser Val Ala Gln Ala Arg
225                 230                 235                 240

Phe Ser Gly Leu Leu Ile Val Lys Thr Val Leu Asp His Ile Leu Gln
                245                 250                 255

Lys Thr Glu Arg Gly Val Arg Leu His Pro Leu Ala Arg Thr Ala Lys
            260                 265                 270

Val Lys Asn Glu Val Asn Ser Leu Lys Ala Ala Leu Ser Ser Leu Ala
        275                 280                 285
```

-continued

```
Lys His Gly Glu Tyr Ala Pro Phe Ala Arg Leu Leu Asn Leu Ser Gly
    290                 295                 300

Val Asn Asn Leu Glu His Gly Leu Phe Pro Ser Thr Ile Gly Asn Cys
305                 310                 315                 320

Thr Arg Ser Arg His Ser Thr Arg Glu Tyr Pro Arg Arg Ser Lys Cys
                325                 330                 335

Trp Arg Thr Val Ser Thr Thr Gly Arg Gly Cys His Xaa Gly Xaa Glu
                340                 345                 350

Ala Thr Pro Thr Ile Cys Arg Val Ser Arg Thr Xaa Pro Ser Trp Thr
                355                 360                 365

Xaa Xaa Ser Gly Lys Glu Asn Ser Tyr Glu Leu Pro Ser Lys Glu
    370                 375                 380

Arg Asn Gln Leu Pro Ala Asn Lys Arg Tyr Gly Asn Ser Lys Lys Arg
385                 390                 395                 400

Ala Pro Gly Gln Ala Asp Arg Ser Tyr His Cys Cys Val Thr Ala Gln
                405                 410                 415

Asn Lys Trp Thr Leu Arg Xaa Xaa Xaa Arg His Ser Leu Ser Arg Thr
                420                 425                 430

His Gln Xaa Xaa Arg Gln Ser Trp Pro Ser Arg Xaa Xaa Ser Asp Xaa
        435                 440                 445

Leu Thr Gly Tyr Asp His Ser Arg Cys Gly Gly Xaa Ser Arg Xaa Trp
    450                 455                 460

Lys Leu Arg Arg Ile Pro Glu Leu Leu Gly Lys Arg His Glu Cys Thr
465                 470                 475                 480

Arg Xaa Leu Gly Pro Ile Arg Ser Arg Arg Gly Arg Gly His
                485                 490                 495

<210> SEQ ID NO 165
<211> LENGTH: 495
<212> TYPE: PRT
<213> ORGANISM: Ebola virus
<220> FEATURE:
<221> NAME/KEY: VARIANT
<222> LOCATION: (1)..(495)
<223> OTHER INFORMATION: X is selenocysteine.

<400> SEQUENCE: 165

Met Asp Ser Arg Pro Gln Lys Ile Trp Met Ala Pro Ser Leu Thr Glu
  1               5                  10                  15

Ser Asp Met Asp Tyr His Lys Ile Leu Thr Ala Gly Leu Ser Val Gln
                20                  25                  30

Gln Gly Ile Val Arg Gln Arg Val Ile Pro Val Tyr Gln Val Asn Asn
            35                  40                  45

Leu Glu Glu Ile Cys Gln Leu Ile Ile Gln Ala Phe Glu Ala Gly Val
    50                  55                  60

Asp Phe Gln Glu Ser Ala Asp Ser Phe Leu Leu Met Leu Cys Leu His
 65                  70                  75                  80

His Ala Tyr Gln Gly Asp Tyr Lys Leu Phe Leu Glu Ser Gly Ala Val
                85                  90                  95

Lys Tyr Leu Glu Gly His Gly Phe Arg Phe Glu Val Lys Lys Arg Asp
                100                 105                 110

Gly Val Lys Arg Leu Glu Glu Leu Leu Pro Ala Val Ser Ser Gly Lys
            115                 120                 125

Asn Ile Lys Arg Thr Leu Ala Ala Met Pro Glu Glu Glu Thr Thr Glu
    130                 135                 140
```

-continued

```
Ala Asn Ala Gly Gln Phe Leu Ser Phe Ala Ser Leu Phe Leu Pro Lys
145                 150                 155                 160

Leu Val Val Gly Glu Lys Ala Cys Leu Arg Lys Val Gln Arg Gln Ile
                165                 170                 175

Gln Val His Ala Glu Gln Gly Leu Ile Gln Tyr Pro Thr Ala Trp Gln
            180                 185                 190

Ser Val Gly His Met Met Val Ile Phe Arg Leu Met Arg Thr Asn Phe
        195                 200                 205

Leu Ile Lys Phe Leu Leu Ile His Gln Gly Met His Met Val Ala Gly
    210                 215                 220

His Asp Ala Asn Asp Ala Val Ile Ser Asn Ser Val Ala Gln Ala Arg
225                 230                 235                 240

Phe Ser Gly Leu Leu Ile Val Lys Thr Val Leu Asp His Ile Leu Gln
                245                 250                 255

Lys Thr Glu Arg Gly Val Arg Leu His Pro Leu Ala Arg Thr Ala Lys
            260                 265                 270

Val Lys Asn Glu Val Asn Ser Leu Lys Ala Ala Leu Ser Ser Leu Ala
        275                 280                 285

Lys His Gly Glu Tyr Ala Pro Phe Ala Arg Leu Leu Asn Leu Ser Gly
    290                 295                 300

Val Asn Asn Leu Glu His Gly Leu Phe Pro Gln Leu Ser Ala Ile Ala
305                 310                 315                 320

Leu Gly Val Ala Thr Ala His Gly Ser Thr Leu Ala Gly Val Asn Val
                325                 330                 335

Gly Glu Gln Tyr Gln Gln Leu Arg Glu Ala Ala Thr Glu Ala Glu Lys
            340                 345                 350

Gln Leu Gln Gln Tyr Ala Glu Ser Arg Glu Leu Asp His Leu Gly Leu
        355                 360                 365

Asp Asp Gln Gly Lys Glu Asn Ser Tyr Glu Leu Pro Ser Glu Lys Glu
    370                 375                 380

Arg Asn Gln Leu Pro Ala Asn Lys Arg Tyr Gly Asn Ser Lys Lys Arg
385                 390                 395                 400

Ala Pro Gly Gln Ala Asp Arg Ser Tyr His Cys Cys Val Thr Ala Gln
                405                 410                 415

Asn Lys Trp Thr Leu Arg Xaa Xaa Xaa Arg His Ser Leu Ser Arg Thr
            420                 425                 430

His Gln Xaa Xaa Arg Gln Ser Trp Pro Ser Arg Xaa Xaa Ser Asp Xaa
        435                 440                 445

Leu Thr Gly Tyr Asp His Ser Arg Cys Gly Xaa Ser Arg Xaa Trp
    450                 455                 460

Lys Leu Arg Arg Ile Pro Glu Leu Leu Gly Lys Arg His Glu Cys Thr
465                 470                 475                 480

Arg Xaa Leu Gly Pro Ile Arg Ser Arg Arg Gly Arg Gly His
                485                 490                 495

<210> SEQ ID NO 166
<211> LENGTH: 47
<212> TYPE: PRT
<213> ORGANISM: Sus scrofa
<220> FEATURE:
<221> NAME/KEY: VARIANT
<222> LOCATION: (1)..(47)
<223> OTHER INFORMATION: X is selenocysteine.

<400> SEQUENCE: 166

Gln Xaa Gly Lys Thr Glu Val Asn Tyr Thr Gln Leu Val Asp Leu His
```

-continued

```
                   1               5                  10                 15
         Ala Arg Tyr Ala Glu Cys Gly Leu Arg Ile Leu Ala Phe Pro Cys Asn
                              20                 25                 30
         Gln Phe Gly Arg Gln Glu Pro Gly Ser Asp Ala Glu Ile Lys Glu
                   35                  40                 45

<210> SEQ ID NO 167
<211> LENGTH: 46
<212> TYPE: PRT
<213> ORGANISM: Saccharomyces cerevisiae
<220> FEATURE:
<221> NAME/KEY: VARIANT
<222> LOCATION: (1)..(46)
<223> OTHER INFORMATION: X is selenocysteine.

<400> SEQUENCE: 167

His Xaa Ala Phe Thr Pro Gln Tyr Lys Glu Leu Glu Tyr Leu Tyr Glu
          1               5                  10                 15
         Lys Tyr Lys Ser His Gly Leu Val Ile Val Ala Phe Pro Cys Gly Gln
                              20                 25                 30
         Phe Gly Asn Gln Glu Phe Glu Lys Asp Lys Glu Ile Asn Lys
                   35                  40                 45

<210> SEQ ID NO 168
<211> LENGTH: 47
<212> TYPE: PRT
<213> ORGANISM: wood
<220> FEATURE:
<221> NAME/KEY: VARIANT
<222> LOCATION: (1)..(47)
<223> OTHER INFORMATION: X is selenocysteine.

<400> SEQUENCE: 168

Gln Xaa Gly Leu Thr Asn Ser Asn Tyr Thr Asp Leu Thr Glu Ile Tyr
          1               5                  10                 15
         Lys Lys Tyr Lys Asp Gln Gly Leu Glu Ile Leu Ala Phe Pro Cys Asn
                              20                 25                 30
         Gln Phe Gly Gly Gln Glu Pro Gly Ser Ile Glu Glu Ile Gln Asn
                   35                  40                 45

<210> SEQ ID NO 169
<211> LENGTH: 46
<212> TYPE: PRT
<213> ORGANISM: nematode
<220> FEATURE:
<221> NAME/KEY: VARIANT
<222> LOCATION: (1)..(46)
<223> OTHER INFORMATION: X is selenocysteine.

<400> SEQUENCE: 169

Tyr Xaa Ala Tyr Thr Met Gln Tyr Arg Asp Phe Asn Pro Ile Leu Gly
          1               5                  10                 15
         Ser Asn Ser Asn Gly Thr Leu Asn Ile Leu Gly Phe Pro Cys Asn Gln
                              20                 25                 30
         Phe Tyr Leu Gln Glu Pro Ala Glu Asn His Glu Leu Leu Asn
                   35                  40                 45

<210> SEQ ID NO 170
<211> LENGTH: 46
<212> TYPE: PRT
<213> ORGANISM: macaque
<220> FEATURE:
<221> NAME/KEY: VARIANT
<222> LOCATION: (1)..(46)
```

<223> OTHER INFORMATION: X is selenocysteine.

<400> SEQUENCE: 170

Tyr Xaa Gly Leu Thr Ala Gln Tyr Pro Glu Leu Asn Ala Leu Gln Glu
 1               5                  10                  15

Glu Leu Lys Pro Tyr Gly Leu Val Val Leu Gly Phe Pro Cys Asn Gln
            20                  25                  30

Phe Gly Lys Gln Glu Pro Gly Asp Asn Lys Glu Ile Leu Pro
        35                  40                  45

<210> SEQ ID NO 171
<211> LENGTH: 46
<212> TYPE: PRT
<213> ORGANISM: rat
<220> FEATURE:
<221> NAME/KEY: VARIANT
<222> LOCATION: (1)..(46)
<223> OTHER INFORMATION: X is selenocysteine.

<400> SEQUENCE: 171

Tyr Xaa Gly Leu Thr Ile Gln Tyr Pro Glu Leu Asn Ala Leu Gln Asp
 1               5                  10                  15

Asp Leu Lys Gln Phe Gly Leu Val Ile Leu Gly Phe Pro Cys Asn Gln
            20                  25                  30

Phe Gly Lys Gln Glu Pro Gly Asp Asn Thr Glu Ile Leu Pro
        35                  40                  45

<210> SEQ ID NO 172
<211> LENGTH: 46
<212> TYPE: PRT
<213> ORGANISM: Homo sapiens
<220> FEATURE:
<221> NAME/KEY: VARIANT
<222> LOCATION: (1)..(46)
<223> OTHER INFORMATION: X is selenocysteine.

<400> SEQUENCE: 172

Tyr Xaa Gly Leu Thr Gly Gln Tyr Ile Glu Leu Asn Ala Leu Gln Glu
 1               5                  10                  15

Glu Leu Ala Pro Phe Gly Leu Val Ile Leu Gly Phe Pro Cys Asn Gln
            20                  25                  30

Phe Gly Lys Gln Glu Pro Gly Glu Asn Ser Glu Ile Leu Pro
        35                  40                  45

<210> SEQ ID NO 173
<211> LENGTH: 46
<212> TYPE: PRT
<213> ORGANISM: Mus sp.
<220> FEATURE:
<221> NAME/KEY: VARIANT
<222> LOCATION: (1)..(46)
<223> OTHER INFORMATION: X is selenocysteine.

<400> SEQUENCE: 173

Tyr Xaa Gly Leu Thr Asp Gln Tyr Leu Glu Leu Asn Ala Leu Gln Glu
 1               5                  10                  15

Glu Leu Gly Pro Phe Gly Leu Val Ile Leu Gly Phe Pro Ser Asn Gln
            20                  25                  30

Phe Gly Lys Gln Glu Pro Gly Glu Asn Ser Glu Ile Leu Pro
        35                  40                  45

<210> SEQ ID NO 174
<211> LENGTH: 46

```
<212> TYPE: PRT
<213> ORGANISM: bovine
<220> FEATURE:
<221> NAME/KEY: VARIANT
<222> LOCATION: (1)..(46)
<223> OTHER INFORMATION: X is selenocysteine.

<400> SEQUENCE: 174

Tyr Xaa Gly Leu Thr Asp Gln Tyr Leu Glu Leu Asn Ala Leu Gln Glu
 1               5                  10                  15

Glu Leu Gly Pro Phe Gly Leu Val Ile Leu Gly Phe Pro Cys Asn Gln
            20                  25                  30

Phe Gly Lys Gln Glu Pro Gly Glu Asn Ser Glu Ile Leu Pro
        35                  40                  45

<210> SEQ ID NO 175
<211> LENGTH: 46
<212> TYPE: PRT
<213> ORGANISM: bovine
<220> FEATURE:
<221> NAME/KEY: VARIANT
<222> LOCATION: (1)..(46)
<223> OTHER INFORMATION: X is selenocysteine.

<400> SEQUENCE: 175

Tyr Xaa Gly Leu Thr Gly Gln Tyr Val Glu Leu Asn Ala Leu Gln Glu
 1               5                  10                  15

Glu Leu Glu Pro Phe Gly Leu Val Ile Leu Gly Phe Pro Cys Asn Gln
            20                  25                  30

Phe Gly Lys Gln Glu Pro Gly Glu Asn Ser Glu Ile Leu Ala
        35                  40                  45

<210> SEQ ID NO 176
<211> LENGTH: 46
<212> TYPE: PRT
<213> ORGANISM: Homo sapiens
<220> FEATURE:
<221> NAME/KEY: VARIANT
<222> LOCATION: (1)..(46)
<223> OTHER INFORMATION: X is selenocysteine.

<400> SEQUENCE: 176

Leu Xaa Gly Thr Thr Thr Arg Asp Phe Thr Gln Leu Asn Glu Leu Gln
 1               5                  10                  15

Cys Arg Phe Pro Arg Arg Leu Val Val Leu Gly Phe Pro Cys Asn Gln
            20                  25                  30

Phe Gly His Gln Glu Asn Cys Gln Asn Glu Glu Ile Leu Asn
        35                  40                  45

<210> SEQ ID NO 177
<211> LENGTH: 47
<212> TYPE: PRT
<213> ORGANISM: bovine
<220> FEATURE:
<221> NAME/KEY: VARIANT
<222> LOCATION: (1)..(47)
<223> OTHER INFORMATION: X is selenocysteine.

<400> SEQUENCE: 177

Leu Xaa Gly Thr Thr Val Arg Asp Tyr Thr Gln Met Asn Asp Leu Gln
 1               5                  10                  15

Arg Arg Leu Gly Pro Arg Gly Leu Val Val Leu Gly Phe Pro Cys Asn
            20                  25                  30

Gln Phe Gly His Gln Glu Asn Ala Lys Asn Glu Glu Ile Leu Asn
```

35                  40                  45

<210> SEQ ID NO 178
<211> LENGTH: 47
<212> TYPE: PRT
<213> ORGANISM: rat
<220> FEATURE:
<221> NAME/KEY: VARIANT
<222> LOCATION: (1)..(47)
<223> OTHER INFORMATION: X is selenocysteine.

<400> SEQUENCE: 178

Leu Xaa Gly Thr Thr Thr Arg Asp Tyr Thr Glu Met Asn Asp Leu Gln
 1               5                  10                  15

Lys Arg Leu Gly Pro Arg Gly Leu Val Val Leu Gly Phe Pro Cys Asn
            20                  25                  30

Gln Phe Gly His Gln Glu Asn Gly Lys Asn Glu Glu Ile Leu Asn
        35                  40                  45

<210> SEQ ID NO 179
<211> LENGTH: 47
<212> TYPE: PRT
<213> ORGANISM: Mus sp.
<220> FEATURE:
<221> NAME/KEY: VARIANT
<222> LOCATION: (1)..(47)
<223> OTHER INFORMATION: X is selenocysteine.

<400> SEQUENCE: 179

Leu Xaa Gly Thr Thr Ile Arg Asp Tyr Thr Glu Met Asn Asp Leu Gln
 1               5                  10                  15

Lys Arg Leu Gly Pro Arg Gly Leu Val Val Leu Gly Phe Pro Cys Asn
            20                  25                  30

Gln Phe Gly His Gln Glu Asn Gly Lys Asn Glu Glu Ile Leu Asn
        35                  40                  45

<210> SEQ ID NO 180
<211> LENGTH: 47
<212> TYPE: PRT
<213> ORGANISM: Homo sapiens
<220> FEATURE:
<221> NAME/KEY: VARIANT
<222> LOCATION: (1)..(47)
<223> OTHER INFORMATION: X is selenocysteine.

<400> SEQUENCE: 180

Leu Xaa Gly Thr Thr Val Arg Asp Tyr Thr Gln Met Asn Glu Leu Gln
 1               5                  10                  15

Arg Arg Leu Gly Pro Arg Gly Leu Val Val Leu Gly Phe Pro Cys Asn
            20                  25                  30

Gln Phe Gly His Gln Glu Asn Ala Lys Asn Glu Glu Ile Leu Asn
        35                  40                  45

<210> SEQ ID NO 181
<211> LENGTH: 47
<212> TYPE: PRT
<213> ORGANISM: rabbit
<220> FEATURE:
<221> NAME/KEY: VARIANT
<222> LOCATION: (1)..(47)
<223> OTHER INFORMATION: X is selenocysteine.

<400> SEQUENCE: 181

Leu Xaa Gly Thr Thr Val Arg Asp Tyr Thr Gln Met Asn Glu Leu Gln
 1               5                  10                  15

-continued

Glu Arg Leu Gly Pro Arg Ala Leu Val Val Leu Gly Phe Pro Cys Asn
                20                  25                  30

Gln Phe Gly His Gln Glu Asn Ala Lys Asn Glu Glu Ile Leu Asn
            35                  40                  45

<210> SEQ ID NO 182
<211> LENGTH: 42
<212> TYPE: PRT
<213> ORGANISM: Coxsackievirus B
<220> FEATURE:
<221> NAME/KEY: VARIANT
<222> LOCATION: (1)..(42)
<223> OTHER INFORMATION: X is selenocysteine.

<400> SEQUENCE: 182

Ile Xaa Arg Gln Trp Lys Leu Thr Gly Cys Arg Cys Asp Leu Gln Met
  1               5                  10                  15

Lys Trp Val Val Lys Tyr Leu Gly Phe Pro Cys Asn Leu Glu His Gln
                20                  25                  30

Val Cys Cys Arg Gly His Tyr Trp Glu Arg
            35                  40

<210> SEQ ID NO 183
<211> LENGTH: 44
<212> TYPE: PRT
<213> ORGANISM: Homo sapiens
<220> FEATURE:
<221> NAME/KEY: VARIANT
<222> LOCATION: (1)..(44)
<223> OTHER INFORMATION: X is selenocysteine.

<400> SEQUENCE: 183

Leu Xaa Gly Thr Thr Ile Arg Asp Tyr Thr Glu Met Asn Asp Leu Gln
  1               5                  10                  15

Lys Arg Leu Gly Leu Val Val Leu Gly Phe Pro Cys Asn Gln Phe Gly
                20                  25                  30

His Gln Val Tyr Gly Ala Arg Trp Val Ala Leu Gly
            35                  40

<210> SEQ ID NO 184
<211> LENGTH: 190
<212> TYPE: PRT
<213> ORGANISM: Entamoeba dispar

<400> SEQUENCE: 184

Met Ser Phe Gln Leu Pro Gln Leu Pro Tyr Ala Tyr Asn Ala Leu Glu
  1               5                  10                  15

Pro His Ile Ser Lys Glu Thr Leu Glu Phe His His Asp Lys His His
                20                  25                  30

Ala Thr Tyr Val Asn Lys Leu Asn Gly Leu Val Lys Gly Thr Glu Gln
            35                  40                  45

Glu His Lys Thr Leu Glu Glu Leu Ile Lys Gln Lys Pro Thr Gln Ala
        50                  55                  60

Ile Tyr Asn Asn Ala Ala Gln Ala Trp Asn His Ala Phe Tyr Trp Lys
 65                 70                  75                  80

Cys Met Cys Gly Cys Gly Val Lys Pro Ser Glu Gln Leu Ile Ala Lys
                85                  90                  95

Leu Thr Ala Ala Phe Gly Gly Leu Glu Glu Phe Lys Lys Lys Glu Thr
            100                 105                 110

Glu Lys Ala Val Gly His Phe Gly Ser Gly Trp Cys Trp Leu Val Glu

```
                115                 120                 125
His Asp Gly Lys Leu Glu Ile Ile Asp Thr His Asp Ala Val Asn Pro
    130                 135                 140

Met Thr Asn Gly Met Lys Pro Leu Leu Thr Cys Asp Val Trp Glu His
145                 150                 155                 160

Ala Tyr Tyr Ile Asp Thr Arg Asn Asn Arg Ala Ala Tyr Leu Glu His
                165                 170                 175

Trp Trp Asn Val Val Asn Trp Lys Phe Val Glu Glu Gln Leu
            180                 185                 190
```

<210> SEQ ID NO 185
<211> LENGTH: 196
<212> TYPE: PRT
<213> ORGANISM: Tetrahymena sp.

<400> SEQUENCE: 185

```
Leu Asn Tyr Glu Tyr Ser Asp Leu Glu Pro Val Leu Ser Ala His Leu
  1               5                  10                  15

Leu Ser Phe His His Gly Lys His His Gln Ala Tyr Val Asn Asn Leu
            20                  25                  30

Asn Ala Thr Tyr Glu Gln Leu Ala Ala Thr Lys Glu Asn Asp Ala
        35                  40                  45

His Lys Ile Ala Thr Leu Gln Ser Ala Leu Arg Phe Asn Leu Gly Gly
    50                  55                  60

His Val Asn His Trp Ile Tyr Trp Asp Asn Leu Ala Pro Val Lys Ser
 65                  70                  75                  80

Gly Gly Gly Val Leu Pro Asp Glu His Ser Pro Leu Thr Lys Ala Ile
                85                  90                  95

Lys Glu Lys Trp Gly Ser Tyr Glu Asn Glu Ile Thr Leu Phe Asn Thr
            100                 105                 110

Arg Thr Ala Ala Ile Gln Gly Ser Gly Trp Gly Trp Leu Gly Tyr Asp
        115                 120                 125

Thr Val Ser Lys Ser Leu Arg Leu Phe Glu Leu Gly Asn Gln Asp Met
    130                 135                 140

Pro Glu Trp Ser Ser Ile Val Pro Leu Leu Thr Ile Asp Val Trp Glu
145                 150                 155                 160

His Ala Tyr Tyr Leu Asp Tyr Gln Asn Leu Arg Pro Lys Tyr Leu Thr
                165                 170                 175

Glu Val Trp Lys Ile Val Asn Trp Arg Glu Val Glu Lys Arg Tyr Leu
            180                 185                 190

Gln Ala Ile Glu
        195
```

<210> SEQ ID NO 186
<211> LENGTH: 240
<212> TYPE: PRT
<213> ORGANISM: bloodfluke

<400> SEQUENCE: 186

```
Met Leu Ala Leu Leu Cys Ser Cys Leu Leu Leu Ala Ala Gly Ala Ser
  1               5                  10                  15

Asp Ala Trp Thr Gly Glu Asp Ser Ala Glu Pro Asn Ser Asp Ser Ala
            20                  25                  30

Glu Trp Ile Arg Asp Met Tyr Ala Lys Val Thr Glu Ile Trp Gln Glu
        35                  40                  45

Val Met Gln Arg Arg Asp Asp Asp Gly Thr Leu His Ala Ala Cys Gln
```

```
                    50                      55                      60
Val Gln Pro Ser Ala Thr Leu Asp Ala Ala Gln Pro Arg Val Thr Gly
 65                      70                      75                      80

Val Val Leu Phe Arg Gln Leu Ala Pro Arg Ala Lys Leu Asp Ala Phe
                     85                      90                      95

Phe Ala Leu Glu Gly Phe Pro Thr Glu Pro Asn Ser Ser Arg Ala
                100                     105                     110

Ile His Val His Gln Phe Gly Asp Leu Ser Gln Gly Cys Glu Ser Thr
                115                     120                     125

Gly Pro His Tyr Asn Pro Leu Ala Val Pro His Pro Gln His Pro Gly
                130                     135                     140

Asp Phe Gly Asn Phe Ala Val Arg Asp Gly Ser Leu Trp Arg Tyr Arg
145                     150                     155                     160

Ala Gly Leu Ala Ala Ser Leu Ala Gly Pro His Ser Ile Val Gly Arg
                165                     170                     175

Ala Val Val Val His Ala Gly Glu Asp Asp Leu Gly Arg Gly Gly Asn
                180                     185                     190

Gln Ala Ser Val Glu Asn Gly Asn Ala Gly Arg Arg Leu Ala Cys Cys
                195                     200                     205

Val Val Gly Val Cys Gly Pro Gly Leu Trp Glu Arg Gln Ala Arg Glu
                210                     215                     220

His Ser Glu Arg Lys Lys Arg Arg Arg Glu Ser Glu Cys Lys Ala Ala
225                     230                     235                     240

<210> SEQ ID NO 187
<211> LENGTH: 114
<212> TYPE: PRT
<213> ORGANISM: rabbit

<400> SEQUENCE: 187

Thr Glu Ile Trp Gln Ala Leu Thr Gln Gln Trp Ala Ala Gln Gly Glu
 1               5                      10                      15

Pro Ala Gly Ala Leu His Ala Val Cys Arg Val Gln Pro Ser Ala Thr
                20                      25                      30

Leu Asp Ala Ala Gln Pro Arg Val Ser Gly Leu Val Val Phe Arg Gln
                35                      40                      45

Leu Gly Pro Gly Ala Gln Leu Glu Ala Phe Phe Asp Leu Leu Glu Gly
        50                      55                      60

Phe Pro Val Glu Ala Asn Leu Ser Ser Arg Ala Ile His Val His Gln
 65                      70                      75                      80

Phe Gly Asp Leu Ser Gln Gly Cys Asp Ser Thr Gly Ala His Tyr Asn
                85                      90                      95

Pro Leu Ala Val Gln His Pro Gln His Pro Gly Asp Phe Gly Asn Phe
                100                     105                     110

Ala Val

<210> SEQ ID NO 188
<211> LENGTH: 244
<212> TYPE: PRT
<213> ORGANISM: rat

<400> SEQUENCE: 188

Met Val Ala Phe Leu Phe Cys Asn Leu Leu Val Ala Cys Gly Ser
 1               5                      10                      15

Val Thr Trp Thr Met Ser Asp Thr Gly Glu Ser Gly Val Asp Leu Ala
                20                      25                      30
```

-continued

```
Asp Arg Leu Asp Leu Val Glu Lys Ile Gly Asp Thr His Ser Lys Asp
        35                  40                  45

Leu Glu Ile Trp Met Glu Leu Gly Lys Gln Arg Glu Ala Asp Ala Arg
 50                  55                  60

Glu Met His Ala Val Cys Arg Val Gln Pro Ser Ala Met Leu Pro Pro
 65                  70                  75                  80

Asp Gln Pro Gln Ile Thr Gly Leu Val Leu Phe Arg Gln Leu Gly Pro
                 85                  90                  95

Ser Ser Arg Leu Glu Ala Ser Phe Asn Leu Glu Gly Phe Pro Ala Glu
                100                 105                 110

Gln Asn Thr Ser Asn His Ala Ile His Val His Glu Phe Gly Asp Leu
            115                 120                 125

Ser Gln Gly Cys Glu Ser Thr Gly Pro His Tyr Asn Pro Leu Gly Val
130                 135                 140

Pro His Pro Gln His Pro Gly Asp Phe Gly Asn Phe Val Val Arg Asp
145                 150                 155                 160

Gly Arg Leu Trp Lys His Arg Met Gly Leu Ala Thr Ser Leu Ala Gly
                165                 170                 175

Pro His Ser Ile Leu Gly Arg Ala Val Val His Ala Gly Glu Asp
                180                 185                 190

Asp Leu Gly Lys Gly Asn Gln Ala Ser Val Gln Asn Gly Asn Ala
            195                 200                 205

Gly Arg Arg Leu Ala Cys Cys Val Val Gly Thr Ser Asn Ser Glu Ala
        210                 215                 220

Trp Glu Ser Gln Thr Lys Glu Arg Lys Lys Trp Arg Trp Glu Ser Glu
225                 230                 235                 240

Cys Lys Thr Thr

<210> SEQ ID NO 189
<211> LENGTH: 195
<212> TYPE: PRT
<213> ORGANISM: Dirofilaria immitis

<400> SEQUENCE: 189

Met Met Gly Ser Phe Ile Phe Leu Leu Ser Ile Ile Ser Ile Asn
 1               5                  10                  15

Tyr Ile Asn Ser Leu His Thr Val His Arg Ser Asn Ile His Arg Asn
                 20                  25                  30

Met His Asn Gly Gly Met Pro Lys Lys Ala Val Ala Val Leu Lys Ser
         35                  40                  45

Asp Thr Val Asn Gly Ile Ile Tyr Phe Gln Gln Asn Asn Arg Ala Ser
 50                  55                  60

Ala Thr Thr Ile Tyr Gly Thr Ile Asn Gly Leu Thr Pro Gly Leu His
 65                  70                  75                  80

Gly Phe His Ile His Gln Tyr Gly Ile Lys Ala Asn Gly Cys Thr Ser
                 85                  90                  95

Ala Ala Ala His Tyr Asn Pro Phe Glu Lys Thr His Gly Arg Pro Thr
            100                 105                 110

Asn Asn Ile Lys His Ile Gly Asp Leu Arg Asn Ile Lys Ala Gly Ala
        115                 120                 125

Asp Gly Val Ala Asn Val Asn Ile Ile Ser Asn His Ile Gln Leu Ser
130                 135                 140

Gly Pro Leu Ser Val Ile Gly Arg Ser Leu Val Val His Ala Asn Pro
145                 150                 155                 160
```

-continued

```
Asp Asp Leu Ser Lys Gly Asn Gly Asp Ala Arg Glu Glu Ser Leu Lys
                165                 170                 175
Thr Gly Asn Ala Gly Ser Arg Ile Val Cys Ser Ile Ile Gly Ile Ala
            180                 185                 190
Pro Ser Thr
        195

<210> SEQ ID NO 190
<211> LENGTH: 201
<212> TYPE: PRT
<213> ORGANISM: Onchocerca armillata

<400> SEQUENCE: 190

Met Ile Asn Ser Phe Ile Val Ile Phe Leu Ser Phe Leu Ile Phe Ile
 1               5                  10                  15
Asn Tyr Ala Asn Leu Val Cys Val Glu Ala Thr His Val Tyr Gly Arg
            20                  25                  30
Arg Ser His Ser Asn Gly Met His Gly Asn Gly Ala Arg Arg Ala Val
        35                  40                  45
Ala Val Leu Arg Gly Asp Ala Gly Val Ser Gly Ile Ile Tyr Phe Gln
    50                  55                  60
Gln Gly Ser Gly Gly Ser Ile Thr Thr Ile Ser Gly Ser Val Ser Gly
65                  70                  75                  80
Leu Thr Pro Gly Leu His Gly Phe His Val His Gln Tyr Gly Asp Gln
                85                  90                  95
Thr Asn Gly Cys Thr Ser Ala Gly Asp His Tyr Asn Pro Phe Gly Lys
            100                 105                 110
Thr His Gly Gly Pro Asn Asp Arg Ile Lys His Ile Gly Asp Leu Gly
        115                 120                 125
Asn Ile Val Ala Gly Ala Asn Gly Val Ala Glu Val Tyr Ile Asn Ser
    130                 135                 140
Tyr Asp Ile Lys Leu Arg Gly Pro Leu Ser Val Ile Gly His Ser Leu
145                 150                 155                 160
Val Val His Ala Asn Thr Asp Asp Leu Gly Gln Gly Thr Gly Asn Met
                165                 170                 175
Arg Glu Glu Ser Leu Lys Thr Gly Asn Ala Gly Ser Arg Leu Ala Cys
            180                 185                 190
Gly Val Ile Gly Ile Ala Ala Val Ser
        195                 200

<210> SEQ ID NO 191
<211> LENGTH: 151
<212> TYPE: PRT
<213> ORGANISM: corn

<400> SEQUENCE: 191

Val Lys Ala Val Ala Val Leu Gly Ser Ser Glu Gly Val Lys Gly Thr
 1               5                  10                  15
Ile Phe Phe Thr Gln Glu Gly Asp Gly Pro Thr Thr Val Thr Gly Ser
            20                  25                  30
Val Ser Gly Leu Lys Pro Gly Leu His Gly Phe His Val His Ala Leu
        35                  40                  45
Gly Asp Thr Thr Asn Gly Cys Met Ser Thr Gly Pro His Tyr Asn Pro
    50                  55                  60
Ala Ser Lys Glu His Gly Ala Pro Glu Asp Glu Asn Arg His Ala Gly
65                  70                  75                  80
```

-continued

```
Asp Leu Gly Asn Val Thr Ala Gly Ala Asp Gly Val Ala Asn Ile Asn
                85                  90                  95

Val Thr Asp Ser Gln Ile Pro Leu Thr Gly Pro Asn Ser Ile Ile Gly
            100                 105                 110

Arg Ala Val Val His Ala Asp Pro Asp Leu Gly Lys Gly Gly
        115                 120                 125

His Glu Leu Ser Lys Ser Thr Gly Asn Ala Gly Gly Arg Val Ala Cys
    130                 135                 140

Gly Ile Ile Gly Leu Gln Gly
145                 150

<210> SEQ ID NO 192
<211> LENGTH: 151
<212> TYPE: PRT
<213> ORGANISM: rice

<400> SEQUENCE: 192

Val Lys Ala Val Ala Val Leu Ala Ser Ser Glu Gly Val Lys Gly Thr
  1               5                  10                  15

Ile Phe Phe Ser Gln Glu Gly Asp Gly Pro Thr Ser Val Thr Gly Ser
             20                  25                  30

Val Ser Gly Ile Lys Pro Gly Leu His Gly Phe His Val His Ala Leu
         35                  40                  45

Gly Asp Thr Thr Asn Gly Cys Met Ser Thr Gly Pro His Phe Asn Pro
     50                  55                  60

Thr Gly Lys Glu His Gly Ala Pro Gln Asp Glu Asn Arg His Ala Gly
 65                  70                  75                  80

Asp Leu Gly Asn Ile Thr Ala Gly Ala Asp Gly Val Ala Asn Val Asn
                 85                  90                  95

Val Ser Asp Ser Gln Ile Pro Leu Thr Gly Ala His Ser Ile Ile Gly
            100                 105                 110

Arg Ala Val Val His Ala Asp Pro Asp Leu Gly Lys Gly Gly
        115                 120                 125

His Glu Leu Ser Lys Thr Thr Gly Asn Ala Gly Gly Arg Val Ala Cys
    130                 135                 140

Gly Ile Ile Gly Leu Gln Gly
145                 150

<210> SEQ ID NO 193
<211> LENGTH: 151
<212> TYPE: PRT
<213> ORGANISM: Nicotiana acuminata

<400> SEQUENCE: 193

Val Lys Ala Val Ala Val Leu Ser Ser Ser Glu Gly Val Ser Gly Thr
  1               5                  10                  15

Ile Phe Phe Thr Gln Asp Gly Asp Ala Pro Thr Thr Val Thr Gly Asn
             20                  25                  30

Val Ser Gly Leu Lys Pro Gly Leu His Gly Phe His Val His Ala Leu
         35                  40                  45

Gly Asp Thr Thr Asn Gly Cys Met Ser Thr Gly Pro His Tyr Asn Pro
     50                  55                  60

Ala Gly Lys Glu His Gly Ala Pro Glu Asp Glu Val Arg His Ala Gly
 65                  70                  75                  80

Asp Leu Gly Asn Ile Thr Val Gly Glu Asp Gly Thr Ala Ser Phe Thr
                 85                  90                  95
```

```
Leu Thr Asp Lys Gln Ile Pro Leu Ala Gly Pro Gln Ser Ile Ile Gly
            100                 105                 110

Arg Ala Val Val His Ala Asp Pro Asp Leu Gly Lys Gly Gly
        115                 120                 125

His Glu Leu Ser Lys Thr Thr Gly Asn Ala Gly Gly Arg Val Ala Cys
        130                 135                 140

Gly Ile Ile Gly Leu Gln Gly
145                 150

<210> SEQ ID NO 194
<211> LENGTH: 151
<212> TYPE: PRT
<213> ORGANISM: sweetpotato

<400> SEQUENCE: 194

Val Lys Ala Val Ala Val Leu Ser Ser Ser Glu Gly Val Ser Gly Thr
  1               5                  10                  15

Ile Phe Phe Ser Gln Glu Gly Asp Gly Pro Thr Thr Val Thr Gly Asn
             20                  25                  30

Val Ser Gly Leu Lys Pro Gly Leu His Gly Phe His Val His Ala Leu
         35                  40                  45

Gly Asp Thr Thr Asn Gly Cys Met Ser Thr Gly Pro His Phe Asn Pro
     50                  55                  60

Ala Gly Lys Glu His Gly Ala Pro Gly Asp Asp Asn Arg His Ala Gly
 65                  70                  75                  80

Asp Leu Gly Asn Ile Thr Val Gly Glu Asp Gly Thr Ala Ser Phe Thr
                 85                  90                  95

Ile Thr Asp Lys Gln Ile Pro Leu Thr Gly Ala Asn Ser Val Ile Gly
            100                 105                 110

Arg Ala Val Val His Gly Asp Pro Asp Asp Leu Gly Lys Gly Gly
        115                 120                 125

His Glu Leu Ser Lys Ser Thr Gly Asn Ala Gly Gly Arg Val Ala Cys
        130                 135                 140

Gly Ile Ile Gly Leu Gln Gly
145                 150

<210> SEQ ID NO 195
<211> LENGTH: 218
<212> TYPE: PRT
<213> ORGANISM: petunia

<400> SEQUENCE: 195

Met Ala Ala His Thr Ile Phe Thr Thr Thr Ser Thr Thr Asn Ser Phe
  1               5                  10                  15

Leu Phe Pro Ile Ala Ser Ser Asn Thr Asn Ser Ala Pro Ser Leu Ser
             20                  25                  30

Ser Ser Phe His Gly Val Ser Leu Lys Val Lys Ser Lys Thr Gln Ser
         35                  40                  45

Leu Thr Leu Ser Ser Val Thr Ser Pro Lys Pro Phe Ile Val Phe Ala
     50                  55                  60

Ala Thr Lys Lys Ala Val Ala Val Leu Lys Gly Thr Ser Asn Val Glu
 65                  70                  75                  80

Gly Val Val Thr Leu Thr Gln Asp Asp Asp Gly Pro Thr Thr Val Lys
                 85                  90                  95

Val Arg Ile Thr Gly Leu Ala Pro Gly Leu His Gly Phe His Leu His
            100                 105                 110
```

```
Glu Phe Gly Asp Thr Thr Asn Gly Cys Met Ser Thr Gly Pro His Phe
            115                 120                 125

Asn Pro Asn Gly Leu Thr His Gly Ala Pro Gly Asp Glu Val Arg His
        130                 135                 140

Ala Gly Asp Leu Gly Asn Ile Glu Ala Asn Ala Ser Gly Val Ala Glu
145                 150                 155                 160

Ala Thr Leu Val Asp Asn Gln Ile Pro Leu Ser Gly Pro Asn Ser Val
                165                 170                 175

Val Gly Arg Ala Leu Val Val His Glu Leu Glu Asp Asp Leu Gly Lys
            180                 185                 190

Gly Gly His Glu Leu Ser Leu Thr Thr Gly Asn Ala Gly Gly Arg Leu
            195                 200                 205

Ala Cys Gly Val Val Gly Leu Thr Pro Ile
210                 215

<210> SEQ ID NO 196
<211> LENGTH: 217
<212> TYPE: PRT
<213> ORGANISM: tomato

<400> SEQUENCE: 196

Met Ala Ala His Ser Ile Phe Thr Thr Thr Ser Thr Thr Asn Ser Phe
1               5                   10                  15

Leu Tyr Pro Ile Ser Ser Ser Ser Ser Pro Asn Ile Asn Ser Ser
            20                  25                  30

Phe Leu Gly Val Ser Ile Asn Val Asn Ala Lys Phe Gly Gln Ser Leu
        35                  40                  45

Thr Leu Tyr Ala Val Thr Thr Pro Lys Pro Leu Thr Val Phe Ala Ala
    50                  55                  60

Thr Lys Lys Ala Val Ala Val Leu Lys Gly Asn Ser Asn Val Glu Gly
65                  70                  75                  80

Val Val Thr Leu Ser Gln Asp Asp Gly Pro Thr Thr Val Asn Val
                85                  90                  95

Arg Ile Thr Gly Leu Ala Pro Gly Leu His Gly Phe His Leu His Glu
            100                 105                 110

Tyr Gly Asp Thr Thr Asn Gly Cys Met Ser Thr Gly Ala His Phe Asn
            115                 120                 125

Pro Asn Lys Leu Thr His Gly Ala Pro Gly Asp Glu Ile Arg His Ala
        130                 135                 140

Gly Asp Leu Gly Asn Ile Val Ala Asn Ala Asp Gly Val Ala Glu Val
145                 150                 155                 160

Thr Leu Val Asp Asn Gln Ile Pro Leu Thr Gly Pro Asn Ser Val Val
                165                 170                 175

Gly Arg Ala Leu Val Val His Glu Leu Glu Asp Asp Leu Gly Lys Gly
            180                 185                 190

Gly His Glu Leu Ser Leu Thr Thr Gly Asn Ala Gly Gly Arg Leu Ala
            195                 200                 205

Cys Gly Val Val Gly Leu Thr Pro Ile
210                 215

<210> SEQ ID NO 197
<211> LENGTH: 202
<212> TYPE: PRT
<213> ORGANISM: pea

<400> SEQUENCE: 197
```

```
Met Ala Ser Gln Thr Leu Val Ser Pro Ser Pro Leu Ser Ser His Ser
 1               5                  10                  15

Leu Leu Arg Thr Ser Phe Ser Gly Val Ser Val Lys Leu Ala Pro Gln
            20                  25                  30

Phe Ser Thr Leu Ala Thr Ser Asn Phe Lys Pro Leu Thr Val Val Ala
        35                  40                  45

Ala Ala Lys Lys Ala Val Ser Val Leu Lys Gly Thr Ser Ala Val Glu
    50                  55                  60

Gly Val Val Thr Leu Thr Gln Asp Asp Glu Gly Pro Thr Thr Val Asn
65                  70                  75                  80

Val Arg Ile Thr Gly Leu Thr Pro Gly Leu His Gly Phe His Leu His
                85                  90                  95

Glu Tyr Gly Asp Thr Thr Asn Gly Cys Ile Ser Thr Gly Pro His Phe
                100                 105                 110

Asn Pro Asn Lys Leu Thr His Gly Ala Pro Glu Asp Glu Ile Arg His
            115                 120                 125

Ala Gly Asp Leu Gly Asn Ile Val Ala Asn Ala Glu Gly Val Ala Glu
        130                 135                 140

Ala Thr Ile Val Asp Asn Gln Ile Pro Leu Thr Gly Pro Asn Ser Val
145                 150                 155                 160

Val Gly Arg Ala Leu Val Val His Glu Leu Gln Asp Asp Leu Gly Lys
                165                 170                 175

Gly Gly His Glu Leu Ser Leu Ser Thr Gly Asn Ala Gly Gly Arg Leu
                180                 185                 190

Ala Cys Gly Val Val Gly Leu Thr Pro Val
            195                 200

<210> SEQ ID NO 198
<211> LENGTH: 221
<212> TYPE: PRT
<213> ORGANISM: spinach

<400> SEQUENCE: 198

Met Ala Ala His Thr Ile Leu Ala Ser Ala Pro Ser His Thr Thr Phe
 1               5                  10                  15

Ser Leu Ile Ser Pro Phe Ser Ser Thr Pro Thr Asn Ala Leu Ser Ser
            20                  25                  30

Ser Leu Gln Ser Ser Ser Phe Asn Gly Leu Ser Phe Lys Leu Ser Pro
        35                  40                  45

Thr Thr Gln Ser Leu Ser Leu Ser Thr Ser Ala Ala Ser Lys Pro Leu
    50                  55                  60

Thr Ile Val Ala Ala Thr Lys Lys Ala Val Ala Val Leu Lys Gly Thr
65                  70                  75                  80

Ser Asn Val Glu Gly Val Val Thr Leu Thr Gln Glu Asp Asp Gly Pro
                85                  90                  95

Thr Thr Val Asn Arg Val Ile Ser Gly Leu Ala Pro Gly Lys His Gly
                100                 105                 110

Phe His Leu His Glu Phe Gly Thr Thr Asn Gly Cys Met Ser Thr Gly
            115                 120                 125

Pro His Phe Asn Pro Asp Lys Lys Thr His Gly Ala Pro Glu Asp Glu
        130                 135                 140

Val Arg His Ala Gly Asp Leu Gly Asn Ile Val Ala Asn Thr Asp Gly
145                 150                 155                 160

Val Ala Glu Ala Thr Ile Val Asp Asn Gln Ile Pro Leu Thr Gly Pro
```

```
                        165                 170                 175
Asn Ser Val Val Gly Arg Ala Leu Val Val His Glu Leu Glu Asp Asp
                    180                 185                 190

Leu Gly Lys Gly Gly His Glu Leu Ser Pro Thr Thr Gly Asn Ala Gly
        195                 200                 205

Gly Arg Leu Ala Cys Gly Val Val Gly Leu Thr Pro Val
    210                 215                 220

<210> SEQ ID NO 199
<211> LENGTH: 150
<212> TYPE: PRT
<213> ORGANISM: Xenopus laevis

<400> SEQUENCE: 199

Val Lys Ala Val Cys Val Leu Ala Gly Ser Gly Asp Val Lys Gly Val
  1               5                  10                  15

Val Arg Phe Glu Gln Gln Asp Asp Gly Asp Val Thr Val Glu Gly Lys
                 20                  25                  30

Ile Glu Gly Leu Thr Asp Gly Asn His Gly Phe His Ile His Val Phe
             35                  40                  45

Gly Asp Asn Thr Asn Gly Cys Leu Ser Ala Gly Pro His Phe Asn Pro
     50                   55                  60

Gln Asn Lys Asn His Gly Ser Pro Lys Asp Ala Asp Arg His Val Gly
 65                  70                  75                  80

Asp Leu Gly Asn Val Thr Ala Glu Gly Gly Val Ala Gln Phe Lys Phe
                 85                  90                  95

Thr Asp Pro Gln Ile Ser Leu Lys Gly Glu Arg Ser Ile Ile Gly Arg
            100                 105                 110

Thr Ala Val Val His Glu Lys Gln Asp Asp Leu Gly Lys Gly Gly Asp
            115                 120                 125

Asp Glu Ser Leu Lys Thr Gly Asn Ala Gly Gly Arg Leu Ala Cys Gly
        130                 135                 140

Val Ile Gly Phe Cys Pro
145                 150

<210> SEQ ID NO 200
<211> LENGTH: 149
<212> TYPE: PRT
<213> ORGANISM: Xenopus laevis

<400> SEQUENCE: 200

Val Lys Ala Val Cys Val Leu Ala Gly Ser Gly Asp Val Lys Gly Val
  1               5                  10                  15

His Phe Glu Gln Gln Asp Glu Gly Ala Val Ser Val Glu Gly Lys Ile
                 20                  25                  30

Glu Gly Leu Thr Asp Gly Leu His Gly Phe His Ile His Val Phe Gly
             35                  40                  45

Asp Asn Thr Asn Gly Cys Met Ser Ala Gly Pro His Phe Asn Pro Glu
     50                   55                  60

Asn Lys Asn His Gly Ala Pro Gly Asp Thr Asp Arg His Val Gly Asp
 65                  70                  75                  80

Leu Gly Asn Val Thr Ala Glu Gly Gly Val Ala Gln Phe Lys Ile Thr
                 85                  90                  95

Asp Ser Leu Ile Ser Leu Lys Gly Pro Asn Ser Ile Ile Gly Arg Thr
            100                 105                 110

Ala Val Val His Glu Lys Ala Asp Asp Leu Gly Lys Gly Gly Asn Asp
```

```
                    115                 120                 125
Glu Ser Leu Lys Thr Gly Asn Ala Gly Gly Arg Leu Ala Cys Gly Val
    130                 135                 140

Ile Gly Tyr Ser Pro
145

<210> SEQ ID NO 201
<211> LENGTH: 153
<212> TYPE: PRT
<213> ORGANISM: Mus sp.

<400> SEQUENCE: 201

Ala Met Lys Ala Val Cys Val Leu Lys Gly Asp Gly Pro Val Gln Gly
  1               5                  10                  15

Thr Ile His Phe Glu Gln Lys Ala Ser Gly Glu Pro Val Val Leu Ser
             20                  25                  30

Gly Gln Ile Thr Gly Leu Thr Glu Gly Gln His Gly Phe His Val His
         35                  40                  45

Gln Tyr Gly Asp Asn Thr Gln Gly Cys Thr Ser Ala Gly Pro His Phe
     50                  55                  60

Asn Pro His Ser Lys Lys His Gly Gly Pro Ala Asp Glu Glu Arg His
 65                  70                  75                  80

Val Gly Asp Leu Gly Asn Val Thr Ala Gly Lys Asp Gly Val Ala Asn
                 85                  90                  95

Val Ser Thr Glu Asp Arg Val Ile Ser Leu Ser Gly Glu His Ser Ile
            100                 105                 110

Ile Gly Arg Thr Met Val Val His Glu Lys Gln Asp Asp Leu Gly Lys
        115                 120                 125

Gly Gly Asn Glu Glu Ser Thr Lys Thr Gly Asn Ala Gly Ser Arg Leu
    130                 135                 140

Ala Cys Gly Val Ile Gly Ile Ala Gln
145                 150

<210> SEQ ID NO 202
<211> LENGTH: 153
<212> TYPE: PRT
<213> ORGANISM: rat

<400> SEQUENCE: 202

Ala Met Lys Ala Val Cys Val Leu Lys Gly Asp Gly Pro Val Gln Gly
  1               5                  10                  15

Val Ile His Phe Glu Gln Lys Ala Ser Gly Glu Pro Val Val Val Ser
             20                  25                  30

Gly Gln Ile Thr Gly Leu Thr Glu Gly Glu His Gly Phe His Val His
         35                  40                  45

Gln Tyr Gly Asp Asn Thr Gln Gly Cys Thr Thr Ala Gly Pro His Phe
     50                  55                  60

Asn Pro His Ser Lys Lys His Gly Gly Pro Ala Asp Glu Glu Arg His
 65                  70                  75                  80

Val Gly Asp Leu Gly Asn Val Ala Ala Gly Lys Asp Gly Val Ala Asn
                 85                  90                  95

Val Ser Ile Glu Asp Arg Val Ile Ser Leu Ser Gly Glu His Ser Ile
            100                 105                 110

Ile Gly Arg Thr Met Val Val His Glu Lys Gln Asp Asp Leu Gly Lys
        115                 120                 125

Gly Gly Asn Glu Glu Ser Thr Lys Thr Gly Asn Ala Gly Ser Arg Leu
```

```
                130             135             140
Ala Cys Gly Val Ile Gly Ile Ala Gln
145                 150
```

<210> SEQ ID NO 203
<211> LENGTH: 152
<212> TYPE: PRT
<213> ORGANISM: guineapig

<400> SEQUENCE: 203

```
Ala Thr Lys Ala Val Cys Val Leu Lys Gly Asp Gly Pro Val Gln Gly
  1               5                  10                  15

Ile Ile His Phe Glu Gln Lys Ala Asn Gly Pro Val Val Lys Gly
                 20                  25                  30

Arg Ile Thr Gly Leu Val Glu Gly Lys His Gly Phe His Val His Glu
             35                  40                  45

Phe Gly Asp Asn Thr Gln Gly Cys Thr Ser Ala Gly Pro His Phe Asn
         50                  55                  60

Pro Leu Ser Lys Lys His Gly Pro Gln Asp Glu Glu Arg His Val
 65                  70                  75                  80

Gly Asp Leu Gly Asn Val Thr Ala Gly Ala Asp Gly Val Ala Asn Val
                 85                  90                  95

Ser Ile Glu Asp Ser Ile Leu Ser Leu Ser Gly Ala Asn Ser Ile Ile
                100                 105                 110

Gly Arg Thr Met Val Val His Glu Lys Pro Asp Asp Leu Gly Lys Gly
            115                 120                 125

Gly Asn Glu Glu Ser Thr Lys Thr Gly Asn Ala Gly Ser Arg Leu Ala
        130                 135                 140

Cys Gly Val Ile Gly Ile Ala Gln
145                 150
```

<210> SEQ ID NO 204
<211> LENGTH: 153
<212> TYPE: PRT
<213> ORGANISM: Homo sapiens

<400> SEQUENCE: 204

```
Ala Thr Lys Ala Val Cys Val Leu Lys Gly Asp Gly Pro Val Gln Gly
  1               5                  10                  15

Ile Ile Asn Phe Glu Gln Lys Glu Ser Asn Gly Pro Val Lys Val Trp
                 20                  25                  30

Gly Ser Ile Lys Gly Leu Thr Glu Gly Leu His Gly Phe His Val His
             35                  40                  45

Glu Phe Gly Asp Asn Thr Ala Gly Cys Thr Ser Ala Gly Pro His Phe
         50                  55                  60

Asn Pro Leu Ser Arg Lys His Gly Gly Pro Lys Asp Glu Glu Arg His
 65                  70                  75                  80

Val Gly Asp Leu Gly Asn Val Thr Ala Asp Lys Asp Gly Val Ala Asp
                 85                  90                  95

Val Ser Ile Glu Asp Ser Val Ile Ser Leu Ser Gly Asp His Cys Ile
                100                 105                 110

Ile Gly Arg Thr Leu Val Val His Glu Lys Ala Asp Asp Leu Gly Lys
            115                 120                 125

Gly Gly Asn Glu Glu Ser Thr Lys Thr Gly Asn Ala Gly Ser Arg Leu
        130                 135                 140

Ala Cys Gly Val Ile Gly Ile Ala Gln
```

```
145                 150

<210> SEQ ID NO 205
<211> LENGTH: 151
<212> TYPE: PRT
<213> ORGANISM: bovine

<400> SEQUENCE: 205

Ala Thr Lys Ala Val Cys Val Leu Lys Gly Asp Gly Pro Val Gln Gly
 1               5                  10                  15

Thr Ile His Phe Glu Ala Lys Gly Asp Thr Val Val Thr Gly Ser
            20                  25                  30

Ile Thr Gly Leu Thr Glu Gly Asp His Gly Phe His Val His Gln Phe
        35                  40                  45

Gly Asp Asn Thr Gln Gly Cys Thr Ser Ala Gly Pro His Phe Asn Pro
    50                  55                  60

Leu Ser Lys Lys His Gly Gly Pro Lys Asp Glu Glu Arg His Val Gly
65                  70                  75                  80

Asp Leu Gly Asn Val Thr Ala Asp Lys Asn Gly Val Ala Ile Val Asp
                85                  90                  95

Ile Val Asp Pro Leu Ile Ser Leu Ser Gly Glu Tyr Ser Ile Ile Gly
            100                 105                 110

Arg Thr Met Val Val His Glu Lys Pro Asp Asp Leu Gly Arg Gly Gly
        115                 120                 125

Asn Glu Glu Ser Thr Lys Thr Gly Asn Ala Gly Ser Arg Leu Ala Cys
    130                 135                 140

Gly Val Ile Gly Ile Ala Lys
145                 150

<210> SEQ ID NO 206
<211> LENGTH: 152
<212> TYPE: PRT
<213> ORGANISM: Sus sp.

<400> SEQUENCE: 206

Ala Thr Lys Ala Val Cys Val Leu Lys Gly Asp Gly Pro Val Gln Gly
 1               5                  10                  15

Thr Ile Tyr Phe Glu Leu Lys Gly Glu Lys Thr Val Leu Val Thr Gly
            20                  25                  30

Thr Ile Lys Gly Leu Ala Glu Gly Asp His Gly Phe His Val His Gln
        35                  40                  45

Phe Gly Asp Asn Thr Gln Gly Cys Thr Ser Ala Gly Pro His Phe Asn
    50                  55                  60

Pro Glu Ser Lys Lys His Gly Gly Pro Lys Asp Gln Glu Arg His Val
65                  70                  75                  80

Gly Asp Leu Gly Asn Val Thr Ala Gly Lys Asp Gly Val Ala Thr Val
                85                  90                  95

Tyr Ile Glu Asp Ser Val Ile Ala Leu Ser Gly Asp His Ser Ile Ile
            100                 105                 110

Gly Arg Thr Met Val Val His Glu Lys Pro Asp Asp Leu Gly Arg Gly
        115                 120                 125

Gly Asn Glu Glu Ser Thr Lys Thr Gly Asn Ala Gly Ser Arg Leu Ala
    130                 135                 140

Cys Gly Val Ile Gly Ile Thr Gln
145                 150
```

```
<210> SEQ ID NO 207
<211> LENGTH: 153
<212> TYPE: PRT
<213> ORGANISM: horse

<400> SEQUENCE: 207
```

| | | | | | | | | | | | | | | |
|---|---|---|---|---|---|---|---|---|---|---|---|---|---|---|
| Ala | Leu | Lys | Ala | Val | Cys | Val | Leu | Lys | Gly | Asp | Gly | Pro | His | Gly |
| 1 | | | | 5 | | | | | 10 | | | | | 15 |
| Val | Ile | His | Phe | Glu | Gln | Gln | Gln | Glu | Gly | Pro | Val | Val | Leu | Lys |
| | | | | 20 | | | | | 25 | | | | | 30 |
| Gly | Phe | Ile | Glu | Gly | Leu | Thr | Lys | Gly | Asp | His | Gly | Phe | His | Val | His |
| | | | | 35 | | | | | 40 | | | | | 45 |
| Glu | Phe | Gly | Asp | Asn | Thr | Gln | Gly | Cys | Thr | Thr | Ala | Gly | Ala | His | Phe |
| | | | | 50 | | | | | 55 | | | | | 60 |
| Asn | Pro | Leu | Ser | Lys | Lys | His | Gly | Gly | Pro | Lys | Asp | Glu | Glu | Arg | His |
| 65 | | | | | 70 | | | | | 75 | | | | | 80 |
| Val | Gly | Asp | Leu | Gly | Asn | Val | Thr | Ala | Asp | Glu | Asn | Gly | Lys | Ala | Asp |
| | | | | 85 | | | | | 90 | | | | | 95 |
| Val | Asp | Met | Lys | Asp | Ser | Val | Ile | Ser | Leu | Ser | Gly | Lys | His | Ser | Ile |
| | | | | 100 | | | | | 105 | | | | | 110 |
| Ile | Gly | Arg | Thr | Met | Val | Val | His | Glu | Lys | Gln | Asp | Asp | Leu | Gly | Lys |
| | | | | 115 | | | | | 120 | | | | | 125 |
| Gly | Gly | Asn | Glu | Glu | Ser | Thr | Lys | Thr | Gly | Asn | Ala | Gly | Ser | Arg | Leu |
| | | | | 130 | | | | | 135 | | | | | 140 |
| Ala | Cys | Gly | Val | Ile | Gly | Ile | Ala | Pro |
| 145 | | | | | 150 |

```
<210> SEQ ID NO 208
<211> LENGTH: 152
<212> TYPE: PRT
<213> ORGANISM: blueshark

<400> SEQUENCE: 208
```

| | | | | | | | | | | | | | | |
|---|---|---|---|---|---|---|---|---|---|---|---|---|---|---|
| Met | Lys | Ala | Val | Cys | Val | Leu | Lys | Gly | Thr | Gly | Glu | Val | Thr | Gly | Thr |
| 1 | | | | 5 | | | | | 10 | | | | | 15 |
| Val | Leu | Phe | Glu | Gln | Ala | Ala | Asp | Gly | Pro | Val | Thr | Leu | Lys | Gly | Ser |
| | | | | 20 | | | | | 25 | | | | | 30 |
| Ile | Thr | Gly | Leu | Thr | Pro | Gly | Lys | His | Gly | Phe | His | Val | His | Ala | Phe |
| | | | | 35 | | | | | 40 | | | | | 45 |
| Gly | Asp | Asn | Thr | Asn | Gly | Cys | Ile | Ser | Ala | Gly | Pro | His | Tyr | Asn | Pro |
| | | | | 50 | | | | | 55 | | | | | 60 |
| Phe | Ser | Lys | Asn | His | Gly | Gly | Pro | Asp | Asp | Glu | Glu | Arg | His | Val | Gly |
| 65 | | | | | 70 | | | | | 75 | | | | | 80 |
| Asp | Leu | Gly | Asn | Val | Glu | Ala | Asn | Gly | Asn | Gly | Val | Ala | Glu | Phe | Glu |
| | | | | 85 | | | | | 90 | | | | | 95 |
| Ile | Lys | Asp | Arg | Gln | Leu | His | Leu | Ser | Gly | Glu | Arg | Ser | Ile | Ile | Gly |
| | | | | 100 | | | | | 105 | | | | | 110 |
| Arg | Thr | Leu | Val | Val | His | Glu | Lys | Glu | Asp | Asp | Leu | Gly | Lys | Gly | Gly |
| | | | | 115 | | | | | 120 | | | | | 125 |
| Asp | Glu | Glu | Ser | Leu | Arg | Thr | Gly | Asn | Ala | Gly | Ser | Arg | Leu | Ala | Cys |
| | | | | 130 | | | | | 135 | | | | | 140 |
| Gly | Val | Ile | Gly | Ile | Ala | Lys | Asp |
| 145 | | | | | 150 |

```
<210> SEQ ID NO 209
<211> LENGTH: 166
```

-continued

```
<212> TYPE: PRT
<213> ORGANISM: loggerhead

<400> SEQUENCE: 209

Ala Thr Val Lys Ala Val Cys Val Leu Lys Gly Glu Asp Pro Val Lys
 1               5                  10                  15

Glu Pro Val Lys Gly Pro Val Lys Glu Pro Val Lys Gly Ile Ile Tyr
                20                  25                  30

Phe Glu Gln Gln Gly Asn Gly Pro Val Thr Leu Ser Gly Ser Ile Thr
            35                  40                  45

Gly Leu Thr Glu Gly Lys His Gly Phe His Val Glu Phe Gly Asp
         50                  55                  60

Asn Thr Asn Gly Cys Thr Ser Ala Gly Ala His Phe Asn Pro Pro Gly
 65                  70                  75                  80

Lys Asn His Gly Gly Pro Gln Asp Asn Glu Arg His Val Gly Asp Leu
                 85                  90                  95

Gly Asn Val Ile Ala Asn Lys Glu Gly Val Ala Glu Val Cys Ile Lys
                100                 105                 110

Asp Ser Leu Ile Ser Leu Thr Gly Ser Gln Ser Ile Ile Gly Arg Thr
            115                 120                 125

Met Val Val His Glu Lys Glu Asp Leu Gly Lys Gly Gly Asn Asp
        130                 135                 140

Glu Ser Leu Lys Thr Gly Asn Ala Gly Ser Arg Leu Ala Cys Gly Val
145                 150                 155                 160

Val Gly Ile Ala Lys Leu
                165

<210> SEQ ID NO 210
<211> LENGTH: 151
<212> TYPE: PRT
<213> ORGANISM: Drosophila melanogaster

<400> SEQUENCE: 210

Val Val Lys Ala Val Cys Val Ile Asn Gly Asp Ala Lys Gly Thr Val
 1               5                  10                  15

Phe Phe Glu Gln Glu Ser Ser Gly Thr Pro Val Lys Val Ser Gly Glu
                20                  25                  30

Val Cys Gly Leu Ala Lys Gly Leu His Gly Phe His Val His Glu Phe
            35                  40                  45

Gly Asp Asn Thr Asn Gly Cys Met Ser Ser Gly Pro His Phe Pro Tyr
         50                  55                  60

Gly Lys Glu His Gly Ala Pro Val Asp Glu Asn Arg His Leu Gly Asp
 65                  70                  75                  80

Leu Gly Asn Ile Glu Ala Thr Gly Asp Cys Pro Thr Lys Val Asn Ile
                 85                  90                  95

Thr Asp Ser Lys Ile Thr Leu Phe Gly Ala Asp Ser Ile Ile Gly Arg
                100                 105                 110

Thr Val Val Val His Ala Asp Ala Asp Asp Leu Gly Gln Gly Gly His
            115                 120                 125

Glu Leu Ser Lys Ser Thr Gly Asn Ala Gly Ala Arg Ile Gly Cys Gly
        130                 135                 140

Val Ile Gly Ile Ala Lys Val
145                 150

<210> SEQ ID NO 211
<211> LENGTH: 154
```

```
<212> TYPE: PRT
<213> ORGANISM: Saccharomyces cerevisiae

<400> SEQUENCE: 211

Met Val Gln Ala Val Ala Val Leu Lys Gly Asp Ala Gly Val Ser Gly
 1               5                  10                  15

Val Val Lys Phe Glu Gln Ala Ser Glu Ser Glu Pro Thr Thr Val Ser
                20                  25                  30

Tyr Glu Ile Ala Gly Asn Ser Pro Asn Ala Glu Arg Gly Phe His Ile
            35                  40                  45

His Glu Phe Gly Asp Ala Thr Asn Gly Cys Val Ser Ala Gly Pro His
        50                  55                  60

Phe Asn Pro Phe Lys Lys Thr His Gly Ala Pro Thr Asp Glu Val Arg
 65                  70                  75                  80

His Val Gly Asp Met Gly Asn Val Lys Thr Asp Glu Asn Gly Val Ala
                85                  90                  95

Lys Gly Ser Phe Lys Asp Ser Leu Ile Lys Leu Ile Gly Pro Thr Ser
               100                 105                 110

Val Val Gly Arg Ser Val Val Ile His Ala Gly Gln Asp Asp Leu Gly
            115                 120                 125

Lys Gly Asp Thr Glu Glu Ser Leu Lys Thr Gly Asn Ala Gly Pro Arg
        130                 135                 140

Pro Ala Cys Gly Val Ile Gly Leu Thr Asn
145                 150

<210> SEQ ID NO 212
<211> LENGTH: 151
<212> TYPE: PRT
<213> ORGANISM: baculovirus

<400> SEQUENCE: 212

Met Lys Ala Ile Cys Ile Ile Ser Gly Asp Val His Gly Lys Ile Tyr
 1               5                  10                  15

Phe Gln Gln Glu Ser Ala Asn Gln Pro Leu Lys Ile Ser Gly Tyr Leu
                20                  25                  30

Leu Asn Leu Pro Arg Gly Leu His Gly Phe His Val His Glu Tyr Gly
            35                  40                  45

Asp Thr Ser Asn Gly Cys Thr Ser Ala Gly Glu His Phe Asn Pro Thr
        50                  55                  60

Asn Glu Asp His Gly Ala Pro Asp Ala Glu Ile Arg His Val Gly Asp
 65                  70                  75                  80

Leu Gly Asn Ile Lys Ser Ala Gly Tyr Asn Ser Leu Thr Glu Val Asn
                85                  90                  95

Met Met Asp Asn Val Met Ser Leu Tyr Gly Pro His Asn Ile Ile Gly
               100                 105                 110

Arg Ser Leu Val Val His Thr Asp Lys Asp Leu Gly Leu Thr Asp
            115                 120                 125

His Pro Leu Ser Lys Thr Thr Gly Asn Ser Gly Gly Arg Leu Gly Cys
        130                 135                 140

Gly Ile Ile Ala Ile Cys Lys
145                 150

<210> SEQ ID NO 213
<211> LENGTH: 184
<212> TYPE: PRT
<213> ORGANISM: bloodfluke
```

<400> SEQUENCE: 213

Met Thr Val Tyr Ser Tyr Leu Val Ile Leu Phe Ile Leu Leu Asp Asn
1               5                   10                  15

Tyr Cys Ser Ala Tyr Gly Tyr Gly Tyr Ser Tyr Tyr His Arg Arg His
            20                  25                  30

Phe Asp Pro Ala Ile Ala Ser Phe Thr Lys Glu Pro Tyr Ile Gly Ala
        35                  40                  45

Val Trp Phe Thr Gln His Gly Asp Tyr Met Tyr Val Asn Gly Ser Val
    50                  55                  60

Ala Gly Leu Pro Pro Gly Lys Leu Leu Gly Thr His Val His Arg Tyr
65                  70                  75                  80

Gly Gly Leu Gly Asn Met Cys Leu Glu Ala Gly Pro His Phe Asn Pro
                85                  90                  95

Phe Asn Gln Arg His Gly Pro Arg His Gly Tyr Pro Arg His Ala Gly
            100                 105                 110

Asp Leu Gly Asn Ile Arg Val Gly Arg Gly Val Ala Lys Phe Asp
        115                 120                 125

Phe Tyr Val Thr Ile Lys Gly Leu Ser Pro Phe Asp Gly Phe Ile Gly
    130                 135                 140

Arg Ala Leu Val Ile His Ala Asn Arg Asp Asp Leu Gly Arg Asn Arg
145                 150                 155                 160

Asp Glu Gly Ser Arg Thr Thr Gly Asn Ser Gly Pro Arg Leu Ala Cys
                165                 170                 175

Ala Thr Ile Gly Phe Arg Ala Pro
            180

<210> SEQ ID NO 214
<211> LENGTH: 125
<212> TYPE: PRT
<213> ORGANISM: Variola virus

<400> SEQUENCE: 214

Met Ala Val Cys Ile Ile Asp His Asp Asn Ile Arg Gly Val Ile Tyr
1               5                   10                  15

Phe Glu Pro Val His Gly Lys Asp Lys Val Leu Gly Ser Val Ile Gly
            20                  25                  30

Leu Lys Ser Gly Thr Tyr Asn Leu Ile Ile His Arg Tyr Gly Asp Ile
        35                  40                  45

Ser Arg Gly Cys Asn Ser Ile Gly Ser Pro Glu Ile Phe Ile Gly Asn
    50                  55                  60

Ile Phe Val Asn Arg Tyr Gly Val Ala Tyr Val Tyr Leu Asp Thr Asp
65                  70                  75                  80

Val Asn Ile Ser Thr Ile Ile Gly Lys Ala Leu Ser Ile Ser Lys Asn
                85                  90                  95

Asp Gln Arg Leu Ala Cys Gly Val Ile Gly Ile Ser Tyr Ile Asn Glu
            100                 105                 110

Lys Ile Ile His Phe Leu Thr Ile Asn Glu Asn Gly Val
        115                 120                 125

<210> SEQ ID NO 215
<211> LENGTH: 194
<212> TYPE: PRT
<213> ORGANISM: Homo sapiens

<400> SEQUENCE: 215

Met Gly Ser Leu Leu Pro Leu Gly Ser Cys Gly Lys Cys Arg Ser Pro

```
                1               5                  10                 15
Gly Glu Leu Ala Glu Gly Arg Leu Ser Ser Leu Val Phe Lys Gly Val
                    20                  25                  30

Gln Ala Leu Gly Leu Ser Pro Ser Ile Ser Tyr Ser Val Trp Pro Arg
            35                  40                  45

Phe Pro Glu Ala Leu Ser Ile Leu Arg Arg Asp Gly Pro Ser Arg Cys
        50                  55                  60

Pro Pro Gly Ala Arg Thr His Cys Ser Ser Val Thr Gln Glu Asn
65                      70                  75                  80

Glu Ala Pro Ser Cys Gly Asp Ser Ser Glu Trp Trp Ser Pro Gln Ser
                    85                  90                  95

Leu Pro Glu Arg His Gly Phe His Glu His Ser Gly Cys Phe Gly Asp
                100                 105                 110

Ser Asn His Phe His Pro Gln Asn Gln Thr His Ser Cys Ser Asn Gly
                115                 120                 125

Val Ile Ala Lys Ala Ala Ser Leu Val Arg Leu Lys Gly His Gly Ser
        130                 135                 140

Pro Ser Asp Glu Arg Gly Arg Met Glu Gln Ser Gly Glu Ile Leu Phe
145                 150                 155                 160

Pro Val Gly Asn Trp Ala Ser Leu Trp Pro Cys Thr Ser Gln Glu Ala
                165                 170                 175

Asp Arg Thr Glu Thr Ser Gly Ala Cys Pro Gln Phe Thr Ser Thr Ser
                180                 185                 190

Leu Glu

<210> SEQ ID NO 216
<211> LENGTH: 194
<212> TYPE: PRT
<213> ORGANISM: Homo sapiens
<220> FEATURE:
<221> NAME/KEY: VARIANT
<222> LOCATION: (1)..(194)
<223> OTHER INFORMATION: X is selenocysteine.

<400> SEQUENCE: 216

Met Gly Ser Leu Leu Pro Leu Gly Ser Cys Gly Lys Xaa Arg Ser Pro
1               5                   10                  15

Gly Glu Leu Ala Glu Gly Arg Leu Ser Ser Leu Val Phe Lys Gly Val
                    20                  25                  30

Gln Ala Leu Gly Leu Ser Pro Ser Ile Ser Tyr Ser Val Trp Pro Arg
            35                  40                  45

Phe Pro Phe Ala Leu Ser Ile Leu Arg Arg Asp Gly Pro Ser Arg Cys
        50                  55                  60

Pro Pro Gly Ala Arg Thr His Cys Ser Ser Val Thr Gln Glu Asn
65                      70                  75                  80

Glu Ala Pro Ser Cys Gly Asp Ser Ser Glu Trp Trp Ser Pro Gln Ser
                    85                  90                  95

Leu Pro Glu Arg His Gly Phe His Glu His Ser Gly Cys Phe Gly Asp
                100                 105                 110

Ser Asn His Phe His Pro Gln Asn Gln Thr His Ser Cys Ser Asn Gly
                115                 120                 125

Val Ile Ala Lys Ala Ala Ser Leu Val Arg Leu Lys Gly His Gly Ser
        130                 135                 140

Pro Ser Asp Glu Arg Gly Arg Met Glu Gln Ser Gly Glu Ile Leu Phe
145                 150                 155                 160
```

```
                                 -continued

Pro Val Gly Asn Trp Ala Ser Leu Trp Pro Xaa Thr Ser Gln Glu Ala
                165                 170                 175

Asp Arg Thr Glu Thr Ser Gly Ala Xaa Pro Gln Phe Thr Ser Thr Ser
            180                 185                 190

Leu Glu
```

SELENOPROTEINS, CODING SEQUENCES AND METHODS

CROSS REFERENCE TO RELATED APPLICATIONS

This application is a Continuation-in-Part of U.S. Provisional Application Ser. No. 60/001,203, filed Jul. 14, 1995, and U.S. Provisional Application Ser. No. 60/003,112, filed Sep. 1, 1995, both abandoned and both of which are incorporated by reference in their entirety herein.

GOVERNMENT RIGHTS

This invention was made, at least in part, with funding from the U.S. Public Health Service Grant AI-30392 from the National Institute of Allergy and Infectious Diseases. Accordingly, the United States Government has certain rights in this invention.

FIELD OF THE INVENTION

The field of this invention is in the area of molecular biology, in particular, the area of coding sequences, nucleic acid secondary structure and gene expression and its regulation, and more specifically, with reference to proteins containing selenocysteine, sequences encoding proteins containing selenocysteine, and methods for identifying coding sequences for selenocysteine-containing proteins.

BACKGROUND OF THE INVENTION

Selenium (Se) is an essential micronutrient that is now known to be incorporated as selenocysteine in a number of selenoproteins, glutathione peroxidase (GPx) being the prototypical example. Selenocysteine is specifically encoded by the UGA codon, and inserted in peptide chains by a cotranslational mechanism that is able to override the normal function of UGA as a termination codon. In eukaryotes, efficient selenocysteine incorporation at UGA codons requires a cellular protein factor and a cis-acting structural signal usually located in the mRNA 3'-untranslated region (3'-UTR), consisting of a selenocysteine insertion sequence (SECIS) in a characteristic stem-loop structure [23,24]. The required protein factor is presumed to be present in certain cells types that express selenoproteins, such as liver cells, lymphocytes, macrophages, thrombocytes, and other blood cells. In such cell types, the presence of a SECIS element in an mRNA is necessary and sufficient for in-frame UGA codons to be translated as selenocysteine.

Dietary Se is critical for proper immune function, and a number of immunomodulatory effects of Se have been documented [Turner and Finch (1991) Proc. Nutr. Soc. 50, 275–285]. Se supplementation increases immunoglobin G synthesis, increased chemotactic responses in neutrophils, and enhancement of both T cell cytotoxicity and proliferation in response to mitogens and antigens [Dhur et al. Comp. Biochem. Physiol. C. 96, 271–280 (1990), 28, 5, 29, 6 and 7]. Impairment of these immune functions can include reduced T cell counts, including reduced CD4+ T cell counts [4, 7, 16], and impaired lymphocyte proliferation and responsiveness [Dhur (1990) supra, Roy et al. Proc. Soc. Exp. Biol. Med. 193, 143–148 (1990); 3–7]. These immunological effects are in addition to various specific disorders that have been associated with Se deficiency [8]. There is a progressive decline in plasma Se and Glutathione peroxidase in ARC and AIDS patients [9–17]. This decline approximately parallels T cell loss or stage of HIV infection, but seems to be particularly noticeable in the terminal stages of AIDS, where Se deficiency is one of the symptoms of the disease.

Over half of plasma Se is in the form of selenoprotein P; its mRNA has 10 UGA selenocysteine (SeC) codons, mostly concentrated in the C-terminal 125 amino acids. It has been suggested to serve as an antioxidant, a Se transport/storage protein, and it attaches to various cell types via a specific receptor. Another mammalian selenoprotein is the type I 5'-iodothyronine deiodinase involved in conversion of T4 thyroid hormone to T3. Se is critical in mammals, including humans, for the maintenance of glutathione-dependent antioxidant status and thyroid T3 hormone levels.

Viruses, and to a lesser extent bacteria, are under a powerful constraint to maximize the information content of their genomes. Some microorganisms have evolved mechanisms to maximize the number of genes and amount of protein coding information in a given length of nucleic acid. For example, by placing overlapping genes in different reading frames of the same nucleotide sequence, coding density can be increased. Another maximization mechanism exploits RNA splicing, a characteristic feature of eukaryotic genes, and possibly a trick that viruses incorporated from their hosts. Alternative RNA splicing allows the modular construction of different proteins containing a common module, avoiding duplication of precious genetic material.

Ribosomal frameshifting can result in the same sort of modular construction, for example in a −1 frameshift, by placing alternate 3' "exons" (modules) in two different reading frames of the same oligonucleotide; when expressed, each is attached to a common module encoded in the 5'-region of the zero reading frame. Multiple frameshift mechanisms, although likely of very low probability, can result in other kinds of modular constructs.

Both overlapping genes and RNA splicing also present new opportunities for various forms of genetic regulation, beyond that attainable by transcriptional regulation alone. The regulation of RNA splicing, along with cotranslational mechanisms like frameshifting and termination suppression enable a more sophisticated yet economical control over the expression of a greater variety of gene products than that attainable with a simple linear arrangement of non-overlapping genes. Retroviruses, for example, utilize a number of elaborate transcriptional and translational control mechanisms in order to influence not only the timing of gene expression, but also to precisely balance the relative quantities of their various gene products. The latter is necessary because structural proteins (products of the retroviral gag and env genes) are needed in much greater quantity than the products of the pol gene, which encodes the viral enzymes protease, reverse transcriptase (RT), and integrase.

Understanding the mechanisms of gene regulation and the extent to which higher organisms, viruses and microorganisms use them, is important in understanding the mechanisms of infectious disease, especially those mechanisms associated with viral and retroviral agents, and those mechanisms associated with the regulation of gene expression in other organisms, including mammals, especially with respect to cancer. The present methods have broad utility in understanding gene regulation, thereby allowing control over gene expression by exploiting the control mechanisms via genetic engineering and/or gene therapy.

SUMMARY OF THE INVENTION

A general method for finding and isolating potential new coding sequences is provided. The method involves an analysis of RNA structure in relation to potential novel open reading frames (ORFs), including those containing UGA codons, the most leaky termination codon. Viral genomic or mRNA, as well as mammalian coding sequences, can be analyzed. UGA termination can be suppressed either by opal suppressor tRNAs (readthrough suppression) with insertion of a conventional amino acid, or by insertion of selenocysteine, under the cotranslational control of specialized RNA structural elements. This analysis reveals locations of potential frameshift sites, and thus novel coding sequences, genes or gene variants, encoded in ORFs that could not otherwise be expressed, because they lack initiation codons. Alternatively, translational readthrough can result in the synthesis of proteins of unexpected sequences. In general, the information thus obtained can be employed to generate predicted amino acid sequences for proteins encoded by these potential ORFs and to prepare nucleic acid constructs to express these proteins in in vitro translation/ expression systems or in vivo in appropriately chosen genetically engineered organisms or cell lines. Application of this method has located a number of previously undetected ORFs that encode novel proteins, including selenoproteins as well as previously undetected ORFs which do not contain selenocysteine. The proteins encoded by the newly identified ORFs can then be examined by procedures well-known in the art for functional similarities to known proteins and tested for that functionality. This method is particularly useful in finding and isolating proteins and the ORFs encoding them which have regulatory function in their natural environment, for example, in the transcriptional or translational regulation of known genes and most particularly in the transcriptional or translational regulation of the known gene genes in which the ORF is located.

The present inventive method has been used to identify the location of a number of novel ORFs in retroviruses including HIV, and in picornaviruses, e.g., coxsackie virus B3, and a number of other RNA viruses as well as certain DNA viruses (See Table 2 for examples). The method has also been successfully applied to mammalian DNA, specifically human sequences, as well (See Table 3 and examples hereinbelow). Several of the proteins, including selenoproteins, encoded by these ORFs can function to regulate gene translation or transcription.

The present invention has allowed the identification and isolation of potential new coding sequences when applied to the analysis of mammalian gene sequences, particularly those from immune system cell genes and oncogenes. The method involves an analysis of the genomic RNA structure in relation to potential novel open reading frames (ORFs), including those containing UGA codons, the most leaky termination codon. Surprisingly, the Se selenoprotein ORFs have been found overlapping other coding sequences. UGA termination can be suppressed either by opal suppressor tRNAs (readthrough suppression) with insertion of a conventional amino acid, or by insertion of selenocysteine under the cotranslational control of specialized RNA structural elements. This analysis reveals locations of potential frameshift sites, and thus novel coding sequences, genes or gene variants, encoded in ORFs that could not otherwise be expressed, because they lack initiation codons. Alternatively, translational readthrough can result in the synthesis of proteins of unexpected sequences. In general, the information thus obtained can be employed to generate predicted amino acid sequences for proteins encoded by these ORFs and to prepare nucleic acid constructs to express these proteins in in vitro translation/expression systems or in vivo in appropriately chosen genetically engineered organisms or cell lines. Application of this method has located a number of previously undetected ORFs that encode novel proteins, including selenoproteins as well as previously undetected ORFs which do not contain selenocysteine. The proteins encoded by the newly identified ORFs are then examined by procedures well-known in the art for functional similarities to known proteins and tested for that functionality. This method is particularly useful in finding and isolating proteins and the ORFs encoding them which have regulatory functions in their natural environment, for example, in the transcriptional or translational regulation of known genes and most particularly in the transcriptional or translational regulation of a known gene in which the ORF is located. In particular, the present method has allowed the recognition of a number of novel ORFs in human T cell genes including those encoding CD4, CD8, IL2-Rα and IL2-Rβ and certain human oncogenes, including bcl.

Identification of the previously undetected open reading frames which encode selenoproteins according to the methods disclosed herein allows the medical or veterinary practitioner to identify disease states in which a patient (or affected animal) can be benefitted by the administration, preferably orally or parenterally, of selenium supplements. Those disease states include, but are not limited to those related to oncogenesis (cancer), certain viral infections, including HIV, hemorrhagic fever viruses including Ebola virus, and/or immunological dysfunction, where host selenium levels are depleted and physiological and immunological processes are negatively impacted.

The present invention also encompasses the cloning and expression, using molecular biological techniques, of the previously undetected open reading frames of the present invention. Once the methods of the present invention have revealed an open reading frame of interest, one of ordinary skill in the art can, without the expense of undue experimentation, generate recombinant DNA molecules suitable for introducing an expressible combination of transcriptional and translation control signal so that expression, independent of frameshift or readthrough suppression mechanisms, can be achieved in a mammalian or bacterial host cell. These techniques are useful for gene therapy; e.f. for introducing negative regulatory proteins of pathogenic viruses, T cells or oncogenesis so as to prevent, delay or ameliorate a disease state) or these molecular biological techniques can be applied to production of the encoded proteins for any purpose desired by the skilled artisan. Alternatively or in addition, antisense constructs, as well understood in the art, can be produced to inhibit production of previously unknown proteins which have deleterious effects in a host organism.

Further objects of the present invention are the coding sequences and the encoded protein and/or selenoprotein products of the open reading frames uncovered by the practice of the detection methods disclosed herein. Prsotein products of the ORFs identified herein can be prepared by cloning and expression methods well-known in the art or by the methods of peptide synthesis. These protein and/or selenoprotein products are useful in a variety of applications as is readily apparent to the ordinary skilled artisan, particularly as regulatory proteins which can up or down regulate gene expression or nucleic acid synthesis.

The protein products including fusion proteins and selenoproteins of the ORFs of this invention can also be employed to prepare antibodies, including protective antibodies. They can also be used, as will be appreciated by those of ordinary skill in the art, to isolate chemical compounds that inhibit their biological function.

BRIEF DESCRIPTION OF THE DRAWINGS

In FIG. 1A, each stem is visible as a pair of lines which are symmetrical with respect to the diagonal. The interpretation is shown in FIG. 1B. The diagram shows that there are only two 5 bp stems in this region of the HIV genome, and that they interlock to form a pseudoknot (PK), because the 3' stem projects from the loop region of the 5' stem (shown by dotted line). The same PK is shown more conventionally in FIG. 2B.

Figures 2A, 2B, 2C:
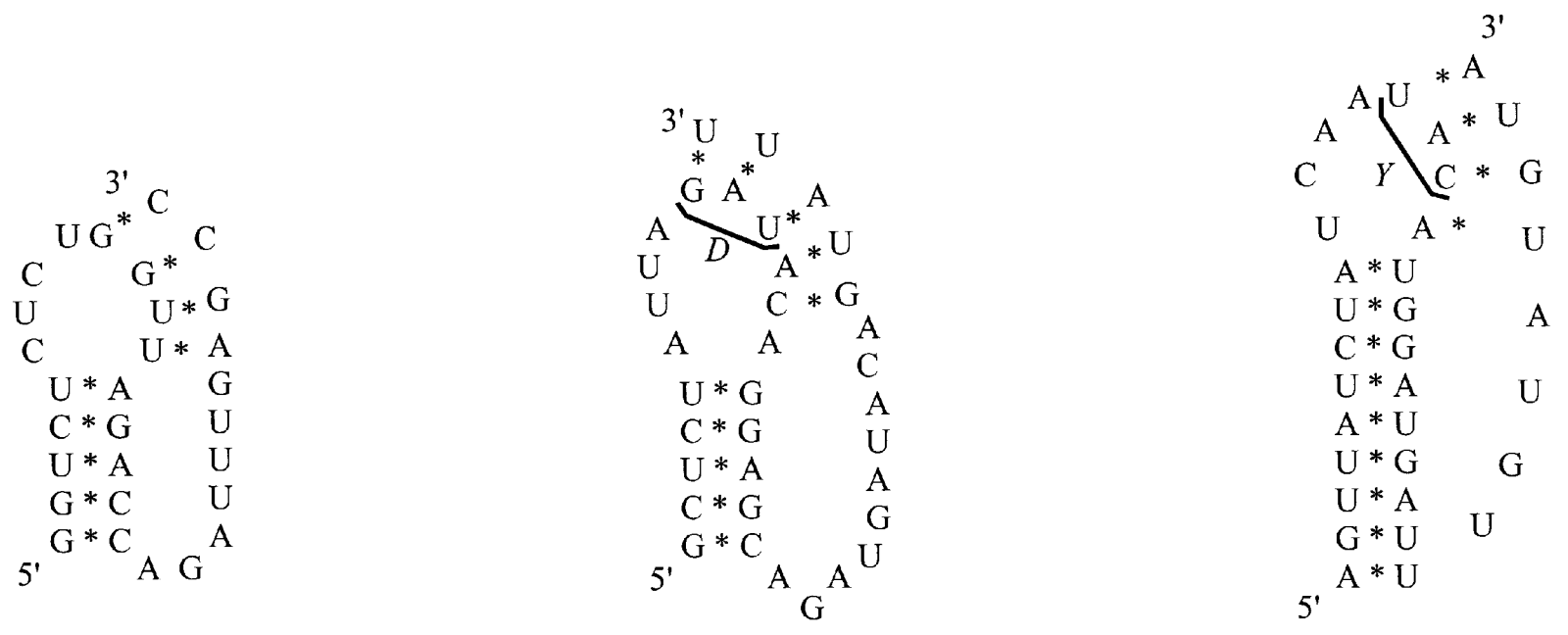

FIGS. 2A–2C show additional pseudoknots in HIV-1. FIG. 2A (SEQ ID NO:3) shows the PK in the TAR region of the long terminal repeat, containing an E2-like palindromic sequence (UGGUUAGACCA) (SEQ ID NO:2). FIG. 2B shows the PK in the protease coding region (SEQ ID NO:1), involving the codons for the DTG consensus sequence. The Asp codon is identified with a "D". FIG. 2C shows the PK in the RT coding region (SEQ ID NO:4), involving the codons for the YMDD (SEQ ID NO:5) consensus sequence; the Tyr codon is indicated with a "Y".

FIGS. 3A–3B show three newly identified PKs in the protease coding regions of HIV-1 (FIG. 3A) (SEQ ID NO:1) (FIG. 3B), CIV (chimpanzee immunodeficiency virus) (SEQ ID NO:6) and SIVsm (FIG. 3C) Simian immunodeficiency virus, (sooty mangabey) (SEQ ID NO:1), all of which are associated with the highly conserved encoded DTG encoded sequence of retroviral proteases. The D is the catalytic aspartate of these proteases.

FIGS. 5A–5C compare the RT YMDD (SEQ ID NO:5) PKs from several primate lentiviruses. The YMDD motif sequence begins at the UAC(Y) following the upper 5' loop. FIG. 5A is for HIV-1 variants (upper case) (SEQ ID NO:4) and SIV chimpanzee (CIV) (SEQ ID NO:9) with differences from HIV-1 shown in lower case; 6 of 9 mutated bases in CIV are on loop regions and the changes in helical regions are consistent with maintaining base pairing, except in the case of one broken base pair, which only shortens the 5' stem by one bp (UA to CA). FIG. 5B shows an alternative conformation of the CIV PK (SEQ ID NO:9), intermediate between the HIV-1 and HIV-2 structures (FIGS. 5A and 5C). FIG. 5C shows the YMDD PK for HIV-2 (SEQ ID NO:10), with base pairings shifted with respect to those seen in HIV-1 (FIG. 5A) although the structural theme is maintained.

(FIG. 10A) (SEQ ID NO:17) Coxsackievirus B5, 0.8 Kcal/mol from global minimum, so only 0.8 DS, p<0.25; (FIG. 10B) (SEQ ID NO:18) Visna retrovirus, 2.4 SD, p<0.01; (FIG. 10C) (SEQ ID NO:19) Polio type 1 Mahoney, 1.3 SD, p<0.2; (FIG. 10D) SEQ ID NO:21 equine infectious anemia virus, 2.9 SD, p<0.003; (FIG. 10E) Coxsackie B3, 4.25 SD, p<0.0001.

FIGS. 11A–11C show predicted PKs associated with non-UGA stop codons (boxed) where termination suppression is suspected, consistent with the demonstrated involvement of PKs in retroviral readthrough suppression. Similar to what has been reported for the type c retroviruses, all 3 of these PKs have a purine-rich consensus sequence (Pu—Pu—C—N—Pu) immediately following the stop codon. The possibility of a third stem region is indicated for A and B by lines connecting complementary bases, presumably these could not be formed at the same time as the 3' stem shown, so a conformational change could be involved. (FIG. 11A) SEQ ID NO:27 At the 3' end of the protease fusion protein, following an ochre stop codon translated as Q. (FIG. 11B) SEQ ID NO:28 At the 3' end of the integrase fusion protein, following an ochre stop codon translated as Q. (FIG. 11C) SEQ ID NO:29 At the 3' end of the RT fusion protein, involving an amber stop codon. This PK lacks the extreme 3' stem seen in the two PKs associated with ochre codons.

FIGS. 12A–12C show additional predicted PKs in HIV-1: the PK schematically shown containing the E2-like palindrome (UGGUUAGACCA) SEQ ID NO:2 in the repeat region of the LTR (FIG. 12A) SEQ ID NO:30; in the integrase region of pol, a PK predicted to direct integrase fusion protein synthesis (FIG. 12B) SEQ ID NO:31; in the env region, a PK predicted to direct synthesis of a gp120 fusion protein (FIG. 12C) SEQ ID NO:32.

FIG. 13 illustrates sequence similarity (26% identity in a 77 residue overlap) between the central portion of the 123 residue CD4 selenoprotein (CD4-SP) and a Cys-rich portion of the mouse mitochondrial capsule selenoprotein (MCSP) SEQ ID NO:33, which has a total of 197 residues. Potential SeC residues encoded by UGA codons are shown as C. UGA can alternatively serve as a codon for Cys, Arg or Trp. This is the unmodified alignment produced by using CD4-SP as a probe to search the PIR 42 (Protein Identification Resources Data Bank) sequence database using the FastA program, as implemented in the GCG program suite (Program Manual for the Wisconsin Package, Ver. 8, Genetics Computer Group, Madison, Wis.). The PAM 250 matrix and other default parameters were used, except the word size was set to 1 for greater sensitivity, and the /OPT parameter was used. This was the second highest ranked hit (significance=7.0 SD) out of over 70,000 protein sequences in the database. UGA encodes Trp in mitochondrial DNA; MCSP is not mitochondrially encoded.

Figure 1A:
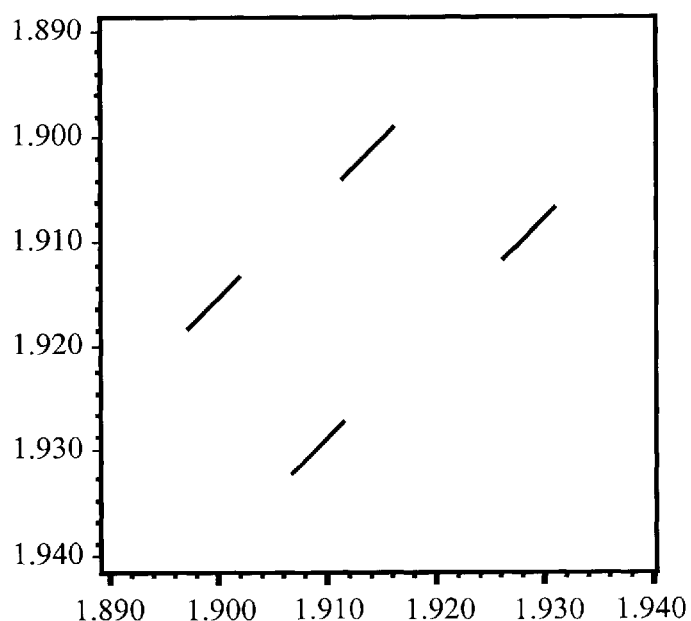
FIGS. 1A and 1B show two plots for detecting pseudoknots by dotplot analysis in the proposed HIV protease frameshift site (nucleotides 1890–1940) (SEQ ID NO:1).

FIGS. 14A–14C illustrate potential stem-loop structures displaying consensus selenocysteine insertion sequences (SECIS elements) found in the following mRNAs: FIG. 14A: CD4, bases 1017–1077 (SEQ ID NO:34) in GenBank #m35160. FIG. 14B: CD8, bases 647–706 (SEQ ID NO:35) in GenBank #m36712. FIG. 14C: HLA-DR invariant chain (p33), bases 544–662 (SEQ ID NO:36) in GenBank #m14765. The potential secondary structures of RNA regions containing the SECIS consensus features (AUG . . . AAA . . . UGR) were predicted using the FOLD program [Zuker & Steigler 1981 *Nucl. Acids Res.* 9:133–148] with updated energy parameters as implemented in the GCG software package.

FIG. 15 illustrates the −1 frameshift sequence in the CD8 beta gene (SEQ ID NO:37) (beginning at position 424 in GenBank #m36712), immediately followed by a potential pseudoknot. Codon-anticodon interactions of the P- and A-site tRNAs are shown schematically both before (below sequence) and after slippage (above sequence), emphasizing that 2 of 3 cognate base pairings would still be maintained after slippage. The mismatched pairs are still purine-pyrimidine in both cases (G:U and A:C). This frameshift site is located just before the beginning of the membrane proximal domain in CD8. A frameshift from the CD8-SP ORF into the main CD8 ORF at this point replaces the N-terminal CDS extracellular domain with a 34 residue selenoprotein module containing 3 selenocysteines. A similar shift site and a significantly larger potential pseudoknot are found beginning at position 535, corresponding precisely to the N-terminal of the transmembrane domain of CD8.

FIGS. 16A–16B illustrate SECIS elements in IL2 receptor subunit mRNAs. Both the IL2-R alpha and beta mRNAs contain consensus selenocysteine insertion sequences (SEQ ID NO:38), $AUG(N)_m AAA(N)_n UGR$, with the potential to form the stem-loop RNA structures characteristic of SECIS elements. FIG. 16A shows that in IL-2R alpha, the putative SECIS is in the 3'-UTR, the usual location in known cellular selenoprotein genes. The region shown is bases 441–480 (SEQ ID NO:39) in GenBank #x03138. The sequence context of the AAA on the loop is identical to that in the known SECIS element in the mammalian type II 5'-deiodinase gene (UAAAG). FIG. 16B shows that in IL-2R beta it is located in the IL-2R beta coding region, but in a location 3' to the major UGA-rich ORFs, relative to which it is a 3'-UTR. The region shown is bases 1475–1545 (SEQ ID NO:40) in GenBank #m26062.

FIG. 17 presents a comparison of the ideal Kozak sequence with the Kozak sequences of the IL2α selenoprotein and that of the IL2α "main" gene. "X" represents a purine:pyrimidine mismatch; ⊕ represents a purine:purine or pyrimidine:pyrimidine mismatch. The Kozak sequence of the IL2α-SP is predicted to occur by chance with a probability of less than $3 \times 10^{-5}$; the probability for chance occurrence of that of the IL2α gene itself is less than $3 \times 10^{-3}$. Thus, that associated with the selenoprotein is a closer match to the ideal and a better candidate than that of the main IL2α gene.

Figure 18A:
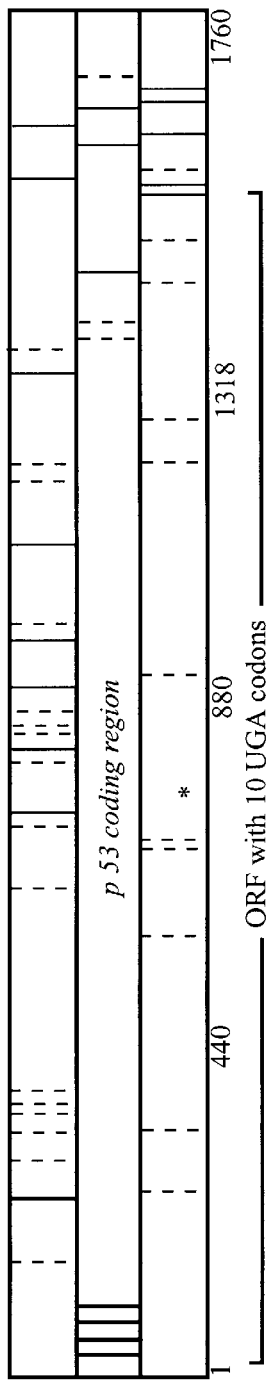
Figure 18B:
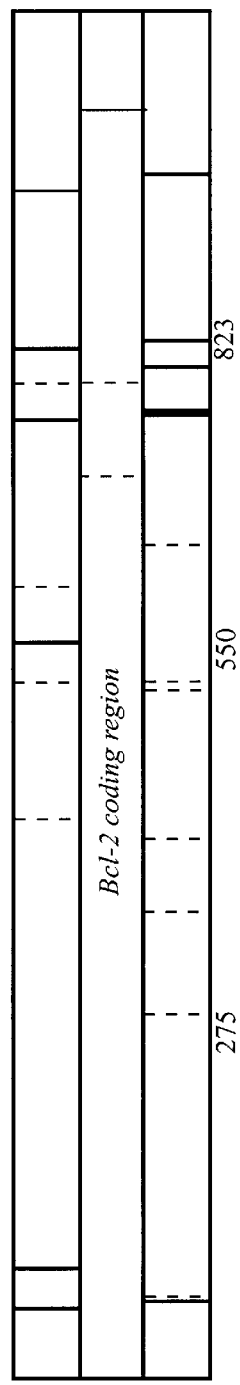
Figure 18C:
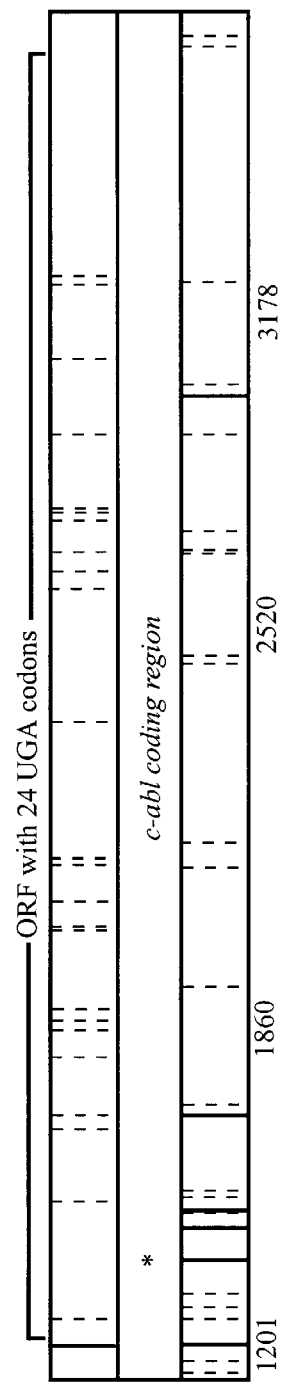

FIGS. 18A–18C illustrate three UGA-rich open reading frames overlapping known genes. All three reading frames of each gene are shown schematically, with UAA and UAG stop codons indicated as solid vertical lines, UGA codons as dashed vertical lines. Both p53 and Bcl-2 terminate in UGA codons, suggesting that small amounts of slightly extended proteins incorporating one or two SeC residues may also be formed as minor products. FIG. 18A gives the entire p53 mRNA, showing that the overlapping +1 ORF with 10 UGA codons (bottom panel) is actually larger than the p53 coding region. A potential frameshift site is shown (*); also see FIG. 15. FIG. 18B provides the 5' (coding) region of the Bcl-2 mRNA, showing an overlapping ORF about the same size as Bcl-2, with 8 UGA codons (bottom panel). FIG. 18C illustrates the C-terminal half of the c-abl coding region, with a huge overlapping ORF containing 24 UGA codons (top panel). A potential frameshift site is shown (*).

Figure 19A:
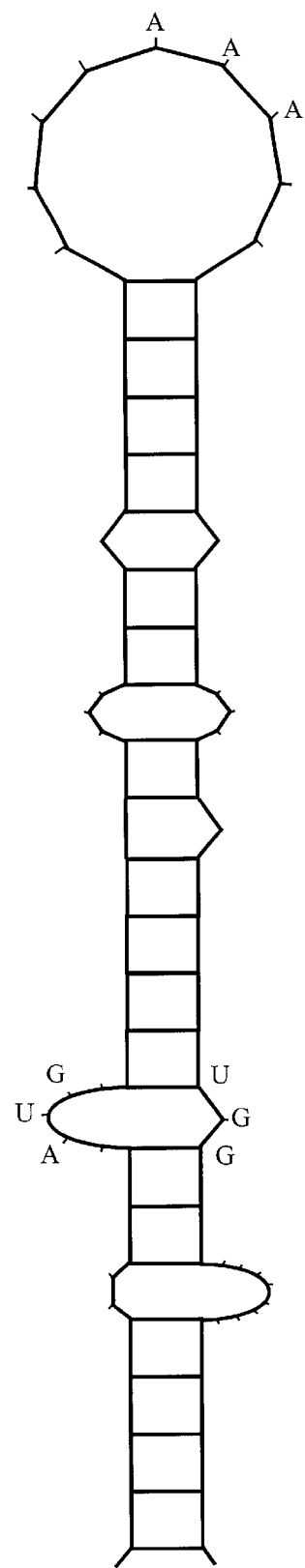
Figure 19B:
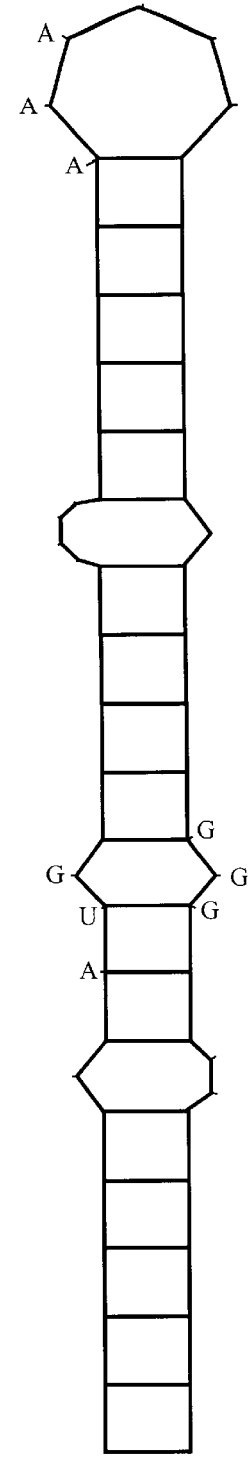

FIGS. 19A–19B illustrates RNA secondary structures predicted for selenocysteine insertion sequences (consensus AUG . . . AAA . . . UGR) in the Bcl-2 and p53 oncogene mRNAs. The characteristic stable stem-loop structures with appropriate spacing between the consensus features can be formed in both cases. The 3'-UTR sequence of c-abl is not available. FIG. 19A illustrates the SECIS element in the 3'-UTR of the Bcl-2 mRNA, bases 1833–1912 (SEQ ID NO:41) in GenBank #m14745; E=−12.9 kcal/mole. FIG. 19B illustrates the SECIS element in the 3'-UTR of the p53 mRNA, bases 1633–1689 (SEQ ID NO:42) in GenBank #K03199; E=−10.1 kcal/mole. In this case one of nine bases differs from the consensus (GGG instead of UGG in the 3' bulge). The Zuker FOLD program as implemented in the GCG software package was used for these calculations (Program Manual for the Wisconsin Package, Ver. Sep. 8, 1994, Genetics Computer Group, Madison, Wis.).

Figure 20:
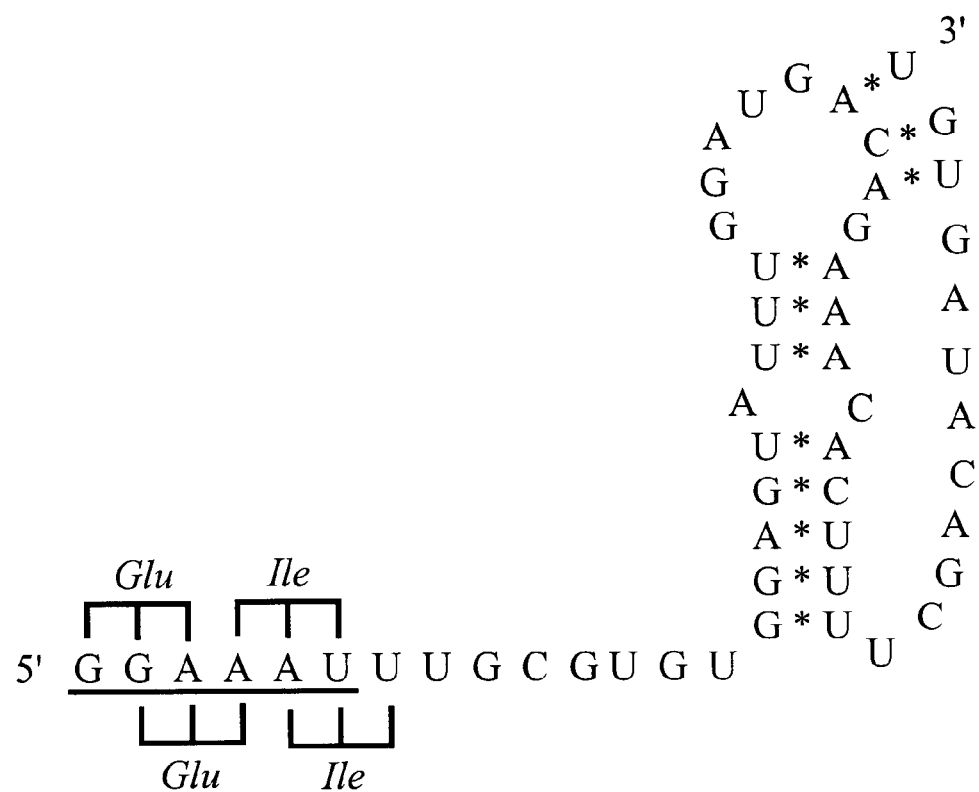

FIG. 20 illustrates the −1 frameshift site in the p53 mRNA, consisting of a near-ideal heptameric-slippery sequence (underlined) and potential RNA pseudoknot, involving bases 809–861 (SEQ ID NO:43) in GenBank #K03199 (p53). The approximate location of this site is indicated by an asterisk. Codon-anticodon interactions of the P- and A-site tRNAs are shown schematically both before (below sequence) and after slippage (above sequence); note that, as with an "ideal" heptamer, this sequence permits the retention of 2 out of 3 cognate base pairs after the shift. A frameshift at this location, from the selenoprotein ORF into the p53 ORF, would produce a fusion protein with an N-terminal selenoprotein module of 160 amino acids with 4 SeC residues, fused to the C-terminal half of the p53 protein. The heptameric frameshift sequence is located 7 nucleotides upstream from the predicted pseudoknot, an optimal distance for efficient frameshifting. The unpaired G at the junction of the 5' and 3' stems is a feature recently shown by Varmus and coworkers to facilitate frameshifting at some retroviral sites. The A-C bulge shown in the major stem probably forms a hydrogen bonded purine-pyrimidine A:C base pair, as these have been observed in some experimental RNA stem structures. A similar frameshift site (not shown) is located near the beginning of the major selenoprotein ORF in the c-abl oncogene, permitting the formation of an N-terminal c-abl/C-terminal selenoprotein hybrid predicted to contain 23 SeC residues.

Figure 21A:
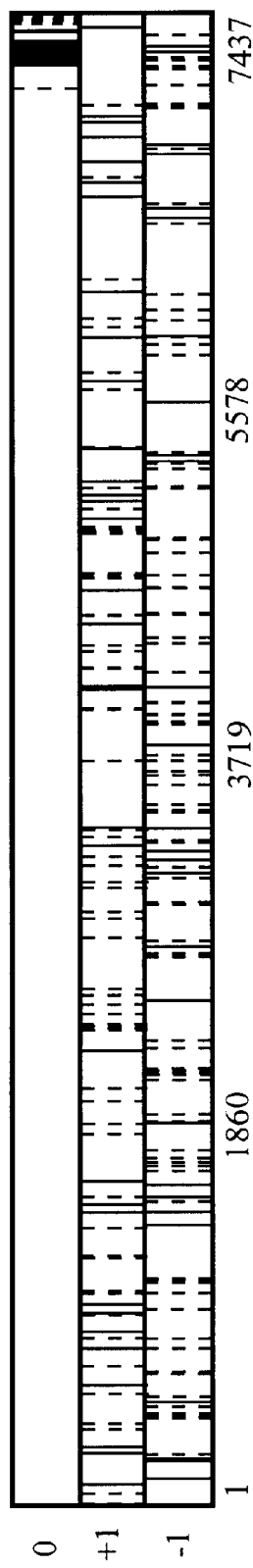
Figure 21B:
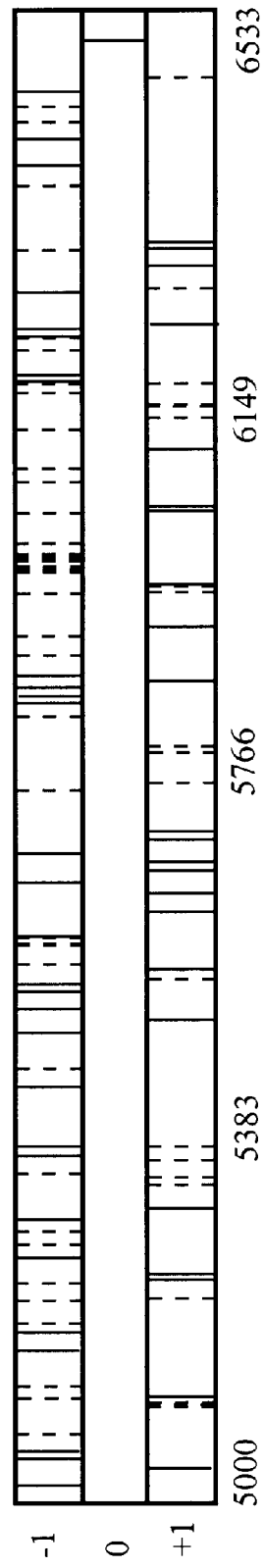

FIGS. 21A and 21B provide schematics of the complete genome of rabbit hemorrhagic fever virus (RHFV) (Genbank accession Z29514) and Haantan virus polymerase gene (Genbank accession X55901), translated in all three reading frames. The dotted lines represent UGA codons and the solid vertical lines represent non-UGA stop codons (UAA and UAG). This analysis is the first step in the general computational strategy for prediction of potential selenoprotein genes. Note the exceptionally high content of UGA codons relative to non-UGA stop codons in both overlapping frames for RHFV, and in the −1 frame for Hantaan virus.

Figure 22:
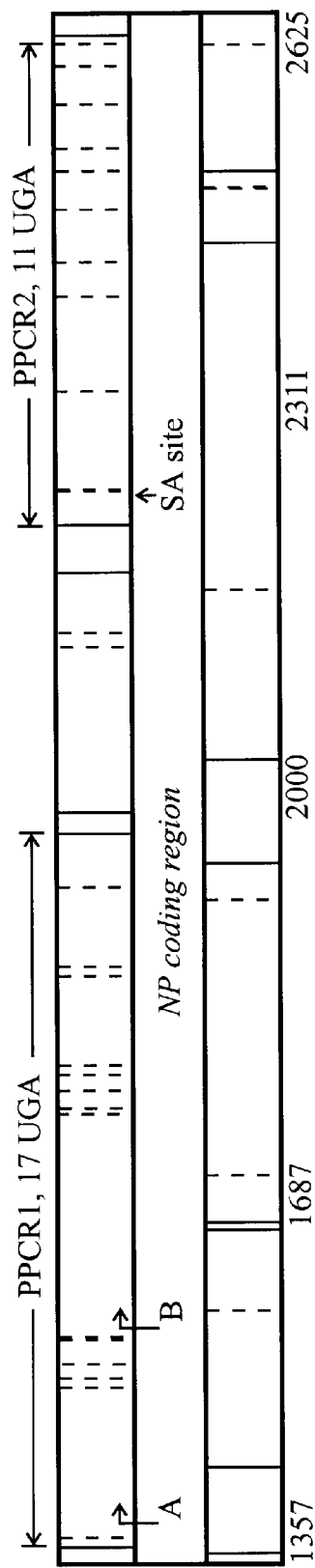

FIG. 22 graphically illustrates the presence of UGA-rich potential protein coding regions (PPCRs) overlapping the Ebola Zaire nucleoprotein (NP) coding region. The figure shows a schematic of the three reading frames for a portion of the NP gene (as in FIG. 21). The dotted lines are UGA stop codons, which can encode selenocysteine. There are two UGA codons. Neither PPCR1 or PPCR2 has a start codon. PPCR1 could be expressed as an NP fusion protein containing a selenoprotein module, by means of a frameshift at either one of two potential −1 frameshift sites, shown with an arrow symbol as A and B (shown in detail in FIGS. 24A and 24B).

Figure 23A:
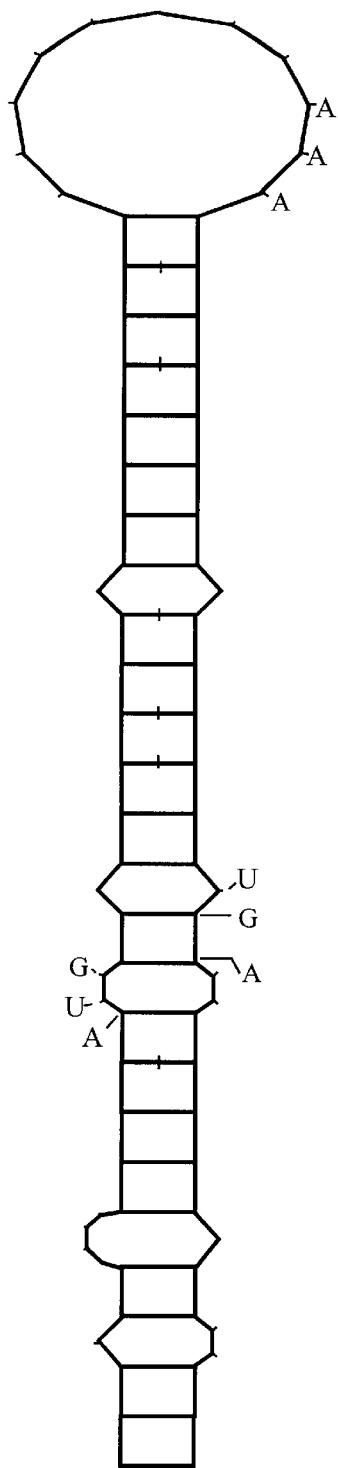
Figure 23B:
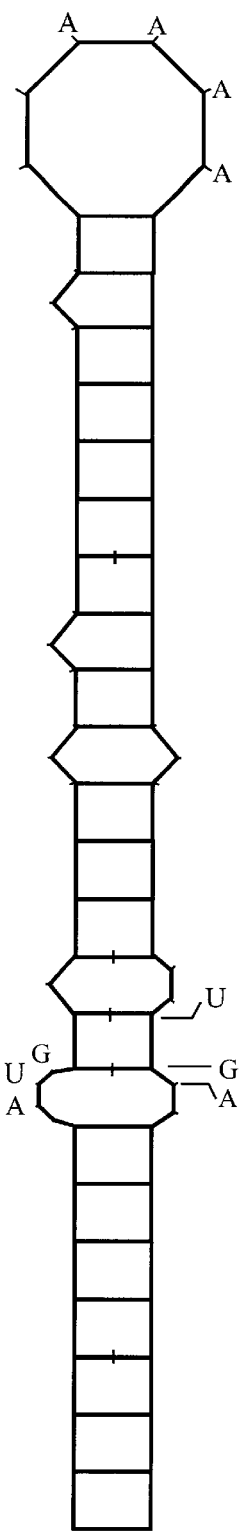
Figure 23C:
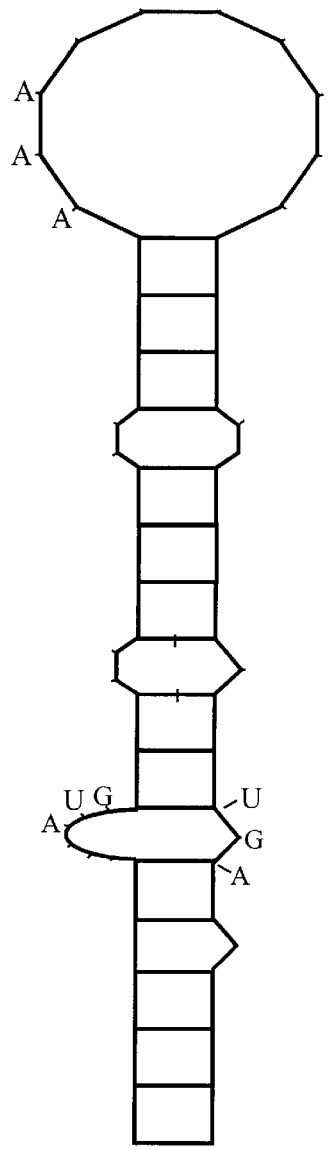

FIGS. 23A–23C illustrate the predicted RNA structures for potential selenocysteine insertion sequences (AUG . . . AAA . . . UGA) in the Ebola virus RNA. FIG. 23A: In the 3'-untranslated region of the nucleoprotein mRNA, bases 2758–2836 (SEQ ID NO:44) in GenBank #L11365; E=−10.1 kcal/mole. FIG. 23B: At the 3' end of the vp35 MRNA, bases 4094–4160 (SEQ ID NO:45); E=−13.4 kcal/mole. FIG. 23C: At the 3' end of the vp30 mRNA, bases 9026–9087 (SEQ ID NO:46); E=−9.4 kcal/mole. Base pairs (shown as ladder rungs) marked by a slash are GU base pairs. Preliminary results indicate that structure A is inactive in a standard assay for eukaryotic SECIS elements.

Figure 24A:
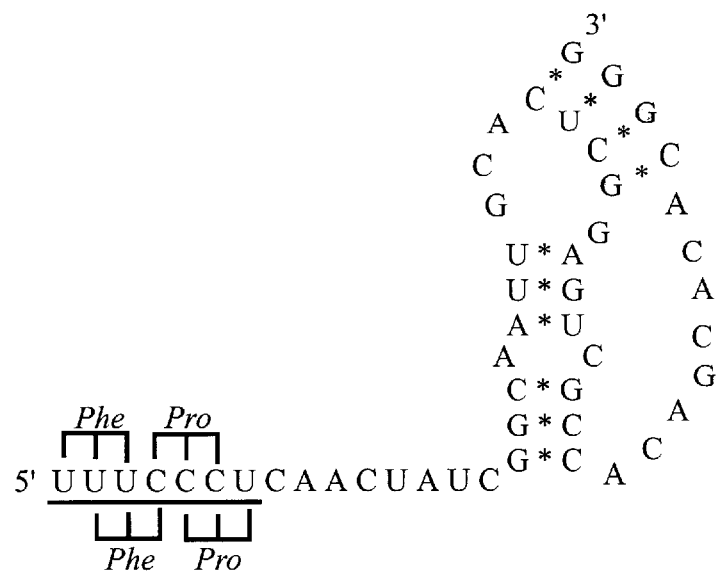
Figure 24B:
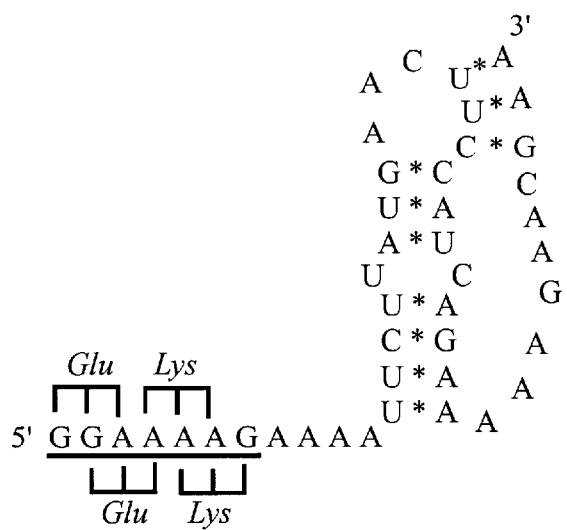

FIGS. 24A–24B (SEQ ID NOS:47 and 48, respectively) give predicted structures at predicted −1 frameshift sites near the beginning of the major UGA-rich pPCR in the Ebola Zaire nucleoprotein (NP mRNA, consisting of slippery sequences (underlined) and potential RNA pseudoknots. The location of these sites are indicated in FIG. 22 by A (beginning at position 1405 in GenBank #L11365) and B (beginning at position 1582). Codon-anticodon interactions of the P- and A-site tRNAs are shown schematically both before (below sequence) and after slippage (above sequence). Slippage on runs of C bases as in site A is known to occur in measles virus.

FIGS. 25A and 25B show predicted −1 frameshift sites associated with GPx-related sequences in CVB3 (FIG. 25A), SEQ ID NO:49 and in some CVB4 strains (FIG. 25B), SEQ ID NO:50. Schematic tRNAs are shown before (below) and after the shift (above) relative to the "slippery" sequences (asterisks denote base pairing)/ Slippage here involves a shift from the overlapping +1 frame into the vp3 protein regions of CVB to five a GPx-vp3 fusion protein.

Figure 26A:
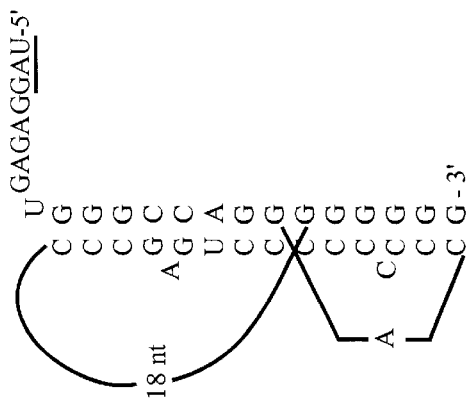
Figure 26B:
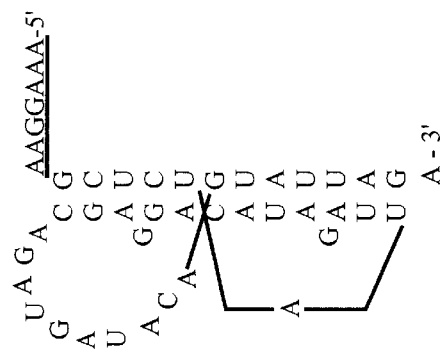
Figure 26C:
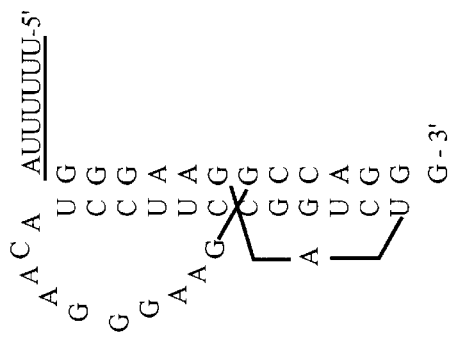

FIGS. 26A–26C illustrate the HIV-1 gag-pol −1 frameshift site (SEQ ID NO:51) and pseudoknot in CPK1 topology compared tot he −1 frameshift in the HIV-1 protease coding region (SEQ ID NO:52). In both cases, the slippery sequence comes right up to the base of he 5' stem of the PK, and the PKs are similar except for several extruded bases in the helices of the HIV-1 protease PK structure. A predicted CPK1, identified in feline leukemia virus (Fe) by Zu et al. *Biochemistry* (1996) 35:4187–4198, is shown (SEQ ID NO:53) for comparison and to illustrate that such single base extrusions are not uncommon.

Figure 27:
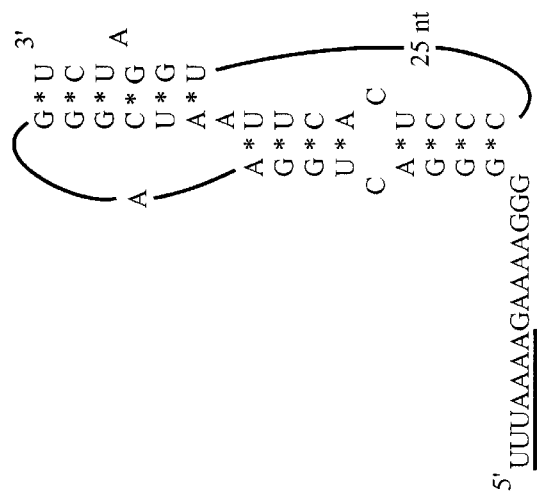

FIG. 27 shows the ideal heptameric −1 frameshift sequence and PK in the nef coding region of HIV-1 (SEQ ID NO:54). Both the PK structure and the heptamer are well conserved in the HIV variants. The overlapping −1 reading frame contains several well conserved UGA codons, and experimental data confirms that this viral sequence induces a −1 frameshift (about 5% efficiency in a standard assay.

FIG. 28 compares codon usage in the HIV-1 nef gene in relation to the conserved UGA codon and the CCCUGA sequence in the overlapping −1 frame. This region is downstream of the frameshift site shown in FIG. 27. As indicated, the nef codons ar i (Leu) and iii (Pro) could use any base at the third position due to the degeneracy of the genetic code, but U is almost always seen in the 76 different HIV isolates, supporting conservation of UGA in the −1 frame (SEQ ID NOS:56 and 57). CCCUGA os a known 1 frameshift (SEQ ID NO:51) signal; it can cause a return to the nef reading frame after insertion of an alternate selenoprotein module encoded in the −1 frame. Conservation of CCCUGA downstream of the first UGA indicates that the latter must be suppressed by readthrough, i.e., the first UGA encodes an amino acid instead of acting as a translation termination signal.

Figure 29:
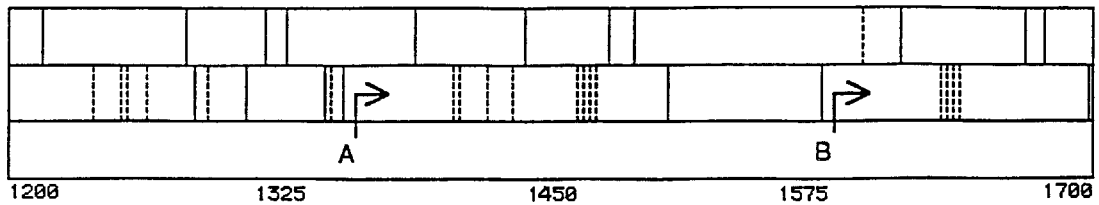

FIG. 29 schematically illustrates the predicted coding regions (PPCRs) overlapping part of the mouse mammary tumor virus (MMTV) gag gene. Numbers correspond to nucleotides in the genomic sequence (Genbank #D 16249). A and B are predicted −1 frameshift sites which can provide entry into ORFS for selenoprotein modules. Dashed lines are UGA codons.

Figures 30A, 30B:
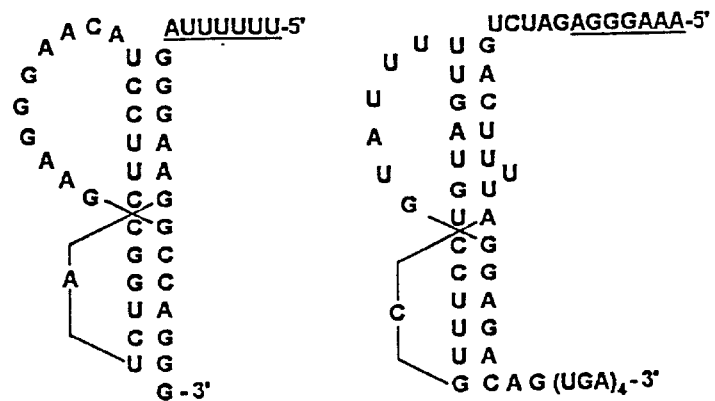

FIGS. 30A–B illustrate the HIV-1 gag-pol −1 frameshift and PK in CPK1 topology (A) and the potential frameshift site B in MMTV (SEQ ID NO:58), with ideal heptamer and CPK1-like PK upstream from four tandem in-frame UGA codons (see FIG. 29).

Figure 31:
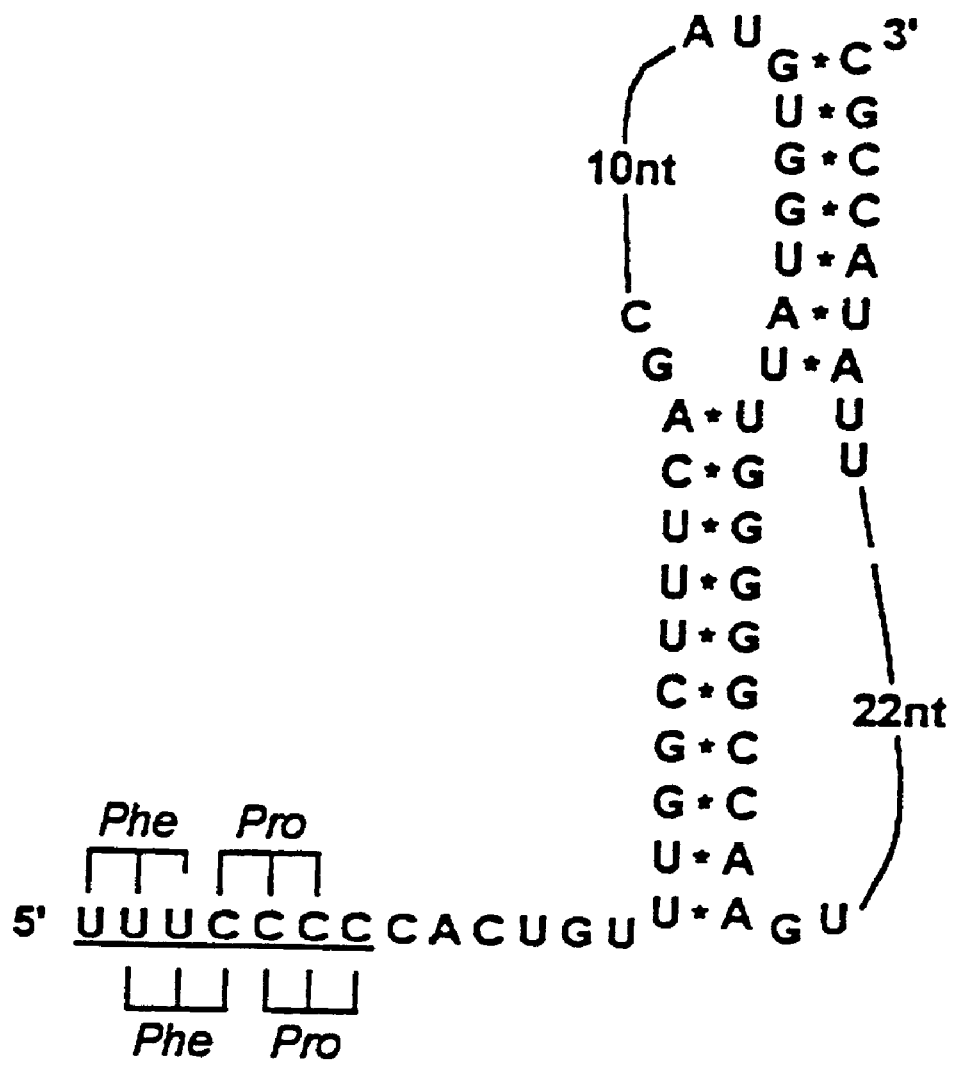

FIG. 31 shows the large PK and heptameric −1 frameshift sequence in hepatitis B virus (SEQ ID NO:59) (Genbank #X51970) overlapping the active site codons of the viral reverse transcriptase. A PK identified in precisely the same location in HIV-1 has been confirmed experimentally.

Figure 32:
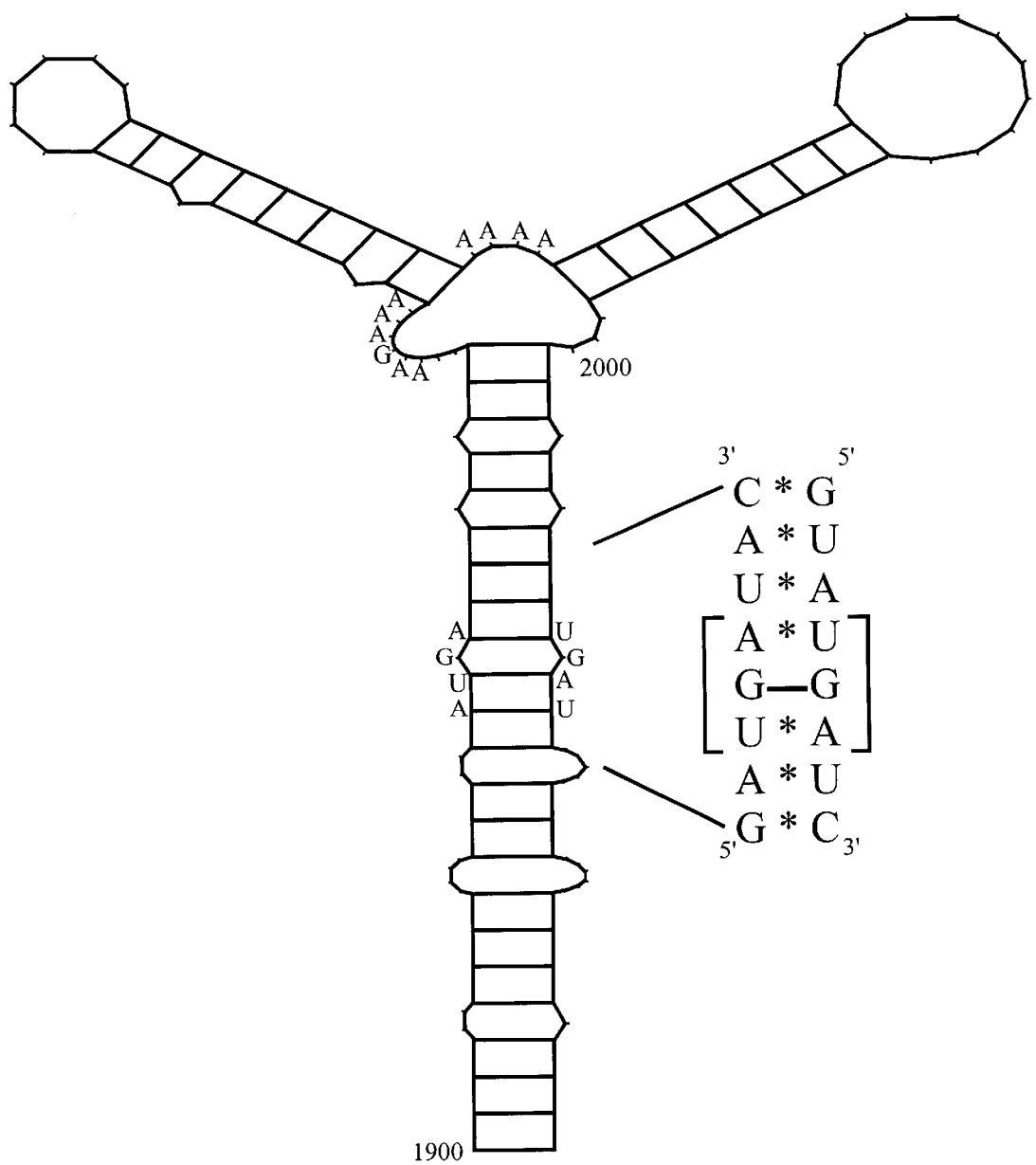

FIG. 32 provides the RNA structure for a portion of the HIV-1 protease coding region (SEQ ID NO:60), where a selenoprotein coding region has been identified in the overlapping −1 reading frame. The two in-frame UGAs (shown in brackets) are located in a complementary regions form a stem with an embedded 5'-AUGA, forced to pair with UGAU-3' as shown in detail in the inset. That structure has features characteristic of a eukaryotic SECIS element, but the AUGA and UGAU involve UGA codons, a situation akin to the bacterial SECIS element. This structure is the global energy minimum predicted using the Zuker FOLD program (−17.2 Kcal/mol).

DETAILED DESCRIPTION OF THE INVENTION

Frameshifting

RNA pseudoknots (PK) are involved in frameshifting and termination suppression. Expression of a gene product by frameshifting is a particularly useful cellular strategy when the product is only required in small amounts relative to another protein. In retroviruses like HIV, the pol gene lacks a start codon, so the pol gene products can only be synthesized as gag-pol fusion proteins, the formation of which is under translational control [1]. The two alternate mechanisms that are used in controlling the relative amounts of gag and pol gene products are ribosomal frameshifting, when genes are partially overlapping in different reading frames

[2], or, less commonly, termination suppression, when the two genes are in the same reading frame, separated by a stop codon [3–5]. Since both of these processes are inefficient, the fusion proteins are only formed infrequently (approximately 5% of the time) when there is either a readthrough of the gag stop codon, or when a −1 frameshift occurs, from gag into the pro or pol reading frame [2,6–9]. Significantly, RNA PKs have been shown to be commonly involved in both processes and must be located 3' to either the stop codon involved in the readthrough [10] or the frameshift site [7].

In frameshifting, the primary role of PK is apparently to cause a pause in translation; in some systems a stem-loop structure alone has been found sufficient. These RNA secondary structures cannot independently induce frameshifts; they act to increase the efficiency of the primary frameshift signal, which is a short RNA sequence of 7 bases or less, often called the "slippery" or "shifty" sequence. Anywhere from 0 to about 12 bases can intervene between the shift sequence and the beginning of the 5' arm of the stem or PK; about 7 bases is optimal for the greatest frameshift efficiency. The shifty sequence should preferably begin about 14 bases before the RNA secondary structure.

The retrovirus gag-pol −1 frameshift site has been extensively studied, and is the basis of the "simultaneous slippage" model developed by Varmus and coworkers [2]. This model involves the translocation of the RNA message by one base while two tRNA molecules are bound to the ribosome, and depends upon a repetitive, "slippery" quality in the message at that point. Detailed molecular analysis has shown that for the most efficient frameshifting to occur, the slippery sequence preferably has the form X XXY YYZ, where triplets represent codons in the zero reading frame. Deviations from this form are known, such as that at the pro-pol frameshift site in the mouse mammary tumor virus (MMTV), which is G GAU UUU [9]. Systematic mutagenesis of the coronavirus heptameric frameshift sequence has shown that considerable deviation from the preferred pattern above can occur without significant loss in frameshift efficiency. In some situations, a lower efficiency frameshift with a less than preferred slippery sequence may function where very low levels of a regulatory protein is required.

In addition to −1 frameshifts, +1 frameshifts have also been reported. There are a diversity of mechanisms for known +1 frameshift sequences. True slippage is apparently not always required and frameshifting with only one tRNA bound to the ribosome P-site seems more the rule than the exception. A common mechanism involves a "hungry" codon in the second position (usually Arg or Ser, but other are possible), which creates a pause due to low cellular levels of the required isoacceptor tRNA, analogous to the pausing effect of RNA secondary structures [93]. Important examples of +1 frameshift sequences include CCC followed by a stop codon, e.g., CCCUGA [94], and CUUAGG [95] or GCGAGU [96], where a combination of a hungry codon (AGG or AGU) and possibly a unique tRNA isoacceptor for the P-site codon (CUU or GCG) facilitate the frameshift by a poorly understood mechanism.

The idea that specific isoacceptor tRNA molecules can be involved in frameshifting at specific codons, and thus that cellular tRNA pools can regulate frameshifting, is gaining support [97]. Consistent with this, it has been shown that the hypermodified forms of tRNA$^{Lys}$ (which, at least in *E. coli*, can contain a modified 2-thio or 2-selenouridine base at the wobble position) have a very unusual anticodon loop confirmation; Watanabe et al. have suggested that this could be the basis of the frequent involvement of Lys codons in frameshift sequences [98].

The UGA Codon

Any of the three stop codons can be suppressed under appropriate circumstances, by means of mutant "suppressor" tRNAs and/or by programmed readthrough involving PKs, as seen in retroviruses [5,26]. Gene regulation by the balancing of readthrough vs. termination of protein synthesis is probably a universal biochemical control mechanism.

Generally speaking, even without including its ability to encode selenocysteine, UGA is probably the most "leaky" of the three stop codons. For example, in Sindbis virus it was observed that an in-frame UGA immediately followed by a C served as a termination suppressor codon, at 10% efficiency, apparently with no other RNA signals required. In an analysis of a large number of eukaryotic genes it was shown that when serving as a termination codon, UGA is rarely followed by a C base [100].

When suppressed by conventional mechanisms, UGA usually encodes an amino acid with a closely related codon, such as Trp, Cys, or Arg, in competition with termination, yielding an extended protein product as well as the terminated product.

As mentioned above, if preceded by CCC, or other shifty codons, an in-frame UGA can be part of a frameshift signal, which can also compete with termination [94,101]. Add to this its exceptional usage to encode Trp in mitochondria and mycoplasma, and its capability to code for selenocysteine in both eukaryotic and prokaryotic genomes, and it is evident that UGA is the most versatile codon in the genetic code. UGA codons are thus of special important in the search for new genes, particularly when the UGAs are highly conserved, or clustered in a potential open reading frame.

In addition to the nonspecific substitution of selenomethionine for methionine that can potentially occur in all proteins when Se is bioavailable, the genomes of both prokaryotic and eukaryotic organisms are known to encode specific selenocysteine (SeC) containing "selenoproteins." Both bacteria and eukaryotes use the UGA codon for SeC, and both utilize a complex cotranslational mechanism for SeC incorporation into polypeptide chains, involving RNA stem-loop structures [Bock et al. (1991) *Mol. Microbiol.* 5:515–20; Berry and Larsen (1993) *Biochem. Soc. Trans.* 21:827–832.

General Method for Finding Potential New Genes

Proteins encoded in large ORFs (open reading frames) with start codons are unmistakable, and no unusual method is required to find them. This invention provides a computer-implemented method of identifying and ultimately isolating gene coding regions that are not immediately apparent. The following is a stepwise description of the method. Specific details are provided in the Experimental section herein. This method applies to nucleic acid sequences of any organism and/or organelle, including among others, viral and eukaryotic sequences, particularly retroviral and other viral sequences and mammalian sequences. An important aspect of this method is the initial treatment of UGA codons as sense codons, rather than stop codons, to initially select potential ORFs. These initially selected ORFs are then scanned for the presence of readthrough suppression signals, frameshift signals, shifty sequences, PKs and possible double frameshifts, all as discussed above and in more detail below, to identify potential genes. Genes encoding selenoproteins are further identified by the presence of a SECIS sequence and a UGA codon.

Step 1. Translate, for example, by computer analysis, the nucleotide sequence of the nucleic acid molecule, the genome or genomic region of interest in all three reading frames (or all six if that is believed to be appropriate for the organism in question, i.e., for double-stranded genomic DNA or RNA). The resulting translation table is modified to differentiate UGA codons from UAA or UAG stop codons, preferably using a distinctive symbol that will highlight them in printouts, so that ORFs containing UGA codons can easily be seen. Organism or organelle-specific deviation from the universal genetic code must be taken into account, e.g., for mitochondria.

Step 2. Search for previously unrecognized ORFs, focusing initially on the largest ones not known to be functional genes. Initially assume UGA is a sense codon, and look for ORFs with clusters of UGA codons, realizing that several small ORFs may actually be combined to form a larger ORF with one or more UGA codons. A computer program that generates a graphical display of ORFs may prove useful, particularly if it can differentiate between the various stop codons.

Step 3. If the 5' region of the ORF in Step 2 overlaps with a known coding region, search for frameshift sequences in the overlap region. The type of frameshift signal (+1 or −1) must be appropriate for the direction of the shift required from the known coding region into the novel ORF.

Step 4. If candidate frameshift sequences are found, analyze for potential RNA structure in the region following the putative shift sequence, looking for major stems or potential PKs beginning no more than about 20 bases past the start (5'-end) of the shifty sequence. There are various techniques for doing this, the most convenient possibly being the use of "dot plots" to predict RNA stems, whereby potential PKs are easily visible as a characteristic pattern, shown in FIGS. 1A and 1B. If a shifty sequence and an appropriately placed stable stem-loop or PK are present, a potential gene has been found. If major RNA structures are known to exist in the region, they must be taken into account as a structure that could facilitate a frameshift or a structure that could be incompatible with the proposed frameshift. The role of RNA structure in many +1 frameshifts is not completely established; it is possible that frameshifts involving "hungry" codons or termination codons (e.g. CCCUGA) may not require additional pausing provided by an RNA structure. But the presence of an RNA structure could contribute to a greater frameshift efficiency.

Step 5. Particularly for quite small ORFs, less than about 100, preferably less than about 90 amino acids encoded, that meet the criteria of steps 3 and 4, the possibility of a second frameshift in the reverse direction should be considered, e.g. a +1 frameshift some distance after a −1 shift. If present, this second signal would most likely be found in the region immediately before the stop codon at the 3' end of the ORF. Such a double frameshift (out of previously known open reading frame and back) corresponds to the replacement of a central protein module encoded in the "zero" reading frame with an alternate module encoded in the −1 reading frame, with the retention of identical N- and C-terminal modules (e.g. several examples in FIG. 4). Successive dual frameshifts in the same direction can also occur, as seen in HTLV.

Step 6. If steps 3 and 4 fail to reveal any frameshift potential, the possibility of expression of the novel ORF lacking an initiation codon by alternative RNA splicing should next be considered. For this mechanism, there must be a splice acceptor sequence identified near the beginning of the ORF that would enable it to be spliced in-frame to another upstream coding region.

Step 7. (Optional) where a candidate open reading frame is found, it is highly desirable to generate multiple alignments of the corresponding region in closely related organisms and preferably in variants or strains of the same organism when it is feasible to do so. Conservation of frameshift signals, PKs, and amino acid sequences increase the possibility that the ORF encodes a protein. This kind of evidence is particularly compelling if the observed conservation cannot be explained in terms of the known overlapping genes, because of the degeneracy of the genetic code.

Step 8. Predicted protein sequences are generated from selected candidate ORFs having the features described above. Predicted amino acid sequences can be used to generate nucleic acid constructs to express the protein (or directly to synthesize the protein, if practical). Expressed proteins can then be tested for functionality.

Step 9. (Optional) Comparative sequence analysis of the predicted protein sequence of the potential ORF is performed, using one or more standard database searching programs and scoring matrices, to see if the predicted protein has significant sequence homology to known proteins. This can provide useful functional information for the novel protein. In addition, one can calculate the isoelectric point, hydrophobicity profile, secondary structure predictions, and searches against databases of known functional protein domains and motifs.

Even aside from its ability to encode selenocysteine, UGA is probably the most "leaky" of the three stop codons, any of which can be suppressed under appropriate circumstances, by means of mutant "suppressor" tRNAs and/or by programmed readthrough involving PKs, as seen in some retroviruses [Hatfield et al. (1992) *Adv Virus Res* 41:193–239]. When suppressed by such "conventional" mechanisms, UGA usually encodes an amino acid with a closely related codon, such as Trp, Cys, or Arg, in competition with termination, yielding a mixture of both the terminated product and an extended protein product. A unit role of the UGA codon is its potential to encode SeC. In eukaryotes, selenocysteine incorporation at UGA depends upon the presence of a protein factor and a structural signal in the mRNA 3'-untranslated region, called an SeC insertion sequence or SECIS element [Berry and Larsen (1993) *Biochem. Soc. Trans.* 21:827–832; Shen et al. (1993) *J. Biol. Chem.* 268:11463–9; Berry et al. (1993) *EMBO J.* 12:3315–3322]. A possibly related stem-loop structure is required in bacteria, but must immediately follow the UGA codon [Bock et al. (1991) *Mol. Microbiol.* 5:515–520].

Finally, as mentioned above, if preceded by CCC or other shifty codons, an in-frame UGA can also be part of a frameshift signal, which may compete with termination and/or readthrough by any of the mechanisms listed above.

Application of Method to Retroviruses

The general method described herein arose out of studies of the relationship between the predicted RNA structure of HIV and the distribution of drug resistance mutations (DRMs) observed for HIV-1 reverse transcriptase (RT) inhibitors. The analysis of Schinazi et al. [16] suggested that non-helical RNA structural regions (loops, bulges and bends) are more mutation-prone than extended helical regions, with which codons for high conserved sequences appear to be more often associated. This was consistent with a previous study that correlated envelope protein hypervariable regions with non-helical RNA structural regions in the env coding region of HIV-1 [17].

Probably due to the very low abundance of Se, and the small number of selenoproteins so far identified (leading to the possibly incorrect impression that they are extremely rare), this possibility apparently remained unconsidered and unexplored until our proposal in 1994 of what in retrospect might be called the "viral selenoprotein theory," which arose initially from an analysis of the genomic structure of HIV-1. We have predicted that several regions of the virus encode selenoproteins, and that certain UGA codons in overlapping reading frames are well conserved in the many HIV-1 isolates that have been sequenced [Taylor et al. (1994) *J. Med. Chem.* 37:2637–2654; Taylor et al. *Computational Medicine, Public Health and Biotechnology; Building a Man in the Machine,* M. Witten, Ed., (World Scientific, London, 1996) Part 1, pp.] which are incorporated in their entirety by reference herein.

In examining the RNA secondary structure-mutation frequency relationship in HIV-1, we discovered several RNA regions similar to PKs, hereafter discussed simply as pseudoknots (PKs). These PKs are precisely associated with highly conserved coding sequences in the HIV pol gene. A PK is a predicted structure in which bases on the loop of an RNA hairpin pair with complementary bases in an upstream or downstream region, forming secondary structures, such as those in FIGS. 1A and 1B. One of these PKs is precisely associated with codons of the highly conserved DTG consensus sequence of retroviral proteases, which includes the catalytic Asp25 of HIV-1 protease (FIG. 2B). Another PK is associated with the highly conserved YMDD (motif C), SEQ ID NO:5 region of RT, which includes two of the three aspartate residues of the RT catalytic triad (FIG. 2C). Variants of these PKs or at least stem-loop structures are found in many other related retroviruses at this same position (see FIGS. 3 and 5). The finding of PK sites so precisely associated with regions encoding key catalytic amino acids of both HIV protease and RT is a strong indication that helical RNA structures are evolutionarily selected in regions encoding critical mutation-intolerant protein sequences.

These PKs were also associated with novel ORFs in HIV as well as in other related retroviruses, strongly indicating that they were directing the synthesis of low levels of novel gene products in HIV via a frameshift mechanism. More specifically, they were directing the synthesis of a fusion protein partly encoded in the –1 reading frame to pol and overlapping with the known protease and RT genes.

Figure 4B:
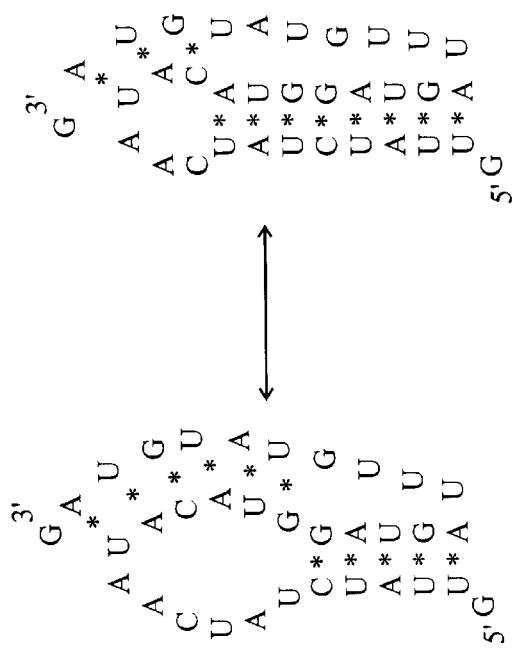
FIGS. 4A–4B compare the known frameshift-directing PK (FIG. 4B) in the HIV-1 gag region (SEQ ID NO:8) with the newly identified PK in the RT coding region (SEQ ID NO:4), associated with the highly conserved YMDD (SEQ ID NO:5) consensus sequence of retroviral reverse transcriptases, placing most of the bases of the YMDD codons into paired regions. The YMDD motif begins at UAC(Y) immediately following the upper 5' loop. This motif includes 2 of 3 Asp residues of the RT catalytic triad. The potential for a zipper-like change in the conformational states, for both PKs, is indicated by arrows.
Figure 4A:
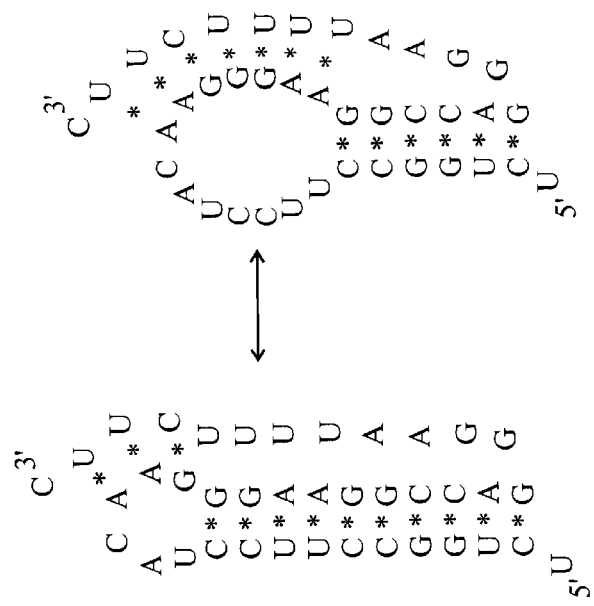

The major stem of the RT pseudoknot of FIG. 2C was predicted using the Zuker FOLD computer program [18], because its 5' stem was sufficiently stable to be predicted in a global fold of the RT-coding RNA [16]. Normally this program is unable to predict PKs because the empirical energy parameters for their relative thermodynamic stability are not accurately known. This RT motif C PK has several topological similarities to the known PK [2,7] at the gag-pol frameshift site (FIG. 4). Both the RT and gag-pol PKs have the zipper-like property of being able to exist in an equilibrium between two extreme conformational states that are both PKs; they also have the same size 5' loop and 3' stem in one of those conformations.

Both of these new PKs in HIV-1 place almost every base of each codon of the respective consensus sequences into a base pair (8 of 9 in protease, 11 of 12 in RT). Based on the statistics reported by Schinazi et al. for the RT coding region (about 57% of total bases were paired in the global minimum energy structure), the probabilities of having that many bases paired in the two consensus sequences purely by chance are $P<0.05$ and $P<0.02$, respectively. The probabilities of having the number of contiguous stacked base pairs observed in the pseudoknots are substantially lower, $p<0.01$ and $P<0.0005$, respectively. This further supports the hypothesis that evolution selects RNA structures with codons for critical conserved sequences in helical regions, suggesting that such structures are less prone to mutation [16].

A comparative analysis of potential RNA structures at these locations (for which a few examples are shown in FIGS. 3A–3C and 5) for various related primate retroviral sequences shows that PK type structures, or at least relatively stable stem structures (for other sequences not shown), are located at these positions in many instances; however, the details of these structures vary considerably. Thus, it is the structural theme of a PK that is conserved rather than identical PK structure being observed in the various examples.

One key RNA pseudoknot predicted in HIV-1, overlapping the codons at the active site of the reverse transcriptase gene and associated with a well-conserved UGA codon in the –1 reading frame, has been confirmed experimentally by chemical and enzymatic cleavage studies [Battigello, et al. (1995) *Bioorg. Med. Chem.* 3:839–849].

Initially, we examined the potential fusion proteins of –1 frameshifts from the pol gene from these PKs. A cursory examination by translation, e.g., computer-implemented translation, of the relevant regions of the reading frame that is –1 with respect to pol indicated stop codons in this reading frame within about 10 amino acids of any potential frameshift sites. Assuming that termination suppression was involved, the translated sequences between the first and second stop codons in the –1 reading frame (only 29 and 13 amino acids long for the protease and RT frameshifts, respectively) were scanned for potential matches against the entire GenBank database, using the FASTDB program. This produced a number of intriguing matches at high levels of significance, particularly with various DNA binding and finger proteins for the short RT –1 frameshift sequence (at 5 to 7 SD significance relative to the database average), and with a number of viral proteins, class I MHC antigens, ribosomal and DNA binding proteins (at 4.5 to 7 SD) for the protease –1 frameshift sequence.

As discussed above, the UGA stop codon can code for selenocysteine, as well as function as a stop codon in conventional contexts. This UGA coding functionality had not previously been observed in retroviruses. The predicted protease and RT fusion proteins that could be expressed under the direction of these pseudoknots, with the insertion of selenocysteine at UGA codons, were translated and studied by database scanning, alignment with similar potential gene products from other primate retroviruses, etc.

Multiple SECIS Elements in the HIV-1 RNA

Assuming that HIV has a selenocysteine insertion mechanism analogous to that of eukaryotes, UGA functioning as a selenocysteine codon would require SECIS-like elements. Using a simple systematic sequence scanning technique, as implemented by computer, followed by predicted RNA folding of the regions of interest, a number of SECIS-like structures were found in the HIV-1 RNA.

An essential feature of SECIS elements is a stem-loop structure displaying a conserved triad of unpaired adenine bases on the loop, e.g., in the context of the sequence UAAAG in the iodothyronine deiodinase (5'-DI) gene [14]. Further down the stem, there is a UGA codon protruding on a bulge, usually with at least two bases of the UGA codon unpaired in the isolated RNA. This UGA apparently combines with the anticodon of a selenocysteine tRNA; the aminoacyl acceptor arm and bound selenocysteine are recognized by the joint action of a special protein translation factor and/or the SECIS loop AAA sequence. In association with this protein factor (believed to be equivalent to the bacterial selB protein [15]), which may bind to the ribosome, the RNA SECIS structure essentially acts as an "attractor" for selenocysteine tRNAs, making them available for insertion at any in-frame UGA codon in the mRNA, and thus, termination suppression of opal stop codons [13, 14]. This complex may also inhibit binding of the termination factor.

Kollmus H, Flohe L, McCarthy J E (1996) Nucleic Acids Res. 24:(7)1195–201 describe a reporter gene system which allows analysis of stop codon suppression in animal cell lines. They have employed the reporter gene system to study the structure-function relationships of SECIS structure. This system relies upon quantification of translational readthrough from the lacZ gene into the luciferase gene obviating the need for enzymatic or immunological estimation of selenoprotein synthesis. The 3'-UTR of the phospholipid hydroperoxide glutathione peroxidase (PHGPx) gene was shown to contain a highly active SECIS element. Mutations in the base-paired sequences of other SECIS elements were used to analyze the significance of primary structure, secondary structure and pairing stability in the stem regions. The results demonstrate that the exact sequences of the paired nucleotides are comparatively unimportant, provided that a consensus combination of length and thermodynamic stability of the base-paired structures is maintained.

Figure 6B:
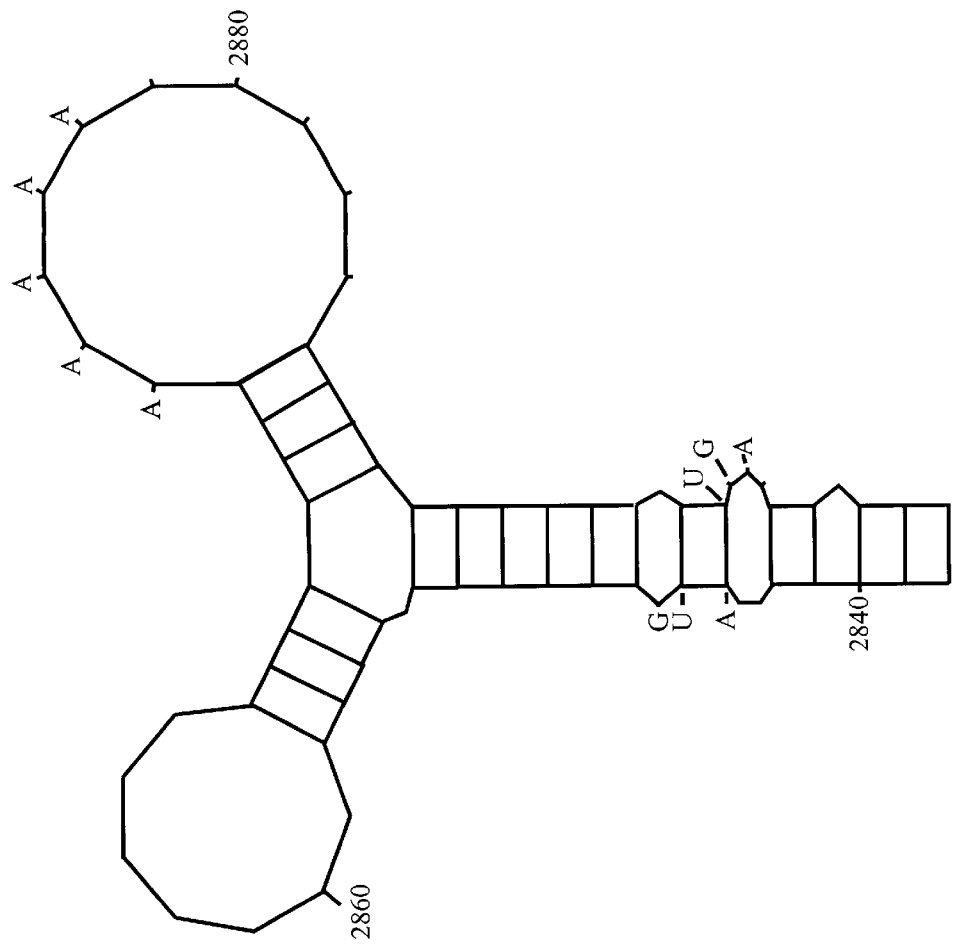
FIG. 6B shows the SECIS element in the HIV RT coding region (SEQ ID NO:12), following a well-conserved UGA codon overlapping the RT active site, energy=−12.9 Kcal/mole.
Figure 6A:
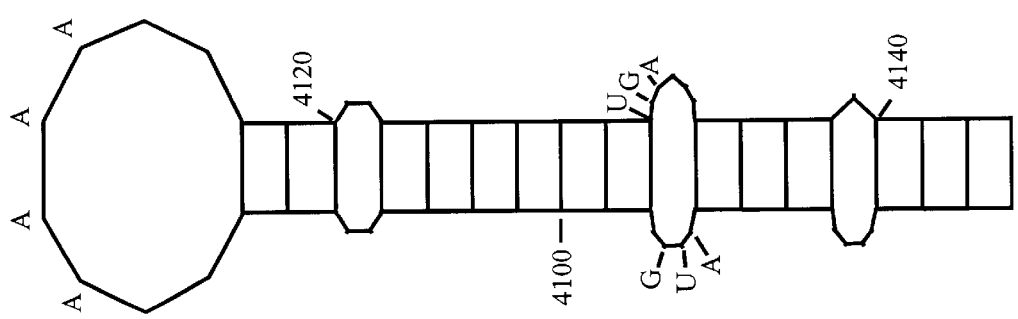
FIG. 6A illustrates the SECIS element in Coxsackievirus B3 (CVB3) SEQ ID NO:11 following an ORF with 8 UGA codons, energy=−8.0 Kcal/mole.

FIGS. 6A–6B show potential SECIS elements from HIV-1 (SEQ ID NO:12) and CVB3 (SEQ ID NO:11). FIG. 6A shows the element found in CVB3 downstream from the ORF with 8 in-frame UGA codons. That element shown in FIG. 6B is located in the HIV-1 RT "thumb" coding region. Both have all the essential features of known SECIS elements located in mammalian selenoprotein genes: an AUG partially paired in a bulge on the 5' arm of the stem, the unpaired adenine triad on the loop, and UGA in a bulge on the 3' arm of the stem [25]. The HIV-1 structure is non-classical because of the presence of an additional stem-loop "sidearm" off the 5' arm of the main stem. Both structures have a near-ideal distance (10–12 base pairs) between the adenine loop and the AUG/UGA consensus bulge regions.

This SECIS in HIV appears to be a fairly stable structure, because it was precisely predicted as a substructure in a global fold of the HIV-1 RT coding region. This substructure is clearly visible at the upper left of the structure in FIG. 2C of Schinazi et al. [16]. The SECIS is in a region 3' to the well conserved UGA codons in the pol coding region of HIV-1 (i.e., in the pro fs, rt1 fs and rt2 fs ORFs).

The SECIS in CVB3 is located 300 nucleotides following the 3' end of the ORF containing 8 in-frame UGA codons. As far as this particular gene of CVB3 is concerned, this is equivalent to a 3'-UTR region, where SECIS elements are always located in mammalian genes. This downstream location apparently gives maximal efficiency of SeC incorporation [14]. This placement strongly indicates that the novel ORF in CVB3 encodes a selenoprotein.

Figure 7:
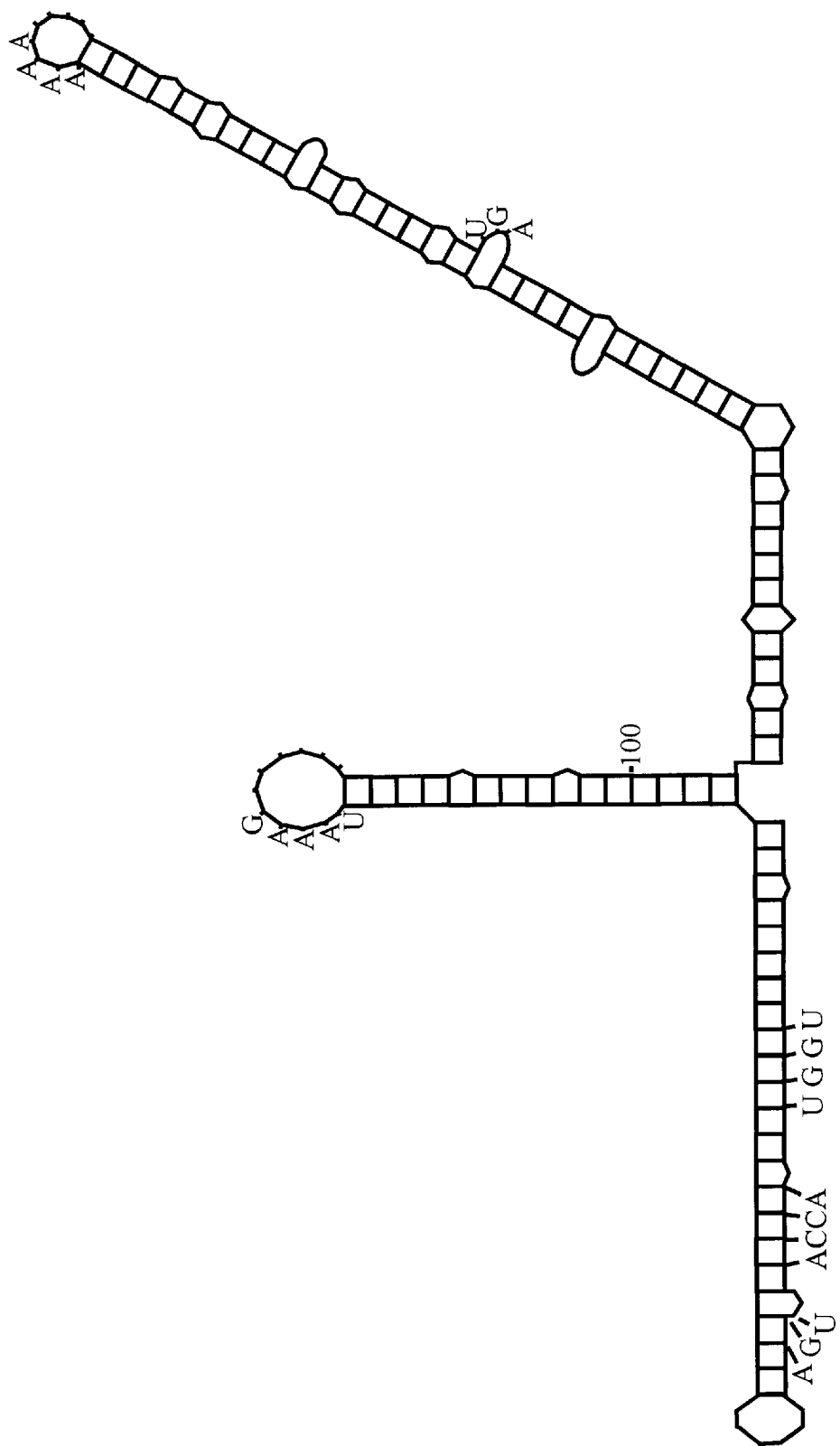
FIG. 7 shows the global minimum energy conformation for the first 250 bases of the 5' end of HIV-1 mRNA (SEQ ID NO:13), showing the TAR element at left, which places an E2-like palindrome (UGGUUAGACCA) SEQ ID NO:2 in the helical stem of TAR. A UGA codon is near the end loop of TAR where the Tat protein is believed to bind. The next major structure (middle stem with UAAAG SECIS motif on loop) is very similar to the 5' DI SECIS loop structure, but there is no UGA displayed on a projecting loop (See FIG. 8). Both these structures are in the LTR repeat region so a second copy is located at the 3' end of HIV-1 mRNA. The third structure (right stem) is in the 5' untranslated region only, and is a predicted SECIS element stem. This entire structure has a predicted global minimum delta F=−78.9 Kcal/mole, and it is significant at 2.4 SD (P<0.01) relative to global minima for random oligonucleotides of the same size and base composition. The TAR stem conformation here is identical to that reported previously by others [23,32].
Figure 8:
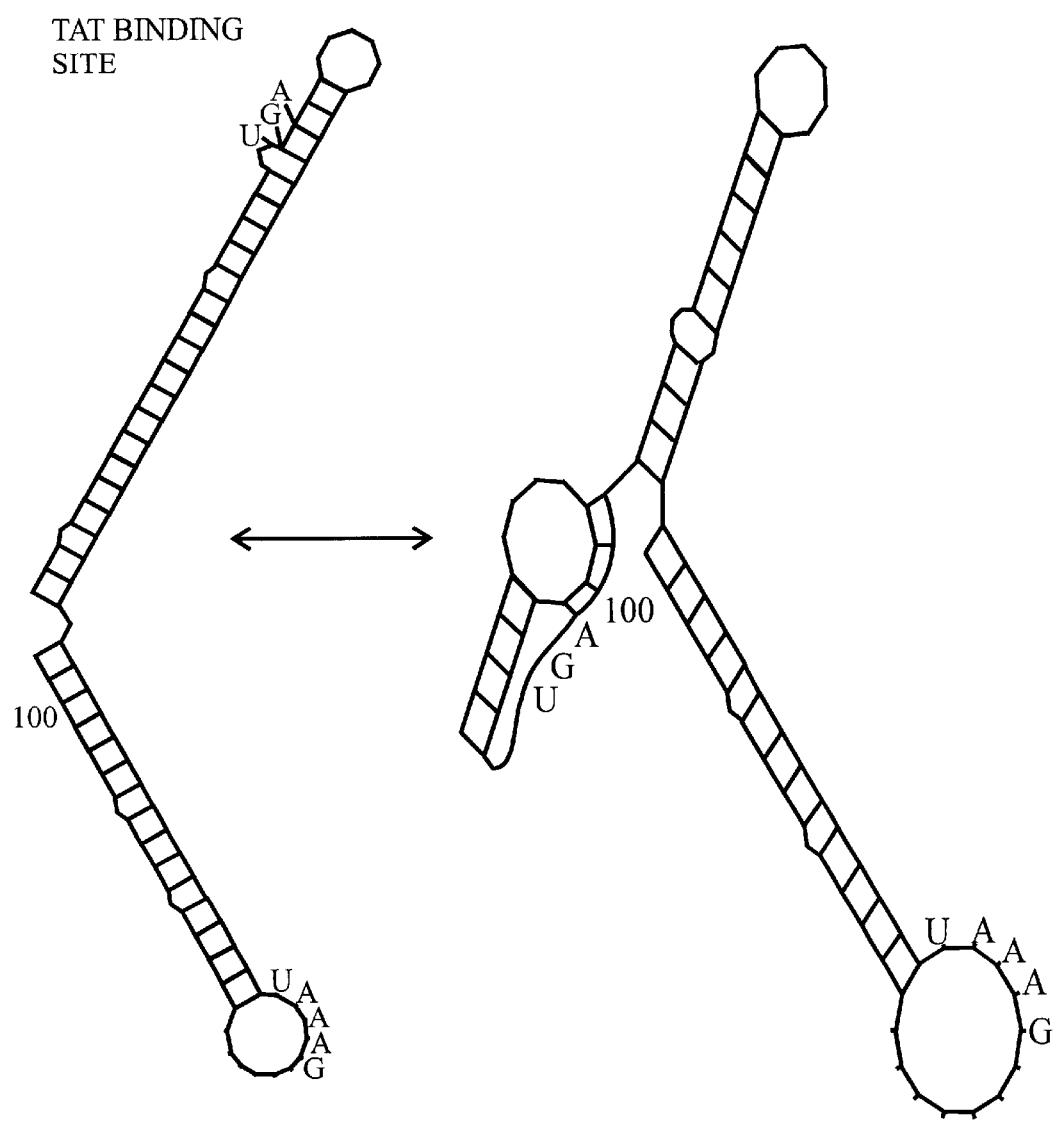
FIG. 8 is an alternative conformation for the TAR stem of FIG. 7 which places the E2-like palindrome in a PK and displays the UGA codon on the 3' loop of the PK, where it works with the SECIS element (UAAAG motif) to serve as a SECIS element at both ends of he HIV-1 mRNA. Because Tat protein binds the TAR stem (left) precisely where the UGA codon is located, Tat binding stabilizes that conformation and inhibits SECIS function. The significance of the structure at right, excluding the PK (which the FOLD program is unable to predict) is 2.0 SD (p<0.01). The free energies of these two structures cannot be directly compared because the free energy contribution of the PK is unknown.
Figure 9C:
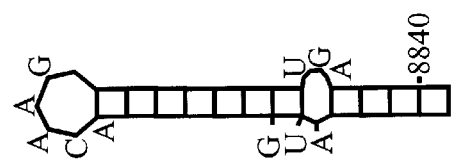
FIGS. 9A–9C show other predicted SECIS elements in the HIV-1 MRNA, located in the integrase coding region, 3.6 SD, p<0.001 (FIG. 9A) SEQ ID NO:14; at the very 3' end of the env coding region, 2.7 SD, p<0.004 (FIG. 9B) SEQ ID NO:15 and just inside the 3' untranslated region, 4.8 SD, p<0.0001 (FIG. 9C).
Figure 9B:
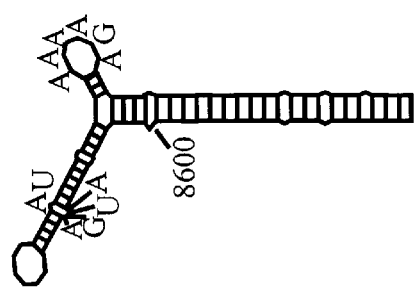
Figure 9A:
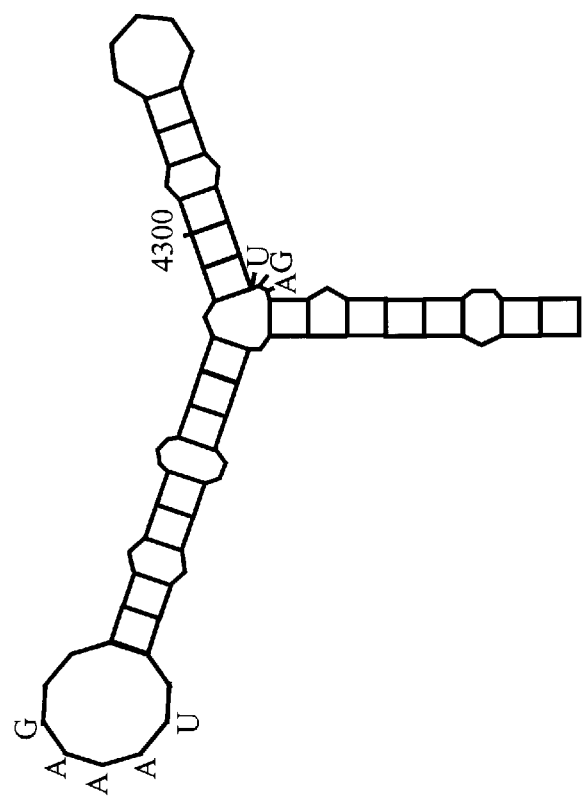

There are six such SECIS stems in the HIV-1 RNA (FIGS. 7–9). Two are identical, being in the R repeat region of the long terminal repeat (LTR), which is the only region of the LTR that would place one at each end of the processed HIV-1 RNA; this structure may also overlap with the "TAR" element" [23] (FIGS. 7 and 8 SEQ ID NO:13). In its 3' location, the adenine-rich potential SECIS motif also serves as the polyadenylation signal. Another SECIS element is in the U5 region of the LTR, and thus in a 5' untranslated region (FIG. 7, right) and two others are in or near the 3' untranslated U3 region (FIG. 9), in addition to the one in the 3' untranslated R region. Another is in the integrase coding region (FIG. 9A SEQ ID NO:14). Several of these have the entire UAAG SECIS motif observed in the mRNA of the cellular 5'-DI gene [14]. The HIV-1 SECIS-like elements are more complex in that several of them have one or more additional stems inserted as side arms off the main SECIS stem, and the one in the LTR repeat region may display the UGA codon on unpaired bases on the 3' loop of a pseudoknot 5' to the SECIS stem (FIGS. 8 and 9). This PK will be discussed later in the context of a potentially critical DNA sequence with which it is associated. These potential SECIS-like RNA structures (FIGS. 7–9) are exceptionally stable in some cases, as demonstrated by a comparison of their free energies to those of randomized sequences [16,24] generally giving probability levels of $10^{-2}$ to $10^{-3}$ or less. These results demonstrate that there are a number of RNA regions in HIV-1 which can function as SECIS elements, thus HIV-1 has the ability to insert selenocysteine at in-frame UGA codons.

Since only one SECIS structure is required in an mRNA for selenocysteine insertion, the existence of multiple potential SECIS elements in HIV-1 suggests that the RNA structure of the viral genome may be optimized to an exceptional degree for the efficient recruitment of selenocysteine tRNAs.

It is also of interest that the preferred cellular tRNA that is packaged in HIV-1 virions and used as a primer for RT is tRNA$^{Lys}$. In *Eschericia coli*, when Se is abundant, up to 50% of the pool of tRNA$^{Lys}$ molecules may contain the modified base 5-[(methylamino)-methyl]-2-selenouridine as the wobble base [25]. As is the case for selenocysteine, the Se in this unusual tRNA comes from the active reduced Se product of the selD protein [15]. Evidence for the existence of a similar modified tRNA$^{Lys}$ has been demonstrated in a mouse leukemia cell line [69]. If this is also true of human cells, it may be more than coincidental the HIV prefers to package a tRNA that can potentially contain Se.

Figure 10A:
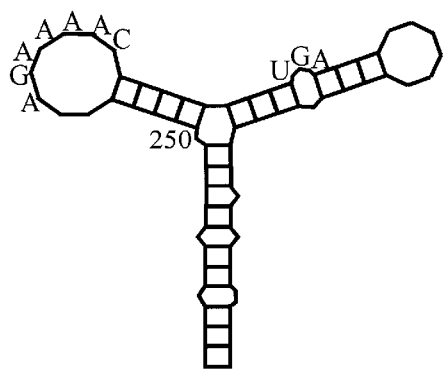
FIGS. 10A–10E provide predicted SECIS elements in other RNA viruses.
Figure 10B:
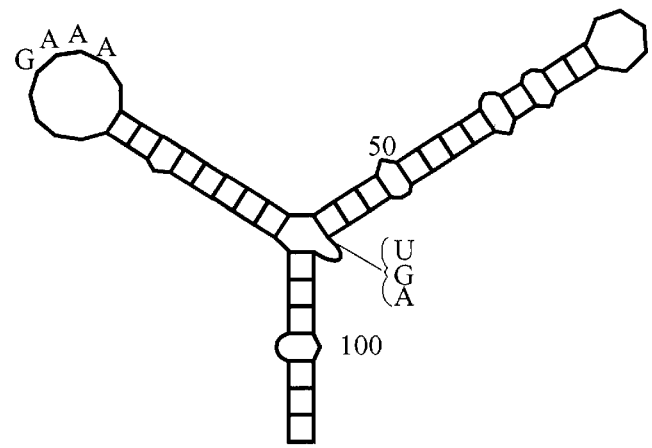
Figure 10C:
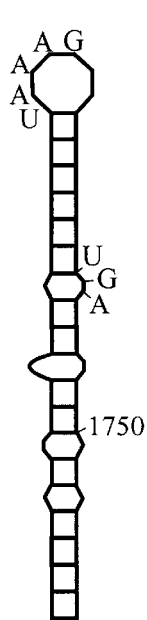
Figure 10D:
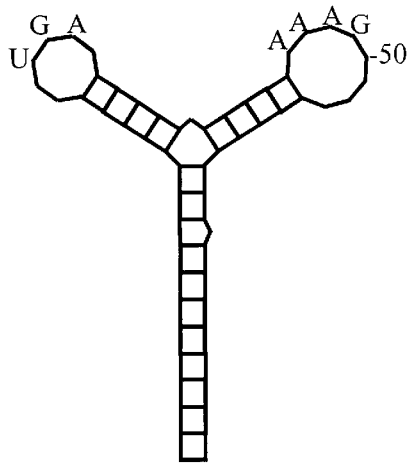
Figure 10E:
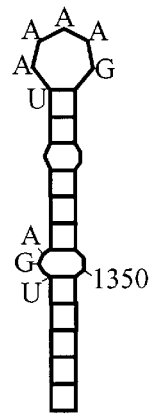

We have found SECIS-like elements in a number of other retroviruses, and in eukaryotic retrotransposons (e.g., Copia), suggesting the Se biochemistry has been used by retroelements throughout evolution and indeed is a hallmark of retroviruses. SECIS elements are also present in other non-retrovirus RNA viruses: picornaviruses including, but not limited to, polio and coxsackie viruses (FIGS. 10A and 10E), hepatitis B virus, which encodes a reverse transcriptase, and thus is a member of the retroid family.

A SeC-containing ORF has also been identified in Ebola virus strain Zaire RNA, where only one frameshift event is needed to translate the SeC-containing coding sequence as an in-frame fusion with the nucleoprotein, and there are several other SeC-containing ORFs as well. Without wishing to be bound by any particular theory, it is postulated that expression of the SeC-containing protein portion contributes to the virulence of the Zaire strain; this is consistent with the reduced virulence of the Reston strain of Ebola virus, which lacks the nucleoprotein-associated SeC-containing sequence. The present inventors have also identified potential SeC-containing ORFS in herpes viruses, Epstein-Barr virus and cytomegalovirus using the methods described herein. Selenoprotein coding sequences are also present in mammalian genes, including, but not limited to, human genes encoding interleukin 2 receptor (SEQ ID NO:39), CD4 (SEQ ID NO:22), CD8 (SEQ ID NO:23) and HLA-DR' (SEQ ID NO:24) (See also Table 9 herein).

Analysis of ORFs in HIV-1

We refer to our original analysis of the ORFs in HIV-1 in Taylor et al. (1994) supra. That reference included Table 1 which referred to potential fusion proteins in HIV-1. The following discussion adds to and modifies the information listed in Table 1 of the reference. Table 1 herein provides a partial summary of fusion protein products of expression from newly identified ORFs in HIV.

The systematic application of the method described herein to the HIV-1 genome has yielded a surprising number of locations where minor gene products, in some cases variants of known proteins, are encoded. The open reading frames of HIV are shown in FIG. 11. The potential frameshift sites and PK structures are shown in FIG. 12, and are discussed hereinbelow. The newly located genes and their corresponding proteins will be referred to by the parent gene regions which they overlap, named in FIG. 12, followed by fs for frameshift, e.g., pro fs for the fusion protein resulting from a frameshift at the indicated site in the protease coding region.

Realizing that the UGA codons in the −1 reading frames downstream from the pseudoknots could be sense codons for selenocysteine, we decoded the sequence for a potential fusion protein (Table 1), beginning as a gag-pol product but switching to the env reading frame (−1 to pol in HIV-1) shortly before the protease pseudoknot. A potential slippery sequence (AAAG GAA in the pol reading frame) was found immediately upstream from the base of the 5' stem of the pseudoknot; this is not an ideal heptameric slippery sequence, but it is as close to the ideal as the MMTV pro-pol heptameric sequence mentioned previously.

Although detailed mechanistic studies of gag-pol frameshifting have suggested slippage while two tRNAs are bound on the ribosome [9] we initially believed another possible scenario here was a frameshift based on slippage while a single lysine tRNA was bound, exploiting the A AAG portion of the slippery sequence listed above. Using this assumption, we predicted the amino acid sequence at the shift site as K/GSS, see Table 1. This assumption has been reconsidered and we now believe that a simultaneous slippage mechanism is active giving the predicted amino acid sequence at the shift site of KE/SS (See Table 1). The proposed shift sequence, the PK and the in-frame UGA codon in the PK region are highly conserved in HIV-1 groups B and D, but the shift sequence in particular has been lost and is clearly non-functional in the predominantly African HIV-1 groups A and O.

It has also been proposed that the role of pseudoknots in frameshifting may be more of an active one than has been previously thought [28], suggesting that the mechanism may not be extremely dependent upon optimally slippery sequences in all cases. Consistent with the nonideal heptameric sequence, this frameshift event is deliberately programmed to be less efficient than that at gag-pol, particularly if the gene product is involved in negative feedback of gene expression, as its similarity to various DNA binding proteins (see below) and the E2 papillomavirus DNA binding domain suggests (FIG. 8).

Searches of the entire PIR database using the complete 69 residue sequence of this hypothetical protease −1 frameshift fusion protein (up to the first non-UGA stop codon SEQ ID NO:26) as a probe produced the most significant hits on HIV and related retroviruses, due to the identity of the first 20 residues with HIV-1 protease. Among the next highest ranked hits are a nonstructural protein of unknown function from ainovirus (a Simbu serogroup bunyavirus; >8 SD), and a number of other viral proteins, a Drosophila gene suppressor and several transforming proteins, and the bovine papillomavirus E2 DNA binding protein, all at >5 SD. Numerous other DNA-binding proteins of various types, viral early proteins, and transcription factors are highly ranked (>4 SD).

Since the retroviral protease is known to cleave gag-pol gene products at a conserved protease cleavage site at the N-terminal of the protease domain after a moderate amount of protease had accumulated in the host cell, the primary product of this gag-pol-frameshift fusion protein would very likely be a product with approximately the first 20 of its N-terminal residues identical to protease, and the rest of its sequence corresponding to a 49 amino acid domain containing two selenocysteine residues (SEQ ID NO:26), the first of which is in a position that is highly conserved in the primate retroviruses (FIGS. 10A–10E).

This first selenocysteine can be aligned with the highly conserved cysteine of the papillomavirus E2 DNA binding domain [29] which is in the center of the DNA recognition helix. This selenocysteine is at the heart of the interaction of this DNA binding protein with its DNA target, which have recently been cocrystallized [30]. The predicted HIV-1 DNA binding protein conforms well to a multiple alignment of various E2 protein DNA-binding domain sequences (FIG. 8) and contains the most essential residues in the correct positions, assuming selenocysteine can substitute for cysteine. The essential tryptophan that is critical for dimerization of this domain [29,30] is correctly placed and is conserved in HIV-1 variants and in chimpanzee immunodeficiency virus (FIG. 8).

Consistent with the requirements for termination suppression of a UAA codon [Feng et al. [10], there is, at the end of the 69 residue region discussed above (SEQ ID NO:26), another pseudoknot (FIG. 16) immediately 3' to the UAA codon. With readthrough suppression, this gene product is extended another 32 amino acids (Table 1 SEQ ID NO:26; lower panel of FIG. 13), making it very close to the length of the aligned E2 DNA binding domains. While the most essential domains for DNA binding and the critical dimerization residues are contained within the upper panel of the alignment shown in FIG. 13, it is likely that maximal DNA binding activity would not be obtained without readthrough of this UAA codon. This is reasonable if the molecule functions primarily as a repressor, since it would be another check against overexpression, which is undesirable for a potent transcriptional regulator. Readthrough extension region also increases the significance scores of alignments to several other DNA binding proteins, for which pairwise sequence alignments at significance levels of 4 to 5 SD can be produced using the entire sequence of the hypothetical HIV-1 protease fusion protein. This, combined with the results of the database searches summarized above, and the fitting of the HIV sequence into the E2 protein multiple alignment, is compelling evidence that this gene encodes a DNA binding protein. As detailed in the legend to FIG. 14, in the putative DNA-recognition helix region, conservation of sequence in the −1 reading frame supports the conclusion that this is a real gene (also see FIG. 15).

Both retroviral proteases and E2-type DNA binding proteins function as dimers. The arrangement of these genes in HIV-1 is consistent with a common dimerization motif (the protease N-terminal region) being attached to two different functional domains (protease and DNA binding activities) encoded by the same nucleic acid sequence in two different reading frames.

An E2-like Dyad-symmetric Sequence at the Very 5' End of the HIV-1 Transcribed Region The papillomavirus E2 DNA binding proteins bind as dimers to a region in DNA with partial dyad symmetry, with the general consensus sequence ACCGNNNNCGGT (SEQ ID NO:61, where N can be any base [29,30]. In keeping with the E2 literature, this partial inverted repeat is termed a palindrome herein. The underlined bases are those that are invariantly conserved in E2 recognition sites for all papillomaviruses. Consistent with the similarity between the potential HIV DNA binding protein and E2 proteins, we have identified a thematically similar but distinct palindromic sequence in the HIV-1 LTR, having the sequence TGGTTAGACCA SEQ ID NO:62. Here, the symmetry is in TGGT pairing with ACCA, with a three-base spacer, as compared to ACCG with CGGT and a four-base spacer in the E2 sequence. In this HIV-1 palindrome, the G pair is at the 5' end, which is the reverse of the E2 sequence. Thus, the sequences are similar in general design but distinct in their details. The HIV-1 E2-like palindrome is located immediately downstream of the TATA box and proposed initiator protein binding site, at the +9 to +19 positions in the LTR, which is a perfect position to block an initiation complex. This region is also contained within the binding site spanned by the so-called leader binding protein, LBP-1, a cellular repressor of HIV expression that inhibits binding of the TATA binding protein [31]. Possible monomer binding versions of the sequence, ACCA or TGGT, are found in several locations in the LTR (around −305, −320, −360, and −400); without wishing to be bound by any particular theory, this is considered to be a negative regulatory region of the HIV-1 enhancer.

Its position in the repeat region of the LTR also places an RNA copy of this palindromic sequence in the TAR element [23,32] at the very 5' end of the HIV-1 RNA and near the 3' end. Consistent with the established pattern that critical or conserved sequences can be associated with helical RNA structures [16,17], this E2-like palindromic sequence in the HIV-1 LTR falls precisely on the stem of the TAR element in the viral RNA (FIG. 7), for which we have found an alternative conformation that is a potential pseudoknot (FIG. 8), which can display an unpaired UGA codon on its 3' loop. This serves as a binding site for the anticodon loops of selenocysteine tRNAs to interact with an unmistakable SECIS stem-loop structure just downstream from the pseudoknot (FIG. 8), since there is no other nearby potentially unpaired UGA codon. Since the Tat protein [23] is known to bind precisely to a bulge on the stem of the TAR element where this UGA codon is located, Tat may inhibit the formation of this pseudoknot, preventing the SECIS from functioning (FIG. 8). Since there may be protein factors that recognize and stabilize RNA pseudoknots, e.g., during frameshifting [28], there could be competition between Tat and any such protein factors. There is precedent for pseudoknots being involved in switching between conformational states as a regulatory mechanism [19].

Given the association between codons for highly conserved sequence motifs and pseudoknots (FIGS. 3A–3C and 5), it is significant that this HIV-1 E2-like sequence also falls precisely on a potential pseudoknot (FIG. 12A). Without wishing to be bound by any particular theory, it is postulated that this is a DNA binding site for a virally encoded protein, or a cellular factor.

Finally, although among viruses this palindromic sequence is quite unique to HIV and its close relatives (where it is usually not precisely identical and is found in varied locations), it is also found in noncoding (intron) regions of several human cytokine-related genes, including the tumor necrosis factor (TNF) receptor gene. Without wishing to be bound by any particular theory, it is postulated that this is a recognition sequence for a virally encoded repressor and that HIV is attempting to resist simulation by cytokines like TNF and to modulate its own expression.

A Conserved Selenoprotein Can Be Expressed as a Reverse Transcriptase -1 Frameshift Fusion Protein Like the pseudoknot in the protease region, the PK at the RT active site coding region (FIG. 4) also has the potential to direct a frameshift and the synthesis of a fusion protein. The best candidate slippery sequence is A AAA CAA in the pol reading frame, which is about 15 bases before the 5' stem of the pseudoknot, although it is not an ideal heptamer. The fusion protein (Table 1) is by necessity a structural analog of RT, identical up to the end of the first major helix of the RT palm domain (helix E) [33], but with the active site YMDD β-hairpin region replaced by a selenocysteine containing module.

As shown in Table 7, this selenocysteine codon is highly conserved in primate retroviruses, indicating this is an expressed gene. The U of the UGA codon is the third position of an Asp codon in the pol reading frame, which, particularly given the high mutation rate of retroviruses, should be a mixture of GAC and GAU (the two possibilities for Asp in the genetic code) if there were no evolutionary selection for U instead of C in the third position. By comparison, the third position of the second Asp codon immediately following is an even mixture of U and C (see the last column of the alignment). Clearly, what is conserved in the UGA codon in the first case is the UGA codon in the −1 reading frame, and possible some structural feature in the RNA.

If the only criterion for evolutionary selection is a requirement for conservation of the Asp of the RT sequence in the pol reading frame, assuming a 50% chance of finding either U or C at this position, the probability of the distribution observed in FIG. 11 arising by chance (U in 33 of 34 sequences) is less than $10^{-8}$. Thus, there is selection based either upon a stringent requirement for RNA secondary structure, or a requirement for conservation of the sequence in the −1 reading frame (the +1 reading frame is ruled out since it has a high density of stop codons in this region). These two factors are interrelated because a protein sequence in the −1 reading frame could not be conserved unless an RNA structure is present to facilitate the frameshift necessary for the expression of that protein.

Although both a UGA codon and an RNA secondary structure are conserved, the UGA codon is more highly conserved than the structure. As discussed previously, the details of the stem-loop or pseudoknot structure found in this location for various retroviruses are highly variable, with those in FIG. 5 being only a closely related sample. When a large set of sequences are compared (Table 7), the A base that pairs with the U of UGA in the HIV-1 RT pseudoknot, which is the first base in the alignment (indicated by an asterisk), is not as well-conserved as the U; this is consistent with the previously mentioned diversity of RNA structures associated with this region of the RT gene. The observation that bases in other positions may pair with the U in various other retroviruses shows that it is the RNA structure that is shifting to accommodate the unchanging UGA codon, and not vice versa. In some structures, e.g., HTLV-2 and BIV (not shown), the U of UGA pairs with a G; in such cases, the stability of the structure would actually be enhanced by a transition of the U to a C, and yet that is almost never observed. In the one case where a CGA is observed rather than a UGA (in SIVagm2, FIGS. 3A–3C), there appears to be a compensatory mutation: slightly downstream from the CGA, an AGA codon seen in other SIVagm variants has mutated to a UGA codon in SIVagm2, potentially encoding a SeC residue eight residues downstream of the CGA codon.

In regard to the conserved UGA codons in the protease fusion protein (FIG. 6), the UGA is not in a stem in a majority of the structures examined. It is on the 3' loop of the HIV-1 and CIV protease pseudoknots (FIG. 3A–3C). Thus, conservation of RNA secondary structure does not explain the conserved UGA codons in the case of the protease fusion protein. On the basis of these considerations and the conservation of the ORFs associated with these genes, the conservation of the UGA codons indicates these are expressed genes and the UGA codons are critical for the encoded proteins.

Database searches using only the −1 frameshift portion of the potential RT fusion protein did not yield an unequivocal picture, as there was not outstanding match to a unique class of proteins. However, there were a number of highly ranked matches to different actual and hypothetical viral proteins, including the most significant match (cytomegalovirus hypothetical UL63 protein, >6 SD), and a protein from vaccinia virus (4.5 SD) that appears to be a thymidine kinase (TK), based on its sequence similarity to other viral kinases. There were matches to several other types of kinases at >3.5 SD and to other ATP utilizing enzymes. Using the entire potential RT fusion protein as a probe, and eliminating hits on RT and viral pol gene sequences (obtained since the N-terminal is identical to HIV-1 RT), several viral TKs were ranked in the top 15 hits (out of >64,000 protein sequences; 4.4 SD).

As with the DNA binding protein discussed above, extension of the product by readthrough suppression, in this case of a UAG stop codon, is indicated by the existence of a potential pseudoknot that was found in the immediate region of the stop codon (FIG. 12C). Addition of this region also gave improved scores (relative to the terminated fusion protein) in pairwise alignments with several TK sequences.

The results are also discussed in terms of the degree to which the various shift sequences and potential PK structures are conserved in the different phylogenetic groupings of HIV-1 sequences established by the analyses of Myers and coworkers, and available online from the Los Alamos HIV sequence database [103]. In particular, we will focus on four groups for which the long terminal repeat (LTR) and pol regions have been aligned: groups A, B, D and O. Of these, group B is by far the largest, and contains essentially all North American and most European isolates, as well as South American and Asian strains. Groups A, D and O are composed almost exclusively of HIV-1 strains from Central and West Africa; of these, the consensus of group D is more similar to group B than that of the other African groups. Most of the potential new genes described here are highly conserved in HIV groups B and D.

A number of primate retroviruses have an ideal or near-ideal −1 shift sequence followed by an RNA structure in the gag coding region, about 800 bases upstream from the known gag-pol frameshift site, which is also shown in Table 4. In HIV-1, the heptameric shift sequence for this novel gag fs is ideal (U UUA AAU). A potential PK with an asymmetric bulge in its 5' stem begins 3 nucleotides after the shift site. The predicted amino acid sequence at the shift site in LN/CM, and the hypothetical protein extends another 58 amino acids, if one counts a UGA codon as a sense codon (the seventh from the C-terminal). The −1 shift sequence and PK are highly conserved in group B, and fairly well in all the other HIV-1 strains except group A, where only about half of the sequences have these features intact.

This heptameric shift sequence is non-ideal (A AAG GAA), but it still permits 2 out of 3 correct base pairs in both shifted P- and A-site tRNAs. It is followed immediately by the potential PK shown in FIG. 2B and schematically as a dot plot in FIGS. 1A and 1B. Assuming a simultaneous slippage mechanism, the predicted amino acid sequence at the shift site is KE/SS. The shift sequence, the PK and the in-frame UGA codon in the PK region are highly conserved in HIV-1 groups B and D, but the shift sequence in particular has been lost and is clearly non-functional in the predominantly African HIV-1 groups A and O.

This pro fs gene product is predicted to be very basic, with a calculated pI of about 11, consistent with a nuclear protein encoding a regulatory DNA binding protein.

The existence of an RT variant, rt1 fs, is indicated by the presence of an ideal heptameric shift sequence (A AAA AAG) just before the RT motif A region. This heptamer is followed by a potential PK at a near-optimal distance of 6 bases. Following an in-frame UGA codon, there is a putative +1 frameshift signal, CUUAGA, which is almost identical to the known Ty retrotransposon +1 shift sequences, except that the second, "hungry" codon is AGA (R) instead of AGG (R) or AGU (S). Significantly, an identical potential +1 frameshift sequence is found following the highly conserved UGA codon in the RT motif C region (rt2 fs in Table 4). For rt1 fs, the predicted amino acid sequence at the −1 shift site is KK/EK, and at the +1 shift site is SL/D. The shift sites, the PK and the in-frame UGA codon are highly conserved in HIV-1 groups B and D. This combination of a −1 followed by a +1 shift replaces the RT motif A region and its highly conserved catalytic Asp with an alternate module having a conserved SeC residue, while retaining the rest of the RT structure.

Another RT variant, rt2 fs, has a non-ideal heptameric shift sequence (A AAU CCA), which is followed by the potential PK overlapping the RT motif C (YMDD SEQ ID NO:5) region (FIG. 2C), at a near-optimal distance of 5 bases. This predicted −1 shift site is two codons downstream from the site suggested previously [hereinabove and 1]; this site has better slip potential and is closer to the PK. There is +1 shift potential of the CUUAGN sequence [95]. As seen with rt1 fs, following the in-frame UGA codons, there is a potential Ty-like +1 shift sequence, CUUAGA. The potential PK (see FIG. 12C) involved in termination suppression of an amber codon at the 3' end of this −1 ORF may also serve to facilitate the +1 frameshift, since it comes exactly 7 nucleotides (the optimal distance) after the CUUAGA sequence. The (revised) predicted amino acid sequence up to and after the −1 shift site is PFRKQNP/RH SEQ ID NO:63; at the +1 shift site it is potentially UL/E (U=SeC in protein code), although since this second UGA codon is immediately followed by a C nucleotide, it may also mediate for opal suppression with insertion of Trp or another amino acid [100]. These shift sites, the PK and the in-frame UGA codons, are highly conserved in HIV-1 groups B and D. As with rt1 fs, these opposed frameshifts are programmed to replace part of the RT active site region (here, the YMDD motif and its catalytic Asp residues) with an SeC-containing module. Because SeC is a significantly acidic amino acid, this substitution is consistent with a biochemical function that is similar or related to that of RT itself.

The potential integrase variant, int fs, was reported previously [1]; the only additional comments to be made here relate to the potential −1 shift sequence. Although the proposed heptamer (A GGA AAA) is not ideal, there is experimental precedent for the involvement of this type of sequence in frameshifting. In a mutational study, Brierley et al. [92] showed that the sequence A GGA AAC had a 1.3% frameshift efficiency in the coronavirus system. The proposed int fs shift sequence is significantly better than that because the potential PK begins 6 nucleotides after the heptamer, which is close to the optimal distance for facilitating a frameshift.

The sequence at the frameshift site is predicted to be GK/ST discussed above; we also discussed suppression of an ochre stop codon at the 3' end of this ORF [1]. This int fs gene (shift site, PK and ORF) is very well conserved in HIV-1 sequence groups B and D, but not in the A and O groups.

This potential env associated frameshift and the sequence at the frameshift site (EK/KS) predicted based on a single tRNA slippage model are described hereinabove and in [1]. The complete −1 shift sequence proposed here (A AAA AGA) involves the same potential hungry Lys codon (AGA) as the putative +1 frameshift sequence (CUUAGA) found near the 3' end of the two rt fs ORFs (FIG. 4). Thus, the single tRNA P-site slippage model seems appropriate in this case [101]. The −1 shift sequence is conserved in all HIV-1 strains. The PK and the in-frame UGA codon are well conserved in HIV-1 groups A, B and D, but in group A the UGA has changed to an Arg codon. The "shifted" gene is believed inactive in group O.

It may be significant that this env fs ORF, which is −1 to the gp41 coding region of env, corresponds precisely to a genomic region that Kubota et al. recently suggested was acquired by HIV from a cellular gene, along with the second coding exon of rev, because there is a base composition different from the rest of the HIV genome [104]. This region of env contains the RNA structure known as the Rev responsive element (RRE), to which the Rev regulatory protein binds.

In addition to the presence of the readthrough of the UGA codon at the 3' end of nef, there is a nef variant expressed by successive −1 and +1 frameshifts, as described above for the rt1 fs and rt2 fs ORFs. The −1 shift sequence is an ideal heptamer (U UUA AAA), followed by a PK at a near-optimal distance of 6 bases. Downstream from an in-frame UGA codon, there is a known +1 frameshift signal, CCUGA [94]. The predicted amino acid sequence at the −1 shift site is LK/RK, and at the +1 shift site LP/DW. The +1 and −1 frameshift sequences, the PK and the in-frame UGA codon are very highly conserved in all four of the major HIV-1 groups examined (all those for which pol and LTR sequence data is also available). Only three HIV sequences out of all the strains in groups A, B, D and O show signs of losing parts of the required sequences, and of those only one strain (HIVMVP5180) has unambiguously lost all potential to express this nef variant.

This region of nef has the two best conserved UGA codons in HIV-1, even more highly conserved that the UGA codon −1 to the YMDD (SEQ ID NO:5) region of RT. The first is the in-frame UGA codon in the nef PK region (FIG. 12), at position 8719, and the second is the UGA codon in the CCUGA +1 frameshift sequence, at position 8755. In both cases, there are only 2 isolates of HIV-1 in groups A, B, D and O in which the UGA is not conserved. Since this region of nef does not overlap with any other known genes, the conservation of these two UGA codons is difficult to explain unless this region of the −1 reading frame is within a real coding sequence or there is some other functional role of the UGA codon. The two UGA codons overlap with nef codons LeuAsp (CU<u>UGA</u>U) and ProAsp (CC<u>UGA</u>Y) respectively. Because of the degeneracy of the genetic code, both Leu (CUN) and PRO (CCN) permit any of the 4 bases in the third position. Thus, the conservation (in both of these cases) of a U in that position in 35 of the 37 isolates by chance alone is wildly improbable, particularly in the light of "A pressure", the tendency of the HIV-1 RT to insert A at a higher frequency than other nucleotides, leading to the high A content of the HIV genome (36%). These are not isolated observations: a higher degree of sequence conservation in the third position of nef codons is seen throughout the entire region of nef shown in Table 4, as compared to the region preceding the −1 frameshift.

Regarding the termination of nef in a UGA codon, we discussed previously the readthrough extension of the nef protein by 33 amino acids if SeC is inserted at this codon. Another alternative that could yield a similar result is the possibility of a readthrough with insertion of Trp [100], possibly competing with SeC insertion as well as termination.

Figure 1B:
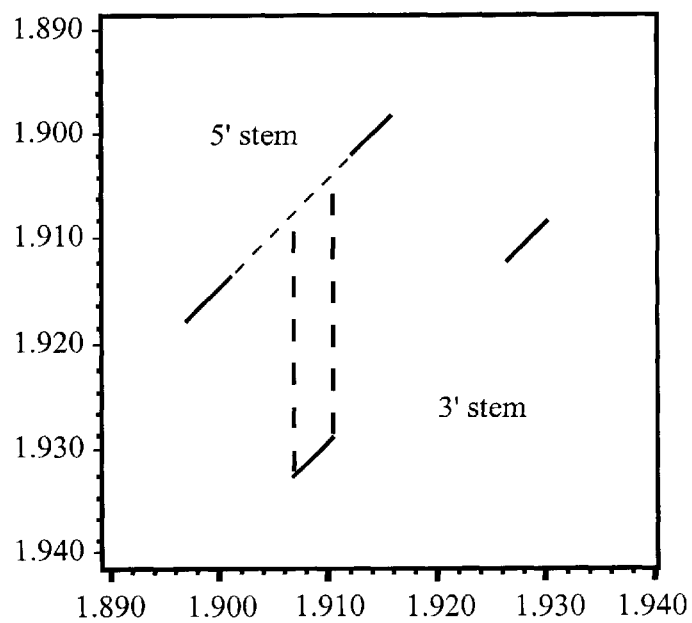

There is a well conserved ORF, contained entirely within the 3'-LTR, −1 to the nef ORF, at the very 3' end of the HIV-1 and HIV-2 genomes (clearly visible in FIGS. 1A and 1B in reference [105]). There are several in-frame UGA codons at the 5' end of this ORF in HIV-1. Comparative sequence analysis with the predicted encoded protein (using FastDB as described previously) revealed a highly significant similarity to the third exon (second coding exon) of HIV-1 Rev protein (significance=5.5 SD< with the Rev match in the top 21 hits out of >70,000 in the PIR database). Although there is some potential for this ORF to be expressed by a −1 frameshift from nef, there are no appropriately placed "ideal" heptameric frameshift sequences.

The possibility that a novel splice acceptor (SA) site might permit the use of this region as an alternate second coding exon of rev was examined. The following candidate SA sequences were found in the nef coding region (compared here to some known SA sites in HIV-1; the actual splice site is shown by G|A, and the number refers to the position of the G):

3' end of intron 1 (5358): AUCCAUUUCAG|A (SEQ ID NO:64)

3' end of intron 2 (7971): AUCG.UUUCAG|A (SEQ ID NO:65)

4a (rev) splice site (5335): ACAA.CAAAAG|A (SEQ ID NO:66)

4a rev site in NL4-3 strain: AUGA.CAAAAG|A (SEQ ID NO:67)

possible new site 1 (8922): AUGACCCUGAG|A (SEQ ID NO:68)

possible new site 2 (8869): AUAAAGGAGAG|A (SEQ ID NO:69)

The rare HIV-1 subtype O (with only two isolates) is clearly unique in regard to this nef frameshift fusion protein overlapping reading frame, because upstream from the first UGA in the −1 frame, it has a UAA stop codon not found in other subtypes, and the UGA has mutated to GGA (Gly).

Excluding the two type O isolates, the first in-frame UGA codon in the overlapping −1 reading frame is present in all but 2 of the remaining 74 nef sequences in the Los Alamos HIV-1 sequence database (one of which has mutated to an AGA (Arg) codon, one to a UAA stop codon). This is remarkable in light of the fact that if only the nef gene in the zero frame is considered, there is no reason for the U of the UGA to be conserved, because the U is the last base of a leucine codon in nef, and due to the degeneracy of the genetic code, any of the four bases should be permitted in that position (FIG. 6). Because of properties inherent in the transcriptional infidelity of reverse transcriptase, the HIV genome also tends toward a high A content ("A pressure"), so in a large set of divergent HIV-1 sequences one would expect to see a high frequency of A bases in the third position of leucine codons, in the absence of overlapping genes.

As detailed in the description of FIG. 7, the same argument applies to the well conserved potential −1 frameshift sequence CCCUGA located slightly downstream. This second UGA is conserved in all but 3 isolates, where it has mutated to an Arg codon, which might still permit it to function as part of a +1 frameshift signal via a hungry codon mechanism.

The extent of conservation of these sequences is essentially identical to the degree of conservation of the nef ORF itself within this set of sequences, i.e. in 3 of 78 HIV-1 related sequences in the database, the zero frame nef ORF is truncated due to premature termination at a stop codon in the middle of the frame (this includes the original HTLV-III sequence first reported by Gallo and coworkers, also called BH10). This may reflect the selective pressure to maintain the nef gene being greater in vivo than in cell culture. Thus, we can fairly say that the sequence and structural features related to this predicted nef fs gene (−1 frameshift signa, UGA and CCCUGA) are as well conserved within this set of HIV-1 sequences as the nef ORF itself.

In summary, the highly conserved UGA codon and CCCUGA sequence in the −1 frame, downstream of an "ideal" heptameric shift and fairly large PK, supports the newly identified selenoprotein module overlapping the nef gene. Simple termination selenocysteine insertion, or opal suppression can occur at this conserved UGA codon. In fact all three possibilities could occur depending upon intracellular conditions, such as the relative abundance of $tRNA_{Sec}$, opal suppressor tRNAs, and release factor.

As an alternative SA for the 3' end of the first coding exon of rev, either of these candidate sites would bring the novel ORF in-frame with the N-terminal coding exon of rev, creating different but related forms of the Rev protein. One essential feature required for these to be functional SA sites is present: there is an upstream potential lariat-forming "CURAY" sequence, CUGAC at 8798, or possibly the (nonideal) CCAAU at 8856. While the potential SA sequence in both of the proposed new sites (GAGA) deviates from the usual SA consensus sequence (CAGA or TAGA), it must be remembered that in HIV-1, the two major splice donor sites (TGGT and CAGT) also differ from the usual donor consensus (AGGT) by a Y/R substitution. In addition, many alternative SA sites in HIV, including the rev sites shown above, have AAGA, demonstrating the precedent for a purine in the position before the highly conserved AG. In both of these sites, the critical AGA is well conserved, an Arg codon in nef; however, of the two, the site #1 AGA is the most conserved. Neither of these potential sites is exceptionally rich in pyrimidines, although there is a very pyrimidine rich sequence from 8872 to 8890, located about 20 nucleotides before site #1 shown above. This is in contrast to many of the known HIV-1 splice acceptor sites, where a pyrimidine rich sequence immediately precedes the region shown. Whether these deviations from the ideal SA consensus could relate to efficiency of splicing (possibly required to be low in this case), or whether this ORF with similarity to rev is expressed at all, remains to be determined.

The placement of the coding regions of rev in different exons can relate to alternative splicing if is used to create two different versions of the protein. Significantly, if SA #1 were used, the proposed alternate C-terminal exon would have an in-frame UGA codon that aligns with an Arg codon in rev. If SA #2 were used, the C-terminal exon would be slightly extended at its 5' end, so that there would be three in-frame UGA codons, all of which align with Arg codons in rev. However, it is possible that this rev2' ORF is not functionally significant, but is merely a vestige of a past duplication within the primate retroviral genome, such as that proposed for the vpx and vpr genes of HIV-2 [106].

The HIV_Nef1 gene product has significant homolgy to various CC, CXC and C type chemokines. See Table 11 for a sequence comparison. In the table, the HIV_Nef1 product (beginning at an internal methionine at position 79) is allignment to various CXC, CC and C type chemokines. UGA codons in HIV_Nef1 are indicated by lower case C. Two of these line up with essential Cys codons of the chemokines at positions indicated by *. Matches to any of the chemokine sequences are shown at the bottom, with identities in letters, similar residues shown by a + and dissimilar or nonconserved residues indicated by a − symbol. The degree of homology to chemokines indicates that the Nef fusion product (at least where UGA encodes SeC or Cys) can function as a chemokine blocking HIV attachment. HIV is now known to use several chemokine receptors (Fusin and CC CKR5) as receptors, in addition to CD4. Chemokines Rantes, Mip1-alpha, and the like are known to block HIV attachment.

Other expression products of new HIV ORFs are disclosed in Table 1. The HIV sequences provided in Table 1 are derived from analysis of the HIV-1 BRU (GenBank #k02013) strain. Similar HIV ORFs to those specifically described in Table 1 are found in other strains of HIV in analogous regions of the coding sequence. Strains other than BRU may have variant coding sequence encoding amino acid sequence somewhat different from those provided in Table 1. Such sequence variants, having variations in ORF sequence of expressed ORF product sequence based on HIV strain differences, are encompassed within this invention.

Analysis of Other Virus Sequences

Coxsackie viruses have been implicated as a probable cofactor in Keshan disease, a classical Se-deficiency disease. Beck et al. have shown that a deficiency of either vitamin E or Se significantly increases the cardiovirulence of CVB3 [107, 108]. We have analyzed the Coxsackie virus CVB3/20 genome for the presence of novel SeC encoding ORFs analogous to those described in HIV, and also for the presence of potential SECIS elements. Two such potential selenoprotein genes are described herein (Table 1). The following ideal heptameric slippery sequence and potential PK are found at the beginning of the VPG coding region of CVB3:

This ORF contains 5 in-frame UGA codons and 5 Cys codons. The potential −1 frameshift (predicted sequence FG/SR) is located immediately following the first two N-terminal amino acids of the VPG protein, which begins with the GF immediately preceding the predicted frameshift. This allows use of the same protease cleavage site to cleave both VPG and this predicted selenoprotein from the polyprotein. Thus the mature selenoprotein, beginning with GFSR, is predicted to contain 122 amino acids. This ORF overlaps the VPG gene and much of the p3-c protease of CVB3.

By translation of CVB3 in all three reading frames using our modified translation table, a selenoprotein coding sequence was found encoded between bases 3442 and 3749 (see Table 1). This ORF has 8 in-frame UGA codons, as well as 8 Cys codons. The predicted protein has a strong similarity to a whole family of proteins that contain epidermal growth factor (EGF) modules, which are commonly found in various cell matrix and cell adhesion proteins [109]. At least 3 other viruses are known to encode EGF homologues [110]. The only known gene with so many in-frame UGA codons is that encoding mammalian selenoprotein P, which has 10 [111]. A region of selenoprotein P also has a strong similarity to a common module of cell matrix and adhesion molecules: the beta chain of integrins and leukocyte adhesion proteins. Such a high density of UGA codons requires an efficient SeC insertion mechanism, and a potential SECIS is located in CVB3 in a region just downstream of (3' to) this ORF.

Analysis of Hemorrhagic Fever Viruses

Hemorrhagic manifestations are the main pathophysiological features of all hemorrhagic fever diseases. The viruses causing hemorrhagic fevers in humans belong to the following groups: togavirus (Chikungunya), flavivirus (Dengue, Yellow fever, Kyansanu forest disease, Omsk Hemorrhagic fever), arenavirus (Argentinean hemorrhagic fever, Bolivian hemorrhagic fever, Lassa fever), filovirus (Ebola, Marburg), phlebovirus (Rift Valley fever), nairovirus (Crimian-Congo Hemorrhagic fever) and hantavirus (Hemorrhagic fever with renal syndrome, nephropathic epidemia). Filovirus infections have several pathological features common with other severe viral hemorrhagic fevers. Among these viruses, filoviruses cause one of the highest fatality rates and the most severe hemorrhagic manifestations. The pathophysiological events that make the filovirus infections of humans so devastating are still obscure. The viruses are pantropic, but no single organ shows sufficient damage to account for either the onset of the severe shock syndrome or the bleeding conditions. Ebola virus (Zaire strain), the most lethal filovirus, is analyzed herein.

Hemorrhage can occur by several mechanisms, which may be interrelated. One is the dysfunction and damage of endothelial cells, which form the inner surface of blood vessels and play a role in the regulation of blood pressure homeostasis, and antithrombogenicity. Endothelial cell lysis is observed in the development of shock lung syndrome often associated with disseminated intravascular coagulation (DIC). Marburg virus replicates in endothelial cells, but there is no direct experimental evidence which links the hemorrhagic manifestations to the virally induced damage to the endothelial cells. Hantaan virus has also been shown to replicate in endothelial cells. Another mechanism in hemorrhagic conditions is induced by complement activation; extensive complement activation precedes onset of shock in Dengue patients.

Another fundamental mechanism in the production of DIC is via the formation of blood clots. The severe hemorrhaging produced by Ebola virus is essentially due to the formation of blood clots, which leads to the obstruction and rupture of small blood capillaries. Thus, the hemorrhagic symptoms may be a consequence of clot formation.

Selenium enhances glutathione peroxidase activity and prostacyclin release in cultured human endothelial cells, cell types implicated in the pathogenesis of some hemorrhagic fevers. There is an increased Prostacyclin 12 (PG12) production with selenium supplementation, whereas there is decreased aortic synthesis of prostacyclin-like compounds in selenium deficient rats. An increase in thromboxane (TXA2) synthesis by rat lung neutrophils was observed during selenium deficiency. Increased bleeding time resulting from selenium supplementation has been observed owing to the increased GSH-Px activity, favoring PG12 over TXA2 formation. In humans, selenium supplementation inhibited in vitro and in vivo production of TXA2 whereas PG12 synthesis was unaffected. Clearly, the net effect of selenium supplementation is an increased PG12/TXA2 ratio, which inhibits clot formation. Thus, one expects selenium to reduce DIC and associated hemorrhagic symptoms. Conversely, virally induced selenium depletion favors hemorrhagic conditions.

Without wishing to be bound by any particular theory, we propose that selenium is involved in the hemorrhagic manifestations in certain viral diseases. Hou and coworkers treated victims of an Asian outbreak of viral hemorrhagic fever with high-dose oral sodium selenite, obtaining dramatic reductions in mortality [Hou et al. (1993) *Zhangua Yiue Zashi.* 73:645–646]. While Hou et al. focused on complement activation as a probable mechanism of action, the possibility that this treatment also helped to counter a virally-induced selenium depletion merits consideration in the light of the viral selenoprotein theory and our recent demonstration of UGA-rich potential protein coding regions (PPCRs) in Ebola virus [Taylor et al. (1996) *J. Orthomolecular Med.* 10:131–138].

There are at least two mechanisms by which selenium might be incorporated into viral proteins; non-specific selenoprotein formation associated with random translational slippage into UGA-rich overlapping reading frames and specific virally encoded selenoproteins biosynthesized under the direction of RNA stem-loop structures.

Viruses are known to frameshift randomly at low frequency, leading to erroneous translational slippage into other frames. Instead of a random distribution of stop codons, Rima noted a bias in the distribution of stop codons in RNA viruses. In paramyxoviruses, there are up to three times the expected number of UGA codons in −1 frame, and up to 1.5 times the expected number of UAG codons in the +1 frame in some genes [Rima, B. K. (1996) *Biochem. Soc. Trans.* 24:1–13]. The present inventors have noted a bias in favor of UGA codons in the overlapping reading frames, particularly the −1 frame, exemplified here in the analyses of rabbit hemorrhagic disease virus, Hantaan virus, and Ebola (FIGS. 21A–21B and 22). With random slippage even though the virus is not programmable to make selenoproteins, it is possible that under specific conditions, probably related to the severity of the infection, this process might lead to a non-specific depletion of selenium in the host.

Alternatively, we find that in some cases UGA-rich overlapping reading frames are associated with potential −1 frameshift sites, including potential RNA pseudoknots that are typically required for the enhancement of frameshifting efficiency [Wyatt and Tinico (1993) in *The RNA World*, R. F. Gesteland, and J. Atkins, Eds., Cold Spring Harbor, pp. 465–496]. This supports programmed synthesis of specific selenoproteins in such cases, which would require a SeC insertion element, an RNA stem-loop structure, somewhere in the viral mRNA [Berry and Larsen (1993) *Biochem. Soc. Trans.* 21:827–32]. Selenoproteins are formed by the translation of UGA as SeC, rather than its normal role as a stop codon.

Predicted selenoproteins are encoded in regions overlapping known genes in HIV-1, coxsackievirus B3, and Ebola virus [Taylor and Ramanathan (1996) *J. Orthomolecular Medicine.* 10:131–138; Taylor et al. (1994) *J Med Chem.* 37:2637–2654; Taylor et al. (1995) *Antiviral Res.* 26:A271–86; Taylor et al. *Computational Medicine, Public Health and Biotechnology: Building a Man in the Machine.* Proceedings of the First World Congress, Austin, Tex. M. Witten, Ed. World Scientific, London. Part 1, pp. 1996].

When candidate selenoprotein or other genes are identified, the hypothetical protein sequence can be compared to known sequences in a protein database to find homologous known proteins. The database search can be done using a program such as FASTA, e.g. as implemented in the GCG software package (Program Manual for the Wisconsin Package, Ver. 8, September 1994, Genetics Computer Group, 575 Science Drive, Madison, Wis. 53711).

Analysis of the Ebola sequence by the methods provided herein revealed two predicted selenoproteins in the −1 reading frame overlapping the major nucleoprotein NP gene, containing 17 and 11 UGA codons, respectively (FIG. 22).

The first PPCR is believed expressed by a ribosomal frameshift from the NP coding region, due to the presence of an "ideal" heptameric shift sequence (UUUCCCU, at site A in FIG. 22), and an RNA PK 8 bases downstream (FIG. 23A). Slippage on a run of Cs has been shown in measles virus [Rima, B. K. (1996) Soc.Trans. 24:1–13]. This frameshift site A comes near the beginning of the predicted selenoprotein, and could permit the formation of a fusion protein consisting of the N-terminal 314 residues of NP fused to a 181 residue C-terminal module potentially containing 16 SeC residues, encoded in the −1 frame (bases 1411 to 1953 in GenBank #L11365; subsequent numbering refers to the same sequence).

Downstream from the first site, there is a second near-ideal frameshift site (FIG. 22B) and potential PK, also in the NP coding region beginning at position 1582 (FIG. 23B SEQ ID NO:45). This second site follows the sixth UGA codon in the PPCR, so a frameshift here yields a potential selenoprotein with only 11 SeC residues. These redundant frameshift sites could provide for either an increased probability of translation or alternate forms of the NP fusion protein.

Significantly, a pyrimidine base following a UGA codon (i.e. UGAY) favors readthrough (e.g. by SeC insertion), whereas a purine base following a UGA codon (UGAR) favors its function as a stop codon [McCaughan et al.]. Of the 17 UGA codons in PPCR1, all except for three near the 5' end are followed by a pyrimidine. All 11 of the UGAs downstream of potential frameshift site B are UGAY, strongly supporting the prediction that this is an expressed selenoprotein coding sequence. The presence of a purine following a UGA does not rule out efficient translation as SeC, because in some cases the requirement for a specific amino acid in the protein necessitates a purine in this position, e.g. in glutathione peroxidases, where there is a UGAG because Gly follows SeC in the protein.

Encoded between bases 2212 and 2598, there is a second UGA-rich predicted selenoprotein coding sequence overlapping the Ebola NP gene. It has 11 UGA codons over 129 residues (FIG. 22). It lacks a start codon but could be expressed from an edited or spliced RNA. RNA editing is the more likely possibility in this case, because RNA editing is known to occur in at least one location in Ebola virus [Sanchez et al. Nat. Acad. Sci., U.S.A. 93:3602–3607]. Because there are no reports of Ebola replication and transcription in the nuclei of infected cells, RNA splicing seems improbable in Ebola. However, there is precedent for nuclear replication/transcription and RNA splicing in a negative, non-segmented, single stranded RNA virus, [Borna disease virus, Cubit et al. (1994) Virus Res. 34:69–79]. There is a potential splice acceptor site very near the beginning of PPCR2, consisting of a CAGA sequence preceded by a pyrimidine rich sequence and an upstream "CURAY" sequence (CUGAC). There are various potential splice donors in the large NP mRNA that could bring this region in-frame to the main NP PPCR or the upstream selenoprotein PPCR with 16 UGAs. Thus, we cannot rule out the possibility that nuclear transcription and splicing of this Ebola mRNA could occur under special circumstances, possibly in the as yet unknown "reservoir" species that is the natural host for Ebola virus.

Table 10 provides the sequences of fusion proteins variants in the Ebola Zaire nucleoprotein (NP region: Ebola _NP1 (SEQ ID NO:164) and Ebola _NP2 (SEQ ID NO:165). Analysis of ORFs in Ebola Zaire have been provided in E. W. Taylor and C. S. Ramanathan (1996) Orthomolecular Medicine 10:131–136, which is incorporated by reference in its entirety herein.

While the PPCRs overlapping the Ebola NP gene are the most striking due to their high content of UGA codons, the analysis revealed several additional predicted selenoprotein PPCRs overlapping other genes, including the vp24, vp30, vp35 and vp40 coding regions, all of which have SeC insertion sequences in their mRNAs (shown for vp30 and vp 335 in FIG. 22). Furthermore, on the Ebola minus strand genomic RNA, there are also potential SeC insertion sequences and several UGA-rich PPCRs (with up to 9 UGAs), some with start codons in the context of Kozak-like sequences, and some potentially expressed from spliced genomic RNAs. Without wishing to be bound by theory, we predict none of the PPCRs on the minus strand are functional, but expression of a protein encoded in a minus strand ORF has been proven in the case of HIV-1 [Michael et al. (1994) J. Virol. 68:979–987].

We have identified a number of genomic regions having the SECIS consensus sequence features as well as the potential to form the necessary RNA stem-loop structures (FIG. 23). Of these, only candidate SECIS A has been tested; it does not direct SeC insertion at a UGA codon in the human deiodinase gene.

Pathogenicity and Potential Selenoproteins in Ebola

One argument for the role of these overlapping UGA-rich PPCRs in pathogenicity in humans involves differences between the Ebola Zaire and Ebola Reston strains. In the Ebola Reston strain, which was devoid of pathogenicity in the three human who were infected, the major potential selenoprotein gene overlapping the NP gene in Ebola Zaire (PPCR1 in FIG. 22) appears to be truncated and is almost certainly inactive. In the Ebola Reston NP mRNA, the UGA-rich PPCRs are disrupted by non-UGA stop codons, there are fewer UGA codons, no analogous frameshift sites or PKs, and no candidate SECIS element in the 3'-UTR. Thus, there is no way that this selenoprotein gene could be specifically expressed in Ebola Reston. This is a definite major difference at the gene level between these strains. This NP-associated selenoprotein gene is also absent in Marburg virus, which also has a lower mortality rate than Ebola Zaire. However, both Marburg and Ebola Reston do have higher than expected densities of UGA codons in overlapping frames, suggesting that the nonspecific selenoprotein synthesis mechanism might still contribute to Se depletion, blood clotting, and hemorrhagic symptoms (Ebola Reston was pathogenic in monkeys).

Selenium deficiency can weaken the immune system's ability to fight viral infection, thus, permitting increased replication, rapid mutation, and facilitating the emergence of more virulent strains, as suggested for coxsackievirus [Beck et al. (1995) Nature Med. 1:433–436]. In addition, virally encoded selenoproteins may be a previously unrecognized contributing factor to increased viral pathogenicity under conditions of Se deficiency. Since any selenoproteins depend on the bioavailability of Se, a rare trace element, we postulate that the presence and activity of such genes in a virus vary with geographical areas and thus be strain specific [Taylor el. Computational Medicine, Public Health and Biotechnology: Building a Man in the Machine. Proceedings of the First world Congress, Austin, Tex. M. Witten, Ed., World Scientific, London, Part 1, pp. 1996]. Specifically, long term selenium deficiency in a host population could lead to the inactivation and loss of such genes. While it would be difficult to predict the effects of such gene loss upon the virulence of the strains involved, it can be a factor contributing to differences in virulence between difference viral strains.

In the case of hemorrhagic fever viruses, the prediction of selenoprotein genes is supported by the known role of Se in regulation of blood clotting. Hemorrhagic conditions are often associated with highly Se-deficient diets in various species, supporting the hypothesis that Se is involved in manifestations of hemorrhagic viral diseases. Nonspecific selenium depletion is supported by the bias towards the usage of UGA codons in −1 frame and the tendency of the virus to frameshift erroneously leading to translational slippage to other frames [Rima (1996) Biochem. Soc. Trans. 24:1–13]. Alternatively, as our analysis of Ebola suggests, the presence of UGA-rich PPCRs and the SECIS elements indicates depletion of host Se by the programmed synthesis of virally encoded selenoproteins.

These selenoproteins may provide antioxidant protection to the Ebola virions in a rapidly degenerating cellular environment. Because these PPCRs overlap the Ebola Zaire NP gene, they can only be expressed as an NP fusion protein. So it is possible that this Se module could be formed as a NP variant comprising a small fraction of the total NP present in virions. This is precisely equivalent to the possibility that some coxsackievirus strains live CVB3 express a viral glutathione peroxidase homologue as a fusion protein to the vp3 capsid protein, permitting attachment a glutathione peroxidase module to the virion surface. In the same way proposed for CVB3, attachment of an antioxidant module to the Ebola virion or release as a soluble factor in the cell may benefit the virus, including defense against oxidative attack by the immune system. If this Ebola NP fusion selenoprotein is formed, incorporated Se may be detectable in Ebola Zaire virions in early infection before cellular stores of SeC become depleted.

In conclusion, our analysis indicates that severe infection by Ebola and certain other hemorrhagic fever viruses can produce extreme Se depletion, resulting in enhanced thrombosis and extensive cellular damage due to lipid peroxidation.

There is merit to the theory that factors like low Se in certain geographic regions contribute to the emergence of new and more virulent viral diseases [Beck et al. (1995) Nature Med. 1:433–436]. Our analysis of hemorrhagic fever viruses shows that a viral requirement or utilization of Se, whether specific or nonspecific, is a significant mechanism contributing to increased viral pathogenicity under conditions of Se depletion in human and animal populations.

Pox Virus Selenoprotein Coding Sequence

Dr. Bernard Moss of NIAID recently reported the newly sequenced genome of the pox virus Molluscum contagiosum [B. Moss, presentation at the conference on "Molecular pathogenesis of viruses," New York, December, 1995]. This virus contains an open reading frame that is highly homologous to the mammalian selenoprotein glutathione peroxidase (GPx), with 80% sequence identity at the amino acid level, and an identically placed in-frame UGA codon.

A Predicted Glutathione Peroxidase Gene in Coxsackieviruses

We identified several potential selenoprotein genes in coxsackie B viruses (CVB) [Taylor et al. in Computational Medicine, Public Health and Biotechnology: Building a Man in the Machine, M. Witten, Ed., (World Scientific, London, 1996), Part 1, pp.], which have been implicated as a probable cofactor in Keshan disease, the classical Se-deficiency disease. Our findings provide an explanation for that cardiovirulence of CVB3 is highly dependent upon the Se status of the host, and that the virus actually mutates into a more virulent form in Se-deficient mice [Beck et al. (1994) J. Med. Viol. 43:166–170; Beck et al. (1995) Nature Med. 1:433–436].

Selenoprotein genes identified in CvB3 included an ORF encoded between bases 3442 and 3749 (SEQ ID NO:78), with a start codon and 8 in-frame UGA codons, as well as Cys codons epidermal growth factor (EGF) modules, commonly found in various extracellular matrix and cell adhesion proteins [Engel, J. (1989) FEBS Lett. 251:1–7]. This match is notable in that 5 out of the 8 UGA codons align precisely with Cys codons in the human EGF protein. Significantly, at least 3 other viruses are known to encode EGF homologues [Opgenorth, et al. (1993) Virol. 192:701–709].

A second predicted selenoprotein in CVB3 is encoded in a PPCR-1 to the main reading frame of CBV3, overlapping the entire vpg gene and much of the p3-c protease coding regions (see SEQ ID NO:79). This lacks a start codon, but could be expressed by a −1 frameshift, due to the presence of an "ideal" heptameric slippery sequence (GGGUUUU, beginning at position 5287) followed by a potential GC-rich PK located near the beginning of the vpg coding region of CBV3. The overlapping reading frame contains 5 in-frame UGA codons as well as 5 Cys codons.

We have discovered in CVB of a candidate GPx gene (see SEQ ID NOS. 80 and 81)—a known selenoprotein—(FIGS. 25A and 25B), which, significantly, is the same selenoprotein gene recently identified by Moss and coworkers in M. contagiosum (supra). This GPx gene in CVB was located by creating a database of all known viral sequences, translating in all six reading frames, and using a mammalian GPx sequence as a database probe for sequence similarities (see legend to FIGS. 25A and 25B). The CVB4 sequence shown (SEQ ID NO:50) was a top hit in the search. Significantly, the region of strong sequence similarity found by the search corresponds precisely to the active site of the GPx protein. In CVB, this sequence overlaps a region of the main polyprotein reading frame that encodes vp3, one of the picornavirus structural (capsid) proteins.

In the CVB4 strain with the highest local similarity to GPx in the overlapping (+1) reading frame (Genbank #S76772), there is no start codon or apparent frameshift site, suggesting that the gene could not be active in that viral strain unless some type of RNA editing or other unusual event is involved. However, in another CVB4 isolate (Genbank #D00149), the overlapping reading frame extends further upstream, and there is a start codon, as well as additional in-frame UGA codons. In CVB3 strains, there is also a start codon, and the entire catalytic site of GPx is present within the span of 43 amino acids, suggesting that a highly truncated yet functional GPx may be encoded in this potential ORF (See SEQ ID NOS. 80 and 81) It is also notable that, at least in CvB3 strains, there is only a single UGA codon, that aligns with the single UGA of GPx that encodes the catalytic SeC.

In both CVB3 and CVB4, downstream of this truncated GPx coding region, sequence similarities to the C-terminal region of GPx can still be observed in the main reading frame, i.e., within the vp3 protein sequence itself. In both the CVB3 and CVB4 strains that have start codons in the GPx-related ORF, there are potential −1 frameshift signals (FIGS. 26A–26C) that could permit this GPx module to be fused to the C-terminal half of vp3, in which certain residues might contribute to the GPx activity, because they match conserved GPx residues in the alignment (e.g. the EILN sequence in FIG. 25B, just past the frameshift site). The predicted fusion protein sequence is shown in FIGS. 25A and 25B as CVB3-FUS, which extends past the end of the CVB sequences in the +1 frame that terminate following the conserved GPx active site sequences.

When the frameshift site is active, out of the many copies of the cp3 protein synthesized, a small percentage (determined by frameshift efficiency and SeC availability) contain a fused GPx module. Because vp3 is a picornavirus structural protein present in about 60 copies per virion, GPx activity is associated with the virion itself. The truncated GPx encoded in the +1 frame can accumulate in infected cells and serve the virus in a regulatory or defensive role, e.g. to antagonize apoptotic defense mechanisms of the immune system that use oxidative processes to kill infected cells [Buttke and Sandstrom (1994) *Free Rad. Res.* 22:389–397].

A bacterial expression vector has been created for the cysteine homologue of a predicted HIV selenoprotein (because it is impossible to directly clone mammalian selenoproteins in bacteria. By mutagenesis, Cys codons were substituted for the two UGA codons in this protein; however, one of these aligns with a conserved Cys codon in the E2 proteins, so the substitution is not necessarily inconsistent with activity. Results indicate that this protein has biological activity, because activation of the promoter of the expression construct leads to growth inhibition in the transfected bacteria (this did not occur with control constructs from which the viral coding sequence was omitted). This result was not unexpected, because the E2-like palindrome in the HIV-1 long terminal repeat as a potential target ford this protein, although extremely rare in human DNA other than in a few cytokine-related genes, is found in a number of bacterial genes associated with intermediary metabolism, leading to a concern about the feasibility of cloning it in bacteria (i.e. if it binds to that palindrome, it could interfere with expression of essential bacterial genes).

Other Viruses that are Predicted to Encode Selenoproteins

Mouse Mammary Tumor Virus (MMTV).

MMTV is a prime candidate for this analysis, because it is believed to be the only retrovirus that has been proven to be sensitive to the chemoprotective effects of Se. In numerous studies, Schrauzer has demonstrated that the incidence of mammary tumors subsequent to infection with MMTV is dramatically reduced by increasing dietary Se [Schrauzer et al. (1989) *Biol. Trace Elem. Res.* 20:169–178]. In regard to human cancer, sequences highly homologous to the MMTV envelope gene occur in 38% of human breast cancer specimens. Dietary Se supplements are useful in reducing the incidence of human breast cancer.

A preliminary examination of MMTV for possible selenoprotein coding potential reveals several regions gene with appropriate frameshift signals capable of accessing PPCRs containing multiple in-frame UGA codons overlapping the MMTV gag. There are two PPCRs in the −1 frame to gag, both having potential −1 frameshift entry sites at their 5' ends. Site A has the potential slip sequence UAAAAGA, which is an excellent candidate for P-site slippage on UAAA, with AGA acting as a "hungry" Arg codon. This is followed 3 bases downstream by a small PK having >50% GC base pairs (not shown). The overlapping PPCR associated with site A has eight in-frame UGA codons. The second UGA-rich PPCR overlapping the MMTV gag gene contains 4 tandem UGA codons downstream of potential frameshift site B (FIG. 29) with an ideal heptameric −1 frameshift sequence (AAAGGGA) and a PK that, like the HIV-1 gag-pol and potential HIV protease PKs (FIGS. 26A–26C), appears to be another example of the Hoffman CPK1 type PK topology (FIG. 30).

Schrauzer has noted antagonism between dietary zinc and the chemoprotective effects of Se against MMTV. Thus, it may be significant that the closely spaced UGA codons in these PPCRs are somewhat reminiscent of the Cys residues in metallothionein, suggesting the possibility of a metal ion chelating role. It should also be noted that the MMTV gag gene encodes a zinc finger module just downstream of the region shown in FIG. 8. Thus, if expressed, these hypothetical selenoproteins would be formed in small amounts as alternative modules to the zinc finger region. Whether they might interact with zinc ions or zinc fingers, contributing to the observed antagonism, remains to be determined.

Hepatitis B virus (HBV).

Of other viruses we have examined, HBV is notable for reduced pathogenicity in Se-supplemented human populations. Although classified as DNA viruses, hepadnaviruses like HBV are closely related to retroviruses in that they utilize an RNA intermediate and encode a reverse transcriptase. Thus, it is highly significant that a potential −1 frameshift sequence and large RNA PK occurs overlapping the region encoding the YMDD active site codons of the HBV reverse transcriptase (FIGS. 10A–10C), because this is precisely the same location where a PK that we predicted in HIV-1 has been confirmed by chemical and enzymatic stability studies. The fact that HIV-1 and HBV have quite divergent slippery sequences and PK topologies suggests that what are being conserved in these two distant relatives are simply the elements necessary to produce a frameshift into the −1 frame, along with its conserved UGA codon overlapping the YMDD sequence of the polymerase.

DNA Viruses.

Compelling evidence for a virally encoded selenoprotein is in a DNA virus; the pox virus *Molluscum contagiosum* was shown to encode an ORF with 80% sequence identity to the known mammalian selenoprotein GPx [reported by B. Moss at conference on "Molecular Pathogenesis of Viruses," December, 1995]. While such a high level of sequence homology may reflect recent acquisition of a cellular gene, the fact that the virus has retained it shows that a virus benefits from encoding its own antioxidant protein, perhaps by regulating oxidant tone within an infected cell possibly repressing its own transcription (since it is typically activated by oxidative stress), and/or for defense against oxidative challenge. The latter could be important in the light of evidence that cytotoxic T-cells can invoke oxidative stress in target cells (e.g. by Fas-mediated stimulation) which triggers apoptosis. A virally-encoded GPx or other antioxidant protein might be used to counter such an attack and permit the infected cell to live longer and ultimately produce more viral progeny.

The fact that DNA viruses can have massive genomes in comparison to most RNA viruses clearly presents greater potential for incorporating specialized genes such as antioxidants or selenoproteins, but at the same time that size can make finding them more difficult. We have observed several quite large UGA-rich PPCRs in certain herpesviruses (e.g. cytomegalovirus and Epstein-Barr), with start codons and up to 11 in-frame UGA codons spanning over 400 amino acids. However, we have so far not been able to find any obvious analogs of known eukaryotic SECIS elements closely associated with these UGA-rich PPCRs.

Analysis of Mammalian Nucleotide Sequences

Since many immune responses are regulated by cytokines, a common factor in some of these observations may be the reported enhancement of interleukin 2 (IL-2) activity by Se. Rather than directly affecting IL-2 levels, increased Se concentrations apparently cause an upregulation of IL-2 receptor (IL-2R) levels, thus potentiating the response to IL-2. It has not yet been determined whether this regulation occurs at the transcriptional or translational level, or via effects on mRNA degradation and stability. Levels of Glutathione peroxidase (GPx), one of the few well characterized mammalian selenoproteins, are also regulated by Se, which acts to stabilize the GPx mRNA.

Selenium deficiency can lead to impaired immune function and reduced T cell counts, as well as various specific disorders. Significantly, in ARC and AIDS patients, a progressive decline in plasma Se and GPx, paralleling T cell loss, has been widely documented. Since evidence now suggests that there is an extremely high turnover of CD4+ T cells in AIDS patients, with billions of new cells lost and replaced daily, any exceptional requirement for Se in lymphocytes could contribute to this progressive Se depletion. Thus, it may be significant that, overlapping the known genes in the +1 reading frame, the mRNAs of several T cell associated genes (CD4, CD8, HLA-DR p33) have open reading frames (ORFs) with as many as 10 in-frame UGA codons (CD4, p33), a clustering which is highly improbable by chance alone, and reminiscent of selenoprotein P, the predominant plasma form of Se. The presence of these ORFs, along with potential stem-loop RNA structures displaying consensus selenocysteine insertion sequences, AUG $(N)_m AAA(N)_n UGR$ (SEQ ID NO:38), suggests that these mRNAs may encode selenoproteins, in addition to the known T cell glycoproteins.

Over half of plasma Se is in the form of selenoprotein P; its mRNA has 10 UGA selenocysteine (SeC) codons, mostly concentrated in the C-terminal 125 amino acids. It has been suggested to serve as an antioxidant, a Se transport/storage protein, and it attaches to various cell types via a specific receptor. Another mammalian selenoprotein is the type I 5'-iodothyronine deiodinase involved in conversion of T4 thyroid hormone to T3. Se is critical in mammals, including humans, for the maintenance of glutathione-dependent antioxidant status and thyroid T3 hormone levels.

To elucidate the molecular basis of the immunopotentiating actions of Se, and thus any possible role for Se in the pathogenesis of AIDS, certain other viral diseases, cancer and normal physiology, certain fundamental questions must be resolved. Perhaps foremost among these is the question of whether the role of Se in leukocytes is limited to its antioxidant function in GPx. In this application, the inventors present evidence to the contrary. An examination of the CD4 and CD8-beta mRNAs revealed that, in the +1 frame overlapping with the main ORF, there are ORFs with start codons and multiple in-frame UGA codons (10 in CD4, 8 in CD8 (SEQ ID NOS:22 and 23)), encoding selenoproteins of 123 and 226 amino acids, respectively. In the mRNA of the invariant chain (p33) of the evolutionarily related MHC Class II molecule HLA-DR, a similar ORF was found in the +1 frame, also with 10 in-frame UGA codons. Such a clustering of UGA codons purely by chance is improbable. In a "blocked" reading frame overlapping a real gene, there should be an essentially random distribution of all three stop codons. Beginning at an arbitrary position (e.g. at a start codon in the "blocked" reading frame), the probability of finding eight consecutive in-frame UGA codons with no intervening UAG or UAA codons is $(1/3)^8$, or $p<2\times10^{-4}$. For 10 UGA codons, as observed in ORFs in both CD4 and HLA-DR, it is $(1/3)^{10}$, which is $p<2\times10^{-5}$. East of these UGA-rich ORFs have a start codon upstream of the first UGA codon, indicating that they encode proteins expressed in vivo.

Moreover, as shown in FIG. 13, the deduced CD4 selenoprotein (CD4-SP, SEQ ID NO:22) amino acid sequence has a highly significant similarity to a Cys-rich region of the sperm mitochondrial capsule selenoprotein (MCSP, SEQ ID NO:33), as determined by a FastA search of over 70,000 protein sequences in the PIR 42 database (significance=7.0 SD in initial scores). There are also several regions of local similarity (e.g. the sequence SCCCXC (SEQ ID NO:82), C=Cys or SeC), and 25% identity overall, to the SeC-rich C-terminal of the human selenoprotein P, which, like the CD4-SP ORF, also has 10 UGA codons.

In eukaryotes, efficient selenocysteine incorporation at UGA codons depends on the presence of a cellular protein factor (equivalent to the bacterial selB protein) and a structural signal in the mRNA 3'-untranslated region (UTR), consisting of a selenocysteine insertion sequence (SECIS) in a characteristic stem-loop structure [Berry et al. EMBO J. 12, 3315–3322 (1993), Berry and Larsen, Biochem. Soc. Trans. 21, 827–832 (1993)]. A possibly related stem-loop structure is required in bacteria, but must immediately follow the UGA codon. A SECIS can also function when placed in a 5'-UTR, or even in trans, when cotransfected on a separate plasmid; however, the efficiency of SeC insertion is highest when the SECIS is in a downstream 3'-UTR location [Berry et al. (1993) supra]. In-frame UGA codons can be translated as SeC with reasonable efficiency as long as there is an upstream or downstream SECIS in the mRNA. The SECIS elements associated with the UGA-containing ORFs of CD4, CD8 and the p33 invariant chain of HLA-DR (FIG. 14) are either in the coding regions (CD4, CD8) or in a 3'-UTR relative to the ORF encoding the predicted selenoprotein (p33). There is an additional 1.2 kbp of the human CD4 3'-UTR for which sequence information is not available. It is possible that one or more additional SECIS elements may be found in that region.

The predicted stem-loop RNA structures (FIG. 14) have all the essential features based on a comparison of known SECIS elements previously identified in mammalian selenoprotein genes: an AUG unpaired or partially paired in a bulge on the 5' arm of the stem, the unpaired adenine triad on the loop, and UGA or UGG in a bulge on the 3' arm of the stem [Berry and Larsen (1993) supra]. These structures also have a near-ideal distance (10–12 base pairs) between the adenine loop and the AUG/UGR consensus bulge regions; the 9 base pairs distance in the CD8 SECIS is compensated by a larger adenine loop.

In all three cases, the start codon for the predicted selenoprotein is downstream from that of the "main" ORF encoding the previously known gene. Thus, selenoprotein synthesis is only initiated on the relatively rare occasions when ribosomal scanning misses the first Met codon, an event which does happen, for example, with many viral genes expressed in mammalian cells. This inefficient initiation is advantageous in selenoprotein synthesis because the ability of cells to synthesize selenoproteins is inherently limited by the low abundance of tRNA$^{sec}$.

In the case of CD4, the UGA-rich ORF in the +1 frame completely overlaps the C-terminal CD4 coding region. The predicted coding sequence (Table 9, SEQ ID NO:22) is between 947–1315 (GenBank #m35160). This selenoprotein can be translated from an alternatively spliced RNA, because there is a potential splice acceptor (SA) site (CCCTGCCCCAG/G, SEQ ID NO:83) about 10 nucleotides upstream from its initiation codon. In a spliced RNA, this Met would be much closer to the 5' cap, where it could be initiated more efficiently. If this SA site were spliced to a potential donor (CAG/GT) at position 35, which is upstream from the CD4 start codon, the Met of the CD4-SP ORF would become the first start codon at the 5' end of the spliced mRNA.

In the CD8-beta mRNA, the selenoprotein is also encoded in the +1 frame, between 329–1006 (GenBank #m36712). It overlaps all but the first 94 N-terminal amino acids of CD8, and extends past its C-terminal by 110 amino acids. Thus, the predicted 226-residue product (Table 9, SEQ ID NO:23), with 8 UGA codons and 11 Cys, is slightly larger than CD8 itself.

In the HLA-DR p33 mRNA, the UGA-rich ORF in the +1 frame completely overlaps the N-terminal half of the p33 gene in the zero frame; the predicted coding sequence is between 60–533 (GenBank #m14765). The start codon is only 4 nucleotides past that of the p33 gene in the zero frame, and the hypothetical selenoprotein has 10 UGA codons and 15 Cys within its 158 residues (Table 9, SEQ ID NO:24).

The only precedent for a nuclear gene having a similar number of in-frame UGA codons is mammalian selenoprotein P, with ten [Hill et al. *Biochem. Soc. Trans.* 21, 832–835 (1993)]. The Cys and SeC-rich C-terminal region of selenoprotein P has a strong similarity to another protein module found in some cell adhesion molecules: the beta chain of integrins and certain leukocyte adhesion proteins like CD18 (both in the top 10 matches, at >6 SD significance in a PIR database search with this region of selenoprotein P as a probe). This similarity could be the basis for the specific binding of selenoprotein P to cells via an as yet uncharacterized receptor [Gomez and Tappel, *Biochim. Biophys. Acta* 979, 20–26 (1989)]. Given that beta-integrin chains are components of a number of leukocyte adhesion proteins and receptors, this integrin/selenoprotein P homology suggests a possible evolutionary relationship between selenoproteins and such molecules. Without wishing to be bound by any particular theory, this is deemed evidence for divergent evolution of the CD4 gene and known selenoproteins (see, e.g., FIG. 13). Because CD4, CD8, MHC proteins, and other members of the immunoglobin superfamily typically share common modules, we predict that similar UGA-rich ORFs will be found overlapping other genes that are important in the immune system. Table 3 presents a summary of examples of known cellular genes in which potential overlapping selenoprotein coding sequences occur.

In Table 9, C̲ represents the amino acid inserted at a UGA codon, this is typically SeC (selenocysteine) but it is known that an Arg, Try or Cys may be inserted at UGA codons. The regions encoding the protein products of Table 9 are CD4 (bases 947–1315 in GenBank #m35160) CD8 (bases 329–1106 in GenBank #m36712) and HLA-DR (bases 60–533 in GenBank #m14765.

Selenoproteins encoded by these ORFs can have a functional role of considerable importance in gene regulation. The analysis indicates that, as well as functioning as independently expressed proteins, they may be used as alternate modules that can be attached to part of the protein encoded in the main ORF by alternative RNA splicing or frameshifting. For example, there is a predicted programmed −1 frameshift in the CD8-SP (FIG. 15), with a near-ideal heptameric shift sequence (G GGA AGG) and a potential pseudoknot that permits a frameshift from the +1 ORF into the main ORF just before the membrane-proximal domain of CD8. A frameshift here leads to the formation of an alternate form of CD8 with the usual extracellular domain replaced by a selenoprotein module, which can have a totally different receptor binding specificity. Although this shift sequence differs from the "ideal" heptameric pattern (X XXY YYZ) in the sixth position [Chammoro et al. *Proc. Natl. Acad. Sci. USA* 89, 713–717 (1992)], it is a variant that still permits 2 out of 3 Watson-Crick base pairs in the codon-anticodon interactions of both tRNAs after slippage (FIG. 15). The distance between the shift sequence and the pseudoknot is 4 nucleotides, well within the range observed in known frameshift sites (0–12 bases), and close to the optimal distance of 6 or 7 bases.

An advantage to the cell for such selenoprotein modules is the potential for redox-regulated rearrangement of disulfide/diselenide/selenosulfide bonds, and consequent conformational changes. This presents opportunities for inducing certain specific cell adhesion reactions or intracellular effects under conditions of oxidative stress, as opposed to others required under more hypoxic conditions.

HLA-DR is an important marker for activated T cells. Thus, if the gene for its invariant chain also encodes a selenoprotein with 10 SeC residues (suggesting a substantial Se requirement), Se is an essential lymphocyte nutritional factor that plays a significant role in T cell function and proliferation. This is consistent with reports that Se supplementation in culture increases the cytotoxicity of killer T cells as well as the proliferation of T cells in response to mitogens and antigens, whereas Se deficiency has the opposite effect, being commonly associated with impaired immune function. This also provides at least a partial explanation for the antiviral and anticancer effects of Se (reviewed in reference, since cellular immunity is the primary defense against viruses and cancer.

An exceptional requirement for Se in the expression and function of these lymphocyte-associated selenoprotein genes can contribute to the decreased levels of CD4+ T cells in Se-deficient animals and humans and decreased plasma Se levels in ARC and AIDS patients with a high rate of CD4+ T cell turnover and depletion. Such genes also support observations suggesting "a priority of Se supply to lymphoid tissues" [Turner and Finch (1991) supra]. Under conditions of severe Se depletion, a compromised ability to express these selenoproteins contributes to T cell anergy, inappropriate apoptosis, or other defects of T cell function. The discovery of selenoprotein genes overlapping HLA-DR and CD4 and the HIV-1 env gene is consistent with this relationship.

T cells require significant quantities of Se for functions other than antioxidant protection via GPx, consistent with competition for Se between viral and cellular selenoprotein synthesis further impairing T cell function in AIDS patients. In addition, as T cell loss progresses, the high turnover rate of T cells in HIV-infected subjects contributes to the decline in plasma Se levels, further compromising both helper and killer T cell functions by inhibiting the formation of the CD4, CD8 and MHC-encoded selenoproteins disclosed herein.

A number of independent observations indicate that the UGA-rich ORFs in T cell associated genes encode selenoproteins: 1) a statistically significant clustering of 8–10 UGA codons in these ORFs, always in the +1 frame relative to the known gene; 2) the presence of start codons upstream of the first UGA in all three cases; 3) at least for the CD4-SP ORF, significant sequence similarities to known selenoproteins (e.g. FIG. 13); 4) the presence of consensus SeC insertion sequences in appropriate potential stem-loop RNA structures (FIG. 14). Furthermore, the existence of selenoproteins with regulatory function is also consistent with the apparent immunopotentiating effects of Se and correlations between CD4+ T-cell counts and plasma Se levels that have been documented in animals, the elderly and HIV-infected patients.

The identification of these UGA-rich ORFs encoding selenoproteins in the human genome is surprising as it is contrary to the conventionally held views that human mRNAs are always monocistronic transcripts, and that human genes almost never overlap. However, such coding density is typical of retroviruses, which in humans preferentially infect T cells. The existence of virus-like genetic processes in T cell genes could reflect co-evolution of T cells and retroviruses.

Analysis of the mRNAs for the alpha and beta subunits of the IL-2R revealed that both have ORFs with multiple in-frame UGA codons overlapping the known genes in either the −1 or the +1 reading frames. In both cases, these ORFs have start codons that are downstream from that of the "main" ORF encoding the known gene. Both mRNAs contain consensus selenocysteine insertion sequences, AUG(N)$_m$AAA(N)$_n$UGR (SEQ ID NO:38), with the potential to form the stem-loop RNA structures characteristic of SECIS elements (FIGS. 15A–15B). In IL-2R alpha, the putative SECIS is in the 3'-UTR, the usual location in known cellular selenoprotein genes [Berry and Larsen (1993) supra]. In IL-2R beta it is located in the IL-2R beta coding region, but in a location 3' to the major UGA-rich ORFs, relative to which it is a 3'-UTR. In contrast, there is no evidence of UGA-rich ORFs or SECIS elements in the mRNA of the IL-2R gamma subunit.

In both the IL-2 alpha and beta subunit mRNAs, the start codon of at least one predicted selenoprotein ORF occurs in the context of a highly distinctive Kozak sequence (FIG. 17), which is a 13 nucleotide sequence that enhances translational initiation, and thus differentiates highly active start codons from those where initiation rarely occurs [Kozak, M., *J. Cell Biol.* 108 (1989): 229–41]. For the novel ORF in IL-2R-alpha, the probability of attaining such a close match to the Kozak consensus by chance can be estimated as $p<3\times10^{-5}$; for that in IL-2R beta, as $p<10^{-3}$ (FIG. 17).

There are several other aspects of these Kozak sequences indicate that these ORFs must encode selenoproteins. For both the IL-2R alpha and beta mRNAs, the Kozak sequences for the selenoprotein ORFs are significantly closer to the "ideal" than those for the (upstream) start codons of the overlapping IL-2R coding regions in the same mRNAs (FIG. 17), being respectively 100 or 5 times less likely to have occurred purely by chance as compared to the Kozak sequences for the IL-2R alpha and beta gene products, which are already significantly non-random. These "stronger" Kozak sequences could help compensate for the downstream position of the start codons for these predicted selenoprotein ORFs, where protein synthesis could only be initiated if ribosomal scanning missed the start codon of the "main" ORF encoding the known gene.

In addition, for the ORF overlapping the IL-2R alpha gene, there is an in-frame UGA codon, embedded in a near-perfect Kozak sequence [Kozak (1989) supra], only 6 bases past the start codon. It makes no sense that this mRNA would be programmed for efficient initiation at this Met codon, only to have to stop after the synthesis of a tripeptide. Thus, the only reasonable explanation is that there must be a readthrough of the UGA "stop" codon. Combined with the presence of an unmistakable SECIS element in the 3'-UTR of the same mRNA (FIG. 16A, SEQ ID NO:39), these observations strongly indicate that the UGA codons in this ORF encode selenocysteine.

In the case of the IL-2R alpha subunit (the "tac antigen"), the UGA-rich ORF in the −1 frame completely overlaps the C-terminal half of IL-2R-alpha. The coding sequence is between 327–740 (GenBank #m14098), and it yields a protein of 138 residues, six of which are selenocysteine. This ORF might also be translated from an alternatively spliced RNA, because there is a potential splice acceptor site (CCUUCCAG|G) at 304/305, about 20 nucleotides upstream from the initiation codon. In a spliced RNA, where it would be much closer to the 5' cap, this Met could be initiated more efficiently. There are also two potential alternative upstream start codons that are not in the context of strong Kozak sequences (at positions 174 and 180 in #m14098), but which might be initiated from the full length mRNA, permitting the formation of larger forms of the protein with up to 190 amino acids and eight selenocysteine residues.

Finally, it is also possible for this selenoprotein module to be expressed as a fusion protein attached to the N-terminal domain of IL-2R-alpha. This is indicated by the presence of a near-ideal−1 frameshift sequence and potential RNA pseudoknot (stems A:A', B:B') beginning at #330, immediately following the Met codon in the −1 ORF:

−1 FRAME SEQ ID NO:86
(330)            GGAAAAUGAAGCCACAGAGAGAA
    UUUAUCAUUUCGUGGUGGGGCAGAUGG
IL-2Ra FRAME GluAsn A B A' B'

A frameshift at this location yields an IL-2R-alpha variant with the first N-terminal 112 residues identical to IL-2R-alpha, but with the C-terminal half replaced by a selenoprotein module of 136 residues. The sequence at the frameshift site is GluAsnSecSer, indicated above in italics. An unpaired A at the junction of the 2 stem regions (between regions B and A') is critical for frameshifting at the mouse mammary tumor virus gag-pro frameshift site [Chen et al. *EMBO J.* 14 (1995): 842–52].

In the IL-2R beta mRNA, there are several UGA-rich ORFs with start codons in both the +1 and −1 reading frames. The identified selenoprotein coding sequence associated with the strongest Kozak sequence (FIG. 26A–26C and 27) is encoded in the +1 frame, between 283–579 (GenBank #m26062). It completely overlaps part of the N-terminal region of IL-2R-beta. The encoded 99-residue protein has six selenocysteines encoded by UGA codons.

In this mRNA, there is the potential for alternative RNA splicing: there is a potential splice donor site at position 548/549 (CAA|GU), and a splice acceptor site at 1296/1297 (CAG|A) preceded by a pyrimidine-rich stretch with only 4 purines in 15 bases). Existance of an intron defined by these splice sites would connect several selenoprotein modules to domains encoded in the IL-2R beta ORF, the removal of such an intron would splice the above-mentioned UGA-rich ORF in the −1 frame to another in the +1 frame following position 1297, creating a large selenoprotein with a total of 9 UGA codons located upstream from the potential SECIS element in this mRNA (FIG. 16A–16B). The mammalian selenoprotein P, which has ten selenocysteine codons [Hill et al. (1993) supra], provides a precedent for a gene having such a high number of in-frame UGA codons.

Our results indicate that the genes encoding the alpha and beta subunits of the IL-2R also encode selenoprotein modules. These mRNAs contain consensus selenocysteine insertion sequences in thermodynamically stable potential stem-loop RNA structures and UGA-rich ORFs with start codons in the context of strong Kozak sequences. In the IL-2R alpha gene, there is an in-frame UGA codon immediately 3' to a Kozak sequence which is very close to the ideal consensus, strongly supporting readthrough of the UGA. Without wishing to be bound by any particular theory, the inventors have ruled out the alternative explanation that these are vestigial genes inactivated by stop codons, but which were active sufficiently recently in evolutionary time to retain their Kozak sequences. The experimental evidence for upregulation of IL-2R by Se provides a direct link between Se levels and IL-2R gene products. Regulation by Se also occurs for other selenoproteins, including GPx.

A number of proto-oncogenes including c-abl and bcl-2, and the p53 tumor suppressor gene, can encode large selenoprotein modules in open reading frames (ORFs) overlapping the known genes. These ORFs contain as many as 24 in-frame UGA codons, which can encode selenocysteine or act as a stop codon (its conventional role).

There are several reasons why these potential genes have escaped detection until now. It has still has not become widely appreciated in the scientific community that the UGA "stop" codon can sometimes encode SeC [Bock et al. *Mol. Microbiol.* 5, 515–520 (1991)]. Conventional analyses of potential protein coding regions in genes usually do not discriminate UGA from the other two stop codons, and thus they fail to reveal that a protein might be encoded by regions containing UGA codons. Such regions are routinely assumed to be inactive due to the presence of stop codons, which is probably true in the vast majority of cases. In addition, prevailing dogma maintains that there is only one gene encoded in a given mammalian mRNA, and that overlapping genes are common only in viruses. Furthermore, there are low concentrations of selenium in biological systems. However, experimental research has uncovered at least 20 new, uncharacterized selenoproteins expressed in some mammalian cells [Behne et al. *Analyst* 120 (1995) 823–825].

For several decades, evidence has accumulated suggesting that low dietary Se is associated with increased cancer risk for a number of cancers, including prostate cancer, and plasma Se levels are often below normal in prostate cancer patients [reviewed in Lanfear et al. *Carcinogenesis* 15(1994) 1387–1392]; however, the underlying mechanisms have remained poorly understood.

Inorganic Se significantly inhibits in vitro growth of the DU-145 prostate cancer cell line at micromolar concentrations comparable to normal plasma Se levels. In addition, even lower concentrations of Se ($10^{-8}$ M) inhibit the ability of cadmium to stimulate the growth of normal prostate epithelial cells by an unknown mechanism.

The bcl-2 oncogene has been implicated in prostate cancer, in which it is often expressed at higher than normal levels. This apparent overexpression appears to inhibit apoptosis by inducing antioxidant defenses. The ultimate effect of Bcl-2 is to inhibit the free radical processes and calcium related effects involved in apoptosis, thus leading to prolonged cell longevity and proliferation. Since the major biochemical functions of Se are in redox related biochemical reactions and antioxidant enzymes, a role for Se and novel selenoproteins in the action of Bcl-2 is mechanistically plausible.

The Se metabolite selenodiglutathione (SDG) is a major intracellular form of Se, produced by the reaction of selenite and glutathione. SDG induces both the synthesis of wild-type p53 protein and apoptosis, and inhibits cell growth [Lanfear et al. (1994) supra], consistent with known antiproliferative and anticancer effects of Se. Furthermore, levels of a number of known selenoproteins like GPx are regulated at the transcription level by Se concentration.

Recently, Facchiano presented theoretical evidence that some eukaryotic genes show evidence of encoding multiple proteins in different overlapping reading frames of a single mRNA [52]. His analysis consists of ignoring stop codons in the alternate frames, translating the full overlapping sequences, and looking for sequence similarities to known proteins. Some of these hypothetical products had significant similarity to known proteins; Facchiano argues that, like some viral genomes, many eukaryotic mRNAs may have been polycistronic in the evolutionary past, and some may still be.

Computer analyses of the p53 and bcl-2 mRNAs revealed that, in the +1 frame overlapping with the main ORF, there are ORFs with multiple in-frame UGA codons (10 in p53, 8 in Bcl-2), encoding selenoproteins of 421 and 226 amino acids, respectively. In the mRNA of the c-abl oncogene, a very large ORF, with an unprecedented 24 in-frame UGA selenocysteine codons distributed over 795 amino acids, was found in the −1 frame. All three of these UGA-rich ORFs have a start codon near the 5' end of the ORF consistent with their encoding expressed genes. The predicted selenoproteins also all have a high cysteine content (p53: 21 cys; Bcl-2: 13 cys; c-abl: 24 cys). See FIGS. 18A–18C and 20.

Such a clustering of UGA codons purely by chance is quite improbable. In a "blocked" reading frame overlapping a real gene, on average there should be an essentially random distribution of all three stop codons, so, beginning at an arbitrary position, the probability of finding 10 consecutive in-frame UGA codons (as in p53) with no intervening UAG or UAA codons is $(1/3)^{10}$, or $p<2\times10^{-5}$. For 24 UGA codons, as observed in an ORF in c-abl, it is $(1/3)^{24}$, which is $p<10^{-11}$. Thus the clustering of UGA codons found in these oncogenes is highly unexpected.

In eukaryotes, efficient selenocysteine incorporation at UGA codons is a cotranslational event that depends upon the presence of +RNA$^{sec}$, a cellular protein factor and a structural signal in the mRNA 3'-untranslated region (UTR), consisting of a selenocysteine insertion sequence (consensus AUG ... AAA ... UGR, where R=purine) in a characteristic stem-loop structure called a SECIS element [Berry and Larsen (1993) supra]. We have identified a SECIS element, required for the translation of the UGA-containing ORFs of p53 and Bcl-2, in the 3'-UTRs (shown in FIGS. 19A–19B); however, most of the 3'-UTR of c-abl is not available in the databases. Based on the large ORF with 24 UGA codons overlapping c-abl, a SECIS is predicted to be present in its 3'-UTR.

In Bcl-2, the consensus SeC insertion sequence in the required stem-loop RNA structure is in the 3'-UTR (FIG. 19A). A potential SECIS in the 3'-UTR of the p53 mRNA deviates from the known SECIS consensus by only one out of nine conserved bases (GGG instead of UGG in the 3' bulge). However, structural diversity has been found in SECIS elements [Berry et al. *EMBO J.* 12, 3315–3322 (1993), Berry and Larsen, *Biochem. Soc. Trans.* 21, 827–832 (1993)]. Subtle variations in the structure and relative stability of these RNA stem-loops may determine the varied efficiency of SeC insertion characteristic of different SECIS elements; this may be a means of regulating the synthesis of different selenoproteins at the translational level [Berry and Larsen (1993) supra]. The minor deviation from the consensus in the putative p53 SECIS may reflect such a control mechanism.

A deeper understanding of the mechanisms of gene regulation in higher organisms, especially in mammals, and particularly in humans, is important in understanding physiological processes and their control. The present methods and disclosure have broader utility in understanding and affecting gene regulation in higher organisms, thereby allowing control over gene expression by exploiting the regulatory mechanisms via genetic engineering and/or gene therapy.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning,* Second Edition, Cold Spring Harbor Laboratory Press, Plainview, N.Y.; Maniatis et al. (1982) *Molecular Cloning,* Cold Spring Harbor Laboratory, Plainview, N.Y.; Wu (ed.) (1993) *Meth. Enzymol.* 218, Part I; Wu (ed.) (1979) *Meth Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics,* Cold Spring Harbor Laboratory Press, Plainview, N.Y.; Old and Primrose (1981) *Principles of Gene Manipulation,* University of California Press, Berkeley; Schleif and Wensink (1982) *Practical Methods in Molecular Biology;* Glover (ed.) (1985) *DNA Cloning* Vol. I and II, IRL Press, Oxford, UK; Hames and Higgins (eds.) (1985) *Nucleic Acid Hybridization,* IRL Press, Oxford, UK; and Setlow and Hollaender (1979) *Genetic Engineering: Principles and Methods,* Vols. 1–4, Plenum Press, New York. Abbreviations and nomenclature, where employed, are deemed standard in the field and commonly used in professional journals such as those cited herein.

EXAMPLES

Example 1

Comparative Sequence Analysis (A) Database Searches.

Hypothetical protein sequences of interest were used as probes to search the PIR 39 (Protein Identification Resources Data Bank) protein database using the FASTDB program (IntelliGenetics, Inc., Mountain View, Calif.). In both database searches and pairwise alignments, cysteine was used in place of selenocysteine in the probe sequences. The database searching algorithm used by FASTDB has been described previously [Brutlag, et al. (1990) *Comp. Appl Biosci.* 6:237–245]. The initial comparison of the query sequence to the database is performed in a manner similar to that used by the FASTP or FASTA programs, except that FASTDB uses the specified similarity matrix in the first pass of the search, rather than in the second pass. The structure-genetic matrix of McLachlan, [McLachlan, A. D. (1972) 64:417–437] which measures a combination of chemical and genetic code similarities, was used as the similarity matrix for database searching. We have found that this combination of searching algorithm and scoring matrix has several benefits, including the finding of optimal alignments to the entire probe sequence, rather than just a small region of optimal local similarity. The values of the various parameters used in the present study were Mismatch penalty, 5; Gap penalty, 2.0; Gap size penalty, 0.26; Joining penalty, 20; K-tuple, 1; Threshold level, 83. The scores of the best match of the probe sequence against each of the target (database) sequences are averaged to give the database mean score and its standard deviation. Significance scores from the database searches are calculated as the difference from the mean divided by the standard deviation. The approach we have used in these database searches is simply to ask, out of the most significant matches, are there hits which represent types of proteins known to occur in viruses, or with biological activities similar to other known viral proteins? Alternatively, if particularly significant matches are observed to multiple examples of a given protein type, it may be worthy of investigation. One of the final criteria has to be: does it make any sense that this virus might encode such a protein?

(B) Pairwise Alignments.

In some cases, the top matches from FASTDB searches were individually compared to the sequence of interest using the BESTFIT or GAP programs (as implemented in the GCG software package [Devereux et al. (1982) *Nucl. Acids Res.* 12:387–395] to generate pairwise alignments. BESTFIT makes an optimal alignment of the best segment of similarity between two sequences, using the local homology algorithm of Smith and Waterman [Smith and Waterman (1981) *Appl. Math.* 2:482–489]. GAP uses the algorithm of Needleman and Wunsch [Needleman and Wunsch (1970) *J. Mol. Biol.* 48:443–453] to generate an optimal alignment of two complete sequences. Unless otherwise specified, the default similarity matrix used for the pairwise alignments was the normalized Dayhoff matrix of Gribskov [Gribskov and Burgess (1984) *Nucl. Acids Res.* 14:6745–6763]. The potential significance of matches was assessed by measuring the deviation of the quality score of the actual alignment from the average quality score calculated by running BESTFIT or GAP with randomized sequences of the same length and amino acid composition. The average quality score and its standard deviation, SD, were determined for 100 alignments of randomized sequences, which were amino acid sequences in this study. Reported percent identities were calculated as no. identities/(sequence length+no. insertions).

(C) Sequences Used.

The HIV-1 BRU sequence, GenBank #K02013, also known as LAI, was used for RNA structure and pseudoknot predictions, analysis of ORFs (FIG. 1), and translation of hypothetical protein sequences (Table 1). FIG. 8 shows predicted structures from the picornaviruses coxsackie B5, #X67706, and polio type 1 Mahoney, #J02281. The following abbreviations have been used (FIGS. 8, 10) for other retroid sequences: VISNA, Visna lentivirus, #M10608; ELAVCG, Equine infectious anemia virus, #M16575; HIVYU, HIV-1, #M93259; HIVJSRF, HIV-1, #M38429; HIVNL43, HIV-1, #M19921; HIVU455A, HIV-1, #M62320; HIVNY5CG, HIV-1, #M38431; HIV1BRU, HIV-1, #K02013; HIVMAL, HIV-1, #K03456; HIVCAM1, HIV-1, #D0112; HIVMN, HIV-1, #M17449; HIVOYI, HIV-1, #M26727; HIV2GH1, HIV-2, #M30895; HIV2ROD, HIV-2, #M15390; HIV2, HIV-2, #A05350; HTLV, HTLV-1, #L02534; SIVAGM1, SIVagm, #Y00295; SIVAGM2, SIVagm, #M66437; SIVAGM3, SIVagm, #M30931; RESIVXX/SIVAGM4, SIVagm, #XO7805; CIV, SIV chimpanzee, #X52154; SIVSYKES, SIV sykes, #L06042; SIVMAND, SIV mandrill; #X15781; SIVACUTE, SIV, #L09211; SIVGAA; SIV, #M80193; SIVMAC, SIV macaque, #M19499; SIVSOOTY, SIV sooty mangabey, #X14307; MMLV, Maloney murine leukemia virus, #J02255; Copia, Retrotransposon Copia, #S03612; Panther, Panther lentivirus, #M95476; FIV, Feline immunodeficiency virus, #M25381; BIV, Bovine immunodeficiency virus, #M32690; PUMA, Puma lentivirus, #U03982.

Example 2

Prediction and Statistical Analysis of RNA Secondary Structure (A) RNA Folding.

The secondary structure of RNA regions was predicted using the FOLD program [Zuker and Steigler (1981) *Nucl. Acids Res.* 9:133–148] with updated energy parameters as implemented in the GCG software package [Devereux et al.1 (1982) supra]. The significance of the stability of such structures can be assessed by measuring the deviation of the free energy of stabilization of the predicted structure from the average calculated for randomized structures of identical size and base composition [Le and Maizel (1989) *J. Theor. Biol.* 138:495–510]. In the present study, the average computed free energy and its standard deviation, SD, were determined from foldings of 30 randomized versions of the nucleotide sequence of interest. The randomized sequence was obtained using the GCG SHUFFLE program. A subroutine was developed which performs the shuffle and folding processes for "n" number of times, the value of "n" given by the user. The difference between the computed free energy of folding and the mean value calculated for the randomized sequences, expressed as the number of SD (z) below the average for the randomized sequences, is a useful metric for assessing the relative stability of the computed folding of the actual sequence relative to that attainable by similarly composed random sequences [Schinazi et al. (1994) *Antimicrob. Agents Chemother.* 38:268–274; Le and Maizel (1989) *J. Theor. Biol.* 138:495–510].

(B) Pseudoknots and SECIS Structures.

Programs like FOLD [Zuker and Steigler (1981) *Nucl. Acids Res.* 9:133–148] and most other global RNA folding programs have not been programmed to predict pseudoknot structures, due in large part to the lack of a comprehensive set of experimental free energy parameters for their relative stability. In the present study, a systematic search for potential pseudoknots was undertaken in regions of interest by a semiautomated method. This involved the use of FOLD in a sliding window type of search for possible stem-loop structures with at least five base pairs in the stem, and loops that were no more than 20 unpaired bases in size. This was followed by a search, within regions no more than 20 bases upstream or downstream from the base of the first stem, for sequences of three or more bases that were the inverse complement to bases on the loop, no more than one base removed from the first stem. In the later stages of the study, analysis of potential open reading frames (FIGS. 1A and 1B) was used to target the regions for the search.

Similarly, potential SECIS stems were found by a systematic sequence scanning method that initially focused on finding occurrences of the 5'-DI SECIS loop motif (UAAAG), with UGA codons either upstream or downstream of the AAA motif. In some cases regions were rapidly eliminated, often by visual inspection of the sequence, due to lack of potential for a stem-loop in the AAA region, under the requirement than no more than one of the three A bases could be paired. Candidate regions were then folded, usually with a sliding window approach, in order to determine the most stable and significant RNA structures in the surrounding region. The thermodynamic stability and statistical significance of the most stable RNA structures were then determined as described in the previous section.

The HIV-1 BRU sequence, GenBank #K02013, also known as LAI, and coxsackievirus B3 strain, #M88483, were used for analysis of ORFs, frameshift sites, RNA structure and PK predictions, and translation of hypothetical protein sequences.

The cDNA+ strand sequences were first translated in all three reading frames with the TRANSLATE program of GCG [*Program Manual for the Wisconsin Package,* Version 8, September 1994, Genetics Computer Group, Madison, Wis.] using a translation table that was modified to insert a unique symbol for TGA.

When a potential novel ORF was located, including those containing TGA codons, the region was examined for potential frameshift sequences, beginning at the 5' end. For regions with potential to be expressed by a −1 frameshift from a known gene, the codon triplets in the −1 frame were examined, because in that frame an ideal heptamer has the pattern XXX YYY, which is easily detected by eye. Even non-ideal sites will usually have at least one homogenous triplet in the −1 reading frame. For a +1 frameshift, the codon triplets in the zero frame must be examined, because that frame contains the A-site hungry codons or stop codons that are typically involved. A P-site codon having shift potential must also be present. Some of the known shift sequences were reviewed above.

When both a potential novel ORF and a −1 shift sequence are found, potential downstream RNA secondary structures (steps and PKs) can be found by various programs and methods. For example, the STEMLOOP and DOTPLOT options of GCG [*Program Manual for the Wisconsin Package,* Version 8, September 1994, Genetics Computer Group, Madison, Wis.] were used to generate FIGS. 1A and 1B, which shows that the two overlapping stems that form the protease PK are the only major stems possible in the region 3' to the proposed shift site.

Hypothetical protein sequences of interest were used as probes to search the PIR 42 (Protein Identification Resources Data Bank) protein sequence database using either the FASTDB program (Intelligenetics, Inc., Mountain View, Calif.) or GCGFASTA [*Program Manual for the Wisconsin Package,* Version 8, September 1994, Genetics Computer Group, Madison, Wis.].

For potential SECIS structures, the secondary structure of RNA regions containing the consensus features (AUG . . . AA . . . UGA) was predicted using the FOLD program [Zuker and Steigler (1981) supra] with updated energy parameters as implemented in the GCG software package [*Program Manual for the Wisconsin Package,* Version 8, September 1994, Genetics Computer Group, Madison, Wis.].

For studies of conservation of these potential genes in the major phylogenetic groups of HIV-1, multiple alignments for various regions of the nucleic acid sequences were downloaded from the HIV sequence database at the Los Alamos National Laboratory. This can be accessed using a www browser such as mosaic; the URL for the database is: http://hiv-web.lanl.gov.

Example 3

SECIS Elements

Regions of the respective mRNAs are tested for the ability to function as SeC insertion sequences, using a vector containing the type I 5'-deiodinase gene (a selenoprotein) and its 3'-UTR region, which contains a well-characterized SECIS element. That SECIS is replaced with SECIS elements from the genes of interest (e.g., FIG. 19). Deiodinase activity is used as a reporter for SeC insertion efficiency. SECIS activity is measured relative to that of the original deiodinase SECIS as a positive control. Positive results in such a test provide compelling evidence that the UGA-rich ORFs in the genes described herein or identified by the methods of the invention encode functional selenoproteins.

Example 4

Frameshift Assays

Sequence analysis revealed heptameric frameshift sequences and RNA pseudoknots that permit the formation of hybrid p53 or oncoproteins containing Se modules (See Table 3). The efficiency of ribosomal frameshifts at such locations is assayed by a standard method using a reporter gene construct provided by Dr. John Atkins, Department of Human Genetics, University of Utah.

Example 5

Cloning, Expression and Characterization of Predicted Selenoproteins

Because there are very significant differences between bacterial and eukaryotic SeC insertion mechanisms, it is essentially impossible to express a cloned human selenoprotein in a bacterial host. For those overlapping selenoprotein ORFs with functional SECIS elements as tested with a reporter gene, eukaryotic expression vectors are constructed for these selenoproteins, including alternate forms such as fusion proteins with parts of the main p53 gene product where there is evidence of active frameshifts, as discussed in Example 4. Because levels of selenoproteins are regulated by the stability and structure of their associated SECIS elements, constructs are made incorporating highly efficient SECIS from the 3'-UTR regions of selenoproteins such as selenoprotein P, to maximize readthrough of UGA codons in the construct and generate maximal levels of the putative selenoproteins in transfection experiments. Using $^{75}$Se labeling, one can monitor the formation and more easily isolate these proteins. These are then used to raise monoclonal antibodies which can be used to investigate differences in the expression of these selenoproteins in normal as opposed to transformed prostate cells. Monoclonal or polyclonal antibodies, preferably monoclonal, specifically reacting with a selenoprotein encoded by a particular coding sequence identified using the present methods may be made by methods known in the art. The antibodies can be raised using the selenoprotein polypeptide or a peptide derived therefrom, preferably from a hydrophilic portion of the selenoprotein.

Example 6

Transfection and Co-transfection Studies

The expression vectors described in Example 5 are used to transfect various prostate tumor cell lines, which can be obtained from the Cap CURE prostate tissue bank or other sources. Co-transfection studies with oncogenes such as Bcl-2 in normal cells reveal any synergy or antagonism between these different gene products. Such studies indicate whether a reduced ability to express these selenoprotein gene products is a factor in tumor development. Because the levels of such selenoproteins are reduced under Se-deficient conditions even without mutations, the resultant imbalance is postulated to be a significant early step in the progression toward increased cell proliferation.

Example 7

Comparative Sequence Analysis of Wild-type and Mutant Genes in Regard to Selenoprotein ORFs Additional computer analyses of wild-type and mutant genes reveal how mutations in oncogenes and p53 associated with cancer progression affect the ORFs identified by the present methods.

It will be understood in the art that the skilled artisan can, without expense or undue experimentation, readily analyze any other DNA sequence to identify the presence of selenoprotein coding sequences using the following steps:

All references and sequence databank entries cited in the present application are incorporated by reference herein. U.S. Provisional Patent Application Serial No. 60/001203, filed Jul. 14, 1995, and U.S. Provisional Patent Application Serial No. 60/003112, filed Sep. 1, 1995, are also hereby incorporated by reference in their entirety.

1. Parslow, T. G. (1993) Post transcriptional Regulation of Human Retro-Viral Gene Expression. In *Human Retroviruses;* Cullen, B. R., Ed.; Oxford University Press: New York; pp. 101–136.
2. Jacks, T.; Power, M. D.; Masiarz, F. R.; Luciw, P. A.; Barr, P. J.; Varmus, H. E. (1988) "Characterization of Ribosomal Frameshifting in HIV-1 gag-pol Gene Expression" *Nature* 331:280–283.
3. Yoshinaka, Y.; Katoh, I.; Copeland, T. D.; Oroszlan, S. (1985) "Murine Leukemia Virus Protease Is Encoded by the gag-pol Gene and Is Synthesized Through Suppression of an Amber Termination Codon" *Proc. Natl. Acad. Sci. USA* 82:1618–1622.
4. Feng, Y. X.; Hatfield, D. L.; Rein, A.; Levin, J. G. (1989) "Translational Readthrough of the Murine Leukemia Virus Gag Gene Amber Codon Does Not Require Virus-Induced Alteration of tRNA" *J. Virol.* 63:2405–2410.
5. Rein, A.; Levin, J. G. (1992) "Readthrough Suppression in the Mammalian Type C Retroviruses and What it Has Taught Us" *New Biol.* 4:283–289.
6. Puglisi, J. D.; Wyatt, J. R.; Tinoco, I., Jr. (1988) "A Pseudoknot RNA Oligonucleotide" *Nature* 331:283–286.
7. Le, S. Y.; Shapiro, B. A.; Chen, J. H.; Nussinov, R.; Maizel, J. V. (1 991) "RNA Pseudoknots Downstream of the Frameshift Sites of Retro-Viruses" *Genet. Anal. Tech. Appl.* 8:191–205.
8. Jacks, T.; Townsley, K.; Varmus, H. E.; Majors, J. (1987) "Two Efficient Ribosomal Frameshifting Events Are Required for Synthesis of Mouse Mammary Tumor Virus Gag-Related Polyproteins" *Proc. Natl. Acad. Sci. USA* 84:4298–4302.
9. Jacks, T.; Madhani, H. D.; Masiarz, F. R.; Varmus, H. E. (1988) "Signals for Ribosomal Frameshifting in the Rouse Sarcoma Virus gag-pol Region" *Cell* 55:447–458.
10. Feng, Y. X.; Yuan, H.; Rein, A.; Levin, J. G. (1992) "Bipartite Signal for Read-Through Suppression in Murine Leukemia Virus mRNA: An Eight-Nucleotide Purine-Rich Sequence Immediately Downstream of the Gag Termination Codon Followed by an RNA Pseudoknot" *J. Virol.* 66:5127–5132.
11. Cohen, E. A.; Lu, Y.; Gottlinger, H.; Dehni, G.; Jalinoos, Y.; Sodroski, J.G.; Haseltine, W. A. (1990) "The T Open Reading Frame of Human Immunodeficiency Virus Type 1" *J. AIDS* 3:601–608.
12. Chamorro, M; Parkin, N.; Varmus, H. E. (1992) "An RNA Pseudoknot and an Optimal Heptameric Shift Site Are Required for Highly Efficient Ribosomal Frameshifting on a Retroviral Messenger RNA" *Proc. Natl. Acad Sci. USA* 89:713–717.
13. Shen, Q.; Chu, F. F.; Newburger, P. E. (1993) "Sequences in the 3'-Untranslated Region of the Human Cellular Glutathione Per-Oxidase Gene Are Necessary and Sufficient for Selenocysteine Incorporation at the UGA Codon" *J. Biol. Chem.* 268:11463–11469.
14. Berry, M. J.; Banu, L.; Harney, J. W.; Larsen, P. R. (1993) "Functional Characterization of the Eukaryotic SECIS Elements Which Direct Selenocysteine Insertion at UGA Codons" *EMBO J.* 12:3315–3322.
15. Bock, A.; Forchhammer, K.; Heider, J.; Leinfelder, W.; Sawers, G.; Veprek, B.; Zinoni, F. (1991) "Selenocysteine: The 21$^{st}$ Amino Acid" *Mol. Microbiol.* 5:515–520.
16. Schinazi, R. F.; Lloyd, R. M., Jr.; Ramanathan, C. S.; Taylor, E. W. (1994) "Antiviral Drug Resistance Mutations in Human Immunodeficiency Virus Type 1 Reverse Transcriptase Occur in Specific RNA Structural Regions" *Antimicrob. Agents Chemother.* 38:268–274.
17. Le, S. Y.; Chen, J. H.; Chatterjee, D.; Maizel, J. V. (1989) "Sequence Divergence and Open Regions of RNA Secondary Structures in the Envelope Regions of the 17 Human Immunodeficiency Virus Isolates" *Nucleic Acids Res.* 17:3275–3288.
18. Zuker, M.; Steigler, P. (1981) "Optimal Computer Folding of Large RNA Sequences Using Thermodynamics and Auxillary Information" *Nucleic Acids Res.* 9:133–148.
19. ten Dam, E.; Pleij, K.; Draper, D. (1992) "Structural and Functional Aspects of RNA Pseudoknots" *Biochemistry* 31:11665–11676.
20. Feng, Y. X.; Levin, J. G.; Hatfield, D. L.; Schaefer, T. S.; Gorelick, R. J.; Rein, A. (1989) "Suppression of UAA and UGA Termination Codons in Mutant Murine Leukemia Viruses" *J. Virol* 63:2870–2873.
21. Feng, Y. X.; Copeland, T. D.; Oroszlan, S.; Rein, A.; Levin, J. G. (1990) "Identification of Amino Acids Inserted During Suppression of UAA and UGA Termination Codons at the gag-pol Junction of Moloney Murine Leukemia Virus" *Proc. Natl. Acad. Sci. USA* 87:8860–8863.
22. Watson, J. D.; Hopkins, N. H.; Roberts, J. W.; Steitz, J. A.; Weiner, A. M. (1987) *Molecular Biology of the Gene*, $4^{th}$ Ed.; Benjamin/Cummings: Menlo Park.
23. Peterlin, B. M.; Adams, M.; Alonso, A.; Baur, A.; Ghosh, S.; Lu, X.; Luo, Y. (1993) "Tat Trans-Activator" In *Human Retroviruses;* Cullen, B. R., Ed.; Oxford University Press: New York; pp. 75–100.
24. Le, S. Y.; Maizel, J. V. (1989) "A Method For Assessing the Statistical Significance of RNA Folding" *J. Theor. Biol.* 138:495–510.
25. Wittwer, A. J.; Stadtman, T. C. (1986) "Biosynthesis of 5-Methylamino-Methyl-2-Selenouridine, a Naturally Occuring Nucleoside in *Escherichia coli* tRNA" *Arch. Biochem. Biophys.* 248:540–550.
26. Hatfield, D. L.; Levin, J. G.; Rein, A.; Oroszlan, S. (1992) "Translational Suppression in Retroviral Gene Expression" *Adv. Virus. Res.* 41:193–239.
27. Heider, J.; Baron, C.; Bock, A. (1992) "Coding From a Distance: Dissection of the mRNA Determinants Required for the Incorporation of Selenocysteine Into Protein" *EMBO J.* 11:3759–3766.
28. Tang, C. K.; Draper, D. E. (1989) "Unusual mRNA Pseudoknot Structure Is Recognized by a Protein Translational Repressor" *Cell* 57:531.
29. Ham, J.; Dostatni, N.; Gauthier, J.-M.; Yaniv, M. (1991) "The Papillomavirus E2 Protein: A Factor With Many Talents" *Trends Biochem. Sci.* 16:440–444.
30. Hegde, R. S.; Grossman, S. R.; Laimins, L. A.; Sigler, P. B. (1992) "Crystal Structure at 1.7 A of the Bovine Papillomavirus-1 E2 DNA-Binding Domain Bound to its DNA Target" *Nature* 359:505–512.
31. Kato, H.; Horikoshi, M.; Roeder, R. G. (1991) "Repression of HIV-1 Transcription by a Cellular Protein" *Science* 251:1476–1479.
32. Berkhout, B. (1992) "Structural Features in TAR RNA of Human and Simian Immunodeficiency Viruses: A Phylogenetic Analysis" *Nucleic Acids Res.* 20:27–31.
33. Jacobo-Molina, A.; Ding, J.; Nanni, R. G.; Clark, A. D., Jr.; Lu, X.; Tantillo, C.; Williams, R. L.; Kamer, G.; Ferris, A. L.; Clark, P.; Hizi, A.; Hughes, S. H.; Arnold, E. (1993) "Crystal Structure of Human Immunodeficiency Virus Type 1 Reverse Transcriptase Complexed With Double-Stranded DNA at 3.0 Å Resolution Shows Bent DNA" *Proc. Natl. Acad. Sci. USA* 90:6320–6324.
34. Cheng, N.; Merrill, B. M.; Painter, G. R.; Frick, L. W.; Furman, P. A. (1993) "Identification of the Nucleotide Binding Site of HIV-1 Reverse Transcriptase Using dTTP as a Photoaffinity Label" *Biochemistry* 32:7630–7634.
35. Kennedy, J. R. (1992) "AIDS—An Autoimmune Module" *Med. Hypotheses* 37:16–19.
36. Katz, D. H. (1993) "AIDS: Primarily a Viral or an Autoimmune Disease?" *Aids Res. Hum. Retrovir.* 9:489–493.
37. Gorbalenya, A. E.; Koonin, E. V.; Donchenko, A. P.; Blinov, V. M. (1988) "A Novel Superfamily of Nucleoside Triphosphate-Binding Motif Containing Proteins Which Are Probably Involved in Duplex Unwinding in DNA and RNA Replication and Recombination. *FEBS Lett.* 235:16–24.
38. Koonin, E. V. (1993) "A Superfamily of ATPases With Diverse Functions Containing Either Classical or Deviant ATP-Binding Motif" *J. Mol. Biol.* 229:1165–1174.
39. Gibbs, J. S.; Desrosiers, R. C. (1993) "Auxiliary Proteins of the Primate Immunodeficiency Viruses" In *Human Retroviruses;* Cullen, B. R., Ed.; Oxford University Press: New York; pp. 137–158.
40. Malim, M.; Cullen, B. (1991) "HIV-1 Structural Gene Expression Requires the Binding of Multiple Rev Monomers to the Viral RRE: Implications for HIV-1 Latency" *Cell* 65:241–248.
41. Beck, K. W.; Schramel, P.; Hedl, A.; Jager, H.; Kaboth, W. (1989) "Trace Element Concentrations in HIV Infected Patients" *Onkologie* 3:43–47.
42. Dworkin, B. M.; Antonecchia, P. P.; Smith, F.; Weiss, L.; Davidian, M.; Rubin, D.; Rosenthal, W. S. (1989) "Reduced Cardiac Selenium Content in the Acquired Immunodeficiency Syndrome" *J. Parenter. Enteral. Nutr.* 13:644–647.
43. Olmsted, L.; Schrauzer, G. N.; Flores-Arce, M.; Dowd, J. (1989) "Selenium Supplementation of Symptomatic Human Immunodeficiency Virus Infected Patients" *Biol. Trace Elem. Res.* 20:59–65.
44. Beck, K. W.; Schramel, P.; Hedl, A.; Jaeger, H.; Kaboth, W. (1990) "Serum Trace Element Levels in HIV-Infected Subjects" *Biol. Trace Elem. Res.* 25:89–96.
45. Allavena, C.; Dousset, B.; May, T.; Amiel, C.; Nabet-Belleville, F.; Canton, P. (1991) "Are Zinc and Selenium Markers of Worsening in HIV Infected Subjects?" *Presse. Med.* 20:1737.
46. Cirelli, A.; Ciardi, M.; de-Simone, C.; Sorice, F.; Giordano, R.; Ciaralli, L.; Costantini, S. (1991) "Serum Selenium Concentration and Disease Progress in Patients With HIV Infection" *Clin. Biochem.* 24:211–214.
47. Schrauzer, G. N.; Sacher, J. (1994) "Selenium in the Maintenance and Therapy of HIV-Infected Patients" *Chem.-Biol. Interact.* 91:199–205.
48. Dworkin, B. M.; Rosenthal, W. S.; Wormser, G. P.; Weiss, L.; Nunez, M.; Joline, C.; Herp, A. (1988) "Abnormalities of Blood Selenium and Glutathione Peroxidase Activity in Patients With Acquired Immunodeficiency Syndrome and AIDS-Related Complex" *Biol. Trace Elem. Res.* 15:167:177.
49. Zazzo, J. F.; Lafont, A.; Darwiche, H.; Sayegh, F.; Camus, F.; Chappuis, P.; Chalas, J.; Benattar, C. (1989) "Is Non Obstructive Myocardiopathy (NOMC) in AIDS Selenium-Deficiency-Related?" In *Selenium in Medicine and Biology;* Neve, J., Fevier, A., Eds,; Walter de Gruyter: Berlin; pp. 281–282.
50. Flohe, L., (1989) "The Selenoprotein Glutathione Peroxidase" In *Glutathione: Chemical, Biochemical and Medical Aspects" Part A;* Dolphin, R. P. D., Avramovic, O., Eds.; Wiley-Interscience: New York; pp. 643–732.
51. LoPresti, J. S.; Fried, J. C.; Spencer, C. A.; Nicoloff, J. T. (1989) "Unique Alterations of Thyroid Hormone Indices in the Acquired Immunodeficiency Syndrome (AIDS)" *Ann. Intern. Med.* 110:970–975.

52. Bourdoux, P. P.; De-Wit, S. A., Servais, G. M.; Clumeck, N.; Bonnyns, M. A. (1991) "Biochemical Thyroid Profile in Patients Infected With the Human Immunodeficiency Virus" *Thyroid* 1:147–149.
53. Nduwayo, L.; Nsabiyumva, F.; Osorio-Salazar, C.; Lecomte, P.; Guilmot, J. L.; Renard, J. P. (1992) "Endocrinological Aspects of Acquired Immunodeficiency Syndrome (AIDS)" *Med. Trop. Mars* 52:139–143.
54. Grunfeld, C.; Pang, M.; Doerrier, W.; Jensen, P.; Shimizu, L.; Feingold, K. R.; Cavalieri, R. R. (1993) "Indices of Thyroid Function and Weight Loss in Human Immunodeficiency Virus Infection and the Acquired Immunodeficiency Syndrome" *Metabolism* 42:1270–1276.
55. Hommes, M. J.; Romijn, J. A.; Endert, E.; Adriaanse, R.; Brabant, G.; Eeftinck-Schattenkerk, J. K.; Wiersinga, W. M.; Sauerwein, H. P. (1993) "Hypothyroid-Like Regulation of the Pituitary-Thyroid Axis in Stable Human Immunodeficiency Virus Infection" *Metabolism* 42:556–561.
56. Byamungu, N.; Mol, K.; Kuhn, E. R. (1991) "Somatostatin Increases Plasma T3 Concentrations in *Tilapia nilotica* in the Presence of Increased Plasma T4 Levels" *Gen. Comp. Endocrinol.* 82:401–406.
57. Geelhoed-Duijvestijn, P. H.; Roelfsema, F.; Schroder-van-der-Elst, J. P.; van-Doorn, J.; van-der-Heide, D. (1992) "Effect of Administration of Growth Hormone On Plasma and Intracellular Levels of Thyroxine and Tri-Iodothyronine in Thyroidectomized Thyroxine-Treated Rats" *J. Endocrinol.* 133:45–49.
58. Roederer, M.; Staal, F. J.; Anderson, M.; Rabin, R.; Raju, P. A.; Herzenberg, L. A.; Herzenberg, L. A. (1993) "Disregulation of Leukocyte Glutathione in AIDS" *Ann. N. Y. Acad. Sci.* 677:113–125.
59. Holroyd, K. J.; Buhl, R.; Borok, Z.; Roum, J. H.; Bokser, A. D.; Grimes, G. J.; Czerski, D.; Cantin, A. M.; Crystal, R. G. (1993) "Correction of Glutathione Deficiency in the Lower Respiratory Tract of HIV Seropositive Individuals by Glutathione Aerosol Treatment" *Thorax* 48:985–989.
60. Kalebic, T.; Kinter, A.; Poli, G.; Anderson, M. E.; Meister, A.; Fauci, A. S. (1991) "Suppression of HIV Expression in Chronically Infected Monocyte Cells by Glutathione, Glutathione Ester, and N-Acetyl Cysteine" *Proc. Natl. Acad. Sci. USA* 88:986–990.
61. Staal, F. J. T.; Anderson, M. T.; Staal, G. E. J.; Herzenberg, L. A.; Gitler, C.; Herzenberg, L. A. (1994) "Redox Regulation of Signal Transduction: Tyrosine Phosphorylation and Calcium Influx" *Proc. Natl. Acad. Sci. USA* 91:3619–3622.
62. *Selenium in Biology and Medicine;* (1987) Combs, G. F., Jr.; Spallholz, J. E., Levander, O. A., Oldfields, J. E., Eds.; Van Nostrand-Reinhold: New York; Vols. A and B.
63. Schrauzer, G. N. (1992) "Selenium. Mechanistic Aspects of Anticarcinogenic Action" *Biol. Trace Elem. Res.* 33:51–62.
64. Schrauzer, G. N.; Molenaar, T.; Kuehn, K.; Waller, D. (1989) "Effect of Simulated American, Bulgarian, and Japanese Human Diets and of Selenium Supplementation on the Incidence of Virally Induced Mammary Tumors in Female Mice" *Biol. Trace Elem. Res.* 20:169–178.
65. Ge, K.-Y.; Bai, J.; Deng, X.-J.; Wu, S.-Q.; Wang, S.-Q.; Xue, A.-N.; Su, C.-Q. (1987) "The Protective Effect of Selenium Against Viral Myocarditis in Mice. In *Selenium in Biology and Medicine;* Combs, G. F., Jr., Spallholz, J. E., Levander, O. A., Oldfields, J. E., Eds.; Van Nostrand-Reinhold: New York; Vol. B; pp. 761–768.
66. Yu, S. Y.; Li, W. G.; Zhu, Y. J.; Yu, W. P.; Hou, C. (1989) "Chemoprevention Trial of Human Hepatitis With Selenium Supplementation in China" *Biol. Trace Elem. Res.* 20:15–22.
67. Balansky, R. M.; Argirova, R. M. (1981) "Sodium Selenite Inhibition of Some Oncogenic RNA Viruses" *Experientia* 37:1194–1195.
68. Lazymovam, Z. A.; Abdullaev, I. I.; Abdullaev, F. I.; Asadullaev, T. A. (1986) "Inhibiting Action of Sodium Selenite on Influenza Virus Reproduction" *Voprosy Virusol.* 31:236–238.
69. Ching, P. S. (1984) "Occurrence of Selenium-Containing tRNAs in Mouse Leukemia Cells" *Proc. Natl. Acad. Sci. USA* 81:3010–3013.
70. Yan, L.; Yee, J. A.; Boylan, L. M.; Spallholz, J. E. (1991) "Effect of Selenium Compounds and Thiols on Human Mammary Tumor Cells" *Biol. Trace Elem. Res.* 30:145–162.
71. Yu, S. Y.; Zhu, Y. J.; Li, W. G.; Huang, Q. S.; Zhi-Huang, C.; Zhang, Q. N.; Hou, C. A. (1991) "A Preliminary Report on the Intervention Trials of Primary Liver Cancer in High-Risk Populations With Nutritional Supplementation of Selenium in China" *Biol. Trace Elem. Res.* 29:289–294.
72. Gelpi, C.; Sontheimer, E. J.; Rodriguez-Sanchez, J. L. (1992) "Autoantibodies Against a Serine tRNA-Protein Complex Implicated in Cotranslational Selenocysteine Insertion" *Proc. Natl. Acad. Sci. USA* 89:9739–9743.
73. Karimpour, I.; Cutler, M.; Shih, D.; Smith, J.; Kleene, K. C. (1992) "Sequence of the Gene Encoding the Mitochondrial Capsule Selenoprotein of Mouse Sperm: Identification of Three In-Phase TGA Selenocysteine Codons" *DNA Cell Biol.* 11:693–699.
74. Bedwal, R. S.; Nair, N.; Sharma, M. P.; Mathur, R. S. (1993) "Selenium—Its Biological Perspectives" *Med. Hypotheses* 41:150–159.
75. Shih, A.; Coutavas, E. E.; Rush, M. G. (1991) "Evolutionary Implications of Primate Endogenous Retroviruses" *Virology* 182:495–502.
76. Katz, R. A.; Skalka, A. M. (1990) "Generation of Diversity in Retroviruses" *Annu. Rev. Genet.* 24:409–445.
77. Talal, N.; Flescher, E.; Dang, H. (1992) "Are Endogenous Retroviruses Involved in Human Autoimmune Disease?" *J. Autoimmun.* 5:61–66.
78. Taylor, E. W.; Jaakkola, J. (1991) "A Transposition of the Reverse Transcriptase Gene Reveals Unexpected Structural Homology to *E. coli* DNA Polymerase I" *Genetica* 84:77–86.
79. Lazcano, A.; Valverde, V.; Hernandez, G.; Gariglio, P.; Fox, G. E.; Oro, J. (1992) "On the Early Emergence of Reverse Transcription Theoretical Basis and Experimental Evidence" *J. Mol. Evol.* 35:524–536.
80. McClure, M. A. (1993) "Evolutionary History of Reverse Transcriptase" In *Reverse Transcriptase;* Skalka, A. M., Goff, S. P., Eds.; Cold Spring Harbor Laboratory Press: New York; pp. 425–444.
81. Storz, G.; Tartaglia, L. A.; Ames, B. N. (1990) "Transcriptional Regulator of Oxidative Stress-Inducible Genes: Direct Activation by Oxidation" *Science* 248:189–194.
82. Vernon, S. D.; Hart, C. E.; Reeves, W. C.; Icenogle, J. P. (1993) "The HIV-1 tat Protein Enhances E2-Dependent Human Papillomavirus 16 Transcription" *Virus Res.* 27:133–145.
83. Burcham, J. L.; Tindall, B.; Marmor, M.; Cooper, D. A.; Berry, G.; Penny, R. (1989) "Incidence and Risk Factors for Human Immunodeficiency Virus Seroconversion in a Cohort of Sydney Homosexual Men" *Med. J. Aust.* 150:634–639.
84. Soderberg, L. S.; Barnett, J. B. (1993) "Inhaled Isobutyl Nitrite Compromises T-Dependent, but Not T-Independent, Antibody Production" *Int. J. Immunopharmacol.* 15:821–827.

85. Brutlag, D. L.; Dautricourt, J.-P.; Maulik, S.; Relph, J. (1990) "Sensitive Similarity Searches of Biological Sequence Databases" *Comput. Appl. Biosci.* 6:237–245.

86. McLachlan, A. D. (1972) "Repeating Sequences and Gene Duplication in Proteins" *J. Mol. Biol.* 64:417–437.

87. Smith, T. F.; Waterman, M. S. (1981) "Comparison of Biosequences" *Adv. Appl. Math.* 2:482–489.

88. Needleman, S. B.; Wunsch, C. D. (1970) "A General Method Applicable to the Search For Similarities in the Amino Acid Sequences of Two Proteins" *J. Mol. Biol.* 48:443–453.

89. Gribskov, M.; Burgess, R. R. (1986) "Sigma Factors From *E. coli*, B. subtilis, Phage SPO1 and Phage T4 Are Homologous Proteins" *Nucleic Acids Res.* 14:6745–6763.

90. Devereux, J.; Haeberli, P.; Smithies, O. (1984) "A Comprehensive Set of Sequence Analysis Programs for the VAX" *Nucl. Acids Res.* 12:387–395.

91. ORFwriter Is a Macintosh Program by Dr. James S. Gibbs; Harvard Medical School (gibbs@husc.harvard.edu).

92. Brierley, I.; Jenner, J. A. (1992) "Mutational Analysis of the 'Slippery-Sequence' Component of a Coronavirus Ribosomal Frameshifting Signal" *J. Mol. Biol.* 227:463–479.

93. Gallant, J.; Lindsley, D. (1993) "Ribosomal Frameshifting at Hungry Codons: Sequence Rules, Directional Specificity and Possible Relationship to Mobile Element Behavior" *Biochem. Soc. Trans.* 21:817–821.

94. de Smit, M. H.; van Duin, J.; van Knippenberg, P. H.; van Eijk, G. H. (1994) "CCC.UGA: A New Site of Ribosomal Frameshifting in *Escherichia coli*" Gene 143:43–47.

95. Belcourt, M. F.; Farabaugh, P. J. (1990) "Ribosomal Frameshifting in the Yeast Retrotransposon Ty: tRNAs Induce Slippage on a 7 Nucleotide Minimal Site" *Cell* 62:339–352.

96. Farabaugh, P. J.; Zhao, H.; Vimaladithan, A. (1993) "A Novel Programmed Frameshift Expresses the POL3 Gene of Retrotransposon Ty3 of Yeast: Frameshifting Without tRNA Slippage" *Cell* 74:93–103.

97. Vimaldithan, A; Farabaugh, P. J. (1994) "Special Peptidyl-tRNA Molecules Can Promote Translational Frameshifting Without Slippage" *Mol. and Cell. Biol.* 14:8107–8116.

98. Watanabe, K.; Hayashi, N.; Oyama, A.; Nishikawa, K.; Ueda, T.; Miura, K. (1994) "Unusual Anticodon Loop Structure Found in *E. coli* Lysine tRNA" *Nucl. Acids Res.* 22:79–87.

99. Barat, C.; Le Grice, S. F. J.; Darlix, J. (1991) "Interaction of HIV-1 Reverse Transcriptase With a Synthetic Form of its Replication Primer, tRNA$^{Lys,3}$" *Nucl. Acids Res.* 19:751–757.

100. Li, G.; Rice, C. M. (1993) "The Signal for Translational Readthrough of a UGA Codon in Sindbis Virus RNA Involves a Single Cytidine Residue Immediately Downstream of the Termination Codon" *J. Virol.* 67:5062–5067.

101. Gramstat, A.; Prufer, D.; Rohde, W. (1994) "The Nucleic Acid-Binding Zinc Finger Protein of Potato Virus M Is Translated by Internal Initiaton as Well as by Ribosomal Frameshifting Involving a Shifty Stop Codon and a Novel Mechanism of P-Site Slippage" *Nucl. Acids Res.* 22:3911–3917.

102. Berry, M. J.; Larsen, R. P. (1993) "Recognition of UGA as a Selenocysteine Codon in Eukaryotes: A Review of Recent Progress" *Biochem. Soc. Trans.* 21:827–832.

103. Myers, G. et al. (1994) "Human Retroviruses and AIDS: A Compilation and Analysis of Nucleic Acid and Amino Acid Sequences" (Los Alamos National Laboratory, Los Alamos, N. Mex.).

104. Kubota, S.; Oroszlan, S.; Hatanaka, M. (1994) "The Origin of Human Immunodeficiency Virus Type-1 Rev Gene. An Evolutionary Hypothesis" *FEBS Lett.* 338:118–121.

105. Gibbs, J. G.; Desrosiers, R. C. (1993) "Auxiliary Proteins of the Primate Immunodeficiency Viruses" In *Human Retroviruses*, Cullen, B. R., Ed.; Oxford University Press: New York.

106. Tristem, M.; Marshall, C.; Karpas, A.; Hill, F. (1992) "Evolution of the Primate Lentiviruses: Evidence From vpx and vpr" *EMBO J.* 11:3405–3412.

107. Beck, M. A.; Kolbeck, P. C.; Rohr, L. H.; Shi, Q.; Morris, V. C.; Levander, O. A. (1994) "Vitamin E. Deficiency Intensifies the Myocardial Injury of Coxsackie B3 Infection of Mice" *J. Nutr.* 124:345–358.

108. Beck, M. A.; Kolbeck, P. C.; Rohr, L. H.; Shi, Q.; Morris, V. C.; Levander, O. A. (1994) "Benign Human Enterovirus Becomes Virulent in Selenium-Deficient Mice" *J. Med. Virol.* 43:166–170.

109. Engel, J. (1989) "EGF-Like Domains in Extracellular Matrix Proteins: Localized Signals for Growth and Differentiation?" *FEBS Lett.* 251:1–7.

110. Opgenorth, A.; Nation, N.; Graham, K.; McFadden, G. (1993) "Transforming Growth Factor Alpha, Shope Fibroma Growth Factor, and Vaccinia Growth Factor Can Replace Myxoma Growth Factor in the Induction of Myxomatosis in Rabbits" *Virol.* 192:701–709.

111. Hill, K. E.; Lloyd, S. R.; Burk, R. F. (1993) "Conserved Features of Selenoprotein P cDNA" *Biochem. Soc. Trans.* 21:832–835.

112. Sandstrom, P. A.; Tebbey, P. W.; Van Cleave, S.; Buttke, T. M. (1994) "Lipid Hydroperoxides Induce Apoptosis in T Cells Displaying a HIV-Associated Glutathione Peroxide Deficiency" *J. Biol Chem.* 269:798–801.

113. Sappey, C.; Legrand-Poels, S.; Best-Belpomme, M.; Favier, A.; Rentier, B.; Piette, J. (1994) "Stimulation of Glutathione Peroxidase Activity Decreases HIV Type 1 Activation After Oxidative Stress" *AIDS Res. Human Retrovir.* 10:1451–1461.

114. Moore, P. S.; Allen, S.; Sowell, A. L.; Van de Pierre, P.; Huff, D. L.; Serufiliria, A.; Nsengumuremyi, F.; Hulley, B. (1993) "Role of Nutritional Status and Weight Loss in HIV Seroconversion Among Rwandan Women" *J. AIDS* 6:611–616.

115. Ziegler, J. L. (1993) "Endemic Kaposi's Sarcoma in Africa and Local volcanic Soils" *Lancet* 342:1348–1351.

116. Zuker, M.; Steigler, P. (1981) "Optimal Computer Folding of Large RNA Sequences Using Thermodynamics and Auxillary Information" *Nucl. Acids Res.* 9:133–148.

117. Program Manual for the Wisconsin Package, Version 8, September 1994, Genetics Computer Group, 575 Science Drive, Madison, Wis., 53711.

TABLE 1

Viral Fusion Protein Sequences[1]

FUSION PROTEIN: HIV_GAG[2] (SEQ ID NO:25)

1 MGARASVLSG GELDRWEKIR LRPGGKKKYK LKHIVWASRE LEFRFAVNPGL

51 LETSEGCRQI LGQLQPSLQT GSEELRSLYN TVATLYCVHQ RIEIKDTKEA

101 LDKIEEEQNK SKKKAQQAAA DTGHSSQVSQ NYPIVQNIQG QMVHQAISPR

151 TLNcmgkssr regfqprsdt hvfsiirrsh ptrfkhhakh sggtssshan 201 vkrdhqUgsc rmg

Comment: This sequence represents fusion protien variants of the N-terminal region of the HIV-1 gag protein, expressed by a -1 frameshift starting from base number 794 (sequence following the frameshift shown in lower case). One variant form tof the fusion protein is terminated at position 206 (ending with the sequence rdhq), i.e. terminated at the UGA codon.

FUSION PROTEIN: HIV_PROTEASE[2] (SEQ ID NO:26)

1 PQITLWQRPL VTIKIGGQLK essiryrsrU ysirrnefar kmetkndrgn 51 wrfyqsktvU sdthrnlwtx̂ syrysisrty tcqhnwkksv dsdwlhfkhs 101 h Comments: This sequence represents fusion protein variants of the N-terminal region of HIV-1 protease, expressed by a -1 frameshift. The ^ represents a site of possible termination suppression, i.e. a non-UGA stop codon folowed by a pseudoknot (as in Taylor et al. (1949) J. Med. Chem. 37:2637–2654, FIG. 12. On Table 1 of our paper the amino acid sequence at the shift site of this fusion protein was given as K/GSS (see text).

Various amino acids with similar anti codons can be substituted at UAA and UGA stop codons by such readthrough mechanisms. Q (glutamine) is the most likely amino acid, but introduction of Y (tyrosine) under these circumstances has occurred, thus x in the sequence resulting from readthrough can be q or y, (lower case being used for frameshifted sequence). Variants include short variants terminating with "nlwt" and longer readthrough variants.

FUSION PROTEIN: HIV_INTEGRASE[2] (SEQ ID NO:70)

1 FLDGIDKAQD EHEKYHSNWR AMASDFNLPP VVAKEIVASC DKCQLKGEAM

51 HGQVDCSPGI WQLDCTHLEG Lsypgssscs qwiyrsrsys srnragnsil 101 sfkisrkmas knntyrqwqq fhqyygqx̂rl lvggnqagiw nslqspksrs 151 sriye Comments: This sequence represents fusion protein variants of HIV integrase resulting from a -1 frameshift in the integrase coding region. The ^ represents a site of possible termination suppression. In the readthrough extended sequence x can be q or y. Variants include short variants ending in "yygq" and longer readthrough variants.

FUSION PROTEIN: HIV_RT1[2] (SEQ ID NO:71)

1 PISPIETVPV KLKPGMDGPK VKQWPLTEEK IKALVEICTE MEKEGKISKI

51 GPENPYNTPV FAIKKKDSTK WRKLVDFREL NKRTQDFWEV QLGIPHPAGL

101 KKekisnstg cgUciffssl DEDFRKYTAF TIPSINNETP GIRYQYNVLP

151 QGWKGSPAIF QSSMTKILEP FRKQNPDIVI YQYMDDLYVG SDLEIGQHRT

201 KIEELRQHLL RWGLTTPDKK HQKEPPFLWM GYELHPDKWT VQPIVLPEKD

251 SWTVNDIQKL VGKLNWASQI YPGIKVRQLC KLLRGTKALT EVIPLTEEAE

301 LELAENREIL KEPVHGVYYD PSKDLIA

Comment: This sequence represents variants of HIV-1 reverse transcriptase with the region encoding the first catalytic Asp replaced by a region encoded in the overlapping -1 frame (lower case), starting from the base number 2437, with a return to the main frame after a +1 frame shift from the base 2492.

FUSION PROTEIN: HIV_RT2[2] (SEQ ID NO:72)

1 PISPIETVPV KLKPGMDGPK VKQWPLTEEK IKALVEICTE MEKEGKISKI

51 GPENPYNTPV FAIKKKDSTK WRKLVDFREL NKTQDFWEV QLGIPHPAGL

101 KKKKSVTVLD VGDAYFSVPL DEDFRKYTAF TIPSINNETP GIRYQYNVLP

TABLE 1-continued

Viral Fusion Protein Sequences[1]

```
151 QGWKGSPAIF QSSMTKILEP FRKQMPrnsy lsihgUfvcr iUlEIGQHRT

201 KIEELRQHLL RWGLTTPDKK HQKEPPFLWM GYELHPDKWT VQPIVLPEKD

251 SWTVNDOQKL VGKLNWASQI YPGIKVRQLC KLLRGTKALT EVIPLTEEAE

301 LELAENREIL KEPVHGVYYD PSKDLIA
```
Comment: This sequence represents variants of HIV-1 reverse transcriptase with the region encoding the second two catalystic Asp residues replaced by a region encoded in the overlapping -1 frame (lower case). starting from the base number 2659, with a return to the main frame after a +1 frame shift from the base 2711.
FUSION PROTEIN: HIV_RT3[2] (SEQ ID NO:73)

```
  1 PISPIETVPV KLKPGMDGPK VKQWPLTEEK IKALVEICTE MEKEGKISKI

51 GPENPYNTPV FAIKKKDSTK WRKLVDFREL NKRTQDFWEV QLGIPHPAGL

101 KKKKSVTVLD VGDAYFSVPL DEDFRKYTAF TIPSINNETP GIRYQYNVLP

151 QGWKGSPAIF QSSMTKILEP FRKtksrhsy lsihgIfvcr iUlrnraaxn 201 knrgaettsv evgtyhtrqk tsertsipld glUtpsU
```
Comment: This sequence represents variants of HIV-1 reverse transcriptase resulting from a -1 frameshift. The ^ indicates a site of possible termination suppression. In the readthrough extended sequence x can be q or y. Variants include short bariants ending with "uraa" and readthrough variants.
FUSION PROTEIN: HIV_NEF1[2] (SEQ ID NO:74)

```
  1 MGGKWSKSSV VGWPTVRERM RRAEPAADGV GAASRDLEKH GAITSSNTAA

51 TNAACAWLEA QEEEEVGFPV TPQVPLRPMT YKAAVDLSHF LKrkggtgra 101 nslptktryp Usvdlphtrl lpUlaelhtr argqistdlw mvlqastsUa 151 r
```
Comment: This sequence represents HIV nef variants expressed by a single -1 frameshift around position 8658—8664. The N-terminal 92 amino acids are identical to the nef protein. The rest of the coding sequence is in the overlapping -1 frame of nef, starting from the base number 8665. In the majority of HIV-1 isolates (but not isolate BRU), the above protein coding sequence is extended by additional amino acids, typically EGRRGQ, sometimes a longer sequence. This reflects the hyperbariability of the HIV-1 nef coding sequence.
FUSION PROTEIN: HIV_NEF2[2] (SEQ ID NO:75)

```
  1 MGGKWSKSSV VGWPTVRERM RRAEPAADGV GAASRDLEKH GAITSSNTAA

51 TNAACAWLEA QEEEEVGFPV TPQVPLRPMT YKAAVDLSHF Lkrkggtgra 101 nslptktryp Usvdlphtrl lpDWQNTYPG PGVRYPLTFG WCYKLVPVEP

151 DKVEEANKGE NTSLLHPVSL HGMDDPEREV LEWRFDSRLA FHHVARELHP

201 EYFKNC
```
Comment: This sequence represents HIV nef variants. There is a return to the main nef reading frame at the conserved +1 frameshift sequence CCCUGA at positions 8752—8757. The sequence encoded in the -1 frame (lower case) starts from the base number 8665, and it returns to the main frame by a +1 frame shift from the base, 8756. By a termination suppression event, this protein can also be extended beyond 'FKNC' as shown for the native nef protein in the previous table (Table 1 of Taylor, E.W. et al. (1994) J. Med. Chem. 37:2637—2654).
FUSION PROTEIN: HIV_BEF3[2] (SEQ ID NO:76)

```
  1 MGGKWSKSSV VGWPTVRERM RRAEPAADGV GAASRDLEKH GAITSSNTAA

51 TNAACAWLEA QEEEEVGFPV TPQVPLRPMT YKAAVDLSHF LKEKGGLEGL

101 IHSQRRQDIL DLWIYHTQGY FPDWQNYTPG PGVRYPLTFG WCYKLVPVEP

151 DKVEEANKGE NTSLLHPVSL HGMDDPEREV LEWRFDSRLA FHHVARELHP

201 EYFKNCUhracykglsagdfpgrrglggtgewralrcci
```
Comments: This sequence represents variants of the HIV nef protein (JMC paper) where the usual termination at the UGA codon following position 206 is suppressed, leading to the extended form shown.

TABLE 1-continued

Viral Fusion Protein Sequences[1]

FUSION PROTEIN: HIV_ENV1[1] (SEQ ID NO:77)
  1 MRVKEKYQHL WRWGWKWGTM LLGILMICSA TEKLWVTVYY GVPVWKEATT

51 TLFCASDAKA YDTEVHNVWA THACVPTDPN PQEVVLVNVT ENFNMWKNDM

101 VEQMHEDIIS LWDQSLKPCV KLTPLCVSLK CTDLGNATNT NSSNTNSSSG

151 EMMMEKGEIK NCSFNISTSI RGKVQKEYAF FYKLDIIPID NDTTSYTLTS

201 CNTSVITQAC PKVSFEPIPI HYCAPAGFAI LKCNNKTFNG TGPCTNVSTV

251 QCTHGIRPVV STQLLLNGSL AEEEVVIRSA NFTDNAKTII VQLNQSVEIN

301 CTRPNNNTRK SIRIQRGPGR AFVITGKIGN MRQAHCNISR AKWNATLKQI

351 ASKLREQFGN NKTIIFKQSS GGDPEIVTHS FNCGGEFFYC NSTQLFNSTW

401 FNSTWSTEGS NNTEGSDTIT LPCRIKQFIN MWQEVGKAMY APPISGQIRC

451 SSNITGLLLT RDGGNNNNGS EIFRPGGGDM RDNWRSELYK YKVVKIEPLG

501 VAPTKAKRRV VQREKkssgn rsfvpwvlgs srkhygrtwn dadgtgqtii 551 vwysaaaeqf aegyUgatas vathslghqa apgknpgcgk ipkgstapgd 601 lgllwkthlh hccalec
Comment: This sequence represents C-terminal modified variants of
the HIV-1 env protein, produced by a -1 frameshift following
position 7347, such that the region shown in lower case, encoded
in the -1 frame, would be fused to the N-terminal of env (upper
case). The underlined region is a possible protease cleavage site.
PROTEIN: CXB3_SP1.PEP[3] (SEQ ID NO:78)
  1 MUYYSQMSVH NGSVLLCVQK QALPNFVURT RSSRGPREUI LPQEIPIPCA

51 FSSWIFRTRU LWRYPKVUAW CHWHCDHGGU RRGGRLCRHPU SPVAGRUCNG

101 TGSEGLCGTA WKCTRLRLY
Comment: This sequence represents variants of a protein that is
homologous to human epidermal growth factor, regions of
thrombospondin, and related proteins. It is encoded in the
-1 reading frame overlapping the main polyprotein. No frameshift
is required because this sequence has its own start codon. It is
encoded between bases 3442 and 3798.
FUSION PROTEIN: CXB3_FUS2.PEP[3] (SEQ ID NO:79)
  1 GPPVYREIKI SVAPETPPPP AIADLLKSVD SEAVREYCKE KGWLVPEINS 51 TLQIEKHVSR AFICLQALTT FVSVAGIIYI IYKLFAGFsr clyrsaqpea 101 qsaypeasks arpclUvrcr ndekelkqge nUiwrvyhag hlUqvgrfat 151 prqtwanhld eUsrgwcarc qgasrqgrhq lrtdttqiep eUecqrhqrl 201 lsqggsgg
Comment: This sequence represents variants of a fusion protein
encoded in the -1 frame (C-terminal half, lower case), overlapping
the vpg coding region. The -1 frame starts from the base number
5293. However, the frameshift site is before the protease cleavage
site at the N-terminal of vpg, so the mature protein is fused to
the upstream product, the known proteins p3A (upper case).
FUSION PROTEIN: CXB3_GPX1.PEP[3] (SEQ ID NO:80)
  1 MLERRSTLWK HTRYLEDMKD LERKYSAFHC NQGTRVFLVGR S
Comment: This sequence represents variants of a truncated
glutathione peroxidase (GPx) enzyme, encoded in the +1 frame
overlapping the main polyprotein between bases 1908 and 2036.
FUSION PROTEIN: CXB3_GPX2.PEP[3] (SEQ ID NO:81)
  1 MLERRSTLWK HTRYLUDPMK DLERKYSAFH CNQGyssvfs rtllgeilny 51 ythwsgsikl tfmfcgsama tgkfllatsp pgagaptkrv damlgthvvw 101 dvglqsscvl cipwisqthy rfvasdeyta ggfitcwyqt nivvpadaqs 151 scyimcfvsa cndfsvrllk dtpfisqqnf fq
Comment: This sequence represents additional variants of the
previous protein (GPx homologues), in which there is a -1
frameshift into the main polyprotein reading frame, making a fusion
product with the C-terminal two thirds of the vp3 structural
protein. The sequence encoded in ht e -1 (main) frame starts from

TABLE 1-continued

Viral Fusion Protein Sequences[1]

base 2009 (lower case in translation). The frameshift sequence and pseudoknot are shown in a separate figure.

[1]UGA codons are shown as U, and can be translated as SeC, Cys, Arg or Trp, or lead to premature termination, depending on conditions in the cell. Sequences at the frameshift sites have been translated according to a single lysine slippage mechanism (E.W. Taylor et al. (1994) J. Med. Chem. 37:2637–2654.
[2]HIV-1 fusion protein sequences are translated from a standard HIV-1 sequence, HIV-1 BRU, GenBank #k02013.
[3]Protein coding sequences are based on those from coxsackievirus b3 strain, GenBank #m88483.

TABLE 2

Examples of viral genomes in which selenoprotein genes have been found overlapping other known viral genes (some have start codons, some are expressed by frameshifting):

| Viral class | Virus type | Virus name | GenBank Acc. # |
|---|---|---|---|
| Retrovirus | Lentivirus | HIV-1 | K02013 |
| Picornavirus | Coxsackievirus | CVB3 | M88483 |
| Flavivirus | | Yellow Fever Virus | K02749 |
| Filovirus | Ebola virus | Ebola Zaire | L11365 |
| Orthomyxovirus | Influenzavirus | Influenza A | J02178 |
| Bunyavirus | | Hantaviris | X55901 |
| Birnavirus | Infectious bursal disease virus | | L19502 |
| Herpesvirus | | Epstein-Barr virus | V01555 |
| Herpesvirus | | Cytomegalovirus | D14980 |
| Herpesvirus | | Human Herpesvirus 6 | I20954 |
| Hepadnavirus | | Hepatitis B | X51970 |

TABLE 3

Examples of known cellular genes in which overlapping selenoprotein genes have been found (some have start codons, some are predicted to be expressed by frameshifting, some by both, giving multiple/alternative protein forms):

| NAME | Genbank Accession # | Comments |
|---|---|---|
| ONCOGENES and PROTO-ONCOGENES: | | |
| c-abl | m14752 | up to 24 UGA codons in ORF |
| bcl2 | M14745 | |
| bcl3 | U05822, other files | |
| lck | U07236 | |
| c-syn | M14333 | |
| elk1 | M25269 | |
| pim1 | M16750 | |
| tel (ets-like gene) | U11732 | |
| c-fos | U01512 | |
| Int1 | X03072 | |
| c-myc | X00364, J00120, K01908, V00501 | |
| TUMOR SUPPRESSOR GENES | | |
| P53 | k03199 | |
| IMMUNOGLOBIN SUPERFAMILY RELATED GENES | | |
| CD4 | M35160 | |
| CD8 | M36712 | |
| HLA-DR | M14765 | |
| TRANSCRIPTION FACTORS | | |
| HUBF | X53390 | |
| LCR-F1 | U08853 | |
| 1L-4 STAT | U16031 | |
| ZFX | X59739 | |
| ZNF6 | X56465 | |
| VHNF1 | X58840 | |
| HNF1 | M57732 | |
| TFIIIC | U06485 | |
| USF | X55666 | |
| B23 | M26697 | |
| MSS1 | D11094 | |
| GATA-3 | X55122 | |
| TRBP | M60801 | |
| HTLF | M94653 | |
| NF-Kappa B | M62399 | |
| BETA INTEGRINS | | |
| Integrin Beta 5 | J05633 | |
| CYTOKINE RECEPTORS | | |
| IL-2R | M14098, M26062 | |
| IL-9R | M84747 | |
| IL-10R | U00672 | |
| TNFR1 | M75866 | |
| CYTOKINES | | |
| IFN-Alpha | M27318 | |
| Leukocyte IFN | V00538 | |
| TNF | M26331 | |
| IFN-Gamma | V00536 | |
| IL-13 | U10307 | |
| GROWTH FACTORS | | |
| PDGF-B | X02811 | |
| TGF-Beta 3 | X14149 | |
| HBGF-R Alpha | M63887 | |
| FGF-R-1 | M34641 | |
| ERBB3 | M29366 | |
| STK-1 | U02687 | |
| EXTRACELLULAR MATRIX PROTEINS | | |
| Thrombospondin | L12350 | Multiple UGA-rich ORFs; one has 30 UGA codons |

TABLE 4

```
GAG (SEQ ID NO:87)
-1 RF:        CysMet
(788) UUUAAAUGCAUGGGUAAAAGUAGUAGAAGAGAAGGCUUUCAGCCCAGAAGUGAUACCCAUGUUUUC
0 RF: LeuAsn    A1    A2          B    A2'  A1'                    B'

GAG-POL* (SEQ ID NO:8)
-1 RF:        ArgGlu
(1631) UUUUUUAGGGAAGAUCUGGCCUUCCUACAAGGGAAGGCCAGGGAAUUUUCUU
0 RF: PheLeu         A          B    A'         B'

PROTEASE (SEQ ID NO:1)
-1 RF:        SerSer                Sec
(1891) AAAGGAAGCUCUAUUAGAUACAGGAGCAGAUGAUACAGUAUU
0 RF: LysGlu  A        B    A'          B'

RT1 (Motif A region) (SEQ ID NO:88)
-RF:          GluLys                  Sec            SerLeu
(2431) AAAAAAGAAAAAUCAGUAACAGUACUGGAUGUGGGUGAUGCAUAUUUUUCAGUUCCCUUAGAU
0 RF: LysLys   A       B    A'         B'            +1 FS Asp RT2 (Motif C region) (SEQ ID NO:4)
-1 RF:        ArgHis                Sec            SecLeu
(2653) AAAUCCAAGCAUAGUUAUCUAUCAAUACAUGGAUGAUUUGUAUGUAGGAUCUGACUUAGAA
0 RF: AsnPro     A       B    A'        B'         +1 FS Glu INTERGRASE (SEQ ID NO:89)
-1 RF:        SerTyr
(4018) AGGAAAAGUUAUCCUGGUAGCAGUUCAUGUAGCCAGUGGAUAUAU
0 RF: GlyLys      A       B    A'       B'

ENV (SEQ ID NO:90)
-1 RF:        LysSer
(7344) AAAAAGAGCAGUGGGAAUAGGAGCUUUGUUCCUUGGGUUCUUGGGAGCAGCAGGAA
0 RF: Lys ?      A       B        A'          B'

NEF (SEQ ID NO:91)
-1 RF:        ArgLys                                    Sec           Pro
(8659) UUUAAAAGAAAAGGGGGGACUGGAAGGGCUAAUUCACUCCCAACGAAGACAAGAUAUCCUUGAUCUGUGGAU-21 nt-CCCUGAU
0 RF: LeuLys      A         B     A'                    B'            +1 FS Asp
```

Potential new frameshift sites in HIV-1. These are shown along with the known gag-pol site (*). Shift sequences are shown in boldface, and potential PK structures indicated by overlining and underlinigin of the stem regions, A:A', B:B'. The predicted amino acid sequences at the frameshift sites are shown in italics, reading from left to right. Numbers refer to the 5' nucleotide. See sections 5.1.1 to 5.1.7 for discussion.

TABLE 5

```
                                  *                                    *
   HIV-1 (SEQ ID NO:93)  TIKIGGQLKGSBIRYRSRCYSIRRNEFARKMETKNDRGNWRFYQSKTVCS.DTHRN.LWT

DPV (SEQ ID NO:94)  CPCLLGTISGNG..NQVKCYSFRVKRWHDRDKY.HHTTTWWAVGGQGSERPGDATV.IVT

BPV-1 (SEQ ID NO:95)  SCFA..LISGTA..NQVKCYRFRVKKNHRHRYE.NCTTTWFTVADNGAERQGQAQI.LIT

CRPV (SEQ ID NO:96)  PPVI..CLKGGH..NQLKCLRYRLKSKHSSLFD.CISTTWSWVDTTSTCRLGSGRM.LIK

HPV-8 (SEQ ID NO:97)  PPVI..LVRGGA..NTLKCFRNRARVRYRGLFK.YFSTTWSWVAGDSTERLGRSRM.LIL

HPV-1 (SEQ ID NO:98)  PPVV..CVKGGA..NQLKCLRYRLKASTQVDFD.SISTTWHWTDRKNTERIGSARM.LVK

HPV-11 (SEQ ID NO:99)  TPIV..QLQGDS..NCLKCFRYRLNDKYKHLFE.LASSTWHWASPEAP.....HKNAIVT

HPV-6 (SEQ ID NO:100)  TPIV..QFQGES..NCLKCFRYRLNRDHRHLFD.LISSTWHWASSKAP.....HKHAIVT

HPV-18 (SEQ ID NO:101)  TPII..HLKGDR..NSLKCLRYRLRKHSDH.YR.DISSTWHWTGAGN......EKTGILT

HPV-16 (SEQ ID NO:102)  TPIV..HLKGDA..NTLKCLRYRFKK.HCTLYT.AVSSTWHWTGHNYK.....HKSAIVT

HPV-33 (SEQ ID NO:103)  APIV..HLKGES..NSLKCLRYRLKP.YNELYS.SMSSTWHWTSDNKN.....SKNGIVT

<—Recog.Helix—>
             HIV      .....QSYRYSISGTYTCNHNWKKSVDSDWLHFKFSH

DPV      ..FKDQSQRSHFLQQVPLPPGMSAHGVTMTVDF
```

TABLE 5-continued

| | |
|---|---|
| BPV-1 | ..FGSPSQRQDFLKHVPLPPGMNISGFTASLDF |
| CRPV | ..FADSEQRDKFLSRVPLPSTTQVFLGNNFYGL |
| HPV-8 | ..FTSAGQREKPDETVKYPKGVDTSYGNLDSL |
| HPV-1 | ..FIDEAQREKFLERVALPRSVSVFLGQFNGS |
| HPV-11 | LTYSSEEQRQQFLNSVKIPPTIRHKVGFMSLHLL |
| HPV-6 | VTYDSEEQRQQFLDVVKIPPTISHKLGFMSLHLL |
| HPV-18 | VTYHSETQRTKFLNTVAIPDSVQILVGYMTMY |
| HPV-16 | LTYDSEWQRDQFLSQVKIPKTITVSTGFMSI |
| HPV-33 | VTFVTGQQQQMFLGTVKIPPTVQISTGFMTLV |

Multiple alignment of the protease -1 frameshift fusion protein (shown complete except for the first eleven residues at the N-terminal, PQITLWQRPLV, (SEQ ID NO:92) which are identical to HIV-1 protease) with a set of papillomavirus E2 protein DNA binding domain sequences. Note similarities (boldfaced) in the DNA recopgnition helix region, with selenocysteine (shown by C plus an asterisk) encoded by UGA aligning with the conserved Cys (underlined) of the E2 proteins. The conserved tryptophan (W,underlined) is important for dimerization and is conserved in HIV-1 variants, CIV and some other primate retroviruses. The most critical DNA binding domains are in the upper panel. Readthrough suppression of a UAA codon by glutamine insertion, at the first Q in the lower panel (Q), aligned with boldfaced glutamates (E), could extend the protein to the length shown this region also conforms to the E2 alignment (e.g., conserved R near the beginning of the lower panel).

TABLE 6

| | | |
|---|---|---|
| | | * * |
| SIVMAND | (SEQ ID NO:104) | SSTRYRSCCYHL |
| SIVAGM3 | (SEQ ID NO:105) | SIIRYGGRCYHY |
| SIVAGM | (SEQ ID NO:106) | VLLGYRGCCFYC |
| SIVSOOTY | (SEQ ID NO:107) | SIIRYRGCRFNC |
| SIVMAC | (SEQ ID NO:108) | SIIGYRGCCFYC |
| HIV2ROD | (SEQ ID NO:109) | SLVRHRGCRLNS |
| HIV1BRU | (SEQ ID NO:110) | SSIRYRSRCYSI |
| HIVYU | (SEQ ID NO:111) | SSIRYRSRCYSI |
| HIV2 | (SEQ ID NO:112) | SFTRHRGCRLNS |
| RESIVXX | (SEQ ID NO:113) | GTARHRGRCHHN |
| SIVACUTE | (SEQ ID NO:114) | SIIRYRGCCFNC |
| SIV1AGM | (SEQ ID NO:115) | SLVRYRSRCHYN |
| SIVGAA | (SEQ ID NO:116) | SIIRYRGCCFNC |
| SIVSYKES | (SEQ ID NO:117) | NVSRYRGRCYYN |
| HIVMAL | (SEQ ID NO:118) | SSIRHRSRCYSI |
| CIV | (SEQ ID NO:119) | SFARYRSCCYSN |

Multiple alignment of the putative protease fusion protein DNA recopgnition helix from a series of primate retroviruses, showing conservation of UGA (selenocysteine codons (shown as C) and other residues. In some of the SIV sequences, two UGA codons are found; all sequences with only one C have arginine (R) in the other position. Conservation of sequence (e.g., the R residues indicated by an asterisk) is improbable unless this is a real gene, because, e.g., the conserved and basein its third codon position, but only A or C at that point will yield an R in the -1 reading frame. Similar arguments apply to the conservation of a UGA codon in the -1 reading frame (see text).

TABLE 7

| | | * SeC |
|---|---|---|
| HIV1BRU | (SEQ ID NO:120) | aucuaucaauacauggaUgau |
| HIVJSRF | (SEQ ID NO:120) | aucuaucaauacauggaUgau |
| HIVYU | (SEQ ID NO:121) | aucuaucaguacauggaUgau |
| HIVNL43 | (SEQ ID NO:120) | aucuaucaauacauggaUgau |
| HIVU455A | (SEQ ID NO:120) | aucuaucaauacauggaUgau |
| HIVNY5CG | (SEQ ID NO:120) | aucuaucaauacauggaUgau |
| COPIA | (SEQ ID NO:122) | guauuauuauauguagaugau |
| HIVMAL | (SEQ ID NO:123) | auauaccaauacauggaUgau |
| HIVCAM1 | (SEQ ID NO:120) | aucuaucaauacauggaUgau |

TABLE 7-continued

| | | |
|---|---|---|
| HIVMN | (SEQ ID NO:120) | aucuaucaauacauggaUgau |
| HIVOYI | (SEQ ID NO:120) | aucuaucaauacauggaUgau |
| HIV2 | (SEQ ID NO:124) | aucguucaguacauggaUgau |
| HIV2ROD | (SEQ ID NO:125) | aucauucaguacauggaugau |
| HIV2GH1 | (SEQ ID NO:126) | cucauccaauacauggaUgau |
| HTLV | (SEQ ID NO:127) | auucuucaauacauggaUgac |
| CIVCG | (SEQ ID NO:128) | auuuaccaauacauggaUgac |
| SIVAGM1 | (SEQ ID NO:129) | uuaguccaguauauggaugac |
| SIVAGM2 | (SEQ ID NO:130) | auuguccaauacauggaCgau |
| SIVAGM3 | (SEQ ID NO:131) | auugugcaauacauggaUgac |
| SIVAGM4 | (SEQ ID NO:132) | auuguacaauacauggaUgau |
| SIVMAND | (SEQ ID NO:133) | uuauaucaauacauggaUgau |
| SIVSOOTY | (SEQ ID NO:134) | cugauccaauacauggaUgac |
| SIVMAC | (SEQ ID NO:135) | uuaguccaguauauggaUgac |
| SIVACUTE | (SEQ ID NO:136) | cugauccaauacauggaUgac |
| SIVSYKES | (SEQ ID NO:137) | cuaauacaguacauggaUgac |
| SIVGAA | (SEQ ID NO:138) | cugauccaauacauggaUgac |
| FIV | (SEQ ID NO:139) | auuuaccaauauauggaUgac |
| PANTHER | (SEQ ID NO:140) | auauaucaauauauggaUgau |
| PUMA | (SEQ ID NO:141) | guauaucaauauauggaUgau |
| BIV | (SEQ ID NO:142) | uuguagavaauauauggaUgau |
| EIAVCG | (SEQ ID NO:143) | uuguaucaauauauggaUgau |
| MMLV | (SEQ ID NO:144) | cugcuacaguacguggaUgac |
| VISNA | (SEQ ID NO:145) | uuuggaauauacauggaUgau |
| | | Y M D D |

Conversation of the UGA codon in the -1 reading frame of the RT YMDD region in primate and other closely related retroviruses. Due to the degeneracy of the genetic code, this conversation cannot be explained by evolutionary selection of the pol gene protein sequence alone, since either GAU or GAC codes for Asp (D). The U of UGA is probably being conserved due to as combined requirement for the UGA codon in the -1 reading frame, assisted by conservation of secondary structure in some specific-cases (see text). In the one case where the UGA is not conserved (SIVagm2), there is evidence of a compensatory mutation: a UGA codon, unique to SIVagm2, is found in the -1 reading frame slightly downstream from the region shown.

TABLE 8

```
 10 DKAQDEHEKYHSNWRAMASDFNLPPVVAKEIVASCDKCQLKGEAMHGQVD 59
    ||||||.:.  ...|.  |    | .||.: ||| . ...|| .   : |
402 dkaqderdwvlnefrtgks....pimvatd.vasrg.idvkgithvfnyd 445

60 CSPGIWQLDCTHLEGKSYPGSSSCSQWIYRSRSYSSRNRAGNSILSF... 106
      ||  . |..|  |:: .:....:...| :.. ....|.  ||||
446 f.pgnte.dyvhrigrtgragakgtaytyftsdnakqarelvsilseakq 493

107 KISRKM........ASKNNTYRQWQQFHQYYGQGRLLVG.GNQA.GIWNS 146
    .|..|:        :.:...|| ...: .  |. |  .| ||.. |. .|
494 didpkleemaryssggrggnyr.rggygr..ggfrrgggygnrnrgfttgs 540

147 LQSPKSRSSR 156
      .| .||..
541 nsaplarsrw 550
```

TABLE 8 shows alignment between the preducted integrase fusion protein (upper sequence SEQ ID NO:84) and the C-terminal end of an *E. coli* RNA helicase (lower segment SEQ ID NO:85) generated using the GAP program with the default normalized Dayhoff matrix, significance 3.7 SD. Gap weight is 1.5, length weight is 0.3, 26% identity. A similar alignment was produced using a PAM 120 matrix, significance score 4.2 SD. The GKS sequence in the second panel, aligned with GRT in the helicase is a known ATPbinding motif.

TABLE 9

CD4 (SEQ ID NO:22)

```
  1 MLALETSPWP LKRKQESCIR KCTWWCCEPL SSRKICPVRC GDPPPLSCCC

51 ACNWRTRRQR SRSGRRRCGC CTLRRGCGSV ECVTRDRSCW NPTSRFCPHG

101 PPRCSQWPCL CWGASPASCF SLG
```

CD8 (SEQ ID NO:23)

```
  1 MQAGSFSISQ ACSRKTVAST SACSSGAPSC PSGRELSCVW LISFPPLPSP

51 PRSPPSRREC AGYPGQRPRRP19 AHFVAPSPLA CWWLASWFCW FPWEWPSTCA

101 AGGGEPGFVS CNNFTNKQRI RFWCPATKRH RSVMSTMWKN ERRDTFNPGE

151 FNGCCSCLLF TAARPFCVCC AWEQLVRGSS GILGRRFHCP QGTSQSVLED

201 CVRNAAHATA SGSCAFPELG PLVVAI
```

HLA-DR p33 (SEQ ID NO:24)

```
  1 MTSATLSPTM SNCPCWAGAL GPRRASAAAE FCTQAFPSEWCLCSSLARPPP

51 PTSCTSSRAG WTNCQSPPRT CSWRTCACSF PSLPSLPCARC AWPPRCCCRR

101 CPWEPCPRGP CRMPPSMATC QRTMCCTCSR MLTPCRCTRH CRGASRRTCD

151 TLRTPWRP
```

Translation of UGA-rich open reading frames, +1 to the main coding region, in CD4, CD8 beta and HLA-DR p33. UGA codons, potentially encoding selenocysteine, are indicated by C.

TABLE 10

Ebola nucleoprotein variants

FUSION PROTEIN: EBOLA_NP1 (SEQ ID NO:164)

```
  1 MDSRPQKIWM APSLTESDMD YHKILTAGLS VQQGIVRQRV IPVYQVNNLE

51 EICQLIIQAF EAGVDFQESA DSFLLMLCLH HAYQGDYKLF LESGAVKYLE

101 GHGFRFEVKK RDGVKRLEEL LPAVSSGKNI KRTLAAMPEE ETTEANAGQF

151 LSFASLFLPK LVVGEKACLR KVQRQIQVHA EQGLIQYPTA WQSVGHMMVI

201 FRLMRTNFLI KFLLIHQGMH MVAGHDANDA VISNSVAQAR FSGLLIVKTV

251 LDHILQKTER GVRLHPLART AKVKNEVNSL KAALSSLAKH GEYAPFARLL

301 NLSGVNNLEH GLfpstignc trsrhstrey prrskcwrtv sttqrgchUg

351 Ueatpticrv srtUpswtUU sgkensyelp sekernqlpa nkrygnskkr 401 apgqadrsyh ccvtaqnkwt lrUUUrhsls rthqUUrqsw psrUUsdUlt 451 gydhsrcggU srUwklrrip ellgkrhect rUlgpirsrr grrgh
```

COMMENT: This sequence represents EBOLA_NP1 cariant fusion proteins having a -1 frameshift starting from base number: 1405. U the amino acid inserted at a UGA codon. UGA can code for SeC, Cys, Trp or Arg.

FUSION PROTEIN: EBOLA_NP2 (SEQ ID NO:165)

```
  1 MDSRPQKIWM APSLTESDMD YHKILTAGLS VQQGIVRQRV IPVYQVNNLE

51 EICQLIIQAF EAGVDFQESA DSFLLMLCLH HAYQGDYKLF LESGAVKYLE

101 GHGFRFEVKK RDGVKRLEEL LPAVSSGKNI KRTLAAMPEE ETTEANAGQF

151 LSFASLFLPK LVVGEKACLR KVQRQIQVHA EQGLIQYPTA WQSVGHMMVI

201 FRLMRTNFLI KFLLIHQGMH MVAGHDANDA VISNSVAQAR FSGLLIVKTV

251 LDHILQKTER GVRLHPLART AKVKNEVNSL KAALSSLAKH GEYAPFARLL

301 NLSGVNNLEH GLFPQLSAIA LGVATAHGST LAGVNVGEQY QQLREAATEA
```

TABLE 10-continued

Ebola nucleoprotein variants

351 EKQLQQYAES RELDHLGLDD Qgkensyelp sekernqlpa nkrygnskkr 401 apgqadrsyh ccvtaqnkwt krUUUrhsls rthqUUrqsw psrUUsdIlt 451 gydhsrcggU srUwklrrip ellgkrhect rUlgpirsrr grrgh
COMMENT: This sequence represents EBOLA_NP1 variant fusion
proteins having a -1 frameshift starting from base number: 1582.
U the amino acid inserted at a UGA codon. UGA can code for SeC,
Cys, Trp or Arg.

TABLE 11

Sequence Comparison if the HIV_Nef1 Fusion Gene Product (Table 1) With Chemokines.

```
                                  1                                               50
      Llchmrat (SEQ ID NO:146)  ..........  .MAPPTRRLL  NAA.LLLLLL  LMATSHQPSG  ..TVVARELR Llgrorat (SEQ ID NO:147)  ..........  .....M.VSA  TRSLLCAALP  VLATSRQATG  ..APVANELR Llgroalpha (SEQ ID NO:148)  ....MARAAL  SAAPSNPRLL  RV..ALLLLL  LVAAGRRAAG  ..ASVATELR Llena78 (SEQ ID NO:149) MSLLSSRAAR  VPGPSSSLCA  LL..VLLLLL  TQPGPIASAG  PAAAVLRELR Llnap1 (SEQ ID NO:150) ..........  .....MTSKL  AV..ALLAAF  LISAALCEGA  VLPRSAKELR Llip10 (SEQ ID NO:151) ..........  .....MNQTA  IL..ICCLIF  LTLSGIQGV.  .PLS..RTVR Llmcp1 (SEQ ID NO:152) ..........  .....MKVSA  AL..LCLLLI  AATFIPQGLA  QPDAINAPVT Llmcp3 (SEQ ID NO:153) .....MWKPM  PSPSNMKASA  AL..LCLLLT  AAAFSPQGLA  QPVGINTSTT Ll4rat (SEQ ID NO:154) ..........  .....MKVST  AF..LCLLLT  VSAFSAQVLA  HPG...IPSA Llranteshu (SEQ ID NO:155) ..........  .....MKVSA  AA..LAVILI  ATALCAPASA  SPYSSDT..TP Llrantesmo (SEQ ID NO:156) ..........  .....MKISA  AA..LTIILT  AAALCAPAPA  SPYGSDT.TP Lllag1 (SEQ ID NO:157) ..........  .....MKLCV  TV..LSLLML  VAAFCSPALS  APMGSDPPTA Llmipbhuma (SEQ ID NO:158) ..........  .....MKLCV  TV..LSLLML  VAAFCSPALS  APMGSDPPTA Lltap2 (SEQ ID NO:159) ..........  .....MKLCV  TV..LSLLML  VAAFCSPALS  APMGSDPPTA Lltap1 (SEQ ID NO:160) ..........  .....MKLCV  TV..LSLLML  VAAFCSLALS  APMGSDPPTA Llmipahuma (SEQ ID NO:161) ..........  .....MQVST  AA...:AVLLC  TMALCN.QFS  ASLAADTPTA Lli309 (SEQ ID NO:162) ..........  .....MQIIT  TA..LVCLLL  AGMWPEDVDS  KSMQV.PFSR Lll1mouse (SEQ ID NO:163) ..........  .....MRLLL  ....LTFLGV  CCLTPWVVEG  VGTEVLEESS HIV_Nef1¹ (SEQ ID NO:74)  (begin #79).....MTYKAp10  AVD.LSHFFK  RKGGTGRANS  LPT..KTRYP
Match of nef1 to chemokines:²           MT+KA  AV-.LS-++-  --+G++RA+S  -PT..-T-+P
```

```
                                  51                                              100
      Llchmrat  C.QCLKTLP.  RVDFENIQSL  TVTPPGPHCT  QTEVIATLKD  GQE.VCLNPQ Llgrorat  C.QCLQTVA.  GIHFKNIQSL  KVMPPGPHCT  QTEVIATLKN  GRE.ACLDPE Llgroalpha  C.QCLQTLQ.  GIHPKNIQSV  NVKSPGPHCA  QTEVIATLKN  GRK..CLNPA Llena78  C.VCLQTTQ.  GVHPKMISNL  QVFAIGPQCS  KVEVVASLKN  GKE.ICLDPE Llnap1  C.QCIKTYSK  PFHPKFIKEL  RVIESGPHCN  NTEIIVKLSD  GRE.LCLDPK Llip10  C.TCISISNQ  PVNPRSLEKL  EIIPASQFCP  RVEIIATMKK  KGEKRCLNPE Llmcp1  C..CYNFTN.  RKISVQRLAS  YRRITSSKCP  KEAIFKTIV   AKE.ICADPR Llmcp3  C..CYRFIN.  KKIPKQRLES  YRRTTSSHCP  REAVIFKTKL  DKE.ICADPT Ll4rat  C..CFRVTN.  KKISFQRLKS  YKIITSSKCP  QTAIVFEIKP  DKM.ICADPK
```

TABLE 11-continued

Sequence Comparison if the HIV_Nef1 Fusion Gene Product
(Table 1) With Chemokines.

```
       Llranteshu  C..CFAYIA.  RPLPRAHIKE  Y.FYTSGKCS  NPAVVFVTRK  NRQ.VCANPE Llrantesmo  C..CFAYLS.  LALPRAHVKE  Y.FYTSSKCS  NLAVVFVTRR  NRQ.VCANPE Lllag1  C..CFSYTA.  RKLPRNFVVD  Y.YETSSLCS  QPAVVFQTKR  SKQ.VCADPS Llmipbhuma C..CFSYTA.  RKLPRNFVVD  Y.YETSSLCS  QPAVVFQTKR  SKQ.VCADPS Lltap2  C..CFSYTA.  RKLPRNFVVD  Y.YETSSLCS  QPAVVFQTKR  GKQ.VCADPS Lltap1  C..CFSYTA.  RKLPRNFVVD  Y.YETSSLCS  QPAVVFQTKR  SKQ.VCADPS Llmipahuma C..CFSYTS.  RQIPQNFIAD  Y.FETSSQCS  KPGVIFLTKR  SRQ.VCADPS Lli309  C..CFSFAE.  QEIPLRAILC  Y.RNTSSICS  NEGLIFKLKR  GKE.ACALDT Lllmouse C.VNLQ.T..  QRLPVQKIKT  Y.IIW..EGA  MRAVIFVTKR  GLK.ICADPE HIV_Nef1  cSVDLPHT..  RLLPcLEALH  T.RARGQIST  DL...WMVLQ  AST.ScAREG
           Match:¹ C-V+L-+T..  R-LP--AEL-  T.RA-GQI+T  +L...++--+  A--.-CA---
                *
                      101                                                141

Llchmrat  APRLQKIIQK  LLKSPSL...  ..........  ..........  .

Llgrorat  APMVQKIKQK  MLKGVPK...  ..........  ..........  .

Llgroalpha  SPIVKKIIEK  MLNSDKSN..  ..........  ..........  .

Llena78  APFLKKVIQK  ILDGGNKEN.  ..........  ..........  .

Llnap1  ENWVQRVVEK  FLKRAENS..  ..........  ..........  .

Llip10   SKAIKNLLKA  VSKEMSKRSP  ..........  ..........  .

Llmcp1  QKWVQDSMDH  LDKQTQTPKT  ..........  ..........  .

Llmcp3  QKWVQDFMKH  LDKKTQTPKL  ..........  ..........  .

Llrat4  KKWVQDAKKY  LGQISQTTKP  ..........  ..........  .

Llranteshu  KKWVREYINS  LEMS......  ..........  ..........  .

Llrantesmo  KKWVQEYINY  LEMS......  ..........  ..........  .

Lllag1  ESWVQEYYD   LELN......  ..........  ..........  .

Llmipbhuma ESWVQEYVYD  LELN......  ..........  ..........  .

Lltap2  ESWVQEYVYD  LELN......  ..........  ..........  .

Lltap1  ESWVQEYVYD  LELN......  ..........  ..........  .

Llmipahuma EEWVQKYVSD  LELSA.....  ..........  ..........  .

Lli309  VGWVQRHRKM  LRHCPSKRK.  ..........  ..........  .

Lllmouse AKWVKAAIKT  VDGRASTRKN  MAETVPTGAQ  RSTSTAVTLT  G

HIV_Nef1  RR.GQ.....  ..........  ..........  ..........  .
           Match¹: ++.-Q
```

¹UGA codons in HIV_Nef1 are indicated by "c".
²Matches to any of the chemokine sequences are shown at the bottom, with identities in letters, similar residues shown by a + and dissimilar or nonreserved residues indicated by a - symbol.

TABLE 12

```
                                  *
  PLHP-GPx-PIG  (SEQ ID NO:166)  QUGKTEVNYTQLVDLHARYAECGLRILAFPCNQFGRQEPGSDA...EIKE

GPx-YEAST     (SEQ ID NO:167)  HUAFTP.QYKELEYLYEKYKSHGLVIVAFPCGQFGNQEFEKDK...EINK
```

TABLE 12-continued

```
HomoGPx-WOOD    (SEQ ID NO:168)  QUGLTNSNYTDLTEIYKKYKDQGLEILAFPCNQFGGQEPGSIE...EIQN GPx-NEMATODE    (SEQ ID NO:169)  YUAYTM.QYRDFNPILGSNSNGTLNILGFPCNQFYLQEPAENH...ELLN GPx-MACAQUE     (SEQ ID NO:170)  YUGLTA.QYPELNALQEELKPYGLVVLGFPCNQFGKQEPGDNK...EILP PreGPx-RAT      (SEQ ID NO:171)  YUGLTI.QYPELNALQDDLKQFGLVILGFPCNQFGKQEPGDNT...EILP GPx-HUMAN       (SEQ ID NO:172)  YUGLTG.QYIELNALQEELAPFGLVILGFPCNQFGKQEPGENS...EILP GPx-MOUSE       (SEQ ID NO:173)  YUGLTD.QYLELNALQEELGPFGLVILGFPSNQFGKQEPGENS...EILP Pre-GPx-RAT     (SEQ ID NO:174)  YUGLTD.QYLELNALQEELGPFGLVILGFPCNQFGKQEPGENS...EILP SelGPx-BOV      (SEQ ID NO:175)  YUGLTG.QYVELNALQEELEPFGLVILGFPCNQFGKQEPGENS...EILA GPx-GI-HUM      (SEQ ID NO:176)  LUGTTTRDFTQLNELQCRF.PRRLVVLGFPCNQFGHQENCQNE...EILN GPx-BOVINE      (SEQ ID NO:177)  LUGTTVRDYTQMNDLQRRLGPRGLVVLGFPCNQFGHQENAKNE...EILN GPx-RAT         (SEQ ID NO:178)  LUGTTTRDYTEMNDLQKRLGPRGLVVLGFPCNQFGHQENGKNE...EILN GPx-MOUSE       (SEQ ID NO:179)  LUGTTIRDYTEMNDLQKRLGPRGLVVLGFPCNQFGHQENGKNE...EILN GPx-HUMAN       (SEQ ID NO:180)  LUGTTVRDYTQMNELQRRLGPRGLVVLGFPCNQFGHQENAKNE...EILN GPx-RABBIT      (SEQ ID NO:181)  LUGTTVRDYTQMNELQERLGPRALVVLGFPCNQFGHQENAKNE...EILN CVB3-FUS(14)    (SEQ ID NO:82)  [LUD.......PMKDLERKYS.......AFHCNQ.GYSSVFSRTLLGEILN CVB3(+1)(14)    (SEQ ID NO:83)   LUD.......PMKDLERKYS.......AFHCNQGTRVFLVGRS    (43) ]

CVB4(+1)(8)     (SEQ ID NO:182)  IURQ.WKLTGCRCDLQMKWV...VKYLGFPCN.LEHQVCCRGH...YWER

GPx-Rel-HUM     (SEQ ID NO:183)  LUGTTIRDYTEMNDLQKRLG...LVVLGFPCNQFGHQVYGARRW...VALG
```

TABLE 13

MULTIPLE SEQUENCES ALIGNMENT SUPEROXIDE DISMUTASE HOMOLOGUE
IN THE ONCOGENE WITH THE KNOWN SUEOXIDE DISMUTASKS

```
                                                 1                                                  50
        Entamoeba-Fe-Cc41 (SEQ ID NO:184) .......... .......... .......... .......... ..........

Tetrahymena-Mn-Cc46 (SEQ ID NO:185) .......... .......... .......... .......... ..........

Bloodfluke-Exsod-Ccex7 (SEQ ID NO:186) ....MLALLC SCLLLAAGAS DAWTGEDASE PNSDSAEW.. ....IRDMYA Rabbit-Exsod-Ccex4 (SEQ ID NO:187) .......... .......... .......... .......... ..........

Rat-Exsod-Coex5 (SEQ ID NO:188) ....MVAELE CNLLLVACGS VTWTMSDTGE SGVDLADRLD LVEKIGDTHS Dirofilaria-Exsod-Ccex2 (SEQ ID NO:189) .......... .......... ........MM GSFI.FLLSI IISINYINSL Onchocarca-Exsod-Ccex3 (SEQ ID NO:190) .......... .......... ........MI MSFIVIFLSF LIFINYANLV Corn-Cc13 (SEQ ID NO:191) .......... .......... .......... .......... ..........

Rice-Cc10 (SEQ ID NO:192) .......... .......... .......... .......... ..........

Nicotiana-Cc35 (SEQ ID NO:193) .......... .......... .......... .......... ..........

Sweetpotato-Cc11 (SEQ ID NO:194) .......... .......... .......... .......... ..........

Petunia-Cc26 (SEQ ID NO:195) MAAHTIFTTT S..TTNSFLF PIASSNTN.. SAPSLSSSFH GVSLKVKSKT Tomato-Cc33 (SEQ ID NO:196) MAAHSIFTTT S..TTNSFLY PISSS...S.. SSPNINSSFL GVSLNVNAKE Pea-Cc32 (SEQ ID NO:197) MASQTLVSP. .........S PLSSH..... ..SLLRTSFS GVSVKLAP..

Spinach-Cc22 (SEQ ID NO:198) MAAHTILASA PSHTTFSLIS PFSSTPTNAL SSSLQSSSFN GLSFKLSPTT Xenopusa-Cc5-2 (SEQ ID NO:199) .......... .......... .......... .......... ..........

Xenopusa-Cc5 (SEQ ID NO:200) .......... .......... .......... .......... ..........
```

TABLE 13-continued

```
            Mouse-Cc16 (SEQ ID NO:201) .......... .......... .......... .......... ..........
              Rat-Cc23 (SEQ ID NO:202) .......... .......... .......... .......... ..........
         Guineapig-Cc7 (SEQ ID NO:203) .......... .......... .......... .......... ..........
             Human-Cc28 (SEQ ID NO:204) .......... .......... .......... .......... ..........
            Bovine-Cc24 (SEQ ID NO:205) .......... .......... .......... .......... ..........
               Pig-Cc21 (SEQ ID NO:206) .......... .......... .......... .......... ..........
             Horse-Cc27 (SEQ ID NO:207) .......... .......... .......... .......... ..........
          Blueshark-Cc4 (SEQ ID NO:208) .......... .......... .......... .......... ..........
        Loggerhead-Cc20 (SEQ ID NO:209) .......... .......... .......... .......... ..........
           Fruitfly-Cc12 (SEQ ID NO:210) .......... .......... .......... .......... ..........
              Yeast-Cc29 (SEQ ID NO:211) .......... .......... .......... .......... ..........
          Baculovirus-Ccx (SEQ ID NO:212) .......... .......... .......... .......... ..........
    Bloodfluke-Exsod-Ccex6 (SEQ ID NO:213) .......... .......... .......... .........M TVYSYLVILF
            Variola-Cc45 (SEQ ID NO:214) .......... .......... .......... .......... ..........
             Treorf-Cc3 (SEQ ID NO:215) .......... .......... ...MGSLLPL GSCGKcRSPG ELAEGRLSSL
                                                   51                                          100
              Entamoeba-Fe-Cc41 .......... .......... .........M SFQLPQLPYA YNALEPHISK
              Tetrahymena-Mn-Cc46 .......... .......... .......... ......LYNE YSDLEPVLSA
           Bloodfluke-Exsod-Ccex7 KVTEIWQEVM QRR....DDD GTLHAACQVQ PSATL..... DAAQPRVTGV
               Rabbit-Exsod-Ccex4 ..TEIWQALT QQWAAQGEPA GALHAVCRVQ PSATL..... DAAQPRVSGL
                  Rat-Exsod-Coex5 KDLEIWMELG KQREA...DA REMHAVCRVQ PSAML..... PPDQPQITGL
             Dirofilaria-Exsod-Ccex2 HT....VHRS NUHRNMHNGG MPKKAVAVLK SD........ .....TVNGI
             Onchocarca-Exsod-Ccex3 CVEATHVYGR RSHSNGMHGN GARRAVAVLR GDA....... .....GVSGI
                         Corn-Cc13 .......... .......... ..VKAVAVLG SSE....... .....GVKGT
                         Rice-Cc10 .......... .......... ..VKAVAVLA SSE....... .....GVKGT
                     Nicotiana-Cc35 .......... .......... ..VKAVAVLS SSE....... .....GVSGT
                   Sweetpotato-Cc11 .......... .......... ..VKAVAVLS SSE....... .....GVSGT
                       Petunia-Cc26 ,PQSLTLSSV TSPKPFIVFA ATKKAVAVLK GTS....... .....NVEGV
                        Tomato-Cc33 .GQSLTLYAV TTPKPLTVFA ATKKAVAVLK GNS....... .....NVEGV
                          Pea-Cc32 ...QFSTLAT SNFKPLTVVA AAKKAVSVLK GTS....... .....AVEGV
                       Spinach-Cc22 QSLSLSTSAA S..KPLTIVA ATKKAVAVLK GTS....... .....NVEGV
                      Xenopusa-Cc5-2 .......... .......... ..VKACVLA GSG....... .....DVKGV
                       Xenopusa-Cc5 .......... .......... ..VKACVLA GSG....... .....DVKGV
                         Mouse-Cc16 .......... .......... .AMKAVCVLK GDG....... .....PVQGT
                          Rat-Cc23 .......... .......... .AMKAVCVLK GDG....... .....PVQGV
                     Guineapig-Cc7 .......... .......... .ATKAVCVLK GDG....... .....PVQGI
                         Human-Cc28 .......... .......... .ATKAVCVLK GDG....... .....PVQGI
                        Bovine-Cc24 .......... .......... .ATKAVCVLK GDG....... .....PVQGT
                           Pig-Cc21 .......... .......... .ATKAVCVLK GDG....... .....PVQGT
                         Horse-Cc27 .......... .......... .ALKAVCVLK GDG....... .....PVHGV
```

TABLE 13-continued

```
         Blueshark-Cc4 .......... ..........  ..MKAVCVLK GTG....... .....EVTGT
       Loggerhead-Cc20 .......... ..........  ATVKAVCVLK GEDPVKEPVK GPVKEPVKGI
          Fruitfly-Cc12 .......... ..........  .VVKAVCVIN GDA....... .....KGT
             Yeast-Cc29 .......... ..........  .MVQAVAVLK GDA....... .....GVSGV
        Baculovirus-Ccx .......... ..........  ..MKAICIIS GD........ .....VHGK
   Bloodfluke-Exsod-Ccex6 ILLDNYVSAY GYGYSYYHRR HFDPAIASFT KE........ .....PYIGA
           Variola-Cc45 .......... ..........  ...MAVCIID HD........ .....NIRGV
             Treorf-Cc3 VFKGVQALGL SPSISYSVWP RFPFALSILR RDGPSRCPPG ARTHCSSSVT
                              101                                         150
        Entamoeba-Fe-Cc41 ETLEFHHDKH HATYVNKLNG LVKGTEQEHK TLEELIKQKP TQAIYNNAAQ
        Tetrahymena-Mn-Cc46 HLLSFHHGKH HQAYVNNLNA TYEQIAAATK ENDAHKIATL QSALRFNLGG
    Bloodfluke-Exsod-Ccex7 VLFRQLAPRA KLDAFFALEG FPTEPNSSSR AIHVHQFGDL SQG.CESTGP
        Rabbit-Exsod-Ccex4 VVFRQLGPGA QLEAFFDLEG FPVEANLSSR AIHVHQFGDL SQG.CDSTGA
          Rat-Exsod-Coex5 VLFRQLGPSS RLEASFNLEG FPAEQNTSNH AIHVHEFGDL SQG.CESTGP
   Dirofilaria-Exsod-Ccex2 IYFQQNNRAS ATTIYGTING LTP....GLH GFHIHQYGIK ANG.CTSAAA
   Onchocarca-Exsod-Ccex3 IYFQQGSGGS ITTISGSVSG LTP....GLH GFHVHQYGDQ TNG.CTSAGD
              Corn-Cc13 IFFTQEGDG. PTTVTGSVGG LKP....GLH GFHVHALGDT TNG.CMSTGP
              Rice-Cc10 IFFSQEGDG. PTSVTGSVSG LKP....GLH GFHVHALGDT TNG.CMSTGP
         Nicotiana-Cc35 IFFTQDGDA. PTTVTGNVSG LKP....GLH GFHVHALGDT TNG.CMSTGP
        Sweetpotato-Cc11 IFFSQEGDG. PTTVTGNVSG LKP....GLH GFHVHALGDT TNG.CMSTGP
            Petunia-Cc26 VTLTQDDDG. PTTVKVRITG LAP....GLH GFHLHEFGDT TNG.CMSTGP
             Tomato-Cc33 VTLSQDDDG. PTTVNVRITG LAP....GLH GFHLHEYGDT TNG.CMSTGA
                Pea-Cc32 VTLTQDDEG. PTTVNVRITG LTP....GLH GFHLHETGDT TNG.CISTGP
            Spinach-Cc22 VTLTQEDDG. PTTVNVRISG LAP....GKH GFHLHEFGDT TNG.CMSTGP
          Xenopusa-Cc5-2 VRFEQQDDGD .VTVEGKIEG LTD....GNH GFHIHVFGDN TNG.CLSAGP
           Xenopusa-Cc5 VHFEQQDEGA .VSVEGKIEG LTD....GLH GFHIHVFGDN TNG.CMSAGP
              Mouse-Cc16 IHFEQKASGE PVVLSGQITG LTE....GQH GFHVHQYGDN TQG.CTSAGP
               Rat-Cc23 IHFEQKASGE PVVVSGQITG LTE....GEH GFHVHQYGDN TQG.CTTAGP
          Guineapig-Cc7 IHFEQKANG. PVVVKGRITG LVE....GKH GFHVHEFGDM TQG,CTSAGP
              Human-Cc28 INFEQKESNG PVKVWGSIKG LTE....GLH GFHVHEFGDN TAG.CTSAGP
             Bovine-Cc24 IHFEAKG.D. TVVVTGSITG LTE....GDH GFHVHQFGDN TQG.CTSAGP
                Pig-Cc21 IYFELKG.EK TVLVTGTIKG LAE....GDH GFHVHQFGDN TQG.CTSAGP
              Horse-Cc27 IHFEQQQEGG PVVLKGFIEG LTK....GDH GFHVHEFGDN TQG.CTTAGA
          Blueshark-Cc4 VLFEQAADG. PVTLKGSITG LTP....GKH GFHVHAFGDN TNG.CISAGP
        Loggerhead-Cc20 IYFEQQGNG. PVILSGSITG LTE....GKH GFHVHEFGDN TNG.CTSAGA
            Fruitfly-Cc12 VFFEQESSGT PVKVSGEVCG LAK....GLH GFHVHEFGDN TNG.CMSSGP
              Yeast-Cc29 VKFEQASESE PTTVSYEIAG LNSPN...AER GFIHEFGDA TNG.CVSAGP
         Baculovirus-Ccx IYFQQESANQ PLKISGYLLN L.PR...GLH GFHVHEYGDT SNG.CTSAGE
    Bloodfluke-Exsod-Ccex6 VWFTQHGDY. .MYVNGSVAG LPPG...KLL GTHVHRYGGL GNM.CLEAGP
            Variola-Cc45 IYFEPVHGKD ..KVLGSVIG LKS....GTY NLIIHRYGDI SRG.CNSIGS
```

TABLE 13-continued

```
              Treorf-Cc3 ....QENE.. APSCGDSSEW WSPQSLPERM GFHEH..... .SG.CFGDSN
CATALYTIC SITE RESIDUES                                  G H H         C 151                                                 200
       Entamoeba-Fe-Cc41 AWNHAFYWKC M....CGCGV KPSEQ..LIA KLTAAFGGLE EFKKKFTEKA
       Tetrahymena-Mn-Cc46 HYNHWIYWDN LAPVKSGGGV LPDEHSPLTK AIKEKWGSYE NFIRLFNTRT
       Bloodfluke-Exsod-Ccex7 HYNPL....A VPHP...... QHPGDFGNF. .AVRDGSLWR YRAGLAASLA
       Rabbit-Exsod-Ccex4 HYNPL....A VQHP...... QHPGDFGNF. .AV....... ..........
            Rat-Exsod-Coex5 HYNPL....G VPHP...... QHPGDFGNF. .VVRDGRLWK HRMGLATSLA
       Dirofilaria-Exsod-Ccex2 HYNPF....E XTHGRPTNNI KHIGDLRNIK .AGADGVANV NIISNHIQLS
       Onchocarca-Exsod-Ccex3 HYNPF....G KTHGGPNDRI KHIGDLGNIV .AGANGVAEV YINSYDIKLR
                    Corn-Cc13 HYNPA....S KEHGAPEDEN RHAGDLGNVT .AGADGVANI NVTDSQIPLT
                    Rice-Cc10 HFNPT....G KEHGAPQDEN RHAGDLGNIT .AGADGVANV NVSDSQIPLT
              Nicotiana-Cc35 HYNPA....G KEHGAPEDEV RHAGDLGNIT .VGEDGTASF TLTDKQIPLA
             Sweetpotato-Cc11 HFPNA....G KEHGAPGDDN RHAGDLGNIT .VGEDGTASF TITDKQIPLT
                 Petunia-Cc26 HFNPN....G LTHGAPGDEV RHAGDLGNIE .ANASGVAEA TLVDNQIPLS
                  Tomato-Cc33 HFNPN....K LTHGAPGDEI RHAGDLGIV. .ANADGVAEV TLVDNQIPLT
                     Pea-Cc32 HFNPN....K LTHGAPEDEI RHAGDLGNIV .ANAEGVAEA TIVDNQIPLT
                 Spinach-Cc22 HFNPD....K KTHGAPEDEV RHAGDLGNIV .ANTDGVAEA TIVDNQIPLT
                Xenopusa-Cc5-2 HFNPQ....N KNHGSPKDAD RHVGDLGNVT .AE.GGVAQF KFTDPQISLK
                 Xenopusa-Cc5 HFNPE....N KNHGAPGDTD RHVGDLGNVT .AE.GGVAQF KITDSLISLK
                  Mouse-Cc16 HFNPH....S KKHGGPADEE RHVGDLGNVT .AGKDGVANV SIEDRVISLS
                    Rat-Cc23 HFNPH....S KKHGGPADEE RHVGDLGNVA .AGKDGVANV SIEDRVISLS
                Guineapig-Cc7 HFNPL....S KKHGGPQDEE RHVGDLGNVT .AGADGVANV SIEDSILSLS
                   Human-Cc28 HFNPL....S RKHGGPKDEE RHVGDLGNVT .ADKDGVADV SIEDSVISLS
                  Bovine-Cc24 HFNPL....S KKHGGPKDEE RHVGDLGNVT .ADKNGVAIV DIVDPLISLS
                     Pig-Cc21 HFNPE....S KKHGGPKDQE RHVGDLGNVT .AGKDGVATV YIEDSVIALS
                   Horse-Cc27 HFNPL....S KKHGGPKDEE RHVGDLGNVT .ADENGKADV DMKDSVISLS
                Blueshark-Cc4 HYNPF....S JNHGGPDDEE RHVGDLGNVE .ANGNGVAEF EIKDRQLHLS
                Loggerhead-Cc20 HFNPP....G KNHGGPQDNE RHVGDLGNVI .ANKEGVAEV CIKDSLISLT
                 Fruitfly-Cc12 HFNPY....G KEHGAPVDEN RHLGDLGNIE .ATGDCPTKV NITDSKITLF
                   Yeast-Cc29 HFNPF....K KTHGAPTDEV RHVGDMGNVK .TDENGVAKG SFKDSLIKLI
               Baculovirus-Ccx HFNPT....N EDHGAPDAEI RHVGDLGNIK SAGYNSLTEV NMMDNVMSLY
          Bloodfluke-Exsod-Ccex6 HFNPF....N QRHGPRGYP RHAGDLGNI. RVGRGGVAKF DFYVTIKGLG
                 Variola-Cc45 .......... .......... ..PEIFIGNI FVNRYGVAYV YL.DTDVNIS
                  Treorf-Cc3 HFHPQ....N QTHSCSNGVI AKAA...... .......... ..........
CATALYTIC SITE RESIDUES H HD          H          K 201                                                 250
       Entamoeba-Fe-Cc41 VGHFGSGWCW LVEHDG..KL EIIDTHDAVN PMTNGMKPLL TCDVWEHAYY
       Tetrahymena-Mn-Cc46 AAIQGSGWGW LGYDTVSKSL RLFELGNQDM PEWSSIVPLL TIDVWEHAYY
       Bloodfluke-Exsod-Ccex7 GPHSIVGRAV VVHAGEDDLG RGG...NQAS VENGNAGRRL ACCVVGVCGP
```

TABLE 13-continued

```
        Rabbit-Exsod-Ccex4  ..........  ..........  ..........  ..........  ..........
           Rat-Exsod-Coex5  GPHSILGRAV  VVHAGEDDLG  KGG...NQAS  VQNGNAGRRL  ACCVVGTSNS
    Dirofilaria-Exsod-Ccex2  GPLSVIGRSL  VVHANPDDLG  KGNGDAREES  LKTGNAGSRI  VCSIIGIAPS
      Onchocarca-Exsod-Ccex3  GPLSVIGHSL  VVHANTDDLG  QGTGNMREES  LKTGNAGSRL  ACGVIGIAAV
                 Corn-Cc13  GPNSIIGRAY  VVHADPDDLG  KGG...HELD  KSTGNAGGRV  ACGIIGLQG.
                 Rice-Cc10  GAHSIIGRAY  VVHADPDDLG  KGG...HELS  KTTGNAGGRV  ACGIIGLQG.
             Nicotiana-Cc35  GPQSIIGRAV  VVHADPDDLG  KGG...HELS  KSTGNAGGRV  ACGIIGLQG.
           Sweetpotato-Cc11  GANSVIGRAV  VVHGDPDDLG  KGG...HELS  KSTGNAGGRV  ACGIIGLQG.
                Petunia-Cc26  GPNSVVGRAL  VVHELEDDLG  KGG...HE.LS LTTGNAGGRL  ACGVVGLTPI
                 Tomato-Cc33  GPNSVVGRAL  VVHELEDDLG  KGG...HE.LS LTTGNAGGRL  ACGVVGLTPI
                    Pea-Cc32  GPNSVVGRAL  VVHELQDDLG  KGG...HE.LS LSTGNAGGRL  ACGCCGLTPV
                Spinach-Cc22  GPNSVVGRAL  VVHELEDDLG  KGG...HE.LS PTTGNAGGRL  ACGVVGLTPV
             Xenopusa-Cc5-2  GERSIIGRTA  VVHEKQDDLG  KGG...DD.ES LKTGNAGGRL  ACGVIGFCP.
               Xenopusa-Cc5  GPNSIIGRTA  VVHEKADDLG  KGG...ND.ES LKTGNAGGRL  ACGVIGYSP.
                 Mouse-Cc16  GEHSIIGRTM  VVHEKQDDLG  KGG...NE.ES TKTGNAGSRL  ACGVIGIAQ.
                   Rat-Cc23  GEHSIIGRTM  VVHEKQDDLG  KGG...NE.ES TKTGNAGSRL  ACGVIGIAQ.
              Guineapig-Cc7  GANSIIGRTM  VVHEKPDDLG  KGG...NE.ES TKTGNAGSRL  ACGVIGIAQ.
                 Human-Cc28  GDHCIIGRTL  VVHEKADDLG  KGG...NE.ES TKTGNAGSRL  ACGVIGIAQ.
                Bovine-Cc24  GEYSIIGRTM  VVHEKPDDLG  RGG...NE.ES TKTGNAGSRL  ACGVIGIAK.
                   Pig-Cc21  GDHSIIGRTM  VVHEKPDDLG  RGG...NE.ES TKTGNAGSRL  ACGIGITQ.
                 Horse-Cc27  GKHSIIGRTM  VVHEKQDDLG  KGG...NE.ES TKTGNAGSRL  ACGVIGIAP.
              Blueshark-Cc4  GERSIIGRTL  VVHEKEDDLG  KGG...DE.ES LRTGNAGSRL  ACGVIGIAKD
             Loggerhead-Cc20  GSQSIIGRTM  VVHEKEDDLG  KGG...ND.ES LKTGNAGSRL  ACGVIGIAKL
                Fruitfly-Cc12  GADSIIGRTV  VVADADDLG   QGG...HE.LS KSTGNAGARI  GCGVIGIAKV
                   Yeast-Cc29  GPTSVVGRSV  VIHAGQDDLG  KGD...TE.ES LKTGNAGPRP  ACGVIGLTN.
              Baculovirus-Ccx  GPHNIIGRSL  VVHTDKDDLG  LTD...HP.LS KTTGNSGGRL  GCGIIAICK.
           Bloodfluke-Exsod-Ccex6  PFDGFIGRAL  VIHANRDDLG  RN...RDE.GS RTTGNSGPRL  ACATIGFRAP
                Variola-Cc45  T...IIGKAL  SI........  ..........  ..........  ...SKNDQRL  ACGVIGISYI
                 Treorf-Cc3  ...SLV.R.L  KGHGSPSD.E  RGRMEQSGEIL FPVGNWASLW  PcTSQEAD..
CATALYTIC SITE RESIDUES                   H    D                     G           C
                                251                              282
             Entamoeba-Fe-Cc41  IDTRNNRAAY  LEHWWNVVNW  KFVEEQL...  ..
           Tetrahymena-Mn-Cc46  LDYQNLRPKY  LTEVWKIVNW  REVEKRYLQA  IE
            Bloodfluke-Exsod-Ccex7  GLWERQAREH  SERKKRRRES  ECKAA.....  ..
              Rabbit-Exsod-Ccex4  ..........  ..........  ..........  ..
                Rat-Exsod-Coex5  EAWESTQK..  .ERKKWRWES  ECKTT.....  ..
         Dirofilaria-Exsod-Ccex2  T.........  ..........  ..........  ..
           Onchocarca-Exsod-Ccex3  S.........  ..........  ..........  ..
                      Corn-Cc13  ..........  ..........  ..........  ..
                      Rice-Cc10  ..........  ..........  ..........  ..
```

TABLE 13-continued

| | |
|---|---|
| Nicotiana-Cc35 | .......... .......... .......... .. |
| Sweetpotato-Cc11 | .......... .......... .......... .. |
| Petunia-Cc26 | .......... .......... .......... .. |
| Tomato-Cc33 | .......... .......... .......... .. |
| Pea-Cc32 | .......... .......... .......... .. |
| Spinach-Cc22 | .......... .......... .......... .. |
| Xenopusa-Cc5-2 | .......... .......... .......... .. |
| Xenopusa-Cc5 | .......... .......... .......... .. |
| Mouse-Cc16 | .......... .......... .......... .. |
| Rat-Cc23 | .......... .......... .......... .. |
| Guineapig-Cc7 | .......... .......... .......... .. |
| Human-Cc28 | .......... .......... .......... .. |
| Bovine-Cc24 | .......... .......... .......... .. |
| Pig-Cc21 | .......... .......... .......... .. |
| Horse-Cc27 | .......... .......... .......... .. |
| Blueshark-Cc4 | .......... .......... .......... .. |
| Loggerhead-Cc20 | .......... .......... .......... .. |
| Fruitfly-Cc12 | .......... .......... .......... .. |
| Yeast-Cc29 | .......... .......... .......... .. |
| Baculovirus-Ccx | .......... .......... .......... .. |
| Bloodfluke-Exsod-Ccex6 | .......... .......... .......... .. |
| Variola-Cc45 | NEKIIHFLTI NENGV..... .......... .. |
| Treorf-Cc3 | ......RTET SGAcPQET.S TSLE...... .. |

The following peptide sequence is translated from H. sapiens mRNA (from base 1055 ro 1639 in clone 210 (SEQ ID NO:216) for TRE oncogene (clone 210, GenBank # C63546). This peptide is a superoxide dismutase homolog of Cu—Zn SOD family based on our observations and has three UGA stop codons denoted as U in the sequence. This peptide is found in all the known isoforms of TRE oncogene and hence all forms of the protein corresponding to this region are encompasses by this invention. SOD is useful as an antioxidant.

1 MGSLLPLGSC GKURSPGELA EGRLSSLVFK GVQALGLSPS ISYSVWPRFP

51 FALSILRRDG PSRCPPGART HCSSSVTQEN EAPSCGDSSE WWSPQSLPER

101 HGFHEHSGCF GDSNHFHPQN QTHSCSNGVI AKAASLVRLK GHGSPSDERG

151 RMEQSGEILF PVGNWASLWP UTSQEADRTE TSGAUPQFTS TSLE

NOTE: Letters below the alignment indicate the highly conserved active site residues in superoxide dismutase enzyme as shown by X-ray crystallographic studies. They were verified to be exactly at the same place in the TRE superoxide homologue by our modeling studies. UGA codons are shown in lower case 'c'.
Connemt: Multiple sequence alignment of this peptide with several known superoxide dismutase is shown in Table 13. Essentially all the important active site residues etc. are conserved in this sequence. This protein has its own start codon so a frameshift is not required for its biosynthesis. It is upstream of the main coding sequence in the mRNA.

What is claimed is:

1. A machine-implementable method for identifying selenoprotein coding sequences within a nucleotide sequence, said method comprising the steps of:

(a) translating in all possible reading frames the nucleotide sequence, wherein the step of translation is carried out treating UGA or TGA as a sense codon, to generate open reading frames (ORFs);

(b) identifying those ORFs having a plurality of UGA or TGA codons and which begin with a translation start codon selected from the group consisting of ATG or AUG or GTG or GUG as independent ORFs and identifying those ORFs which do not begin with a translation start codon selected from the group consisting of ATG or AUG or GTG or GUG as frameshift ORFs;

(c) identifying ORFs not containing internal in-frame UGA or TGA codons which correspond to known coding sequences;

(d) selecting those frameshift ORFs identified in step (b) which overlap a known coding sequence identified in step (c), and identifying frameshift ORFs wherein a −1 or a +1 frameshift sequence is located within overlapping of said coding sequences, wherein the −1 or +1 nature of the frameshift sequence matches the −1 or +1 nature of the frameshift required to change reading frame from that of the known coding sequence to that of the ORF identified in step (b) and identifying in the 3' untranslated region of the newly identified coding sequence, a SECIS element structure;

(e) as an alternative to step (d), selecting those independent ORFs identified in step (b) and analyzing for the presence of a SECIS element structure in the 3' untranslated region of the independent ORF, so that a selenoprotein coding sequence is identified;

whereby a frameshift-generated selenocysteine-containing fusion protein coding sequence is identified in step (d) or a selenoprotein coding sequence is identified in step (e).

2. The method of claim 1 wherein said nucleotide sequence is a viral nucleotide sequence from genomic RNA, mRNA, cDNA or DNA.

3. The method of claim 2 wherein said viral nucleotide sequence is from human immunodeficiency virus, simian immunodeficiency virus, hepatitis virus B, coxsackievirus B3, coxsackievirus B4, ebolavirus or another hemorrhagic fever virus, including but not limited to Hantaan virus and rabbit hemorrhagic virus.

4. The method of claim 1 wherein said nucleotide sequence is a mammalian cellular nucleotide sequence from genomic DNA, mRNA or cDNA.

5. The method of claim 4 wherein said nucleotide sequence comprises a coding sequence for a mammalian protein selected from the group consisting of bcl-2, p53, c-abl, interleukin-2 CD4, CD8 and HLA-DR.

6. The method of claim 1 further comprising the step of analyzing said sequence for a RNA pseudoknot or a stem structure within about 20 nucleotides after the frameshift sequence in step (d).

7. The method of claim 1 further comprising, after step b, the step of selecting frameshift ORFs which encode less than about 100 amino acids, analyzing for a second frameshift sequence downstream of the first frameshift sequence, wherein the second frameshift sequence is opposite in effect to that of the first frameshift sequence, whereby a selenocysteine-containing fusion protein resulting from two frameshift events is identified.

8. The method of claim 1 wherein no independent ORFs and no frameshift-dependent ORFS are identified in step (d) or step (e), further comprising the step of analyzing for splice sequences such that, where said UGA or TGA-containing ORF is flanked by splice sequences, a selenoprotein module is identified which is expressed via mRNA splicing.

9. A selenoprotein encoded in the genome of a virus, wherein the coding sequence of said selenoprotein is genetically engineered for expression in a nucleic acid construct.

10. A selenoprotein of claim 9 encoded in the genome of a virus selected from the group consisting of a retrovirus, a DNA virus or a filovirus.

11. A selenoprotein of claim 9 encoded in the genome of a human immunodificiency virus (HIV).

12. A selenoprotein of claim 11 selected from the group consisting of those proteins having the sequences identified as HIV_GAG, HIV_PROTEASE, HIV_INTEGRASE, HIV_RT1, HIV_RT2, HIV_RT3, HIV_NEF1, HIV_NEF2, HIV_NEF3, OR HIV_ENV1.

13. A selenoprotein of claim 9 encoded in the genome of an Ebola Zaire virus.

14. A selenoprotein of claim 9 encoded in the genome of a Coxsackie virus.

15. A selenoprotein encoded within a human gene selected from the group consisting of CD4, CD8, HLA-D8, alpha-IL-2R and beta-IL-2R, wherein the coding sequence of said selenoprotein is genetically engineered for expression in a nucleic acid construct.

16. A selenoprotein encoded within an oncogene, proto-oncogene or tumor suppressor gene selected from the group consisting of c-abl, bcl-2 and p53, wherein a nucleotide sequence encoding said selenoprotein is genetically engineered for expression in a nucleic acid construct.

* * * * *

UNITED STATES PATENT AND TRADEMARK OFFICE
CERTIFICATE OF CORRECTION

PATENT NO.    : 6,303,295 B1
DATED         : October 16, 2001
INVENTOR(S)   : Taylor et al.

It is certified that error appears in the above-identified patent and that said Letters Patent is hereby corrected as shown below:

<u>Title Page,</u>
Item [56], OTHER PUBLICATIONS, please replace "Unleases Jeckyll-Hyde Virus" with -- Unleashes Jekyll-Hyde Virus --.

<u>Column 4,</u>
Line 50, please replace "Prsotein" with -- Protein --.

<u>Column 9,</u>
Line 59, please replace "tot he" with -- to the --.
Line 61, please replace "of he 5' stem" with -- of the 5' stem --.

<u>Column 10,</u>
Line 16, please replace "os a known" with -- is a known --.

<u>Column 14,</u>
Line 34, please replace "A unit" with -- A unique --.

<u>Column 28,</u>
Line 3, please replace "allignment" with -- alignment --.

<u>Column 34,</u>
Line 47, please replace "80 and 81)" with -- 80 and 81). --.

<u>Column 35,</u>
Line 14, please replace "in bacteria." with -- in bacteria). --.

<u>Column 42,</u>
Lines 13-16, please delete the following:
" -1 FRAME SEQ ID NO:86
(330)   GGAAAAUGAA<u>GCCAC</u>A<u>GAGA</u>GAA
        UUUAUCA<u>UUUC</u>GUGGUGGGGCAGAUGG
Il-2Ra FRAME G1uAsn A B A´ B´"
and insert the following:
--       -1 FRAME         *SecSer*            _____
(330)   GG<u>AAAAU</u>GAA<u>GCCAC</u>A<u>GAGA</u>GAAUUUAUCA<u>UUUC</u>GUGGUGGGG
        CAGAUGG IL-2Ra FRAME          *G1uAsn*        A         B         A´        B´ --

Page 1 of 6

UNITED STATES PATENT AND TRADEMARK OFFICE
CERTIFICATE OF CORRECTION

PATENT NO. : 6,303,295 B1
DATED : October 16, 2001
INVENTOR(S) : Taylor et al.

It is certified that error appears in the above-identified patent and that said Letters Patent is hereby corrected as shown below:

Column 58 and 59,
Table 1, under the heading of FUSION PROTEIN: HIV_GAG (SEQ ID NO: 25), please replace the amino acid residues 41-50, "LEFRFAVNPGL" with
-- LERFAVNPGL --.
Table 1, line approximately 11, please replace "one variant form tof" with -- one variant form of --.
Table 1, the second line from the bottom, replace the amino acid residues 81-90, "NKTQDFWEV" with -- NKRTQDFWWEV --.

Columns 59 and 60,
Table 1, line 1, replace the amino acid residues 171-180, "FRKQMPrnsy"
with -- FRKQNPrhsy --.
Table 1, line 3, replace the amino acid residues 251-260, "SWTVNDOQKL"
with -- SWTVNDIQKL --.
Table 1, line 14, under the heading of FUSION PROTEIN: HIV_RT3 (SEQ ID NO:73), replace the amino acid residues 181-190, "IsihgIfvcr" with -- lsihgUfvcr --.
Table 1, line 19, in the comment section, replace "short bariants" with -- short variants --.
Table 1, line 33, in the comment section, replace "hyperbariability" with
-- hypervariability --.
Table 1, in the bottom section, replace the heading, " FUSION PROTEIN:HIV_BEF3" with -- FUSION PROTEIN:HIV_NEF3 --.

Columns 61 and 62,
Table 1, under the heading of FUSION PROTEIN: HIV_ENV1 (SEQ ID NO:77), replace the amino acid residues, 321-330, "AFVITGKIGN" with -- AFVTIGKIGN --.
Table 1, under the heading of PROTEIN:CXB3_SP1 PEP (SEQ ID NO:78), replace the amino acid residues, 81-90, "RRGGRLCRHPU" with -- RRGRLCRHPU --.
Table 1, under the heading of FUSION PROTEIN:CXB3_FUS2.PEP (SEQ ID NO:79), replace the amino acid residues, 191-200, "eUecqrhqrl" with -- eUevqrhqrl --.
Table 1, under the heading of FUSION PROTEIN: CXB3_GPX1.PEP (SEQ ID NO:80), replace the amino acid residues 11-20, "HTRYLEDMKD" with -- HTRYLUPMKD --.
Table 1, under the heading of FUSION PROTEIN:CXB3_GPX2.PEP (SEQ ID NO:81), replace the amino acid residues 71-80, "tgkfllatsp" with -- tgkfllaysp --.
Table 1, last line in the bottom comment section, replace "encoded in ht e-1" with
-- encoded in the -1 --.

UNITED STATES PATENT AND TRADEMARK OFFICE
CERTIFICATE OF CORRECTION

PATENT NO.   : 6,303,295 B1
DATED        : October 16, 2001
INVENTOR(S)  : Taylor et al.

It is certified that error appears in the above-identified patent and that said Letters Patent is hereby corrected as shown below:

Columns 65 and 66,
Table 4, in the sequence under the heading of RT1 (Motif A region) (SEQ ID NO: 88), replace "UAUU" with -- UAUU --.
Table 4, in the sequence under the heading of RT2 (Motif C region) (SEQ ID NO:4), replace the triplet codon for Arg from "AAG" to -- AGA --.
Table 5, near the bottom, align the phrase, "←Recog. Helix →" right below the amino acid sequence, "GES..NSLKCLRYRLKP" of HPV-33.
Table 5, line 2, replace the last part of the sequence for CRPV, "FLGNNFYGL" with -- FLGNFYGL --.

Column 70,
Table 7, line 6, delete the sequence for BIV and insert -- uuguaucaauauauggaUgau --.
Table 7, the sequence for VISNA should be aligned as follows:
-- uuuggaauauacauggaUgau
            Y M D D --.
Table 8, in the last part of the third aligned sequence pair, replace the sequence, "gfttgs" with -- gftgs --.

Columns 70, 71 and 72,
Table 9, under the heading of CD4, replace the amino acid residues, 81-90, "ECVTRDRSCW" with -- CCVTRDRSCW --.

Columns 71 and 72,
Table 9, under the heading of CD8, delete "p19" after the residue 70.
Table 9, under the heading of HLA-DR p33, replace the residues 31-40, "FCTQAFPSEWC" with -- PCTQAFPSWC --.
Table 10, in the comment section, replace "EBOLA_NP1 cariant fusion" with -- EBOLA_NP1 variant fusion --.

Columns 73 and 74,
Table 10, in the second line, replace the residues 441-450, "psrUUsdIlt" with -- psrUUsdUlt --.
Table 11, in the title, replace "comparison if" with -- comparison of --.
Table 11, in the sequence for Llmipahuma (SEQ ID NO:161), replace ":AVLLC" with -- LAVLLC --.
Table 11, in the sequence for HIV_Nefl, delete "p10" after the sequence "MTYKA".

UNITED STATES PATENT AND TRADEMARK OFFICE
CERTIFICATE OF CORRECTION

PATENT NO. : 6,303,295 B1
DATED : October 16, 2001
INVENTOR(S) : Taylor et al.

It is certified that error appears in the above-identified patent and that said Letters Patent is hereby corrected as shown below:

Columns 75 and 76,
Table 11, middle section, the HIV_Nef1 and the match sequences should be aligned as follows:
HIV_Nef1    csVDLPHT.. RLLPcLAELH T.RARGQIST DL...WMVLQ AST.ScAREG
Match:[1]    C-V+L-+T.. R-LP--AEL-    T.RA-GAI+T +L...++--+ A--,-CA---

Columns 77 and 78,
Table 12, last line, in the last part of the GPx-Rel-HUM sequence, replace "...QVYGARRW..." with -- ... QVYGARW... --.
Table 13, second line in the title, replace "SUEOXIDE" with -- SUPEROXIDE --.

Columns 77-86,
Table 13, in the left hand column, replace all occurrences of "Rat-Exsod-Coex5" with -- Rat-Exsod-Ccex5 --.
Table 13, between the residues 1 and 50, replace the sequence for Bloodfluke-Exsod-Ccex7, "DAWGEDASE" with -- DAWGEDSAE --.
Table 13, between the residues 1 and 50, replace the sequence for Rat-Exsod-Ccex5, "MVAELE" with -- MVAFLF --.

Columns 79-80,
Table 13, between the residues 51 and 100, replace the sequence for Tetrahymena-Mn-Cc46, "LYNE" with -- LNYE --.
Table 13, between the residues 51-100, replace the sequence for Dirofilaria-Exsod-Ccex2, "NUHRNMHNGG" with -- NIHRNMHNGG --.

Columns 81-82,
Table 13, line 6, replace the sequence for Bloodfluke-Exsod-Ccex6, "ILLDNYVSAY" with -- ILLDNYCSAY --.
Table 13, between the residues 101 and 150, replace the sequence for Corn-Cc13, "PTTVTGSVGG" with -- PTTVTGSVSG --.
Table 13, between the residues 101 and 150, replace the sequence for Pea-Cc32, "GFHLHETGDT" replace with -- GFHLHEYGDT --
Table 13, between the residues 101 and 150, replace the sequence for Guineapig-Cc7, "GFHVHEFGDM" with -- GFHVHEFGDN --.
Table 13, between the residues 101 and 150, replace the sequence for Yeast-Cc29, "LNSPN", with -- NSPN --.

UNITED STATES PATENT AND TRADEMARK OFFICE
CERTIFICATE OF CORRECTION

PATENT NO.    : 6,303,295 B1
DATED         : October 16, 2001
INVENTOR(S)   : Taylor et al.

It is certified that error appears in the above-identified patent and that said Letters Patent is hereby corrected as shown below:

Columns 83-84,
Table 13, between the residues 151 and 200, replace the sequence for Tetrahymena-Mn-Cc46, "HYNHWIYWDN" with -- HVNHWIYWDN --.
Table 13, between the residues 151 and 200, replace the sequence for Dirofilaria-Exsod-Ccex2, "XTHGRPTNNI" with -- KTHGRPTNNI --.
Table 13, between the residues 151 and 200, replace the sequence for Tomato-Cc33, "RHAGDLGIV" with -- RHAGDLGNIV --.
Table 13, between the residues 151 and 200, replace the sequence for Blueshark-Cc4, "JNHGGPDDEE" with -- KNHGGPDDEE --.
Table 13, between the residues 151 and 200, replace the sequence for Bloodfluke-Exsod-Ccex6, "QRHGPRGYP" with -- QRHGPRHGYP --.
Table 13, between the residues 151 and 200, replace the sequence for CATALYTIC SITE RESIDUES, "H HD" with -- H HP --.

Columns 85-86,
Table 13, line 5, replace the sequence for Corn Cc13, "GPNSIIGRAY VVHADPDDLG KGG... HELD" with -- GPNSIIGRAV VVHADPDDLG KGG...HELS --.
Table 13, line 6, replace the sequence for Rice-Cc10, "GAHSIIGRAY" with -- GAHSIIGRAV --.
Table 13, line 7, replace the sequence for Nicotiana-Cc35, "KSTGNAGGRV" with -- KTTGNAGGRV --.
Table 13, line 11, replace the sequence for Pea-Cc32, "ACGCCGLTPV" with -- ACGVVGLTPV --.
Table 13, line 23, replace the sequence for Loggerhead-Cc20, "ACGVGIAKL" with -- ACGVVGIAKL --.
Table 13, line 24, replace the sequence for Fluitfly-Ccl2, "VVADADDLG" with -- VVHADADDLG --.
.

UNITED STATES PATENT AND TRADEMARK OFFICE
CERTIFICATE OF CORRECTION

PATENT NO. : 6,303,295 B1
DATED : October 16, 2001
INVENTOR(S) : Taylor et al.

It is certified that error appears in the above-identified patent and that said Letters Patent is hereby corrected as shown below:

<u>Columns 85-86 (cont'd),</u>
Table 13, lines 29 and 30, the sequence for CATALYTIC SITE RESIDUES, "G    C" should be aligned with the sequence for Treorf-Cc3 as follows:
-- ...SLV.R.L KGHGSPSD.E    RGRMEQSGEIL    FPVGNWASLW PCTSQEAD..
              H     D                              G                  C --.

Signed and Sealed this

Fifteenth Day of July, 2003

JAMES E. ROGAN
*Director of the United States Patent and Trademark Office*